US011072635B2

(12) United States Patent
Chen et al.

(10) Patent No.: US 11,072,635 B2
(45) Date of Patent: *Jul. 27, 2021

(54) MACROCYCLIC BROAD SPECTRUM ANTIBIOTICS

(71) Applicants: RQX PHARMACEUTICALS, INC., La Jolla, CA (US); GENENTECH, INC., South San Francisco, CA (US)

(72) Inventors: Yongsheng Chen, Shanghai (CN); Peter Andrew Smith, San Francisco, CA (US); Tucker Curran Roberts, San Diego, CA (US); Robert I. Higuchi, Solana Beach, CA (US); Prasuna Paraselli, San Diego, CA (US); Michael F. T. Koehler, Palo Alto, CA (US); Jacob Bradley Schwarz, San Ramon, CA (US); James John Crawford, San Francisco, CA (US); Cuong Q. Ly, Burlingame, CA (US); Huiyong Hu, Fremont, CA (US); Zhiyong Yu, Shanghai (CN)

(73) Assignees: RQX Pharmaceuticals, Inc., La Jolla, CA (US); Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/777,509

(22) PCT Filed: Nov. 21, 2016

(86) PCT No.: PCT/CN2016/106597
§ 371 (c)(1),
(2) Date: May 18, 2018

(87) PCT Pub. No.: WO2017/084629
PCT Pub. Date: May 26, 2017

(65) Prior Publication Data
US 2020/0239519 A1 Jul. 30, 2020

Related U.S. Application Data

(63) Continuation-in-part of application No. PCT/CN2016/105043, filed on Nov. 8, 2016, and a continuation-in-part of application No. PCT/CN2015/095165, filed on Nov. 20, 2015.

(30) Foreign Application Priority Data

Nov. 20, 2015 (WO) ................ PCT/CN2015/095165
Nov. 8, 2016 (WO) ................ PCT/CN2016/105043

(51) Int. Cl.
C07K 7/06 (2006.01)
A61P 31/04 (2006.01)
A61K 9/00 (2006.01)
A61K 45/06 (2006.01)

(52) U.S. Cl.
CPC ................ *C07K 7/06* (2013.01); *A61P 31/04* (2018.01); *A61K 9/0014* (2013.01); *A61K 45/06* (2013.01)

(58) Field of Classification Search
CPC ........... C07K 7/06; A61P 31/04; A61K 45/06; A61K 9/0014
See application file for complete search history.

(56) References Cited

U.S. PATENT DOCUMENTS

| | | | |
|---|---|---|---|
| 3,128,280 | A | 4/1964 | Rorig |
| 5,204,328 | A | 4/1993 | Nutt et al. |
| 6,025,350 | A | 2/2000 | Masamune et al. |
| 6,048,694 | A | 4/2000 | Bramucci et al. |
| 6,951,840 | B2 | 10/2005 | Belvo et al. |
| 9,187,524 | B2 | 11/2015 | Romesberg et al. |
| 9,309,285 | B2 | 4/2016 | Roberts et al. |
| 10,392,422 | B2 | 8/2019 | Roberts et al. |
| 10,501,493 | B2 | 12/2019 | Roberts et al. |
| 2003/0130172 | A1 | 7/2003 | Belvo et al. |
| 2004/0024178 | A1 | 2/2004 | Ashman et al. |
| 2005/0153876 | A1 | 7/2005 | Cameron et al. |
| 2007/0099885 | A1 | 5/2007 | Endermann et al. |
| 2008/0275018 | A1 | 11/2008 | Endermann et al. |
| 2008/0300231 | A1 | 12/2008 | Endermann et al. |
| 2013/0130985 | A1 | 5/2013 | Alewood et al. |
| 2013/0244929 | A1 | 9/2013 | Gallant et al. |
| 2013/0281360 | A1 | 10/2013 | Romesberg et al. |
| 2014/0249073 | A1 | 9/2014 | Roberts et al. |
| 2015/0045286 | A1 | 2/2015 | Romesberg et al. |

(Continued)

FOREIGN PATENT DOCUMENTS

| | | |
|---|---|---|
| CN | 1675236 A | 9/2005 |
| CN | 103159830 A | 6/2013 |

(Continued)

OTHER PUBLICATIONS

US 10,351,595 B2, 07/2019, Roberts et al. (withdrawn)
Bundgaard, Design of Prodrugs, 1985, chapter 1, p. 1. (Year: 1985).*
Silverman, Prodrugs and Drug Delivery Systems, The Organic Chemistry of Drug Design and Drug Action, pp. 352-399, 1992 (Year : 1992).*
Wolff, Burger's Medicinal Chemistry and Drug Discover, fifth edition, vol. 1, Principles and Practice, 1995, 976-977 (Year: 1995).*

(Continued)

*Primary Examiner* — Sudhakar Katakam
(74) *Attorney, Agent, or Firm* — Alston & Bird LLP

(57) ABSTRACT

Provided herein are antibacterial compounds, wherein the compounds in some embodiments have broad spectrum bioactivity. In various embodiments, the compounds act by inhibition of bacterial type 1 signal peptidase (SpsB), an essential protein in bacteria. Pharmaceutical compositions and methods for treatment using the compounds described herein are also provided.

20 Claims, No Drawings

(56) References Cited

U.S. PATENT DOCUMENTS

| | | | |
|---|---|---|---|
| 2017/0073370 | A1 | 3/2017 | Roberts et al. |
| 2017/0088582 | A1 | 3/2017 | Roberts et al. |
| 2018/0327367 | A1 | 11/2018 | Chen et al. |
| 2020/0024309 | A1 | 1/2020 | Smith et al. |
| 2020/0239519 | A1 | 7/2020 | Chen et al. |
| 2020/0255476 | A1 | 8/2020 | Petronijevic et al. |
| 2020/0377463 | A1 | 12/2020 | Koehler et al. |

FOREIGN PATENT DOCUMENTS

| | | | |
|---|---|---|---|
| CN | 103788176 A | | 5/2014 |
| JP | 2018135357 A | | 8/2018 |
| JP | 2018184435 A | | 11/2018 |
| WO | WO 1998/017679 | A1 | 4/1998 |
| WO | WO-0114346 | A1 | 3/2001 |
| WO | WO-03106480 | A1 | 12/2003 |
| WO | WO 2011/109441 | A1 | 9/2011 |
| WO | WO-2011112441 | A1 | 9/2011 |
| WO | WO-2012036907 | A2 | 3/2012 |
| WO | WO-2012166665 | A2 | 12/2012 |
| WO | WO-2013138187 | A1 | 9/2013 |
| WO | WO-2014081886 | A1 | 5/2014 |
| WO | WO-2015179441 | A2 | 11/2015 |
| WO | WO-2017064629 | A1 | 4/2017 |
| WO | WO 2017/084629 | A1 | 5/2017 |
| WO | WO-2017084630 | A1 | 5/2017 |
| WO | WO 2018/149419 | A1 | 8/2018 |
| WO | WO 2018/183198 | A1 | 10/2018 |
| WO | WO 2019/067498 | A2 | 4/2019 |

OTHER PUBLICATIONS

Banker, Modem Pharmaceutics, 1996, third edition, p. 596. (Year: 1996).*

Bruton et al. Lipopeptide substrates for SpsB, the *Staphylococcus aureus* type I signal peptidase: design, conformation and conversion to α-ketoamide inhibitors. European Journal of Medicinal Chemistry 38:351-356. (2003).

Butler et al. Natural Products—The Future Scaffold for Novel Antibiotics. Biochemical Pharmacology 71:919-929 (2006).

Dufour et al. Total Synthesis of Arlomycin A2, a Signal Peptidase I (SPaseI) Inhibitor. J. P. Synlett 15:2355-2359 (2008).

Holtzel et al. Arylomycins A and B, new biaryl-bridged lipopeptide antibiotics produced by *Streptomyces* sp. Tu 6075. Antibot (Tokyo) 55(6):571-577 (2002).

Liu et al. Efforts toward broadening the spectrum of arylomycin antibiotic activity. Biorg Med Chem Lett 23:5654-5659 (2013).

Liu et al. Synthesis and Characterization of the Arylomycin Lipoglycopeptide Antibiotics and the Crystallographic Analysis of Their Complex with Signal Peptidase. J Am Chem Soc 133:17869-17877 (2011).

Paetzel et al. Crystallographic and biophysical analysis of a bacterial signal peptidase in complex with a lipopeptide-based inhibitor. J Biol Chem 279(29):30781-30790 (2004).

PCT/CN2016/106597 International Search Report and Written Opinion dated Mar. 8, 2017.

PCT/CN2016/106597 Supplementary International Search Report dated Jul. 5, 2017.

PCT/CN2016/106598 International Search Report and Written Opinion dated Mar. 2, 2017.

PCT/CN2016/106598 Supplementary International Search Report dated Jun. 12, 2017.

PCT/US2012/39727 International Preliminary Report on Patentability dated Dec. 2, 2013.

PCT/US2012/39727 International Search Report and Written Opinion dated Jan. 3, 2013.

PCT/US2013/071093 International Preliminary Report on Patentability dated Jun. 4, 2015.

PCT/US2013/071093 International Search Report and Written Opinion dated Apr. 1, 2014.

PCT/US2014/051151 International Preliminary Report on Patentability dated Feb. 25, 2016.

PCT/US2015/031631 International Preliminary Report on Patentability dated Dec. 1, 2016.

PCT/US2015/031631 International Search Report and Written Opinion dated Nov. 3, 2015.

Roberts et al. Initial efforts toward the optimization of arylomycins for antibiotic activity. J Am Chem Soc 129:15830-15838 (2007).

Roberts et al. Initial efforts toward the optimization of arylomycins for antibiotic activity. J Med Chem. 54(14):4954-4963 (2011).

Roberts et al. Synthesis and Biological Characterization of Arylomycin B Antibiotics. J. Nat. Prod. 74:956-961 (2011).

Schimana et al. Arylomycins A and B, new biaryl-bridged lipopeptide antibiotics produced by *Streptomyces* sp. Tü 6075. I. Taxonomy, fermentation, isolation and biological activities. J Antibiot (Tokyo) 55(6):565-570 (2002).

Smith et al. Broad Spectrum Antibiotic Activity of the Arylomycin Natural Products Is Masked by Natural Target Mutations. Chem Biol 17:1223-1231 (2010).

Therien et al. Broadening the Spectrum of β-Lactam Antibiotics through Inhibition of Signal Peptidase Type 1. Antimicrobial Agents and Chemotherapy. 56:4662-4670 (2012).

U.S. Appl. No. 14/086,908 Office Action dated Jan. 5, 2015.

U.S. Appl. No. 14/086,908 Office Action dated May 29, 2015.

U.S. Appl. No. 14/123,024 Office Action dated May 1, 2015.

U.S. Appl. No. 14/123,024 Office Action dated May 19, 2016.

U.S. Appl. No. 14/123,024 Office Action dated Oct. 15, 2015.

Berge et al., "Pharmaceutical Salts," Journal of Pharmaceutical Science, 66(1):1-19, (1977).

Bockstael et al., "Evaluation of the type I signal peptidase as antibacterial target for biofilm-associated infections of *Staphylococcus* epidermidis," Microbiology, 155(11):3719-3729, (2009).

Chen et al., "Highly Regioselective Halogenation of Pyridine N-Oxide: Practical Access to 2-Halo-Substituted Pyridines," Org. Lett., 17(12):2948-2951, (2015).

Clardy et al., "New antibiotics from bacterial natural products," Nature Biotechnology, 24:1541-1550, (2006).

Deangelis et al., "Generating active "L-Pd(0)" via Neutral or Cationic π-Allylpalladium Complexes Featuring Biaryl/Bipyrazolylphosphines: Synthetic, Mechanistic, and Structure-Activity Studies in Challenging Cross-Coupling Reactions," Journal of Organic Chemistry, 80(13):6794-6813, (2015).

Dufour et al., "Intramolecular Suzuki-Miyaura Reaction for the Total Synthesis of Signal Peptidase Inhibitors, Arylomycins A(2) and B(2)," Chemistry: A European Journal, 16(34):10523-10534, (2010).

Freireich et al., "Quantitative comparison of toxicity of anticancer agents in mouse, rat, hamster, dog, monkey, and man," Cancer Chemotherapy Rep., 50(4):219-244, (1966).

Johansson Seechurn et al., "Air-Stable Pd(R-allyl)LC1 (L=Q-Phos), P(t-Bu)3, etc.) Systems for C-C/N Couplings: Insight into the Structure-Activity Relationship and Catalyst Activation Pathway," Journal of Organic Chemistry, 76(19):7918-7932, (2011).

Kohlmann et al., "Fragment Growing and Linking Lead to Novel Nanomolar Lactate Dehydrogenase Inhibitors," J. Med. Chem., 56(3):1023-1040, (2013).

Musial-Siwek et al., "A Small Subset of Signal Peptidase Residues are Perturbed by Signal Peptide Binding," Chem Biol Drug Des., 72(2):140-146, (2008).

Nilsson et al., "A signal peptide with a proline next to the cleavage site inhibits leader peptidase when present in a sec-independent protein," FEBS Letters, 299(3):243-246, (1992).

Reetz et al., "Direct geminal dimethylation of ketones and exhaustive methylation of carboxylic acid chlorides using dichlorodimethyltitanium," Chem. Ber., 118(3):1050-1057, (1985).

Schmitt et al., "Synthesis of Mono- and Bis(fluoroalkyl)pyrimidines from FARs, Fluorinated Acetoacetates, and Malononitrile Provides Easy Access to Novel High-Value Pyrimidine Scaffolds," Chemistry, 24(6):1311-1316, (2018).

Steinmetz et al., "Thuggacins, macrolide antibiotics active against Mycobacterium tuberculosis: isolation from myxobacteria, structure elucidation, conformation analysis and biosynthesis," Chemistry, 13(20):5822-5832, (2007).

(56) References Cited

OTHER PUBLICATIONS

Tan and Romesberg, "Latent antibiotics and the potential of the arylomycins for broad-spectrum antibacterial activity," Medicinal Chemistry Communications, 3(8):916-925, (2012).
Will et al., "Analysis of mitochondrial function using phosphorescent oxygen-sensitive probes," Nature Protocols, 1(6):2563-2572, (2006).
PCT/US2011/049967 International Preliminary Report on Patentability dated Mar. 19, 2013.
PCT/US2011/049967 International Search Report and Written Opinion dated Apr. 6, 2012.
PCT/US2013/029913 International Preliminary Report on Patentability dated Sep. 16, 2014.
PCT/US2013/029913 International Search Report and Written Opinion dated Aug. 1, 2013.
PCT/US2018/024351 International Search Report and Written Opinion dated Jun. 11, 2018.
PCT/US2018/024351 International Preliminary Report on Patentability dated Oct. 1, 2019.
PCT/US2018/052791 International Preliminary Report on Patentability dated Mar. 31, 2020.
Australian Application No. 2016357926, Examination Report No. 1 dated May 26, 2020.
Iranian Application No. 139850140003004248,Office Action dated May 13, 2020, including English translation.
Japanese Application No. 2017-513597, Office Action dated May 20, 2020, including English translation.
Australian Application No. 2016357927, Examination Report No. 1 dated Jun. 5, 2020.
European Application No. 16840309.5, Article 94(3) Communication dated Jun. 18, 2020.
U.S. Appl. No. 16/539,947, Non-Final Office Action dated Jun. 30, 2020.
Braun et al., "Imp/OstA is required for cell envelope biogenesis in *Escherichia coli*," Molecular Microbiology, 45(5):1289-1302, (2002).
Buzder-Lantos et al., "Substrate based peptide aldehyde inhibits bacterial type I signal peptidase," Bioorg Med Chem Lett,19:2880-2883, (2009).
Gould, Philip L., "Salt Selection for Basic Drugs," Int J. Pharm., 33:201-217, (1986).
Hallander et al., "Synergism Between Aminoglycosides and Cephalosporins with Antipseudomonal Activity: Interaction Index and Killing Curve Method," Antimocrob. Agents Chemother., 22:743-752, (1982).
Luo et al., "Crystallographic analysis of bacterial signal peptidase in ternary complex with arylomycin A2 and a beta-sultam inhibitor," Biochemistry, 48(38):8976-8984, (2009).
Mandal et al., "Lipopeptides in microbial infection control: scope and reality for industry," Biotechnol Adv., 31(2):338-345, (2013).
Michaux et al., "Stereocontrolled routes to β,β'-disubstituted α-amino acids," Chem. Soc. Rev., 38:2093-2116, (2009).

Morisaki et al., "A Putative Bacterial ABC Transporter Circumvents the Essentiality of Signal Peptidase," Mbio, 7(5):e00412-16, (2016).
PCT/CN2016/106597 International Preliminary Report on Patentability dated May 22, 2018.
PCT/CN2016/106598 International Preliminary Report on Patentability dated May 22, 2018.
PCT/CN2018/076957 International Search Report and Written Opinion dated Jun. 8, 2018.
ROBERTS et al., "Structural and Initial Biological Analysis of Synthetic Arylomycin A2," J Am Chem Soc., 129(51):15830-8, (2007).
Schallenberger et al., "Type I Signal Peptidase and Protein Secretion and *Stphylococcus aureus*," J Bacterol, 94(10):2677-86, (2012).
Smith et al., "Optimized arylomycins are a new class of Gram-negative antibiotics," Nature, 561(7722):189-194, (2018).
Van Bambeke et al., "The bacterial envelope as a target for novel anti-MRSA antibiotics," Trends in Pharmacological Sciences, 29:124-134, (2008).
West, Solid State Chemistry and its Applications.. Wiley, New York. pp. 358 & 365. (1988).
PCT/US2018/052791 International Search Report and Written Opinion dated Apr. 17, 2019.
U.S. Appl. No. 15/777,499, Non-Final Office Action dated Mar. 19, 2020.
U.S. Appl. No. 15/312,614 Office Action dated Jul. 17, 2018.
U.S. Appl. No. 15/358,100 Office Action dated Aug. 3, 2018.
U.S. Appl. No. 15/358,100 Office Action dated Nov. 26, 2018.
U.S. Appl. No. 15/777,499 Office Action dated Mar. 20, 2019.
U.S. Appl. No. 15/777,499 Office Action dated Oct. 3, 2019.
WIPO Application No. PCT/US2014/051151, PCT International Search Report and Written Opinion of the International Searching Authority dated Nov. 7, 2014.
Japanese Application No. 2017-513597, Office Action dated May 15, 2019, including English translation.
Brown et al., "New natural products as new leads for antibacterial drug discovery," Bioorganic and Medicinal Chemistry Letters, 24(2):413-418, (2014).
PubChem-CID-53377499, "Compound Summary (8S,11S,14S)-3,17,18-Trihydroxy-14-[[2-[[(2R)-2-[[(2R)-3-hydroxy-2-(methylamino)propanoyl]amino]propanoyl]amino]acetyl]-methylamino]-11-methyl-10,13-dioxo-9,12-diazatricyclo[13.3.1.12,6]icosa-1(18),2,4,6(20),15(19),16-hexaene-8-carboxylic acid," (Oct. 5, 2011).
PCT/US2020/034670 International Search Report and Written Opinion dated Sep. 30, 2020.
Smith, Michael B., Description and Table of Contents, *March's Advanced Organic Chemistry: Reactions, Mechanisms, and Structure*, 8th Ed., Hoboken, NJ: Wiley, 2144 pages, (Nov. 2019).
Wang et al., "Application of Nitrile in Drug Design," Chinese Journal of Organic Chemistry, 32:1643-1652, (Dec. 2012) (epub. Apr. 2012).

\* cited by examiner

MACROCYCLIC BROAD SPECTRUM ANTIBIOTICS

CROSS-REFERENCE

This application is a U.S. National Stage entry of PCT International Application PCT/CN2016/106597, filed Nov. 21, 2016, which claims the benefit of PCT International Application PCT/CN2016/105043, filed Nov. 8, 2016, and PCT International Application PCT/CN2015/095165, filed Nov. 20, 2015, both of which are incorporated by reference in their entirety.

BACKGROUND OF THE INVENTION

Antibiotic resistance is a serious and growing phenomenon in contemporary medicine and has emerged as a major public health concern of the 21st century. Therefore, novel classes of broad-spectrum antibiotics, especially those that target novel mechanisms of action, are needed to treat multidrug-resistant pathogens.

SUMMARY OF THE INVENTION

Described herein are novel macrocyclic compounds for the treatment of microbial infections, such as for the treatment of bacterial infections. In various embodiments, the present disclosure provides lipopeptide macrocyclic compounds for the treatment of bacterial infections. In various embodiments, the present disclosure provides classes and subclasses of chemical compounds structurally related to arylomycin for the treatment of bacterial infections. In various embodiments, the macrocyclic compounds act by inhibition of bacterial type 1 signal peptidase (SpsB), an essential protein in bacteria.

In one aspect described herein is a compound of Formula (I):

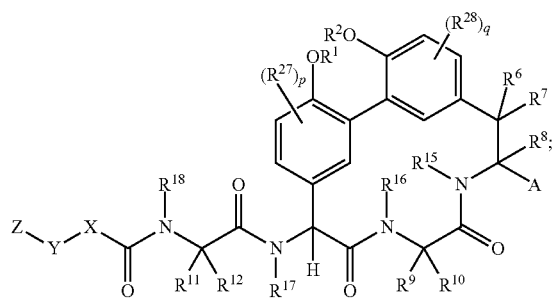

Formula (I)

wherein:

$R^1$ and $R^2$ are each independently H, —($C_1$-$C_6$)alkyl, —($C_1$-$C_6$)alkyl-$OR^{23}$, —$CH_2CH(OH)CH_2NH_2$, —$CH_2CH$(heterocycloalkyl)$CH_2NH_2$, —$CH_2C(O)NH_2$, —$CH_2C(O)N(H)CH_2CN$, —($C_1$-$C_6$)alkyl-C(O)$OR^{23}$, —($C_1$-$C_6$)alkyl-$NR^{21}R^{22}$, —($C_1$-$C_6$)alkyl-C(O)$NR^{25}R^{26}$, —($C_1$-$C_6$)alkyl-N($R^{23}$)C(O)($C_1$-$C_6$)alkyl$NR^{21}R^{22}$, or —($C_1$-$C_6$)alkyl-C(O)N($R^{23}$)($C_1$-$C_6$)alkyl, or optionally substituted heterocycloalkyl;

$R^6$, $R^7$, and $R^8$ are each independently H, or —($C_1$-$C_6$)alkyl;

$R^9$ is H, —($C_1$-$C_6$)haloalkyl, or —($C_3$-$C_6$)cycloalkyl;

$R^{10}$ is H, or —($C_1$-$C_6$)alkyl;

$R^{11}$ and $R^{12}$ are each independently H, —$NH_2$, —($C_1$-$C_6$)alkyl, —($C_1$-$C_6$)alkyl-$OR^{23}$, —($C_1$-$C_6$)alkyl-$SR^{23}$, —($C_1$-$C_6$)alkyl-C(O)$OR^{23}$, —($C_1$-$C_6$)alkyl-$NR^{21}R^{22}$, —($C_1$-$C_6$)alkyl-C(O)$NR^{25}R^{26}$, —($C_1$-$C_6$)alkyl-S(O)—($C_1$-$C_6$)alkyl, —($C_1$-$C_6$)alkyl-N(H)CH═NH, N(H)C(NH)$NH_2$, —($C_1$-$C_6$)alkyl-heterocycloalkyl, optionally substituted —($C_1$-$C_6$)alkyl-N(H)heterocycloalkyl, or —($C_1$-$C_6$)alkyl-heteroaryl; or $R^{11}$ and $R^{18}$ are combined to form an optionally substituted heterocycloalkyl ring, and $R^{12}$ is H;

$R^{15}$, $R^{16}$, $R^{17}$, and $R^{18}$ are each independently H, —($C_3$-$C_6$)cycloalkyl, —($C_1$-$C_6$)alkyl-$OR^{23}$, —($C_1$-$C_6$)alkyl-C(O)$OR^{23}$, or —($C_1$-$C_6$)alkyl-$NR^{21}R^{22}$;

A is —CN, —$CH_2CN$, —CH═CHCN, —$CH_2N$(H)C(O)$CH_2CN$, —$CH_2N$(H)C(O)N(H)$R^{24}$, —C(O)N(H)$R^{34}$, —C(O)N(H)C($R^{23}$)$_2$C(O)$OR^{29}$, —C(O)N(H)C($R^{23}$)$_2$C(O)$NR^{32}R^{33}$, —C(O)N(H)C($R^{23}$)$_2$C═$NR^{30}$, —C(O)N(H)$SO_3H$, —C(O)N(H)$SO_2$CH═$CH_2$, —C(O)N(H)N($R^{24}$)C(O)CH═$CH_2$, —C(O)N(H)N($R^{24}$)C(O)$CH_2Cl$,

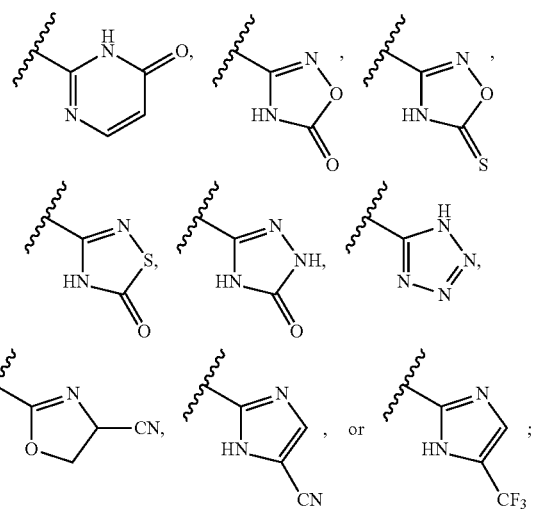

X is optionally substituted —($C_1$-$C_6$)alkyl-, —($C_2$-$C_6$)alkenyl-, —($C_2$-$C_6$)alkynyl-, —($C_3$-$C_7$)cycloalkyl-, optionally substituted heterocycloalkyl, optionally substituted aryl, optionally substituted heteroaryl, —N($R^{24}$)($C_1$-$C_6$)alkyl-, —N($R^{24}$)($C_6$-$C_{10}$)aryl-, or —$SO_2$($C_1$-$C_6$)alkyl-;

Y is a bond, optionally substituted —($C_1$-$C_6$)alkyl-, —($C_2$-$C_6$)alkenyl-, —($C_2$-$C_6$)alkynyl-, —($C_1$-$C_6$)alkyl-N($R^{24}$)($C_1$-$C_6$)alkyl-, —O($C_6$-$C_{10}$)aryl-, —N($R^{24}$)($C_1$-$C_6$)alkyl-, —N($R^{24}$)$SO_2$($C_1$-$C_6$)alkyl-, —N($R^{24}$)C(O)($C_1$-$C_6$)alkyl-, —C(O)($C_1$-$C_6$)alkyl-, —$SO_2$($C_1$-$C_6$)alkyl-, —C(O)NH($C_1$-$C_6$)alkyl-, —($C_3$-$C_7$)cycloalkyl-, optionally substituted —C(O)N($R^{24}$)aryl-, optionally substituted —N($R^{24}$)C(O)aryl-, optionally substituted —N($R^{24}$)$SO_2$aryl-, optionally substituted aryl, or optionally substituted heteroaryl;

Z is H, halogen, —$NH_2$, —CN, —$CF_3$, —$CO_2H$, —($C_1$-$C_{12}$)alkyl, —($C_2$-$C_{12}$)alkenyl, —($C_2$-$C_{12}$)alkynyl, —C(O)$NR^{25}R^{26}$, —N($R^{24}$)($C_1$-$C_{12}$)alkyl, —N($R^{24}$)C(O)($C_1$-$C_{12}$)alkyl, optionally substituted —($C_3$-$C_7$)cycloalkyl, —($C_1$-$C_6$)alkyl-heterocycloalkyl, optionally substituted aryl, or optionally substituted heteroaryl;

each $R^{21}$ and $R^{22}$ is independently H, —($C_1$-$C_6$)alkyl, —($C_1$-$C_6$)heteroalkyl, —($C_1$-$C_6$)alkyl-$CO_2H$, —C(O)($C_1$-$C_6$)alkyl, —C(O)N($R^{31}$)$_2$, —$SO_2N$($R^{31}$)$_2$; or $R^{21}$ and $R^{22}$ and the nitrogen atom to which they are attached form a heterocycloalkyl ring;

each $R^{31}$ is independently H or —($C_1$-$C_6$)alkyl; or two $R^{31}$ and the nitrogen atom to which they are attached form a heterocycloalkyl ring;
each $R^{23}$ is independently H or —($C_1$-$C_6$)alkyl;
each $R^{24}$ is independently H or —($C_1$-$C_6$)alkyl;
each $R^{25}$ and $R^{26}$ is independently H or optionally substituted —($C_1$-$C_6$)alkyl; or $R^{25}$ and $R^{26}$ and the nitrogen atom to which they are attached form a heterocycloalkyl ring;
each $R^{27}$ is independently halogen, —($C_1$-$C_6$)alkyl, or —($C_1$-$C_6$)heteroalkyl;
each $R^{28}$ is independently halogen, —($C_1$-$C_6$)alkyl, or —($C_1$-$C_6$)heteroalkyl;
$R^{29}$ is —$CH_2C(O)NH_2$ or optionally substituted aryl;
$R^{30}$ is

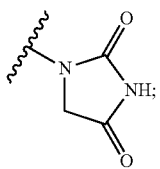 [SMILES: *N1CC(=O)NC1=O]

$R^{32}$ is H or —($C_1$-$C_6$)alkyl;
$R^{33}$ is —$CH_2CN$, —$OC(O)(C_1$-$C_6)$alkyl, or —$SO_2NH_2$;
$R^{34}$ is —OH, —$NH_2$, —CN, —$CH_2CH_2CN$, —$O(C_1$-$C_6)$alkyl, —$C(O)(C_1$-$C_6)$alkyl, —$SO_2NH_2$,

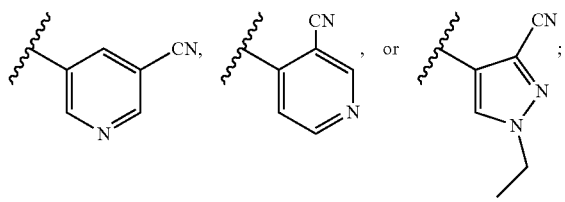

p is 0, 1, or 2; and
q is 0, 1, or 2;
or a pharmaceutically acceptable salt, solvate, or prodrug thereof.

In another embodiment described herein is a compound of Formula (I) having the structure of Formula (Ia):

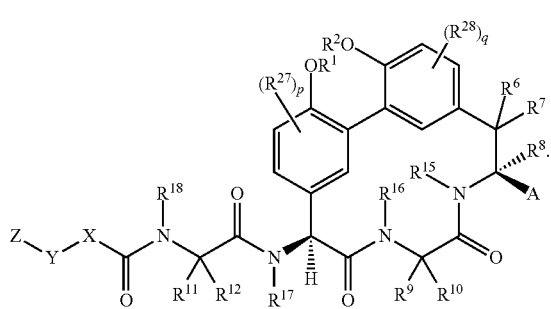

Formula (Ia)

In another embodiment described herein is a compound of Formula (I) or Formula (Ia) wherein $R^6$, $R^7$, and $R^8$ are H. In another embodiment described herein is a compound of Formula (I) or Formula (Ia) wherein $R^{15}$ and $R^{16}$ are H.

In another embodiment described herein is a compound of Formula (I) having the structure of Formula (Ib):

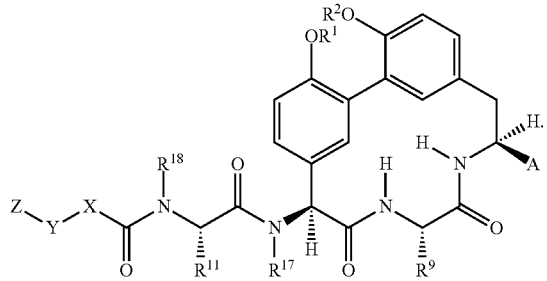

Formula (Ib)

In one embodiment is a compound of Formula (I), (Ia), or (Ib) wherein $R^{17}$ is —$CH_3$. In a further embodiment is a compound of Formula (I), (Ia), or (Ib) wherein $R^{18}$ is H. In a further embodiment is a compound of Formula (I), (Ia), or (Ib) wherein $R^9$ is —($C_1$-$C_6$)alkyl. In a further embodiment is a compound of Formula (I), (Ia), or (Ib) wherein $R^9$ is —$CH_3$.

In another embodiment described herein is a compound of Formula (I) having the structure of Formula (Ic):

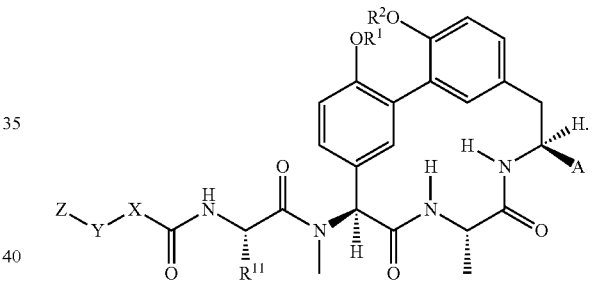

Formula (Ic)

In a further embodiment is a compound of Formula (I), (Ia), (Ib), or (Ic) wherein $R^{11}$ is —($C_1$-$C_6$)alkyl-$OR^{23}$. In a further embodiment is a compound of Formula (I), (Ia), (Ib), or (Ic) wherein $R^{11}$ is —$CH_2CH_2OH$. In a further embodiment is a compound of Formula (I), (Ia), (Ib), or (Ic) wherein $R^{11}$ is —($C_1$-$C_6$)alkyl. In a further embodiment is a compound of Formula (I), (Ia), (Ib), or (Ic) wherein $R^{11}$ is —($C_1$-$C_6$)alkyl-$NR^{21}R^{22}$. In a further embodiment is a compound of Formula (I), (Ia), (Ib), or (Ic) wherein $R^{11}$ is —($C_1$-$C_6$)alkyl-$NH_2$. In a further embodiment is a compound of Formula (I), (Ia), (Ib), or (Ic) wherein $R^{11}$ is —$CH_2NH_2$. In a further embodiment is a compound of Formula (I), (Ia), (Ib), or (Ic) wherein $R^{11}$ is —$CH_2CH_2CH_2NH_2$. In a further embodiment is a compound of Formula (I), (Ia), (Ib), or (Ic) wherein $R^{11}$ is —$CH_2CH_2CH_2CH_2NH_2$. In a further embodiment is a compound of Formula (I), (Ia), (Ib), or (Ic) wherein $R^{11}$ is —$CH_2CH_2NH_2$. In a further embodiment is a compound of Formula (I), (Ia), (Ib), or (Ic) wherein $R^1$ and $R^2$ are each independently H, or —($C_1$-$C_6$)alkyl-$NR^{21}R^{22}$. In a further embodiment is a compound of Formula (I), (Ia), (Ib), or (Ic) wherein $R^1$ and $R^2$ are each independently —($C_1$-$C_6$)alkyl-$NR^{21}R^{22}$. In a further embodiment is a compound of Formula (I), (Ia), (Ib), or (Ic) wherein $R^1$ and $R^2$ are each —$CH_2CH_2NH_2$.

In another embodiment described herein is a compound of Formula (I) having the structure of Formula (Id):

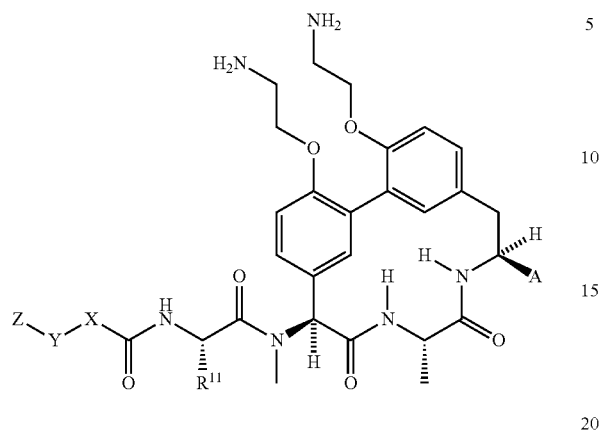

Formula (Id);

wherein $R^{11}$ is —CH$_2$NH$_2$, —CH$_2$CH$_2$NH$_2$, or —CH$_2$CH$_2$CH$_2$NH$_2$.

In a further embodiment is a compound of Formula (I), (Ia), (Ib), (Ic), or (Id) wherein X is optionally substituted aryl. In a further embodiment is a compound of Formula (I), (Ia), (Ib), (Ic), or (Id) wherein X is optionally substituted phenyl. In a further embodiment is a compound of Formula (I), (Ia), (Ib), (Ic), or (Id) wherein X is optionally substituted heteroaryl. In a further embodiment is a compound of Formula (I), (Ia), (Ib), (Ic), or (Id) wherein X is optionally substituted pyridine or optionally substituted pyrimidine. In a further embodiment is a compound of Formula (I), (Ia), (Ib), (Ic), or (Id) wherein X is optionally substituted —(C$_1$-C$_6$)alkyl-. In a further embodiment is a compound of Formula (I), (Ia), (Ib), (Ic), or (Id) wherein Y is optionally substituted aryl. In a further embodiment is a compound of Formula (I), (Ia), (Ib), (Ic), or (Id) wherein Y is optionally substituted phenyl. In a further embodiment is a compound of Formula (I), (Ia), (Ib), (Ic), or (Id) wherein Y is optionally substituted heteroaryl. In a further embodiment is a compound of Formula (I), (Ia), (Ib), (Ic), or (Id) wherein Y is optionally substituted —(C$_1$-C$_6$)alkyl-. In a further embodiment is a compound of Formula (I), (Ia), (Ib), (Ic), or (Id) wherein Y is —O—(C$_1$-C$_6$)alkyl-. In a further embodiment is a compound of Formula (I), (Ia), (Ib), (Ic), or (Id) wherein Y is —N(H)—(C$_1$-C$_6$)alkyl-. In a further embodiment is a compound of Formula (I), (Ia), (Ib), (Ic), or (Id) wherein Y is a bond. In a further embodiment is a compound of Formula (I), (Ia), (Ib), (Ic), or (Id) wherein Z is —(C$_1$-C$_6$)alkyl. In a further embodiment is a compound of Formula (I), (Ia), (Ib), (Ic), or (Id) wherein Z is optionally substituted aryl. In a further embodiment is a compound of Formula (I), (Ia), (Ib), (Ic), or (Id) wherein Z is optionally substituted phenyl. In a further embodiment is a compound of Formula (I), (Ia), (Ib), (Ic), or (Id) wherein Z is optionally substituted heteroaryl. In a further embodiment is a compound of Formula (I), (Ia), (Ib), (Ic), or (Id) wherein Z is optionally substituted —(C$_3$-C$_7$)cycloalkyl. In a further embodiment is a compound of Formula (I), (Ia), (Ib), (Ic), or (Id) wherein Z is halogen.

In a further embodiment is a compound of Formula (I), (Ia), (Ib), (Ic), or (Id) wherein —X—Y—Z is

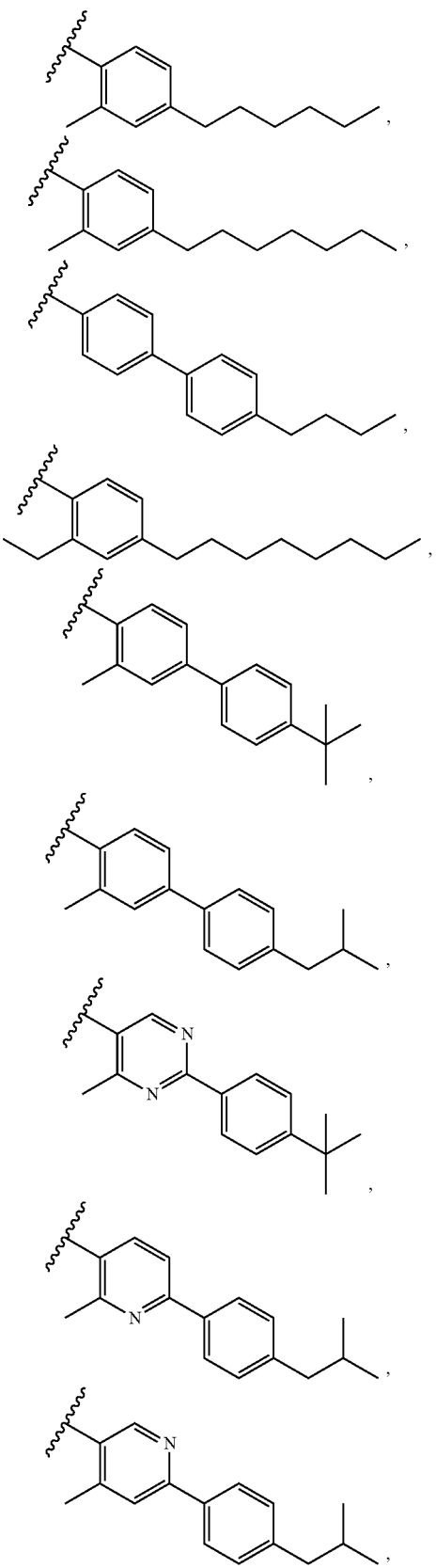

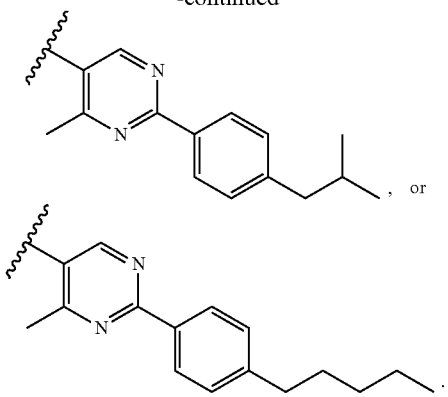

In another aspect is a pharmaceutical composition comprising a compound of Formula (I), (Ia), (Ib), (Ic), or (Id), or a pharmaceutically acceptable salt, pharmaceutically acceptable solvate, or pharmaceutically acceptable prodrug thereof, and a pharmaceutically acceptable excipient thereof.

In another aspect is the use of a compound of Formula (I), (Ia), (Ib), (Ic), or (Id), or a pharmaceutically acceptable salt, pharmaceutically acceptable solvate, or pharmaceutically acceptable prodrug thereof, for the preparation of a medicament for the treatment of a bacterial infection in a patient.

In another embodiment is a method for treating a bacterial infection in a mammal comprising administering to the mammal a compound of Formula (I), (Ia), (Ib), (Ic), or (Id), or a pharmaceutically acceptable salt, pharmaceutically acceptable solvate, or pharmaceutically acceptable prodrug thereof, at a frequency and for a duration sufficient to provide a beneficial effect to the mammal. In another embodiment, the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In another embodiment the bacterial infection is an infection involving a Gram-negative bacteria. In another embodiment, administering comprises a topical administration.

In a further embodiment are methods of treating a mammal in need of such treatment comprising administering to the mammal a second therapeutic agent. In another embodiment, the second therapeutic agent is not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid. In another embodiment, the second therapeutic agent is a β-lactam antibiotic. In another embodiment, the β-lactam antibiotic is selected from penicillins, monobactams, cephalosporins, cephamycins, and carbapenems. In another embodiment, the β-lactam antibiotic is selected from Azlocillin, Amoxicillin, Ampicillin, Doripenem, Meropenem, Biapenem, Cefamandole, Imipenem, Mezlocillin, Cefmetazole, Cefprozil, Piperacillin/tazobactam, Carbenicillin, Cefaclor, Cephalothin, Ertapenem, Cefazolin, Cefepime, Cefonicid, Cefoxitin, Ceftazidime, Oxacillin, Cefdinir, Cefixime, Cefotaxime, Cefotetan, Cefpodoxime, Ceftizoxime, Ceftriaxone, Faropenem, Mecillinam, Methicillin, Moxalactam, Ticarcillin, Tomopenem, Ceftobiprole, Ceftaroline, Flomoxef, Cefiprome, and Cefozopran. A further embodiment comprises administering a β-lactamase inhibitor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a bacterial SPase plays a role in the biochemical mechanisms involved in the disease or malcondition such that a therapeutically beneficial effect can be achieved by acting on the enzyme. "Acting on" SPase can include binding to SPase and/or inhibiting the bioactivity of an SPase.

The expression "effective amount", when used to describe therapy to an individual suffering from a disorder, refers to the amount of a compound described herein that is effective to inhibit or otherwise act on SPase in the individual's tissues wherein SPase involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds described herein are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds described herein can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "0-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R)$_2$, OC(O)N(R')$_2$, C(S)N(R')$_2$, (CH$_2$)$_{0-2}$N(R')C(O)R', (CH$_2$)$_{0-2}$N(R')N(R)$_2$, N(R')N(R')C(O)R', N(R')N(R')C(O)OR', N(R')N(R')CON(R')$_2$, N(R)SO$_2$R', N(R)SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as 0, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

The term "alkylene" means a linear saturated divalent hydrocarbon radical of one to six carbon atoms or a branched saturated divalent hydrocarbon radical of one to six carbon atoms unless otherwise stated, such as methylene, ethylene, propylene, 1-methylpropylene, 2-methylpropylene, butylene, pentylene, and the like.

The term "carbonyl" means C=O.

The terms "carboxy" and "hydroxycarbonyl" mean COOH.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group.

Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "heterocycloalkyl" ring is a cycloalkyl ring containing at least one heteroatom. A heterocycloalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a heterocycloalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzodioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "thioalkoxy" refers to an alkyl group previously defined attached to the parent molecular moiety through a sulfur atom.

The term "glycosyloxyoxy" refers to a glycoside attached to the parent molecular moiety through an oxygen atom.

The term "alkoxycarbonyl" represents as ester group; i.e. an alkoxy group, attached to the parent molecular moiety through a carbonyl group such as methoxycarbonyl, ethoxycarbonyl, and the like.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x-C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1-C_6)$ perfluoroalkyl, more preferred is —$(C_1-C_3)$perfluoroalkyl, most preferred is —$CF_3$.

The term "$(C_x-C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkylene, more preferred is —$(C_1-C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" or "aminocarbonyl" group is a group of the formula C(O)NR$_2$, wherein R can be H, alkyl, aryl, etc.

The term "azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

The term "ring derived from a sugar" refers to a compound that forms a ring by removing the hydrogen atoms from two hydroxyl groups of any sugar.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds described herein may take the form of salts. The term "salts" embraces addition salts of free acids or free bases which are compounds described herein. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds of the present disclosure.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the present disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I), (Ia), (Ib), (Ic), or (Id) compounds, for example in their purification by recrystallization. All of these salts may be prepared by conventional means from the corresponding compound according to Formula (I), (Ia), (Ib), (Ic), or (Id) by reacting, for example, the appropriate acid or base with the compound according to Formula (I), (Ia), (Ib), (Ic), or (Id). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Further examples of prodrugs include boronate esters which can be hydrolyzed under physiological conditions to afford the corresponding boronic acid. Conventional procedures for the selection and preparation of suitable prodrug derivatives are described, for example, in "Design of Prodrugs", ed. H. Bundgaard, Elsevier, 1985.

In addition, where features or aspects of the present disclosure are described in terms of Markush groups, those skilled in the art will recognize that the presently described compounds is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the present disclosure are described in terms of Markush groups, those skilled in the art will recognize that the present disclosure is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present disclosure further embraces isolated compounds according to Formula (I), (Ia), (Ib), (Ic), or (Id). The expression "isolated compound" refers to a preparation of a compound of Formula (I), (Ia), (Ib), (Ic), or (Id), or a mixture of compounds according to Formula (I), (Ia), (Ib), (Ic), or (Id), wherein the isolated compound has been separated from the reagents used, and/or byproducts formed, in the synthesis of the compound or compounds.

"Isolated" does not mean that the preparation is technically pure (homogeneous), but it is sufficiently pure to compound in a form in which it can be used therapeutically. Preferably an "isolated compound" refers to a preparation of a compound of Formula (I), (Ia), (Ib), (Ic), or (Id) or a mixture of compounds according to Formula (I), (Ia), (Ib), (Ic), or (Id), which contains the named compound or mixture of compounds according to Formula (I), (Ia), (Ib), (Ic), or (Id) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds described herein and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds Described Herein

Tautomerism

Within the present disclosure it is to be understood that a compound of Formula (I), (Ia), (Ib), (Ic), or (Id) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the present disclosure encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

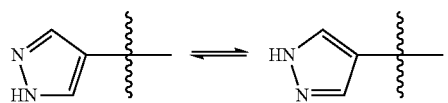

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

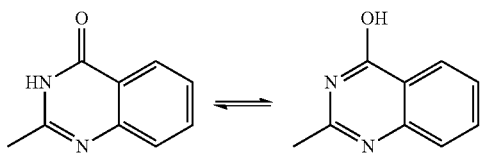

is an example of tautomerism. Accordingly, a structure depicted herein as one tautomer is intended to also include the other tautomer.

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking is A>B>C>D. The lowest ranking atom, D is oriented away from the viewer.

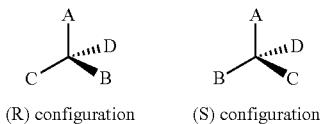

(R) configuration     (S) configuration

The present disclosure is meant to encompass diastereomers as well as their racemic and resolved, diastereomerically and enantiomerically pure forms and salts thereof.

Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound described herein, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present disclosure therefore includes any possible stable rotamers of formula (I) which are biologically active in the treatment of cancer or other proliferative disease states.

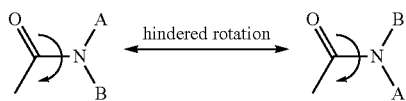

Regioisomerism

In some embodiments, the compounds described herein have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

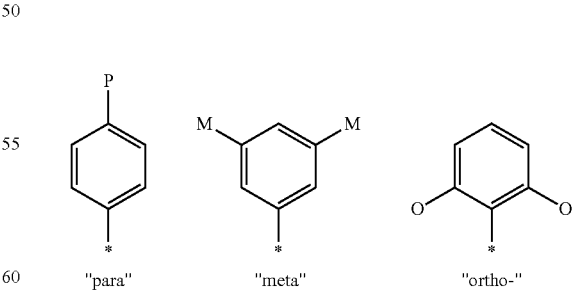

"para"     "meta"     "ortho-"

In various embodiments, the compound or set of compounds, such as are among the inventive compounds or are used in the inventive methods, can be any one of any of the combinations and/or sub-combinations of the above-listed embodiments.

Compounds

In one aspect described herein are compounds of Formula (I):

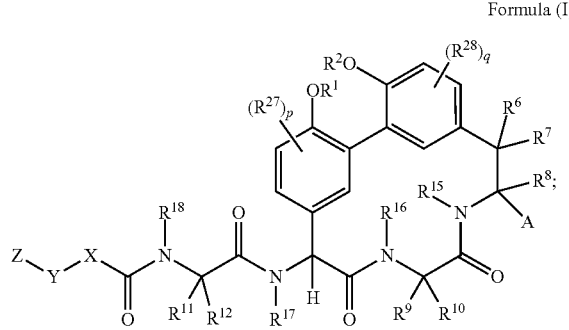

Formula (I)

wherein:
R¹ and R² are each independently H, —(C₁-C₆)alkyl-OR²³, —CH₂CH(OH)CH₂NH₂, —CH₂CH(heterocycloalkyl)CH₂NH₂, —CH₂C(O)NH₂, —CH₂C(O)N(H)CH₂CN, —(C₁-C₆)alkyl-C(O)OR²³, —(C₁-C₆)alkyl-NR²¹R²², —(C₁-C₆)alkyl-C(O)NR²⁵R²⁶, N(R²³)C(O)(C₁-C₆)alkylNR²¹R²², or —(C₁-C₆)alkyl-C(O)N(R²³)(C₁-C₆)alkyl, or optionally substituted heterocycloalkyl;

R⁶, R⁷, and R⁸ are each independently H, or —(C₁-C₆)alkyl;
R⁹ is H, —(C₁-C₆)haloalkyl, or —(C₃-C₆)cycloalkyl;
R¹⁰ is H, or —(C₁-C₆)alkyl;
R¹¹ and R¹² are each independently H, —NH₂, —(C₁-C₆)alkyl, —(C₁-C₆)alkyl-OR²³, —(C₁-C₆)alkyl-SR²³, —(C₁-C₆)alkyl-C(O)OR²³, —(C₁-C₆)alkyl-NR²¹R²², —(C₁-C₆)alkyl-C(O)NR²⁵R²⁶, —(C₁-C₆)alkyl-S(O)—(C₁-C₆)alkyl, —(C₁-C₆)alkyl-N(H)CH=NH, —(C₁-C₆)alkyl-N(H)C(NH)NH₂, —(C₁-C₆)alkyl-heterocycloalkyl, optionally substituted —(C₁-C₆)alkyl-N(H)heterocycloalkyl, or —(C₁-C₆)alkyl-heteroaryl; or R¹¹ and R¹⁸ are combined to form an optionally substituted heterocycloalkyl ring, and R¹² is H;

R¹⁵, R¹⁶, R¹⁷, and R¹⁸ are each independently H, —(C₃-C₆)cycloalkyl, —(C₁-C₆)alkyl-OR²³, —(C₁-C₆)alkyl-C(O)OR²³, or —(C₁-C₆)alkyl-NR²¹R²²;

A is —CN, —CH₂CN, —CH=CHCN, —CH₂N(H)C(O)CH₂CN, —CH₂N(H)C(O)N(H)R²⁴, —C(O)N(H)R³⁴, —C(O)N(H)C(R²³)₂C(O)OR²⁹, —C(O)N(H)C(R²³)₂C(O)NR³²R³³, —C(O)N(H)C(R²³)₂C=NR³⁰, —C(O)N(H)SO₃H, —C(O)N(H)SO₂CH=CH₂, —C(O)N(H)N(R²⁴)C(O)CH=CH₂, —C(O)N(H)N(R²⁴)C(O)CH₂Cl,

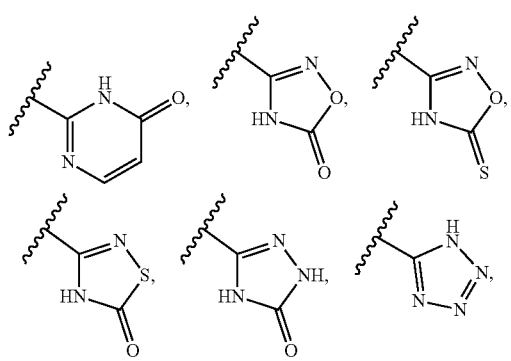

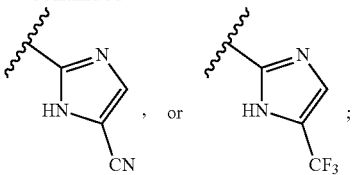

X is optionally substituted —(C₁-C₆)alkyl-, —(C₂-C₆)alkenyl-, —(C₂-C₆)alkynyl, —(C₃-C₇)cycloalkyl-, optionally substituted heterocycloalkyl, optionally substituted aryl, optionally substituted heteroaryl, —N(R²⁴)(C₁-C₆)alkyl-, —N(R²⁴)(C₆-C₁₀)aryl-, or —SO₂(C₁-C₆)alkyl-;

Y is a bond, optionally substituted —(C₁-C₆)alkyl-, —(C₂-C₆)alkenyl-, —(C₂-C₆)alkynyl, —(C₁-C₆)alkyl-N(R²⁴)(C₁-C₆)alkyl-, —O—(C₁-C₆)alkyl-, —O(C₆-C₁₀)aryl-, —N(R²⁴)(C₁-C₆)alkyl-, —N(R²⁴)SO₂(C₁-C₆)alkyl-, —N(R²⁴)C(O)(C₁-C₆)alkyl-, —C(O)(C₁-C₆)alkyl-, —S(C₁-C₆)alkyl-, —SO₂(C₁-C₆)alkyl-, —C(O)NH(C₁-C₆)alkyl-, —(C₃-C₇)cycloalkyl-, optionally substituted —C(O)N(R²⁴)aryl-, optionally substituted —N(R²⁴)C(O)aryl-, optionally substituted —N(R²⁴)SO₂aryl-, optionally substituted aryl, or optionally substituted heteroaryl;

Z is H, halogen, —NH₂, —CN, —CF₃, —CO₂H, —(C₁-C₁₂)alkyl, —(C₂-C₁₂)alkenyl, —(C₂-C₁₂)alkynyl, —C(O)NR²⁵R²⁶, —N(R²⁴)(C₁-C₁₂)alkyl, —N(R²⁴)C(O)(C₁-C₁₂)alkyl, optionally substituted —(C₃-C₇)cycloalkyl, —(C₁-C₆)alkyl-heterocycloalkyl, optionally substituted aryl, or optionally substituted heteroaryl;

each R²¹ and R²² is independently H, —(C₁-C₆)alkyl, —(C₁-C₆)heteroalkyl, —(C₁-C₆)alkyl-CO₂H, —C(O)(C₁-C₆)alkyl, —C(O)N(R³¹)₂, —SO₂N(R³¹)₂; or R²¹ and R²² and the nitrogen atom to which they are attached form a heterocycloalkyl ring;

each R³¹ is independently H or —(C₁-C₆)alkyl; or two R³¹ and the nitrogen atom to which they are attached form a heterocycloalkyl ring;

each R²³ is independently H or —(C₁-C₆)alkyl;
each R²⁴ is independently H or —(C₁-C₆)alkyl;
each R²⁵ and R²⁶ is independently H or optionally substituted —(C₁-C₆)alkyl; or R²⁵ and R²⁶ and the nitrogen atom to which they are attached form a heterocycloalkyl ring;

each R²⁷ is independently halogen, —(C₁-C₆)alkyl, or —(C₁-C₆)heteroalkyl;
each R²⁸ is independently halogen, —(C₁-C₆)alkyl, or —(C₁-C₆)heteroalkyl;
R²⁹ is —CH₂C(O)NH₂ or optionally substituted aryl;
R³⁰ is

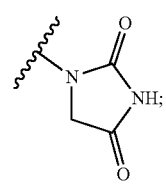 [SMILES: *N1CC(=O)NC1=O]

R³² is H or —(C₁-C₆)alkyl;
R³³ is —CH₂CN, —OC(O)(C₁-C₆)alkyl, or —SO₂NH₂;
R³⁴ is —OH, —NH₂, —CN, —CH₂CH₂CN, —O(C₁-C₆)alkyl, —C(O)(C₁-C₆)alkyl, —SO₂NH₂,

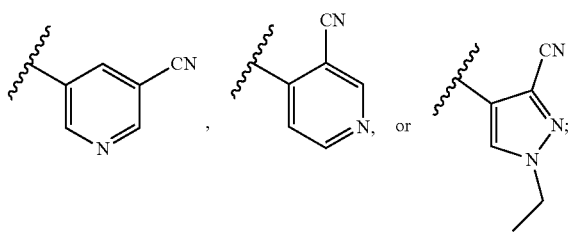

p is 0, 1, or 2; and
q is 0, 1, or 2;
or a pharmaceutically acceptable salt, solvate, or prodrug thereof.

In one embodiment is a compound of Formula (I) wherein $R^6$, $R^7$, and $R^8$ are H.

In another embodiment is a compound of Formula (I) wherein $R^{15}$ and $R^{16}$ are H.

In one embodiment is a compound of Formula (I) wherein $R^{17}$ is —($C_1$-$C_6$)alkyl. In another embodiment is a compound of Formula (I) wherein $R^{17}$ is —$CH_3$. In another embodiment is a compound of Formula (I) wherein $R^{17}$ is —$CH_2CH_3$. In another embodiment is a compound of Formula (I) wherein $R^{17}$ is —($C_3$-$C_6$)cycloalkyl. In another embodiment is a compound of Formula (I) wherein $R^{17}$ is cyclopropyl. In another embodiment is a compound of Formula (I) wherein $R^{17}$ is —($C_1$-$C_6$)alkyl-C(O)$OR^{23}$. In another embodiment is a compound of Formula (I) wherein $R^{17}$ is —$CH_2CH_2OH$. In another embodiment is a compound of Formula (I) wherein $R^{17}$ is —($C_1$-$C_6$)alkyl-$NR^{21}R^{22}$. In another embodiment is a compound of Formula (I) wherein $R^{17}$ is —$CH_2CH_2NH_2$. In another embodiment is a compound of Formula (I) wherein $R^{17}$ is H.

In another embodiment is a compound of Formula (I) wherein $R^{18}$ is H.

In another embodiment is a compound of Formula (I) wherein $R^{10}$ is H.

In another embodiment is a compound of Formula (I) wherein $R^{10}$ is H and $R^9$ is —($C_1$-$C_6$)alkyl. In another embodiment is a compound of Formula (I) wherein $R^{10}$ is H and $R^9$ is —$CH_3$. In another embodiment is a compound of Formula (I) wherein $R^{10}$ is H and $R^9$ is —$CH_2CH_3$. In another embodiment is a compound of Formula (I) wherein $R^{10}$ is H and $R^9$ is —($C_1$-$C_6$)haloalkyl. In another embodiment is a compound of Formula (I) wherein $R^{10}$ is H and $R^9$ is —$CH_2F$. In another embodiment is a compound of Formula (I) wherein $R^{10}$ is H and $R^9$ is —$CHF_2$. In another embodiment is a compound of Formula (I) wherein $R^{10}$ is H and $R^9$ is —($C_3$-$C_6$)cycloalkyl. In another embodiment is a compound of Formula (I) wherein $R^{10}$ is H and $R^9$ is cyclopropyl. In another embodiment is a compound of Formula (I) wherein $R^{10}$ is H and $R^9$ is H.

In another embodiment is a compound of Formula (I) wherein $R^{12}$ is H.

In another embodiment is a compound of Formula (I) wherein $R^{12}$ is H and $R^{11}$ is —($C_1$-$C_6$)alkyl. In another embodiment is a compound of Formula (I) wherein $R^{12}$ is H and $R^{11}$ is —$CH_3$. In another embodiment is a compound of Formula (I) wherein $R^{12}$ is H and $R^{11}$ is —($C_1$-$C_6$)alkyl-$OR^{23}$. In another embodiment is a compound of Formula (I) wherein $R^{12}$ is H and $R^{11}$ is —$CH_2OH$. In another embodiment is a compound of Formula (I) wherein $R^{12}$ is H and $R^{11}$ is —$CH_2CH_2OH$. In another embodiment is a compound of Formula (I) wherein $R^{12}$ is H and $R^{11}$ is —($C_1$-$C_6$)alkyl. In another embodiment is a compound of Formula (I) wherein $R^{12}$ is H and $R^{11}$ is —($C_1$-$C_6$)alkyl-$NR^{21}R^{22}$. In another embodiment is a compound of Formula (I) wherein $R^{12}$ is H and $R^{11}$ is —($C_1$-$C_6$)alkyl-$NH_2$. In another embodiment is a compound of Formula (I) wherein $R^{12}$ is H and $R^{11}$ is —$CH_2NH_2$. In another embodiment is a compound of Formula (I) wherein $R^{12}$ is H and $R^{11}$ is —$CH_2CH_2NH_2$. In another embodiment is a compound of Formula (I) wherein $R^{12}$ is H and $R^{11}$ is —$CH_2CH_2CH_2NH_2$. In another embodiment is a compound of Formula (I) wherein $R^{12}$ is H and $R^{11}$ is —$CH_2CH_2CH_2CH_2NH_2$. In another embodiment is a compound of Formula (I) wherein $R^{12}$ is H and $R^{11}$ is —($C_1$-$C_6$)alkyl-CN. In another embodiment is a compound of Formula (I) wherein $R^{12}$ is H and $R^{11}$ is —$CH_2CN$. In another embodiment is a compound of Formula (I) wherein $R^{12}$ is H and $R^{11}$ is —($C_1$-$C_6$)alkyl-C(O)$NR^{25}R^{26}$. In another embodiment is a compound of Formula (I) wherein $R^{12}$ is H and $R^{11}$ is —$CH_2C(O)NH_2$. In another embodiment is a compound of Formula (I) wherein $R^{12}$ is H and $R^{11}$ is —$CH_2CH_2C(O)NH_2$. In another embodiment is a compound of Formula (I) wherein $R^{12}$ is H and $R^{11}$ is —($C_1$-$C_6$)alkyl-heteroaryl. In another embodiment is a compound of Formula (I) wherein $R^{12}$ is H and $R^{11}$ is H.

In another embodiment is a compound of Formula (I) wherein $R^{11}$ and $R^{18}$ are combined to form an optionally substituted heterocycloalkyl ring and $R^{12}$ is H.

In another embodiment is a compound of Formula (I) wherein p is 1 and $R^{27}$ is halogen. In another embodiment is a compound of Formula (I) wherein p is 1 and $R^{27}$ is optionally substituted —($C_1$-$C_6$)alkyl. In another embodiment is a compound of Formula (I) wherein q is 0, p is 1 and $R^{27}$ is halogen. In another embodiment is a compound of Formula (I) wherein q is 0, p is 1 and $R^{27}$ is optionally substituted —($C_1$-$C_6$)alkyl. In another embodiment is a compound of Formula (I) wherein q is 1 and $R^{28}$ is halogen. In another embodiment is a compound of Formula (I) wherein q is 1 and $R^{28}$ is optionally substituted —($C_1$-$C_6$)alkyl. In another embodiment is a compound of Formula (I) wherein p is 0, q is 1 and $R^{28}$ is halogen. In another embodiment is a compound of Formula (I) wherein p is 0, q is 1 and $R^{28}$ is optionally substituted —($C_1$-$C_6$)alkyl.

In another embodiment is a compound of Formula (I) wherein p is 0, and q is 0.

In another embodiment is a compound of Formula (I) wherein $R^1$ and $R^2$ are each independently H, or —($C_1$-$C_6$)alkyl-$NR^{21}R^{22}$. In another embodiment is a compound of Formula (I) wherein $R^1$ and $R^2$ are each H. In another embodiment is a compound of Formula (I) wherein $R^1$ and $R^2$ are each independently —($C_1$-$C_6$)alkyl-$NR^{21}R^{22}$. In another embodiment is a compound of Formula (I) wherein $R^1$ is H, and $R^2$ is —($C_1$-$C_6$)alkyl-$NR^{21}R^{22}$. In another embodiment is a compound of Formula (I) wherein $R^1$ is —($C_1$-$C_6$)alkyl-$NR^{21}R^{22}$, and $R^2$ is H. In another embodiment is a compound of Formula (I) wherein $R^1$ is H, and $R^2$ is —$CH_2CH_2NH_2$. In another embodiment is a compound of Formula (I) wherein $R^1$ is —$CH_2CH_2NH_2$, and $R^2$ is H. In another embodiment is a compound of Formula (I) wherein $R^1$ and $R^2$ are each —$CH_2CH_2NH_2$.

In another embodiment is a compound of Formula (I) wherein A is —CN. In another embodiment is a compound of Formula (I) wherein A is —$CH_2CN$. In another embodiment is a compound of Formula (I) wherein A is —CH=CHCN. In another embodiment is a compound of Formula (I) wherein A is —$CH_2N(H)C(O)CH_2CN$. In another embodiment is a compound of Formula (I) wherein A is —$CH_2N(H)C(O)N(H)R^{24}$. In another embodiment is a compound of Formula (I) wherein A is —C(O)N(H)$R^{34}$. In another embodiment is a compound of Formula (I) wherein A is —C(O)N(H)C($R^{23}$)$_2$C(O)$OR^{29}$. In another embodiment is a compound of Formula (I) wherein A is —C(O)N(H)C(R$^{23}$)$_2$C(O)NR$^{32}$R$^{33}$. In another embodiment is a compound of Formula (I) wherein A is C(O)N(H)C(R$^{23}$)$_2$C=NR$^{30}$. In another embodiment is a compound of Formula (I) wherein A is —C(O)N(H)SO$_3$H. In another embodiment is a compound of Formula (I) wherein A is —C(O)N(H)SO$_2$CH=CH$_2$. In another embodiment is a compound of Formula (I) wherein A is C(O)N(H)N(R$^{24}$)C(O)CH=CH$_2$. In another embodiment is a compound of Formula (I) wherein A is —C(O)N(H)N(R$^{24}$)C(O)CH$_2$Cl.

In another embodiment is a compound of Formula (I) wherein A is —C(O)N(H)R$^{34}$, wherein R$^{34}$ is —OH. In another embodiment is a compound of Formula (I) wherein A is —C(O)N(H)R$^{34}$, wherein R$^{34}$ is —NH$_2$. In another embodiment is a compound of Formula (I) wherein A is —C(O)N(H)R$^{34}$, wherein R$^{34}$ is —CN. In another embodiment is a compound of Formula (I) wherein A is —C(O)N(H)R$^{34}$, wherein R$^{34}$ is —CH$_2$CH$_2$CN. In another embodiment is a compound of Formula (I) wherein A is —C(O)N(H)R$^{34}$, wherein R$^{34}$ is —O(C$_1$-C$_6$)alkyl. In another embodiment is a compound of Formula (I) wherein A is —C(O)N(H)R$^{34}$, wherein R$^{34}$ is —C(O)(C$_1$-C$_6$)alkyl. In another embodiment is a compound of Formula (I) wherein A is —C(O)N(H)R$^{34}$, wherein R$^{34}$ is —SO$_2$NH$_2$. In another embodiment is a compound of Formula (I) wherein A is —C(O)N(H)R$^{34}$, wherein R$^{34}$ is

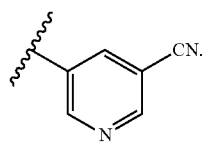 [SMILES: *c1cncc(C#N)c1]

In another embodiment is a compound of Formula (I) wherein A is —C(O)N(H)R$^{34}$, wherein R$^{34}$ is

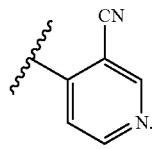

In another embodiment is a compound of Formula (I) wherein A is —C(O)N(H)R$^{34}$, wherein R$^{34}$ is

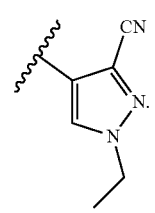 [SMILES: *c1cn(CC)nc1C#N]

In another embodiment is a compound of Formula (I) wherein A is

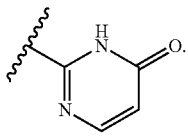 [SMILES: *c1nccc(=O)[nH]1]

In another embodiment is a compound of Formula (I) wherein A is

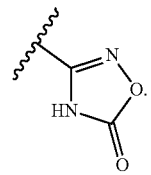

In another embodiment is a compound of Formula (I) wherein A is

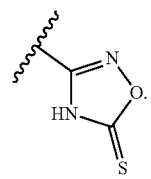

In another embodiment is a compound of Formula (I) wherein A is

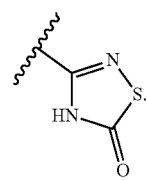

In another embodiment is a compound of Formula (I) wherein A is

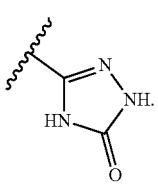

In another embodiment is a compound of Formula (I) wherein A is

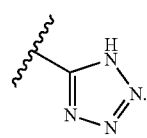

In another embodiment is a compound of Formula (I) wherein A is

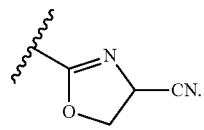 [SMILES: *C1=NC(C#N)CO1]

In another embodiment is a compound of Formula (I) wherein A is

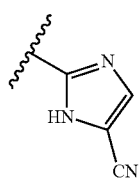

In another embodiment is a compound of Formula (I) wherein A is

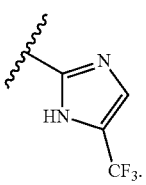

In another embodiment is a compound of Formula (I) wherein X is optionally substituted aryl. In another embodiment is a compound of Formula (I) wherein X is optionally substituted phenyl. In another embodiment is a compound of Formula (I) wherein X is optionally substituted heteroaryl. In another embodiment is a compound of Formula (I) wherein X is optionally substituted pyridine or optionally substituted pyrimidine. In another embodiment is a compound of Formula (I) wherein X is optionally substituted —($C_1$-$C_6$)alkyl-. In another embodiment is a compound of Formula (I) wherein Y is optionally substituted aryl. In another embodiment is a compound of Formula (I) wherein Y is optionally substituted phenyl. In another embodiment is a compound of Formula (I) wherein Y is optionally substituted heteroaryl. In another embodiment is a compound of Formula (I) wherein Y is optionally substituted —($C_1$-$C_6$)alkyl-. In another embodiment is a compound of Formula (I) wherein Y is —O—($C_1$-$C_6$)alkyl-. In another embodiment is a compound of Formula (I) wherein Y is —N(H)—($C_1$-$C_6$)alkyl-. In another embodiment is a compound of Formula (I) wherein Y is a bond. In another embodiment is a compound of Formula (I) wherein Z is —($C_1$-$C_6$)alkyl. In another embodiment is a compound of Formula (I) wherein Z is optionally substituted aryl. In another embodiment is a compound of Formula (I) wherein Z is optionally substituted phenyl. In another embodiment is a compound of Formula (I) wherein Z is optionally substituted heteroaryl. In another embodiment is a compound of Formula (I) wherein Z is optionally substituted —($C_3$-$C_7$)cycloalkyl. In another embodiment is a compound of Formula (I) wherein Z is halogen.

In another embodiment is a compound of Formula (I) wherein —X—Y—Z is

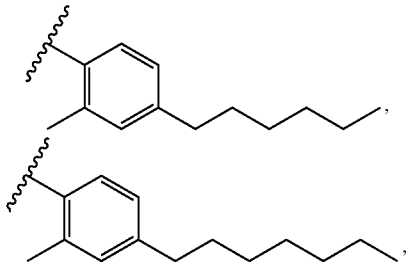

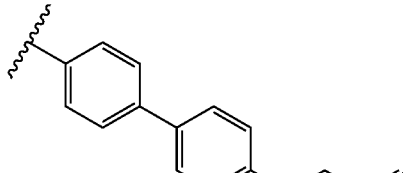

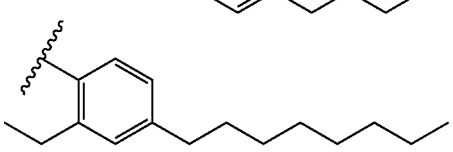

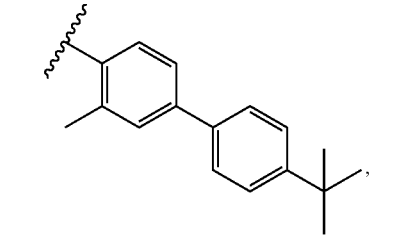

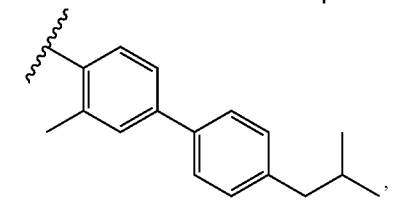

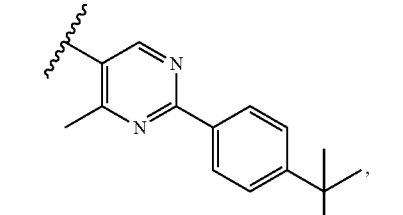

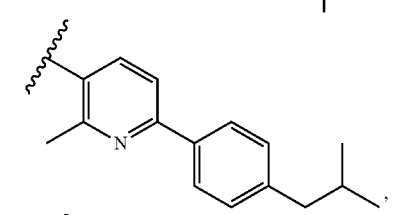

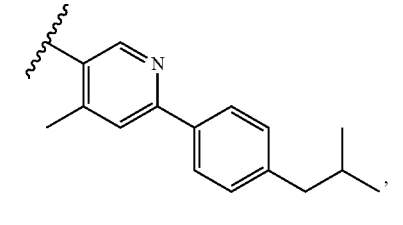

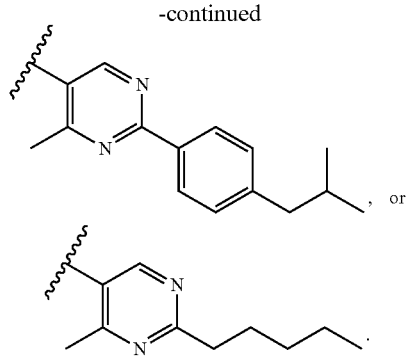, or

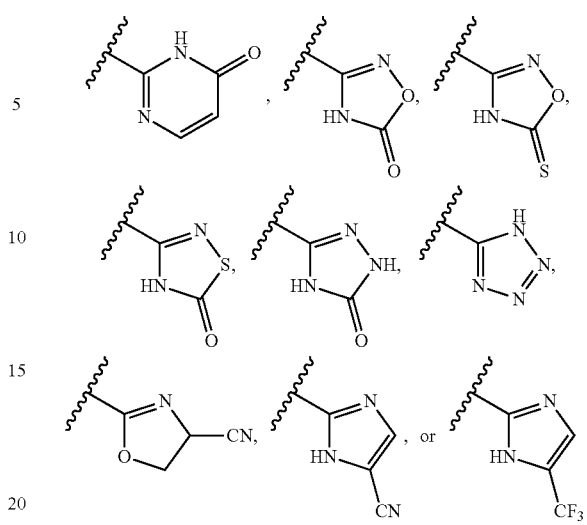

In another embodiment is a compound of Formula (I) having the structure of Formula (Ia):

Formula (Ia)

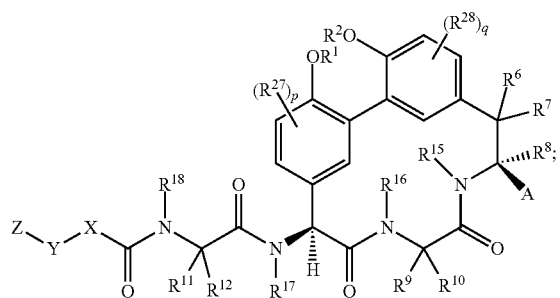

wherein:

$R^1$ and $R^2$ are each independently H, —($C_1$-$C_6$)alkyl, —($C_1$-$C_6$)alkyl-$OR^{23}$, —$CH_2CH(OH)CH_2NH_2$, —$CH_2CH$(heterocycloalkyl)$CH_2NH_2$, —$CH_2C(O)NH_2$, —$CH_2C(O)N$(H)$CH_2CN$, —($C_1$-$C_6$)alkyl-C(O)$OR^{23}$, —($C_1$-$C_6$)alkyl-$NR^{21}R^{22}$, —($C_1$-$C_6$)alkyl-C(O)$NR^{25}R^{26}$, —($C_1$-$C_6$)alkyl-N($R^{23}$)C(O)($C_1$-$C_6$)alkyl$NR^{21}R^{22}$, or —($C_1$-$C_6$)alkyl-C(O)N($R^{23}$)($C_1$-$C_6$)alkyl, or optionally substituted heterocycloalkyl;

$R^6$, $R^7$, and $R^8$ are each independently H, or —($C_1$-$C_6$)alkyl;

$R^9$ is H, —($C_1$-$C_6$)alkyl, —($C_1$-$C_6$)haloalkyl, or —($C_3$-$C_6$)cycloalkyl;

$R^{10}$ is H, or —($C_1$-$C_6$)alkyl;

$R^{11}$ and $R^{12}$ are each independently H, —$NH_2$, —($C_1$-$C_6$)alkyl, —($C_1$-$C_6$)alkyl-$OR^{23}$, —($C_1$-$C_6$)alkyl-$SR^{23}$, —($C_1$-$C_6$)alkyl-C(O)$OR^{23}$, —($C_1$-$C_6$)alkyl-$NR^{21}R^{22}$, —($C_1$-$C_6$)alkyl-CN, —($C_1$-$C_6$)alkyl-C(O)$NR^{25}R^{26}$, —($C_1$-$C_6$)alkyl-S(O)—($C_1$-$C_6$)alkyl, —($C_1$-$C_6$)alkyl-N(H)CH=NH, —($C_1$-$C_6$)alkyl-N(H)C(NH)$NH_2$, —($C_1$-$C_6$)alkyl-heterocycloalkyl, optionally substituted —($C_1$-$C_6$)alkyl-N(H)heterocycloalkyl, or —($C_1$-$C_6$)alkyl-heteroaryl; or $R^{11}$ and $R^{18}$ are combined to form an optionally substituted heterocycloalkyl ring, and $R^{12}$ is H;

$R^{15}$, $R^{16}$, $R^{17}$, and $R^{18}$ are each independently H, —($C_1$-$C_6$)alkyl, —($C_3$-$C_6$)cycloalkyl, —($C_1$-$C_6$)alkyl-$OR^{23}$, —($C_1$-$C_6$)alkyl-C(O)$OR^{23}$, or —($C_1$-$C_6$)alkyl-$NR^{21}R^{22}$;

A is —CN, —$CH_2CN$, —CH=CHCN, —$CH_2N$(H)C(O)$CH_2CN$, —$CH_2N$(H)C(O)N(H)$R^{24}$, —C(O)N(H)$R^{34}$, —C(O)N(H)C($R^{23}$)$_2$C(O)$OR^{29}$, —C(O)N(H)C($R^{23}$)$_2$C(O)$NR^{32}R^{33}$, —C(O)N(H)C($R^{23}$)$_2$C=$NR^{30}$, —C(O)N(H)$SO_3H$, —C(O)N(H)$SO_2CH$=$CH_2$, —C(O)N(H)N($R^{24}$)C(O)CH=$CH_2$, —C(O)N(H)N($R^{24}$)C(O)$CH_2Cl$,

X is optionally substituted —($C_1$-$C_6$)alkyl-, —($C_2$-$C_6$)alkenyl-, —($C_2$-$C_6$)alkynyl-, —($C_3$-$C_7$)cycloalkyl-, optionally substituted heterocycloalkyl, optionally substituted aryl, optionally substituted heteroaryl, —O—($C_1$-$C_6$)alkyl-, —N($R^{24}$)($C_1$-$C_6$)alkyl-, —N($R^{24}$)($C_6$-$C_{10}$)aryl-, or —$SO_2$($C_1$-$C_6$)alkyl-;

Y is a bond, optionally substituted —($C_1$-$C_6$)alkyl-, —($C_2$-$C_6$)alkenyl-, —($C_2$-$C_6$)alkynyl-, —($C_1$-$C_6$)alkyl-N($R^{24}$)($C_1$-$C_6$)alkyl-, —O—($C_1$-$C_6$)alkyl-, —O($C_6$-$C_{10}$)aryl-, —N($R^{24}$)($C_1$-$C_6$)alkyl-, —N($R^{24}$)$SO_2$($C_1$-$C_6$)alkyl-, —N($R^{24}$)C(O)($C_1$-$C_6$)alkyl-, —C(O)($C_1$-$C_6$)alkyl-, —S($C_1$-$C_6$)alkyl-, —$SO_2$($C_1$-$C_6$)alkyl-, —C(O)NH($C_1$-$C_6$)alkyl-, —($C_3$-$C_7$)cycloalkyl-, optionally substituted —C(O)N($R^{24}$)aryl-, optionally substituted —N($R^{24}$)C(O)aryl-, optionally substituted —N($R^{24}$)$SO_2$aryl-, optionally substituted aryl, or optionally substituted heteroaryl;

Z is H, halogen, —$NH_2$, —CN, —$CF_3$, —$CO_2H$, —($C_1$-$C_{12}$)alkyl, —($C_2$-$C_{12}$)alkenyl, —($C_2$-$C_{12}$)alkynyl, —C(O)$NR^{25}R^{26}$, —N($R^{24}$)($C_1$-$C_{12}$)alkyl, —N($R^{24}$)C(O)($C_1$-$C_{12}$)alkyl, optionally substituted —($C_3$-$C_7$)cycloalkyl, —($C_1$-$C_6$)alkyl-heterocycloalkyl, optionally substituted aryl, or optionally substituted heteroaryl;

each $R^{21}$ and $R^{22}$ is independently H, —($C_1$-$C_6$)alkyl, —($C_1$-$C_6$)heteroalkyl, —($C_1$-$C_6$)alkyl-$CO_2H$, —C(O)($C_1$-$C_6$)alkyl, —C(O)N($R^{31}$)$_2$, —$SO_2N$($R^{31}$)$_2$; or $R^{21}$ and $R^{22}$ and the nitrogen atom to which they are attached form a heterocycloalkyl ring;

each $R^{31}$ is independently H or —($C_1$-$C_6$)alkyl; or two $R^{31}$ and the nitrogen atom to which they are attached form a heterocycloalkyl ring;

each $R^{23}$ is independently H or —($C_1$-$C_6$)alkyl;

each $R^{24}$ is independently H or —($C_1$-$C_6$)alkyl;

each $R^{25}$ and $R^{26}$ is independently H or optionally substituted —($C_1$-$C_6$)alkyl; or $R^{25}$ and $R^{26}$ and the nitrogen atom to which they are attached form a heterocycloalkyl ring;

each $R^{27}$ is independently halogen, —($C_1$-$C_6$)alkyl, or —($C_1$-$C_6$)heteroalkyl;

each $R^{28}$ is independently halogen, —($C_1$-$C_6$)alkyl, or —($C_1$-$C_6$)heteroalkyl;

$R^{29}$ is —$CH_2C(O)NH_2$ or optionally substituted aryl;

$R^{30}$ is

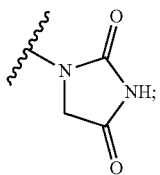 [SMILES: *N1CC(=O)NC1=O]

$R^{32}$ is H or —($C_1$-$C_6$)alkyl;
$R^{33}$ is —$CH_2CN$, —OC(O)($C_1$-$C_6$)alkyl, or —$SO_2NH_2$;
$R^{34}$ is —OH, —$NH_2$, —CN, —$CH_2CH_2CN$, —O($C_1$-$C_6$)alkyl, —C(O)($C_1$-$C_6$)alkyl, —$SO_2NH_2$,

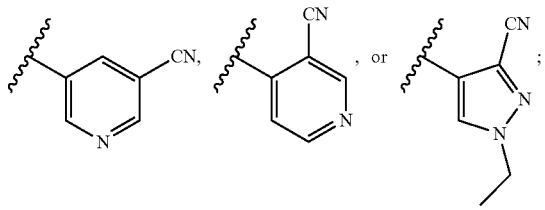

p is 0, 1, or 2; and
q is 0, 1, or 2;
or a pharmaceutically acceptable salt, solvate, or prodrug thereof.

In one embodiment is a compound of Formula (Ia) wherein $R^6$, $R^7$, and $R^8$ are H.

In another embodiment is a compound of Formula (Ia) wherein $R^{15}$ and $R^{16}$ are H.

In one embodiment is a compound of Formula (Ia) wherein $R^{17}$ is —($C_1$-$C_6$)alkyl. In another embodiment is a compound of Formula (Ia) wherein $R^{17}$ is —$CH_3$. In another embodiment is a compound of Formula (Ia) wherein $R^{17}$ is —$CH_2CH_3$. In another embodiment is a compound of Formula (Ia) wherein $R^{17}$ is —($C_3$-$C_6$)cycloalkyl. In another embodiment is a compound of Formula (Ia) wherein $R^{17}$ is cyclopropyl. In another embodiment is a compound of Formula (Ia) wherein $R^{17}$ is —($C_1$-$C_6$)alkyl-C(O)$OR^{23}$. In another embodiment is a compound of Formula (Ia) wherein $R^{17}$ is —$CH_2CH_2OH$. In another embodiment is a compound of Formula (Ia) wherein $R^{17}$ is —($C_1$-$C_6$)alkyl-$NR^{21}R^{22}$. In another embodiment is a compound of Formula (Ia) wherein $R^{17}$ is —$CH_2CH_2NH_2$. In another embodiment is a compound of Formula (Ia) wherein $R^{17}$ is H.

In another embodiment is a compound of Formula (Ia) wherein $R^{18}$ is H.

In another embodiment is a compound of Formula (Ia) wherein $R^{10}$ is H.

In another embodiment is a compound of Formula (Ia) wherein $R^{10}$ is H and $R^9$ is —($C_1$-$C_6$)alkyl. In another embodiment is a compound of Formula (Ia) wherein $R^{10}$ is H and $R^9$ is —$CH_3$. In another embodiment is a compound of Formula (Ia) wherein $R^{10}$ is H and $R^9$ is —$CH_2CH_3$. In another embodiment is a compound of Formula (Ia) wherein $R^{10}$ is H and $R^9$ is —($C_1$-$C_6$)haloalkyl. In another embodiment is a compound of Formula (Ia) wherein $R^{10}$ is H and $R^9$ is —$CH_2F$. In another embodiment is a compound of Formula (Ia) wherein $R^{10}$ is H and $R^9$ is —$CHF_2$. In another embodiment is a compound of Formula (Ia) wherein $R^{10}$ is H and $R^9$ is —($C_3$-$C_6$)cycloalkyl. In another embodiment is a compound of Formula (Ia) wherein $R^{10}$ is H and $R^9$ is cyclopropyl. In another embodiment is a compound of Formula (Ia) wherein $R^{10}$ is H and $R^9$ is H.

In another embodiment is a compound of Formula (Ia) wherein $R^{12}$ is H.

In another embodiment is a compound of Formula (Ia) wherein $R^{12}$ is H and $R^{11}$ is —($C_1$-$C_6$)alkyl. In another embodiment is a compound of Formula (Ia) wherein $R^{12}$ is H and $R^{11}$ is —$CH_3$. In another embodiment is a compound of Formula (Ia) wherein $R^{12}$ is H and $R^{11}$ is —($C_1$-$C_6$)alkyl-$OR^{23}$. In another embodiment is a compound of Formula (Ia) wherein $R^{12}$ is H and $R^{11}$ is —$CH_2OH$. In another embodiment is a compound of Formula (Ia) wherein $R^{12}$ is H and $R^{11}$ is —$CH_2CH_2OH$. In another embodiment is a compound of Formula (Ia) wherein $R^{12}$ is H and $R^{11}$ is —($C_1$-$C_6$)alkyl. In another embodiment is a compound of Formula (Ia) wherein $R^{12}$ is H and $R^{11}$ is —($C_1$-$C_6$)alkyl-$NR^{21}R^{22}$. In another embodiment is a compound of Formula (Ia) wherein $R^{12}$ is H and $R^{11}$ is —($C_1$-$C_6$)alkyl-$NH_2$. In another embodiment is a compound of Formula (Ia) wherein $R^{12}$ is H and $R^{11}$ is —$CH_2NH_2$. In another embodiment is a compound of Formula (Ia) wherein $R^{12}$ is H and $R^{11}$ is —$CH_2CH_2NH_2$. In another embodiment is a compound of Formula (Ia) wherein $R^{12}$ is H and $R^{11}$ is —$CH_2CH_2CH_2NH_2$. In another embodiment is a compound of Formula (Ia) wherein $R^{12}$ is H and $R^{11}$ is —$CH_2CH_2CH_2CH_2NH_2$. In another embodiment is a compound of Formula (Ia) wherein $R^{12}$ is H and $R^{11}$ is —($C_1$-$C_6$)alkyl-CN. In another embodiment is a compound of Formula (Ia) wherein $R^{12}$ is H and $R^{11}$ is —$CH_2CN$. In another embodiment is a compound of Formula (Ia) wherein $R^{12}$ is H and $R^{11}$ is —($C_1$-$C_6$)alkyl-C(O)$NR^{25}R^{26}$. In another embodiment is a compound of Formula (Ia) wherein $R^{12}$ is H and $R^{11}$ is —$CH_2C(O)NH_2$. In another embodiment is a compound of Formula (Ia) wherein $R^{12}$ is H and $R^{11}$ is —$CH_2CH_2C(O)NH_2$. In another embodiment is a compound of Formula (Ia) wherein $R^{12}$ is H and $R^{11}$ is —($C_1$-$C_6$)alkyl-heteroaryl. In another embodiment is a compound of Formula (Ia) wherein $R^{12}$ is H and $R^{11}$ is H.

In another embodiment is a compound of Formula (Ia) wherein $R^{11}$ and $R^{18}$ are combined to form an optionally substituted heterocycloalkyl ring and $R^{12}$ is H.

In another embodiment is a compound of Formula (Ia) wherein p is 1 and $R^{27}$ is halogen. In another embodiment is a compound of Formula (Ia) wherein p is 1 and $R^{27}$ is optionally substituted —($C_1$-$C_6$)alkyl. In another embodiment is a compound of Formula (I) wherein q is 0, p is 1 and $R^{27}$ is halogen. In another embodiment is a compound of Formula (I) wherein q is 0, p is 1 and $R^{27}$ is optionally substituted —($C_1$-$C_6$)alkyl. In another embodiment is a compound of Formula (Ia) wherein q is 1 and $R^{28}$ is halogen. In another embodiment is a compound of Formula (Ia) wherein q is 1 and $R^{28}$ is optionally substituted —($C_1$-$C_6$)alkyl. In another embodiment is a compound of Formula (Ia) wherein p is 0, q is 1 and $R^{28}$ is halogen. In another embodiment is a compound of Formula (Ia) wherein p is 0, q is 1 and $R^{28}$ is optionally substituted —($C_1$-$C_6$)alkyl.

In another embodiment is a compound of Formula (Ia) wherein p is 0, and q is 0.

In another embodiment is a compound of Formula (Ia) wherein $R^1$ and $R^2$ are each independently H, or —($C_1$-$C_6$)alkyl-$NR^{21}R^{22}$. In another embodiment is a compound of Formula (Ia) wherein $R^1$ and $R^2$ are each H. In another embodiment is a compound of Formula (Ia) wherein $R^1$ and $R^2$ are each independently —($C_1$-$C_6$)alkyl-$NR^{21}R^{22}$. In another embodiment is a compound of Formula (Ia) wherein $R^1$ is H, and $R^2$ is —($C_1$-$C_6$)alkyl-$NR^{21}R^{22}$. In another embodiment is a compound of Formula (Ia) wherein $R^1$ is —(C$_1$-C$_6$)alkyl-NR$^{21}$R$^{22}$, and R$^2$ is H. In another embodiment is a compound of Formula (Ia) wherein R$^1$ is H, and R$^2$ is —CH$_2$CH$_2$NH$_2$. In another embodiment is a compound of Formula (Ia) wherein R$^1$ is —CH$_2$CH$_2$NH$_2$, and R$^2$ is H. In another embodiment is a compound of Formula (Ia) wherein R$^1$ and R$^2$ are each —CH$_2$CH$_2$NH$_2$.

In another embodiment is a compound of Formula (Ia) wherein A is —CN. In another embodiment is a compound of Formula (Ia) wherein A is —CH$_2$CN. In another embodiment is a compound of Formula (Ia) wherein A is —CH═CHCN. In another embodiment is a compound of Formula (Ia) wherein A is —CH$_2$N(H)C(O)CH$_2$CN. In another embodiment is a compound of Formula (Ia) wherein A is —CH$_2$N(H)C(O)N(H)R$^{24}$. In another embodiment is a compound of Formula (Ia) wherein A is —C(O)N(H)R$^{34}$. In another embodiment is a compound of Formula (Ia) wherein A is —C(O)N(H)C(R$^{23}$)$_2$C(O)OR$^{29}$. In another embodiment is a compound of Formula (Ia) wherein A is —C(O)N(H)C(R$^{23}$)$_2$C(O)NR$^{32}$R$^{33}$. In another embodiment is a compound of Formula (Ia) wherein A is C(O)N(H)C(R$^{23}$)$_2$C═NR$^{30}$. In another embodiment is a compound of Formula (Ia) wherein A is —C(O)N(H)SO$_3$H. In another embodiment is a compound of Formula (Ia) wherein A is —C(O)N(H)SO$_2$CH═CH$_2$. In another embodiment is a compound of Formula (Ia) wherein A is C(O)N(H)N(R$^{24}$)C(O)CH═CH$_2$. In another embodiment is a compound of Formula (Ia) wherein A is —C(O)N(H)N(R$^{24}$)C(O)CH$_2$Cl.

In another embodiment is a compound of Formula (Ia) wherein A is —C(O)N(H)R$^{34}$, wherein R$^{34}$ is —OH. In another embodiment is a compound of Formula (Ia) wherein A is —C(O)N(H)R$^{34}$, wherein R$^{34}$ is —NH$_2$. In another embodiment is a compound of Formula (Ia) wherein A is —C(O)N(H)R$^{34}$, wherein R$^{34}$ is —CN. In another embodiment is a compound of Formula (Ia) wherein A is —C(O)N(H)R$^{34}$, wherein R$^{34}$ is —CH$_2$CH$_2$CN. In another embodiment is a compound of Formula (Ia) wherein A is —C(O)N(H)R$^{34}$, wherein R$^{34}$ is —O(C$_1$-C$_6$)alkyl. In another embodiment is a compound of Formula (Ia) wherein A is —C(O)N(H)R$^{34}$, wherein R$^{34}$ is —C(O)(C$_1$-C$_6$)alkyl. In another embodiment is a compound of Formula (Ia) wherein A is —C(O)N(H)R$^{34}$, wherein R$^{34}$ is —SO$_2$NH$_2$. In another embodiment is a compound of Formula (Ia) wherein A is —C(O)N(H)R$^{34}$, wherein R$^{34}$ is

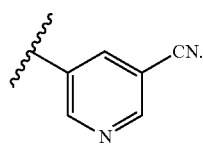 [SMILES: *c1cncc(C#N)c1]

In another embodiment is a compound of Formula (Ia) wherein A is —C(O)N(H)R$^{34}$, wherein R$^{34}$ is

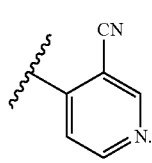

In another embodiment is a compound of Formula (Ia) wherein A is —C(O)N(H)R$^{34}$, wherein R$^{34}$ is

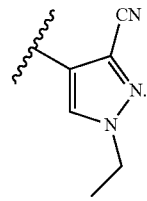 [SMILES: *c1cn(CC)nc1C#N]

In another embodiment is a compound of Formula (Ia) wherein A is

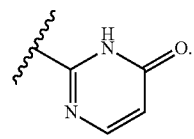

In another embodiment is a compound of Formula (Ia) wherein A is

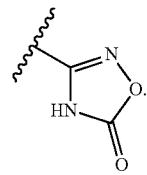 [SMILES: *c1noc(=O)[nH]1]

In another embodiment is a compound of Formula (Ia) wherein A is

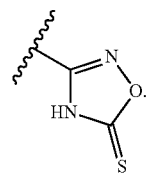 [SMILES: *c1noc(=S)[nH]1]

In another embodiment is a compound of Formula (Ia) wherein A is

In another embodiment is a compound of Formula (Ia) wherein A is

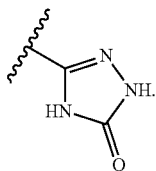 [SMILES: *c1n[nH]c(=O)[nH]1]

In another embodiment is a compound of Formula (Ia) wherein A is

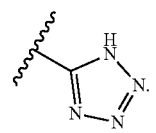

In another embodiment is a compound of Formula (Ia) wherein A is

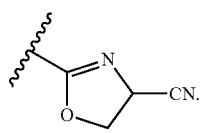 [SMILES: *C1=NC(C#N)CO1]

In another embodiment is a compound of Formula (Ia) wherein A is

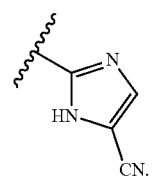 [SMILES: *c1ncc(C#N)[nH]1]

In another embodiment is a compound of Formula (Ia) wherein A is

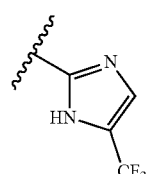

In another embodiment is a compound of Formula (Ia) wherein X is optionally substituted aryl. In another embodiment is a compound of Formula (Ia) wherein X is optionally substituted phenyl. In another embodiment is a compound of Formula (Ia) wherein X is optionally substituted heteroaryl. In another embodiment is a compound of Formula (Ia) wherein X is optionally substituted pyridine or optionally substituted pyrimidine. In another embodiment is a compound of Formula (Ia) wherein X is optionally substituted —($C_1$-$C_6$)alkyl-. In another embodiment is a compound of Formula (Ia) wherein Y is optionally substituted aryl. In another embodiment is a compound of Formula (Ia) wherein Y is optionally substituted phenyl. In another embodiment is a compound of Formula (Ia) wherein Y is optionally substituted heteroaryl. In another embodiment is a compound of Formula (Ia) wherein Y is optionally substituted —($C_1$-$C_6$)alkyl-. In another embodiment is a compound of Formula (Ia) wherein Y is —O—($C_1$-$C_6$)alkyl-. In another embodiment is a compound of Formula (Ia) wherein Y is —N(H)—($C_1$-$C_6$)alkyl-. In another embodiment is a compound of Formula (Ia) wherein Y is a bond. In another embodiment is a compound of Formula (Ia) wherein Z is —($C_1$-$C_6$)alkyl. In another embodiment is a compound of Formula (Ia) wherein Z is optionally substituted aryl. In another embodiment is a compound of Formula (Ia) wherein Z is optionally substituted phenyl. In another embodiment is a compound of Formula (Ia) wherein Z is optionally substituted heteroaryl. In another embodiment is a compound of Formula (Ia) wherein Z is optionally substituted —($C_3$-$C_7$)cycloalkyl. In another embodiment is a compound of Formula (Ia) wherein Z is halogen.

In another embodiment is a compound of Formula (Ia) wherein —X—Y—Z is

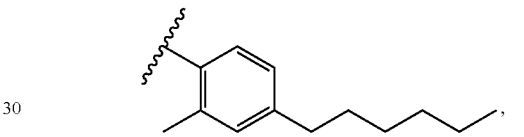

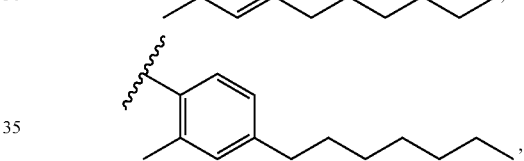

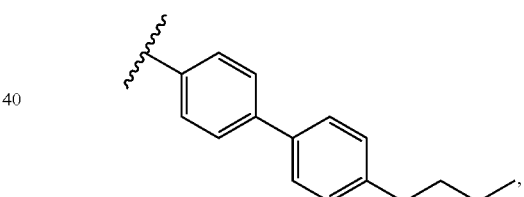

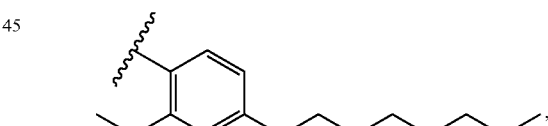

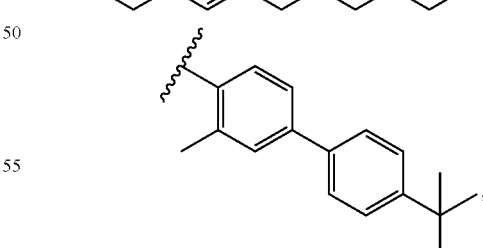

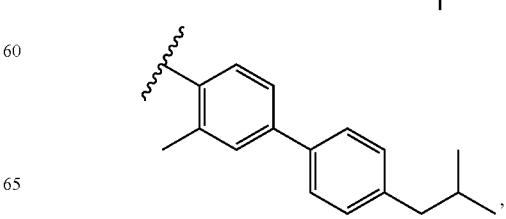

-continued

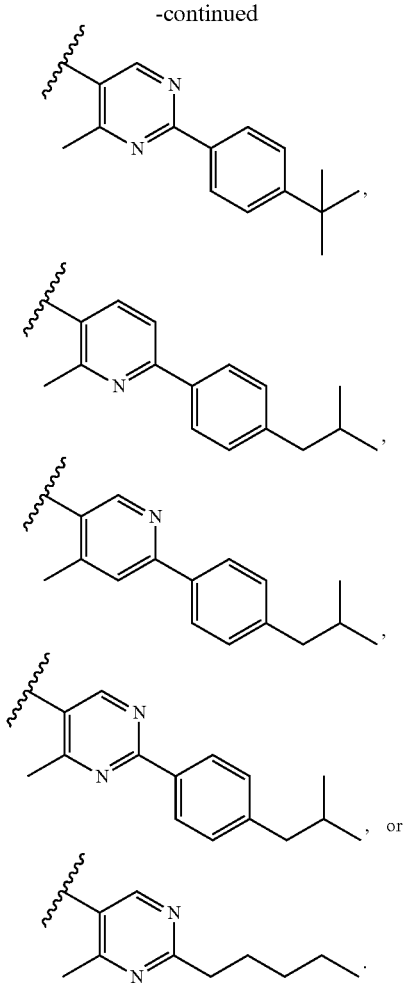

In another embodiment is a compound of Formula (I) having the structure of Formula (Ib):

Formula (Ib)

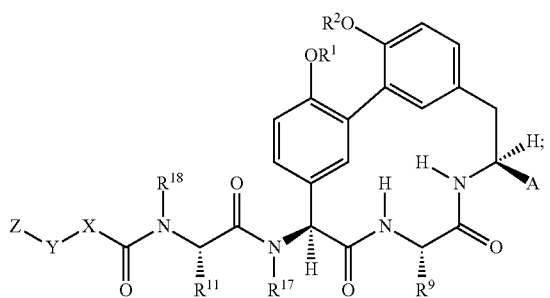

wherein:
R$^1$ and R$^2$ are each independently H, —(C$_1$-C$_6$)alkyl, —(C$_1$-C$_6$)alkyl-OR$^{23}$, —CH$_2$CH(OH)CH$_2$NH$_2$, —CH$_2$CH(heterocycloalkyl)CH$_2$NH$_2$, —CH$_2$C(O)NH$_2$, —CH$_2$C(O)N(H)CH$_2$CN, —(C$_1$-C$_6$)alkyl-C(O)OR$^{23}$, —(C$_1$-C$_6$)alkyl-NR$^{21}$R$^{22}$, —(C$_1$-C$_6$)alkyl-C(O)NR$^{25}$R$^{26}$, —(C$_1$-C$_6$)alkyl-N(R$^{23}$)C(O)(C$_1$-C$_6$)alkylNR$^{21}$R$^{22}$, or —(C$_1$-C$_6$)alkyl-C(O)N(R$^{23}$)(C$_1$-C$_6$)alkyl, or optionally substituted heterocycloalkyl;
R$^9$ is H, —(C$_1$-C$_6$)alkyl, —(C$_1$-C$_6$)haloalkyl, or —(C$_3$-C$_6$)cycloalkyl;
R$^{11}$ is H, —NH$_2$, —(C$_1$-C$_6$)alkyl, —(C$_1$-C$_6$)alkyl-OR$^{23}$, —(C$_1$-C$_6$)alkyl-SR$^{23}$, —(C$_1$-C$_6$)alkyl-C(O)OR$^{23}$, —(C$_1$-C$_6$)alkyl-NR$^{21}$R$^{22}$, —(C$_1$-C$_6$)alkyl-CN, —(C$_1$-C$_6$)alkyl-C(O)NR$^{25}$R$^{26}$, —(C$_1$-C$_6$)alkyl-S(O)—(C$_1$-C$_6$)alkyl, —(C$_1$-C$_6$)alkyl-N(H)CH=NH, —(C$_1$-C$_6$)alkyl-N(H)C(NH)NH$_2$, —(C$_1$-C$_6$)alkyl-heterocycloalkyl, optionally substituted —(C$_1$-C$_6$)alkyl-N(H)heterocycloalkyl, or —(C$_1$-C$_6$)alkyl-heteroaryl; or R$^{11}$ and R$^{18}$ are combined to form an optionally substituted heterocycloalkyl ring;
R$^{17}$ and R$^{18}$ are each independently H, —(C$_1$-C$_6$)alkyl, —(C$_3$-C$_6$)cycloalkyl, —(C$_1$-C$_6$)alkyl-OR$^{23}$, —(C$_1$-C$_6$)alkyl-C(O)OR$^{23}$, or —(C$_1$-C$_6$)alkyl-NR$^{21}$R$^{22}$;
A is —CN, —CH$_2$CN, —CH=CHCN, —CH$_2$N(H)C(O)CH$_2$CN, —CH$_2$N(H)C(O)N(H)R$^{24}$, —C(O)N(H)R$^{34}$, —C(O)N(H)C(R$^{23}$)$_2$C(O)OR$^{29}$, —C(O)N(H)C(R$^{23}$)$_2$C(O)NR$^{32}$R$^{33}$, —C(O)N(H)C(R$^{23}$)$_2$C=NR$^{30}$, —C(O)N(H)SO$_3$H, —C(O)N(H)SO$_2$CH=CH$_2$, —C(O)N(H)N(R$^{24}$)C(O)CH=CH$_2$, —C(O)N(H)N(R$^{24}$)C(O)CH$_2$Cl,

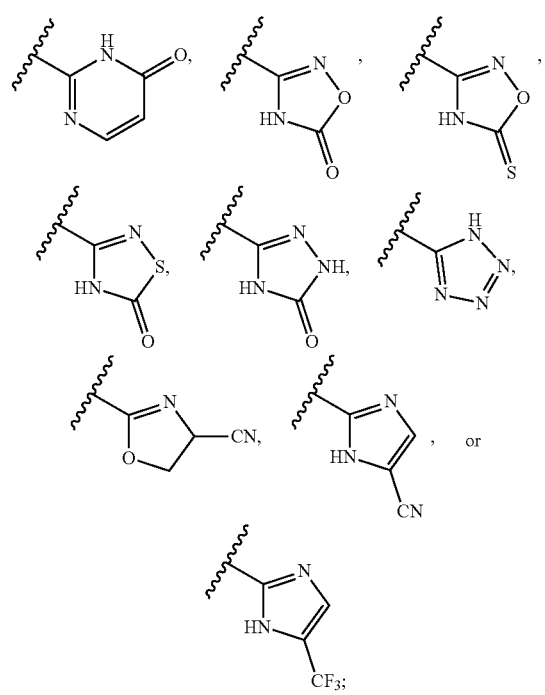

X is optionally substituted —(C$_1$-C$_6$)alkyl-, —(C$_2$-C$_6$)alkenyl-, —(C$_2$-C$_6$)alkynyl, —(C$_3$-C$_7$)cycloalkyl-, optionally substituted heterocycloalkyl, optionally substituted aryl, optionally substituted heteroaryl, —O—(C$_1$-C$_6$)alkyl-, —N(R$^{24}$)(C$_1$-C$_6$)alkyl-, —N(R$^{24}$)(C$_6$-C$_{10}$)aryl-, or —SO$_2$(C$_1$-C$_6$)alkyl-;
Y is a bond, optionally substituted —(C$_1$-C$_6$)alkyl-, —(C$_2$-C$_6$)alkenyl-, —(C$_2$-C$_6$)alkynyl, —(C$_1$-C$_6$)alkyl-N(R$^{24}$)(C$_1$-C$_6$)alkyl-, —O—(C$_1$-C$_6$)alkyl-, —O(C$_6$-C$_{10}$)aryl-, —N(R$^{24}$)(C$_1$-C$_6$)alkyl-, —N(R$^{24}$)SO$_2$(C$_1$-C$_6$)alkyl-, —N(R$^{24}$)C(O)(C$_1$-C$_6$)alkyl-, —C(O)(C$_1$-C$_6$)alkyl-, —S(C$_1$-C$_6$)alkyl-, —SO$_2$(C$_1$-C$_6$)alkyl-, —C(O)NH(C$_1$-C$_6$)alkyl-, —(C$_3$-C$_7$)cycloalkyl-, optionally substituted —C(O)N(R$^{24}$)aryl-, optionally substituted —N(R$^{24}$)C(O)aryl-, optionally substituted —N(R$^{24}$)SO$_2$aryl-, optionally substituted aryl, or optionally substituted heteroaryl;
Z is H, halogen, —NH$_2$, —CN, —CF$_3$, —CO$_2$H, —(C$_1$-C$_{12}$)alkyl, —(C$_2$-C$_{12}$)alkenyl, —(C$_2$-C$_{12}$)alkynyl, —C(O)NR$^{25}$R$^{26}$, —O—(C$_1$-C$_{12}$)alkyl, —N(R$^{24}$)(C$_1$-

$C_{12}$)alkyl, —N($R^{24}$)C(O)($C_1$-$C_{12}$)alkyl, optionally substituted —($C_3$-$C_7$)cycloalkyl, —($C_1$-$C_6$)alkyl-heterocycloalkyl, optionally substituted aryl, or optionally substituted heteroaryl;

each $R^{21}$ and $R^{22}$ is independently H, —($C_1$-$C_6$)alkyl, —($C_1$-$C_6$)heteroalkyl, —($C_1$-$C_6$)alkyl-$CO_2H$, —C(O)($C_1$-$C_6$)alkyl, —C(O)N($R^{31}$)$_2$, —$SO_2$N($R^{31}$)$_2$; or $R^{21}$ and $R^{22}$ and the nitrogen atom to which they are attached form a heterocycloalkyl ring;

each $R^{31}$ is independently H or —($C_1$-$C_6$)alkyl; or two $R^{31}$ and the nitrogen atom to which they are attached form a heterocycloalkyl ring;

each $R^{23}$ is independently H or —($C_1$-$C_6$)alkyl;
each $R^{24}$ is independently H or —($C_1$-$C_6$)alkyl;
each $R^{25}$ and $R^{26}$ is independently H or optionally substituted —($C_1$-$C_6$)alkyl; or $R^{25}$ and $R^{26}$ and the nitrogen atom to which they are attached form a heterocycloalkyl ring;

$R^{29}$ is —$CH_2$C(O)$NH_2$ or optionally substituted aryl;
$R^{30}$ is

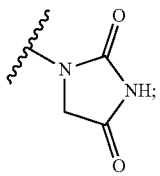 [SMILES: *N1CC(=O)NC1=O]

$R^{32}$ is H or —($C_1$-$C_6$)alkyl;
$R^{33}$ is —$CH_2CN$, —OC(O)($C_1$-$C_6$)alkyl, or —$SO_2NH_2$; and
$R^{34}$ is —OH, —$NH_2$, —CN, —$CH_2CH_2CN$, —O($C_1$-$C_6$)alkyl, —C(O)($C_1$-$C_6$)alkyl, —$SO_2NH_2$,

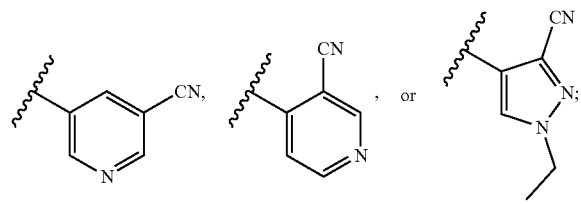

or a pharmaceutically acceptable salt, solvate, or prodrug thereof.

In one embodiment is a compound of Formula (Ib) wherein $R^{17}$ is —($C_1$-$C_6$)alkyl. In another embodiment is a compound of Formula (Ib) wherein $R^{17}$ is —$CH_3$. In another embodiment is a compound of Formula (Ib) wherein $R^{17}$ is —$CH_2CH_3$. In another embodiment is a compound of Formula (Ib) wherein $R^{17}$ is —($C_3$-$C_6$)cycloalkyl. In another embodiment is a compound of Formula (Ib) wherein $R^{17}$ is cyclopropyl. In another embodiment is a compound of Formula (Ib) wherein $R^{17}$ is —($C_1$-$C_6$)alkyl-C(O)$OR^{23}$. In another embodiment is a compound of Formula (Ib) wherein $R^{17}$ is —$CH_2CH_2OH$. In another embodiment is a compound of Formula (Ib) wherein $R^{17}$ is —($C_1$-$C_6$)alkyl-$NR^{21}R^{22}$. In another embodiment is a compound of Formula (Ib) wherein $R^{17}$ is —$CH_2CH_2NH_2$. In another embodiment is a compound of Formula (Ib) wherein $R^{17}$ is H.

In another embodiment is a compound of Formula (Ib) wherein $R^{18}$ is H.

In another embodiment is a compound of Formula (Ib) wherein $R^5$ is H.

In another embodiment is a compound of Formula (Ib) wherein $R^4$ is H. In another embodiment is a compound of Formula (Ib) wherein $R^4$ is —($C_1$-$C_6$)alkyl. In another embodiment is a compound of Formula (Ib) wherein $R^4$ is —$CH_3$. In another embodiment is a compound of Formula (Ib) wherein $R^4$ is —$CH_2CH_3$. In another embodiment is a compound of Formula (Ib) wherein $R^4$ is —($C_1$-$C_6$)alkyl-OH. In another embodiment is a compound of Formula (Ib) wherein $R^4$ is —$CH_2OH$. In another embodiment is a compound of Formula (Ib) wherein $R^4$ is —($C_3$-$C_6$)cycloalkyl. In another embodiment is a compound of Formula (Ib) wherein $R^4$ is cyclopropyl. In another embodiment is a compound of Formula (Ib) wherein $R^4$ is —C(O)$NH_2$.

In another embodiment is a compound of Formula (Ib) wherein $R^4$ and $R^5$ and the carbon atom to which they are attached form a cyclopropyl ring.

In another embodiment is a compound of Formula (Ib) wherein $R^9$ is —($C_1$-$C_6$)alkyl. In another embodiment is a compound of Formula (Ib) wherein $R^9$ is —$CH_3$. In another embodiment is a compound of Formula (Ib) wherein $R^9$ is —$CH_2CH_3$. In another embodiment is a compound of Formula (Ib) wherein $R^9$ is —($C_1$-$C_6$)haloalkyl. In another embodiment is a compound of Formula (Ib) wherein $R^9$ is —$CH_2F$. In another embodiment is a compound of Formula (Ib) wherein $R^9$ is —$CHF_2$. In another embodiment is a compound of Formula (Ib) wherein $R^9$ is —($C_3$-$C_6$)cycloalkyl. In another embodiment is a compound of Formula (Ib) wherein $R^9$ is cyclopropyl. In another embodiment is a compound of Formula (Ib) wherein $R^9$ is H.

In another embodiment is a compound of Formula (Ib) wherein $R^{11}$ is —($C_1$-$C_6$)alkyl. In another embodiment is a compound of Formula (Ib) wherein $R^{11}$ is —$CH_3$. In another embodiment is a compound of Formula (Ib) wherein $R^{11}$ is —($C_1$-$C_6$)alkyl-$OR^{23}$. In another embodiment is a compound of Formula (Ib) wherein $R^{11}$ is —$CH_2OH$. In another embodiment is a compound of Formula (Ib) wherein $R^{11}$ is —$CH_2CH_2OH$. In another embodiment is a compound of Formula (Ib) wherein $R^{11}$ is —($C_1$-$C_6$)alkyl. In another embodiment is a compound of Formula (Ib) wherein $R^{11}$ is —($C_1$-$C_6$)alkyl-$NR^{21}R^{22}$. In another embodiment is a compound of Formula (Ib) wherein $R^{11}$ is —($C_1$-$C_6$)alkyl-$NH_2$. In another embodiment is a compound of Formula (Ib) wherein $R^{11}$ is —$CH_2NH_2$. In another embodiment is a compound of Formula (Ib) wherein $R^{11}$ is —$CH_2CH_2NH_2$. In another embodiment is a compound of Formula (Ib) wherein $R^{11}$ is —$CH_2CH_2CH_2NH_2$. In another embodiment is a compound of Formula (Ib) wherein $R^{11}$ is —$CH_2CH_2CH_2CH_2NH_2$. In another embodiment is a compound of Formula (Ib) wherein $R^{11}$ is —($C_1$-$C_6$)alkyl-CN. In another embodiment is a compound of Formula (Ib) wherein $R^{11}$ is —$CH_2CN$. In another embodiment is a compound of Formula (Ib) wherein $R^{11}$ is —($C_1$-$C_6$)alkyl-C(O)$NR^{25}R^{26}$. In another embodiment is a compound of Formula (Ib) wherein $R^{11}$ is —$CH_2C(O)NH_2$. In another embodiment is a compound of Formula (Ib) wherein $R^{11}$ is —$CH_2CH_2C(O)NH_2$. In another embodiment is a compound of Formula (Ib) wherein $R^{11}$ is —($C_1$-$C_6$)alkyl-heteroaryl. In another embodiment is a compound of Formula (Ib) wherein $R^{11}$ is H.

In another embodiment is a compound of Formula (Ib) wherein $R^{11}$ and $R^{18}$ are combined to form an optionally substituted heterocycloalkyl ring.

In another embodiment is a compound of Formula (Ib) wherein $R^1$ and $R^2$ are each independently H, or —($C_1$-$C_6$)alkyl-$NR^{21}R^{22}$. In another embodiment is a compound of Formula (Ib) wherein $R^1$ and $R^2$ are each H. In another embodiment is a compound of Formula (Ib) wherein $R^1$ and $R^2$ are each independently —($C_1$-$C_6$)alkyl-$NR^{21}R^{22}$. In another embodiment is a compound of Formula (Ib) wherein $R^1$ is H, and $R^2$ is —($C_1$-$C_6$)alkyl-$NR^{21}R^{22}$. In another embodiment is a compound of Formula (Ib) wherein $R^1$ is —($C_1$-$C_6$)alkyl-$NR^{21}R^{22}$, and $R^2$ is H. In another embodiment is a compound of Formula (Ib) wherein $R^1$ is H, and $R^2$ is —$CH_2CH_2NH_2$. In another embodiment is a compound of Formula (Ib) wherein $R^1$ is —$CH_2CH_2NH_2$, and $R^2$ is H. In another embodiment is a compound of Formula (Ib) wherein $R^1$ and $R^2$ are each —$CH_2CH_2NH_2$.

In another embodiment is a compound of Formula (Ib) wherein A is —CN. In another embodiment is a compound of Formula (Ib) wherein A is —$CH_2CN$. In another embodiment is a compound of Formula (Ib) wherein A is —CH=CHCN. In another embodiment is a compound of Formula (Ib) wherein A is —$CH_2N(H)C(O)CH_2CN$. In another embodiment is a compound of Formula (Ib) wherein A is —$CH_2N(H)C(O)N(H)R^{24}$. In another embodiment is a compound of Formula (Ib) wherein A is —$C(O)N(H)R^{34}$. In another embodiment is a compound of Formula (Ib) wherein A is —$C(O)N(H)C(R^{23})_2C(O)OR^{29}$. In another embodiment is a compound of Formula (Ib) wherein A is —$C(O)N(H)C(R^{23})_2C(O)NR^{32}R^{33}$. In another embodiment is a compound of Formula (Ib) wherein A is $C(O)N(H)C(R^{23})_2C=NR^{30}$. In another embodiment is a compound of Formula (Ib) wherein A is —$C(O)N(H)SO_3H$. In another embodiment is a compound of Formula (Ib) wherein A is —$C(O)N(H)SO_2CH=CH_2$. In another embodiment is a compound of Formula (Ib) wherein A is $C(O)N(H)N(R^{24})C(O)CH=CH_2$. In another embodiment is a compound of Formula (Ib) wherein A is —$C(O)N(H)N(R^{24})C(O)CH_2Cl$.

In another embodiment is a compound of Formula (Ib) wherein A is —$C(O)N(H)R^{34}$, wherein $R^{34}$ is —OH. In another embodiment is a compound of Formula (Ib) wherein A is —$C(O)N(H)R^{34}$, wherein $R^{34}$ is —$NH_2$. In another embodiment is a compound of Formula (Ib) wherein A is —$C(O)N(H)R^{34}$, wherein $R^{34}$ is —CN. In another embodiment is a compound of Formula (Ib) wherein A is —$C(O)N(H)R^{34}$, wherein $R^{34}$ is —$CH_2CH_2CN$. In another embodiment is a compound of Formula (Ib) wherein A is —$C(O)N(H)R^{34}$, wherein $R^{34}$ is —O($C_1$-$C_6$)alkyl. In another embodiment is a compound of Formula (Ib) wherein A is —$C(O)N(H)R^{34}$, wherein $R^{34}$ is —$C(O)(C_1$-$C_6)$alkyl. In another embodiment is a compound of Formula (Ib) wherein A is —$C(O)N(H)R^{34}$, wherein $R^{34}$ is —$SO_2NH_2$. In another embodiment is a compound of Formula (Ib) wherein A is —$C(O)N(H)R^{34}$, wherein $R^{34}$ is

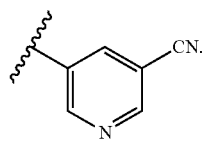 [SMILES: *c1cncc(C#N)c1]

In another embodiment is a compound of Formula (Ib) wherein A is —$C(O)N(H)R^{34}$, wherein $R^{34}$ is

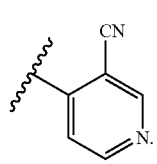

In another embodiment is a compound of Formula (Ib) wherein A is —$C(O)N(H)R^{34}$, wherein $R^{34}$ is

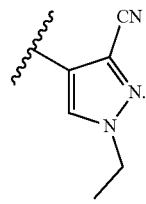 [SMILES: *c1cn(CC)nc1C#N]

In another embodiment is a compound of Formula (Ib) wherein A is

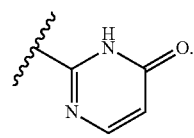

In another embodiment is a compound of Formula (Ib) wherein A is

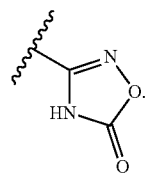 [SMILES: *c1noc(=O)[nH]1]

In another embodiment is a compound of Formula (Ib) wherein A is

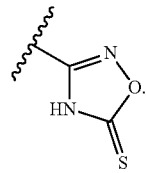 [SMILES: *c1noc(=S)[nH]1]

In another embodiment is a compound of Formula (Ib) wherein A is

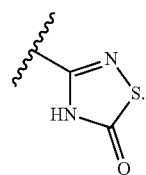 [SMILES: *c1nsc(=O)[nH]1]

In another embodiment is a compound of Formula (Ib) wherein A is

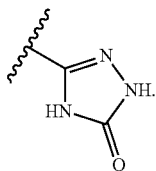 [SMILES: *c1n[nH]c(=O)[nH]1]

In another embodiment is a compound of Formula (Ib) wherein A is

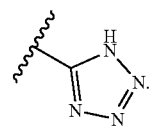

In another embodiment is a compound of Formula (Ib) wherein A is

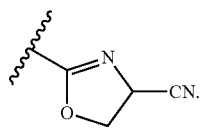 [SMILES: *C1=NC(C#N)CO1]

In another embodiment is a compound of Formula (Ib) wherein A is

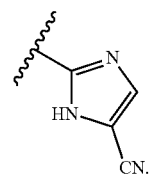 [SMILES: *c1ncc(C#N)[nH]1]

In another embodiment is a compound of Formula (Ib) wherein A is

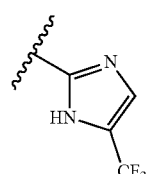

In another embodiment is a compound of Formula (Ib) wherein X is optionally substituted aryl. In another embodiment is a compound of Formula (Ib) wherein X is optionally substituted phenyl. In another embodiment is a compound of Formula (Ib) wherein X is optionally substituted heteroaryl. In another embodiment is a compound of Formula (Ib) wherein X is optionally substituted pyridine or optionally substituted pyrimidine. In another embodiment is a compound of Formula (Ib) wherein X is optionally substituted —($C_1$-$C_6$)alkyl-. In another embodiment is a compound of Formula (Ib) wherein Y is optionally substituted aryl. In another embodiment is a compound of Formula (Ib) wherein Y is optionally substituted phenyl. In another embodiment is a compound of Formula (Ib) wherein Y is optionally substituted heteroaryl. In another embodiment is a compound of Formula (Ib) wherein Y is optionally substituted —($C_1$-$C_6$)alkyl-. In another embodiment is a compound of Formula (Ib) wherein Y is —O—($C_1$-$C_6$)alkyl-. In another embodiment is a compound of Formula (Ib) wherein Y is —N(H)—($C_1$-$C_6$)alkyl-. In another embodiment is a compound of Formula (Ib) wherein Y is a bond. In another embodiment is a compound of Formula (Ib) wherein Z is —($C_1$-$C_6$)alkyl. In another embodiment is a compound of Formula (Ib) wherein Z is optionally substituted aryl. In another embodiment is a compound of Formula (Ib) wherein Z is optionally substituted phenyl. In another embodiment is a compound of Formula (Ib) wherein Z is optionally substituted heteroaryl. In another embodiment is a compound of Formula (Ib) wherein Z is optionally substituted —($C_3$-$C_7$)cycloalkyl. In another embodiment is a compound of Formula (Ib) wherein Z is halogen.

In another embodiment is a compound of Formula (Ib) wherein —X—Y—Z is

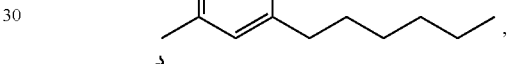

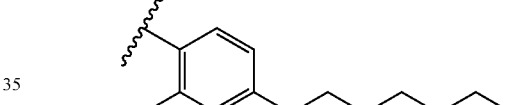

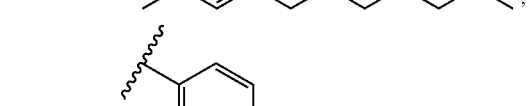

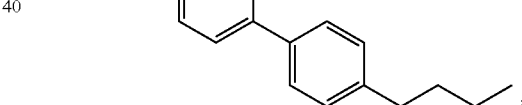

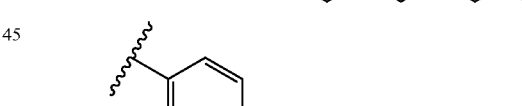

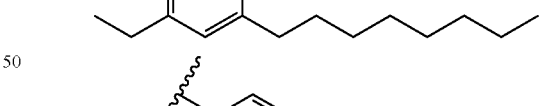

-continued

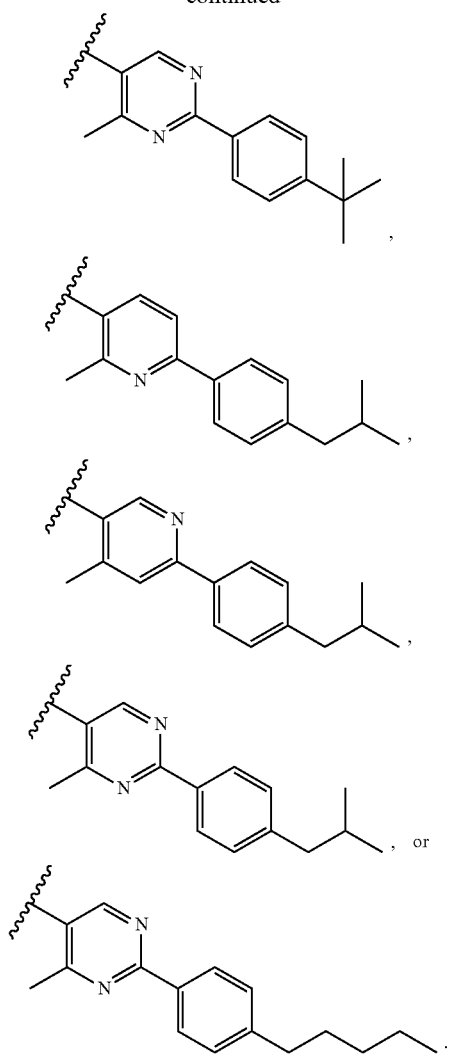

,

,

,

, or

.

In another embodiment is a compound of Formula (I) having the structure of Formula (Ic):

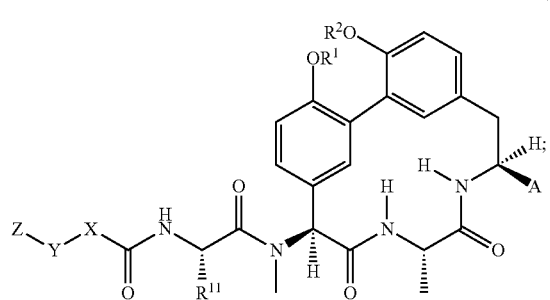

Formula (Ic)

wherein:
R¹ and R² are each independently H, —(C₁-C₆)alkyl, —(C₁-C₆)alkyl-OR²³, —CH₂CH(OH)CH₂NH₂, —CH₂CH(heterocycloalkyl)CH₂NH₂, —CH₂C(O)NH₂, —CH₂C(O)N(H)CH₂CN, —(C₁-C₆)alkyl-C(O)OR²³, —(C₁-C₆)alkyl-NR²¹R²², —(C₁-C₆)alkyl-C(O)NR²⁵R²⁶, —(C₁-C₆)alkyl-N(R²³)C(O)(C₁-C₆)alkylNR²¹R²², or —(C₁-C₆)alkyl-C(O)N(R²³)(C₁-C₆)alkyl, or optionally substituted heterocycloalkyl;

R¹¹ is H, —NH₂, —(C₁-C₆)alkyl, —(C₁-C₆)alkyl-OR²³, —(C₁-C₆)alkyl-SR²³, —(C₁-C₆)alkyl-C(O)OR²³, —(C₁-C₆)alkyl-NR²¹R²², —(C₁-C₆)alkyl-CN, —(C₁-C₆)alkyl-C(O)NR²⁵R²⁶, —(C₁-C₆)alkyl-S(O)—(C₁-C₆)alkyl, —(C₁-C₆)alkyl-N(H)CH=NH, —(C₁-C₆)alkyl-N(H)C(NH)NH₂, —(C₁-C₆)alkyl-heterocycloalkyl, optionally substituted —(C₁-C₆)alkyl-N(H)heterocycloalkyl, or —(C₁-C₆)alkyl-heteroaryl;

A is —CN, —CH₂CN, —CH=CHCN, —CH₂N(H)C(O)CH₂CN, —CH₂N(H)C(O)N(H)R²⁴, —C(O)N(H)R³⁴, —C(O)N(H)C(R²³)₂C(O)OR²⁹, —C(O)N(H)C(R²³)₂C(O)NR³²R³³, —C(O)N(H)C(R²³)₂C=NR³⁰, —C(O)N(H)SO₃H, —C(O)N(H)SO₂CH=CH₂, —C(O)N(H)N(R²⁴)C(O)CH=CH₂, —C(O)N(H)N(R²⁴)C(O)CH₂Cl,

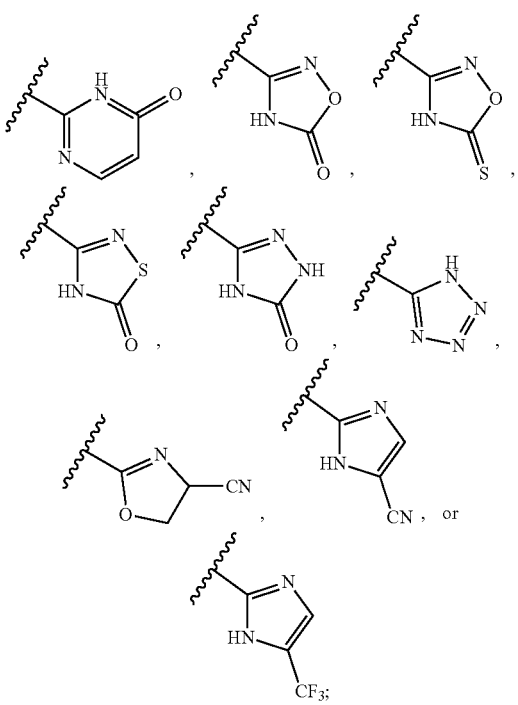

X is optionally substituted —(C₁-C₆)alkyl-, —(C₂-C₆)alkenyl-, —(C₂-C₆)alkynyl, —(C₃-C₇)cycloalkyl-, optionally substituted heterocycloalkyl, optionally substituted aryl, optionally substituted heteroaryl, —O—(C₁-C₆)alkyl, —N(R²⁴)(C₁-C₆)alkyl-, —N(R²⁴)(C₆-C₁₀)aryl-, or —SO₂(C₁-C₆)alkyl-;

Y is a bond, optionally substituted —(C₁-C₆)alkyl-, —(C₂-C₆)alkenyl-, —(C₂-C₆)alkynyl, —(C₁-C₆)alkyl-N(R²⁴)(C₁-C₆)alkyl-, —O—(C₁-C₆)alkyl-, —O(C₆-C₁₀)aryl-, —N(R²⁴)(C₁-C₆)alkyl-, —N(R²⁴)SO₂(C₁-C₆)alkyl-, —N(R²⁴)C(O)(C₁-C₆)alkyl-, —C(O)(C₁-C₆)alkyl-, —S(C₁-C₆)alkyl-, —SO₂(C₁-C₆)alkyl-, —C(O)NH(C₁-C₆)alkyl-, —(C₃-C₇)cycloalkyl-, optionally substituted —C(O)N(R²⁴)aryl-, optionally substituted —N(R²⁴)C(O)aryl-, optionally substituted —N(R²⁴)SO₂aryl-, optionally substituted aryl, or optionally substituted heteroaryl;

Z is H, halogen, —NH₂, —CN, —CF₃, —CO₂H, —(C₁-C₁₂)alkyl, —(C₂-C₁₂)alkenyl, —(C₂-C₁₂)alkynyl, —C(O)NR²⁵R²⁶, —N(R²⁴)(C₁-C₁₂)alkyl, —N(R²⁴)C(O)(C₁-C₁₂)alkyl, optionally substituted —(C₃-C₇)cycloalkyl, —($C_1$-$C_6$)alkyl-heterocycloalkyl, optionally substituted aryl, or optionally substituted heteroaryl;

each $R^{21}$ and $R^{22}$ is independently H, —($C_1$-$C_6$)alkyl, —($C_1$-$C_6$)heteroalkyl, —($C_1$-$C_6$)alkyl-$CO_2$H, —C(O)($C_1$-$C_6$)alkyl, —C(O)N($R^{31}$)$_2$, —$SO_2$N($R^{31}$)$_2$; or $R^{21}$ and $R^{22}$ and the nitrogen atom to which they are attached form a heterocycloalkyl ring;

each $R^{31}$ is independently H or —($C_1$-$C_6$)alkyl; or two $R^{31}$ and the nitrogen atom to which they are attached form a heterocycloalkyl ring;

each $R^{23}$ is independently H or —($C_1$-$C_6$)alkyl;
each $R^{24}$ is independently H or —($C_1$-$C_6$)alkyl;
each $R^{25}$ and $R^{26}$ is independently H or optionally substituted —($C_1$-$C_6$)alkyl; or $R^{25}$ and $R^{26}$ and the nitrogen atom to which they are attached form a heterocycloalkyl ring;

$R^{29}$ is —$CH_2$C(O)$NH_2$ or optionally substituted aryl;
$R^{30}$ is

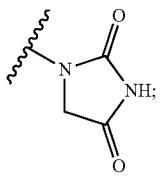 [SMILES: *N1CC(=O)NC1=O]

$R^{32}$ is H or —($C_1$-$C_6$)alkyl;
$R^{33}$ is —$CH_2$CN, —OC(O)($C_1$-$C_6$)alkyl, or —$SO_2NH_2$; and
$R^{34}$ is —OH, —$NH_2$, —CN, —$CH_2CH_2$CN, —O($C_1$-$C_6$)alkyl, —C(O)($C_1$-$C_6$)alkyl, —$SO_2NH_2$,

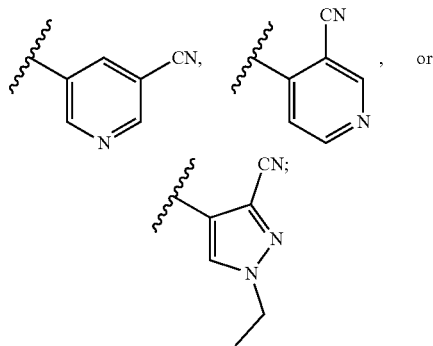

or a pharmaceutically acceptable salt, solvate, or prodrug thereof.

In another embodiment is a compound of Formula (Ic) wherein $R^{11}$ is —($C_1$-$C_6$)alkyl. In another embodiment is a compound of Formula (Ic) wherein $R^{11}$ is —$CH_3$. In another embodiment is a compound of Formula (Ic) wherein $R^{11}$ is —($C_1$-$C_6$)alkyl-O$R^{23}$. In another embodiment is a compound of Formula (Ic) wherein $R^{11}$ is —$CH_2$OH. In another embodiment is a compound of Formula (Ic) wherein $R^{11}$ is —$CH_2CH_2$OH. In another embodiment is a compound of Formula (Ic) wherein $R^{11}$ is —($C_1$-$C_6$)alkyl. In another embodiment is a compound of Formula (Ic) wherein $R^{11}$ is —($C_1$-$C_6$)alkyl-N$R^{21}R^{22}$. In another embodiment is a compound of Formula (Ic) wherein $R^{11}$ is —($C_1$-$C_6$)alkyl-$NH_2$. In another embodiment is a compound of Formula (Ic) wherein $R^{11}$ is —$CH_2NH_2$. In another embodiment is a compound of Formula (Ic) wherein $R^{11}$ is —$CH_2CH_2NH_2$. In another embodiment is a compound of Formula (Ic) wherein $R^{11}$ is —$CH_2CH_2CH_2NH_2$. In another embodiment is a compound of Formula (Ic) wherein $R^{11}$ is —$CH_2CH_2CH_2CH_2NH_2$. In another embodiment is a compound of Formula (Ic) wherein $R^{11}$ is —($C_1$-$C_6$)alkyl-CN. In another embodiment is a compound of Formula (Ic) wherein $R^{11}$ is —$CH_2$CN. In another embodiment is a compound of Formula (Ic) wherein $R^{11}$ is —($C_1$-$C_6$)alkyl-C(O)N$R^{25}R^{26}$. In another embodiment is a compound of Formula (Ic) wherein $R^{11}$ is —$CH_2$C(O)$NH_2$. In another embodiment is a compound of Formula (Ic) wherein $R^{11}$ is —$CH_2CH_2$C(O)$NH_2$. In another embodiment is a compound of Formula (Ic) wherein $R^{11}$ is —($C_1$-$C_6$)alkyl-heteroaryl. In another embodiment is a compound of Formula (Ic) wherein $R^{11}$ is H.

In another embodiment is a compound of Formula (Ic) wherein $R^1$ and $R^2$ are each independently H, or —($C_1$-$C_6$)alkyl-N$R^{21}R^{22}$. In another embodiment is a compound of Formula (Ic) wherein $R^1$ and $R^2$ are each H. In another embodiment is a compound of Formula (Ic) wherein $R^1$ and $R^2$ are each independently —($C_1$-$C_6$)alkyl-N$R^{21}R^{22}$. In another embodiment is a compound of Formula (Ic) wherein $R^1$ is H, and $R^2$ is —($C_1$-$C_6$)alkyl-N$R^{21}R^{22}$. In another embodiment is a compound of Formula (Ic) wherein $R^1$ is —($C_1$-$C_6$)alkyl-N$R^{21}R^{22}$, and $R^2$ is H. In another embodiment is a compound of Formula (Ic) wherein $R^1$ is H, and $R^2$ is —$CH_2CH_2NH_2$. In another embodiment is a compound of Formula (Ic) wherein $R^1$ is —$CH_2CH_2NH_2$, and $R^2$ is H. In another embodiment is a compound of Formula (Ic) wherein $R^1$ and $R^2$ are each —$CH_2CH_2NH_2$.

In another embodiment is a compound of Formula (Ic) wherein A is —CN. In another embodiment is a compound of Formula (Ic) wherein A is —$CH_2$CN. In another embodiment is a compound of Formula (Ic) wherein A is —CH=CHCN. In another embodiment is a compound of Formula (Ic) wherein A is —$CH_2$N(H)C(O)$CH_2$CN. In another embodiment is a compound of Formula (Ic) wherein A is —$CH_2$N(H)C(O)N(H)$R^{24}$. In another embodiment is a compound of Formula (Ic) wherein A is —C(O)N(H)$R^{34}$. In another embodiment is a compound of Formula (Ic) wherein A is —C(O)N(H)C($R^{23}$)$_2$C(O)O$R^{29}$. In another embodiment is a compound of Formula (Ic) wherein A is —C(O)N(H)C($R^{23}$)$_2$C(O)N$R^{32}R^{33}$. In another embodiment is a compound of Formula (Ic) wherein A is C(O)N(H)C($R^{23}$)$_2$C=N$R^{30}$. In another embodiment is a compound of Formula (Ic) wherein A is —C(O)N(H)$SO_3$H. In another embodiment is a compound of Formula (Ic) wherein A is —C(O)N(H)$SO_2$CH=$CH_2$. In another embodiment is a compound of Formula (Ic) wherein A is C(O)N(H)N($R^{24}$)C(O)CH=$CH_2$. In another embodiment is a compound of Formula (Ic) wherein A is —C(O)N(H)N($R^{24}$)C(O)$CH_2$Cl.

In another embodiment is a compound of Formula (Ic) wherein A is —C(O)N(H)$R^{34}$, wherein $R^{34}$ is —OH. In another embodiment is a compound of Formula (Ic) wherein A is —C(O)N(H)$R^{34}$, wherein $R^{34}$ is —$NH_2$. In another embodiment is a compound of Formula (Ic) wherein A is —C(O)N(H)$R^{34}$, wherein $R^{34}$ is —CN. In another embodiment is a compound of Formula (Ic) wherein A is —C(O)N(H)$R^{34}$, wherein $R^{34}$ is —$CH_2CH_2$CN. In another embodiment is a compound of Formula (Ic) wherein A is —C(O)N(H)$R^{34}$, wherein $R^{34}$ is —O($C_1$-$C_6$)alkyl. In another embodiment is a compound of Formula (Ic) wherein A is —C(O)N(H)$R^{34}$, wherein $R^{34}$ is —C(O)($C_1$-$C_6$)alkyl. In another embodiment is a compound of Formula (Ic) wherein A is —C(O)N(H)$R^{34}$, wherein $R^{34}$ is —$SO_2NH_2$. In another embodiment is a compound of Formula (Ic) wherein A is —C(O)N(H)$R^{34}$, wherein $R^{34}$ is

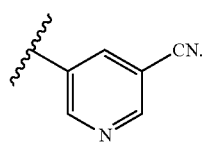 [SMILES: *c1cncc(C#N)c1]

In another embodiment is a compound of Formula (Ic) wherein A is —C(O)N(H)R³⁴, wherein R³⁴ is

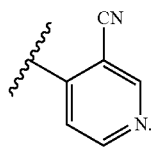

In another embodiment is a compound of Formula (Ic) wherein A is —C(O)N(H)R³⁴, wherein R³⁴ is

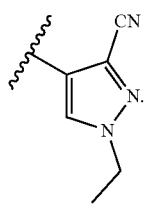

In another embodiment is a compound of Formula (Ic) wherein A is

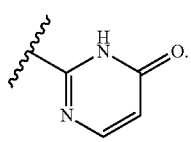

In another embodiment is a compound of Formula (Ic) wherein A is

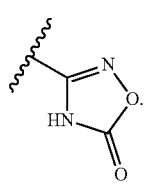 [SMILES: *c1noc(=O)[nH]1]

In another embodiment is a compound of Formula (Ic) wherein A is

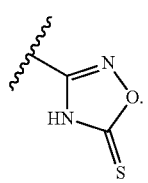 [SMILES: *c1noc(=S)[nH]1]

In another embodiment is a compound of Formula (Ic) wherein A is

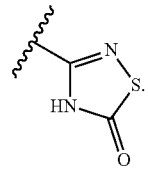 [SMILES: *c1nsc(=O)[nH]1]

In another embodiment is a compound of Formula (Ic) wherein A is

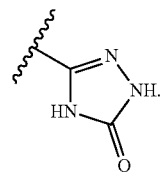 [SMILES: *c1n[nH]c(=O)[nH]1]

In another embodiment is a compound of Formula (Ic) wherein A is

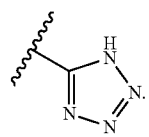

In another embodiment is a compound of Formula (Ic) wherein A is

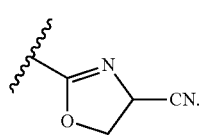 [SMILES: *C1=NC(C#N)CO1]

In another embodiment is a compound of Formula (Ic) wherein A is

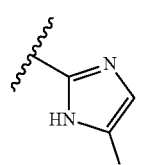

In another embodiment is a compound of Formula (Ic) wherein A is

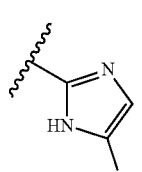

In another embodiment is a compound of Formula (Ic) wherein X is optionally substituted aryl. In another embodiment is a compound of Formula (Ic) wherein X is optionally substituted phenyl. In another embodiment is a compound of Formula (Ic) wherein X is optionally substituted heteroaryl. In another embodiment is a compound of Formula (Ic) wherein X is optionally substituted pyridine or optionally substituted pyrimidine. In another embodiment is a compound of Formula (Ic) wherein X is optionally substituted —(C$_1$-C$_6$)alkyl-. In another embodiment is a compound of Formula (Ic) wherein Y is optionally substituted aryl. In another embodiment is a compound of Formula (Ic) wherein Y is optionally substituted phenyl. In another embodiment is a compound of Formula (Ic) wherein Y is optionally substituted heteroaryl. In another embodiment is a compound of Formula (Ic) wherein Y is optionally substituted —(C$_1$-C$_6$)alkyl-. In another embodiment is a compound of Formula (Ic) wherein Y is —O—(C$_1$-C$_6$)alkyl-. In another embodiment is a compound of Formula (Ic) wherein Y is —N(H)—(C$_1$-C$_6$)alkyl-. In another embodiment is a compound of Formula (Ic) wherein Y is a bond. In another embodiment is a compound of Formula (Ic) wherein Z is —(C$_1$-C$_6$)alkyl. In another embodiment is a compound of Formula (Ic) wherein Z is optionally substituted aryl. In another embodiment is a compound of Formula (Ic) wherein Z is optionally substituted phenyl. In another embodiment is a compound of Formula (Ic) wherein Z is optionally substituted heteroaryl. In another embodiment is a compound of Formula (Ic) wherein Z is optionally substituted —(C$_3$-C$_7$)cycloalkyl. In another embodiment is a compound of Formula (Ic) wherein Z is halogen.

In another embodiment is a compound of Formula (Ic) wherein —X—Y—Z is

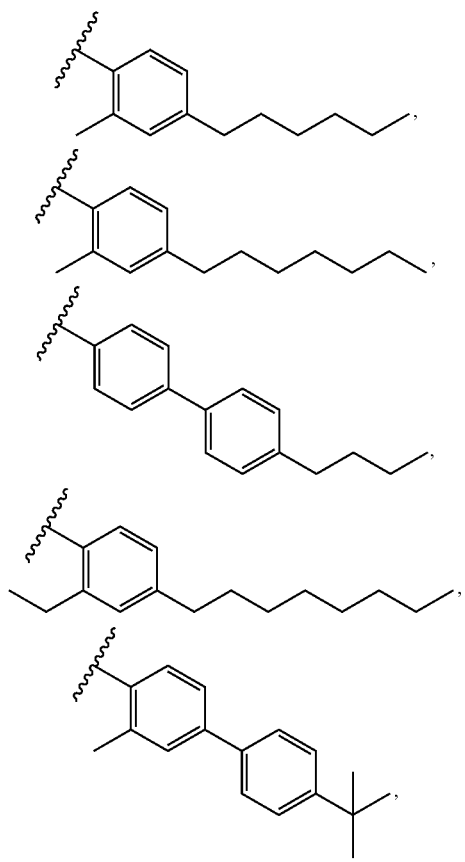

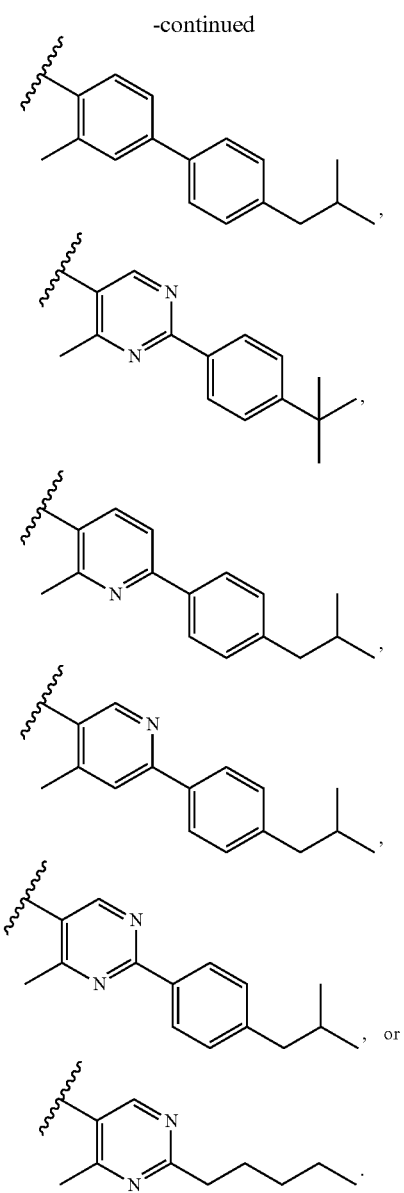

In another embodiment is a compound of Formula (I) having the structure of Formula (Id):

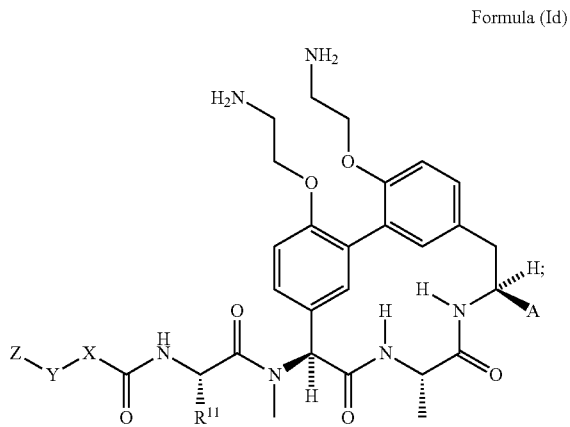

Formula (Id)

wherein:

$R^{11}$ is —$CH_2NH_2$, —$CH_2CH_2NH_2$, or —$CH_2CH_2CH_2NH_2$;

A is —CN, —$CH_2$CN, —CH=CHCN, —$CH_2$N(H)C(O)$CH_2$CN, —$CH_2$N(H)C(O)N(H)$R^{24}$, —C(O)N(H)$R^{34}$, —C(O)N(H)C($R^{23}$)$_2$C(O)O$R^{29}$, —C(O)N(H)C($R^{23}$)$_2$C(O)N$R^{32}R^{33}$, —C(O)N(H)C($R^{23}$)$_2$C=N$R^{30}$, —C(O)N(H)SO$_3$H, —C(O)N(H)SO$_2$CH=CH$_2$, —C(O)N(H)N($R^{24}$)C(O)CH=CH$_2$, —C(O)N(H)N($R^{24}$)C(O)CH$_2$Cl,

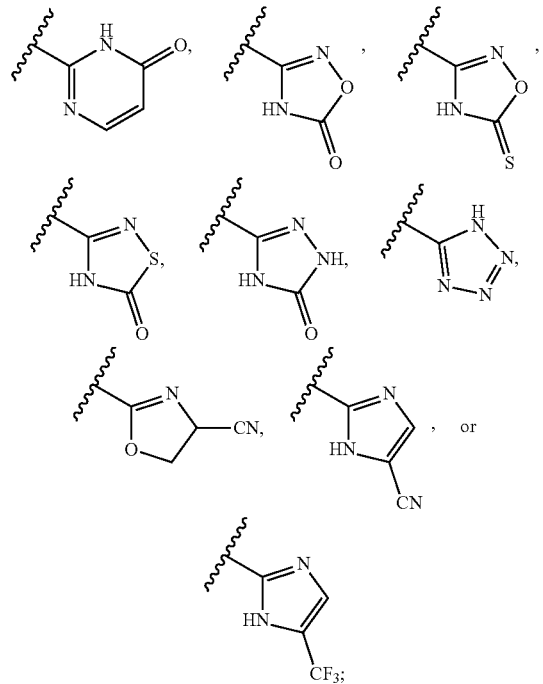

$R^{30}$ is

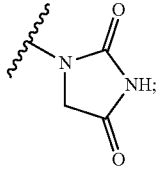 [SMILES: *N1CC(=O)NC1=O]

$R^{32}$ is H or —($C_1$-$C_6$)alkyl;
$R^{33}$ is —$CH_2$CN, —OC(O)($C_1$-$C_6$)alkyl, or —SO$_2$NH$_2$; and
$R^{34}$ is —OH, —NH$_2$, —CN, —$CH_2CH_2$CN, —O($C_1$-$C_6$)alkyl, —C(O)($C_1$-$C_6$)alkyl, —SO$_2$NH$_2$,

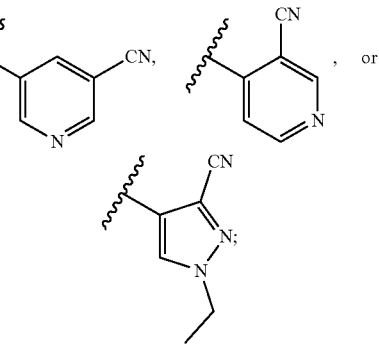

or a pharmaceutically acceptable salt, solvate, or prodrug thereof.

In one embodiment is a compound of Formula (Id) wherein $R^{11}$ is —$CH_2NH_2$. In another embodiment is a compound of Formula (Id) wherein $R^{11}$ is —$CH_2CH_2NH_2$. In another embodiment is a compound of Formula (Id) wherein $R^{11}$ is —$CH_2CH_2CH_2NH_2$.

In another embodiment is a compound of Formula (Id) wherein A is —CN. In another embodiment is a compound of Formula (Id) wherein A is —$CH_2$CN. In another embodiment is a compound of Formula (Id) wherein A is —CH=CHCN. In another embodiment is a compound of Formula (Id) wherein A is —$CH_2$N(H)C(O)$CH_2$CN. In another embodiment is a compound of Formula (Id) wherein A is —$CH_2$N(H)C(O)N(H)$R^{24}$. In another embodiment is a compound of Formula (Id) wherein A is —C(O)N(H)$R^{34}$. In another embodiment is a compound of Formula (Id) wherein A is —C(O)N(H)C($R^{23}$)$_2$C(O)O$R^{29}$. In another embodiment is a compound of Formula (Id) wherein A is —C(O)N(H)C($R^{23}$)$_2$C(O)N$R^{32}R^{33}$. In another embodiment is a compound of Formula (Id) wherein A is C(O)N(H)C($R^{23}$)$_2$C=N$R^{30}$. In another embodiment is a compound of Formula (Id) wherein A is —C(O)N(H)SO$_3$H. In another embodiment is a compound of Formula (Id) wherein A is —C(O)N(H)SO$_2$CH=CH$_2$. In another embodiment is a compound of Formula (Id) wherein A is C(O)N(H)N($R^{24}$)C(O)CH=CH$_2$. In another embodiment is a compound of Formula (Id) wherein A is —C(O)N(H)N($R^{24}$)C(O)CH$_2$Cl.

In another embodiment is a compound of Formula (Id) wherein A is —C(O)N(H)$R^{34}$, wherein $R^{34}$ is —OH. In another embodiment is a compound of Formula (Id) wherein A is —C(O)N(H)$R^{34}$, wherein $R^{34}$ is —NH$_2$. In another embodiment is a compound of Formula (Id) wherein A is —C(O)N(H)$R^{34}$, wherein $R^{34}$ is —CN. In another embodiment is a compound of Formula (Id) wherein A is —C(O)N(H)$R^{34}$, wherein $R^{34}$ is —$CH_2CH_2$CN. In another embodiment is a compound of Formula (Id) wherein A is —C(O)

X is optionally substituted —($C_1$-$C_6$)alkyl-, —($C_2$-$C_6$)alkenyl-, —($C_2$-$C_6$)alkynyl, —($C_3$-$C_7$)cycloalkyl-, optionally substituted heterocycloalkyl, optionally substituted aryl, optionally substituted heteroaryl, —O—($C_1$-$C_6$)alkyl-, —N($R^{24}$)($C_1$-$C_6$)alkyl-, —N($R^{24}$)($C_6$-$C_{10}$)aryl-, or —SO$_2$($C_1$-$C_6$)alkyl-;

Y is a bond, optionally substituted —($C_1$-$C_6$)alkyl-, —($C_2$-$C_6$)alkenyl-, —($C_2$-$C_6$)alkynyl-, —($C_1$-$C_6$)alkyl-N($R^{24}$)($C_1$-$C_6$)alkyl-, —O—($C_1$-$C_6$)alkyl-, —O($C_6$-$C_{10}$)aryl-, —N($R^{24}$)($C_1$-$C_6$)alkyl-, —N($R^{24}$)SO$_2$($C_1$-$C_6$)alkyl-, —N($R^{24}$)C(O)($C_1$-$C_6$)alkyl-, —C(O)($C_1$-$C_6$)alkyl-, —S($C_1$-$C_6$)alkyl-, —SO$_2$($C_1$-$C_6$)alkyl-, —C(O)NH($C_1$-$C_6$)alkyl-, —($C_3$-$C_7$)cycloalkyl-, optionally substituted —C(O)N($R^{24}$)aryl-, optionally substituted —N($R^{24}$)C(O)aryl-, optionally substituted —N($R^{24}$)SO$_2$aryl-, optionally substituted aryl, or optionally substituted heteroaryl;

Z is H, halogen, —NH$_2$, —CN, —CF$_3$, —CO$_2$H, —($C_1$-$C_{12}$)alkyl, —($C_2$-$C_{12}$)alkenyl, —($C_2$-$C_{12}$)alkynyl, —C(O)N$R^{25}R^{26}$, —N($R^{24}$)($C_1$-$C_{12}$)alkyl, —N($R^{24}$)C(O)($C_1$-$C_{12}$)alkyl, optionally substituted —($C_3$-$C_7$)cycloalkyl, —($C_1$-$C_6$)alkyl-heterocycloalkyl, optionally substituted aryl, or optionally substituted heteroaryl;

each $R^{23}$ is independently H or —($C_1$-$C_6$)alkyl;

each $R^{24}$ is independently H or —($C_1$-$C_6$)alkyl;

$R^{25}$ and $R^{26}$ is independently H or optionally substituted —($C_1$-$C_6$)alkyl; or $R^{25}$ and $R^{26}$ and the nitrogen atom to which they are attached form a heterocycloalkyl ring;

$R^{29}$ is —$CH_2$C(O)NH$_2$ or optionally substituted aryl;

N(H)R³⁴, wherein R³⁴ is —O(C₁-C₆)alkyl. In another embodiment is a compound of Formula (Id) wherein A is —C(O)N(H)R³⁴, wherein R³⁴ is —C(O)(C₁-C₆)alkyl. In another embodiment is a compound of Formula (Id) wherein A is —C(O)N(H)R³⁴, wherein R³⁴ is —SO₂NH₂. In another embodiment is a compound of Formula (Id) wherein A is —C(O)N(H)R³⁴, wherein R³⁴ is

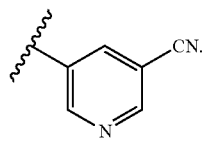 [SMILES: *c1cncc(C#N)c1]

In another embodiment is a compound of Formula (Id) wherein A is —C(O)N(H)R³⁴, wherein R³⁴ is

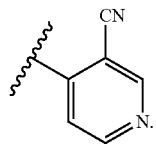 [SMILES: *c1ccncc1C#N]

In another embodiment is a compound of Formula (Id) wherein A is —C(O)N(H)R³⁴, wherein R³⁴ is

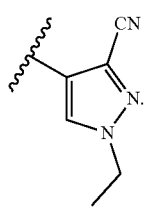

In another embodiment is a compound of Formula (Id) wherein A is

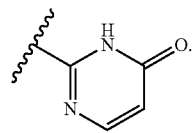 [SMILES: *c1nccc(=O)[nH]1]

In another embodiment is a compound of Formula (Id) wherein A is

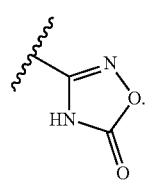 [SMILES: *c1noc(=O)[nH]1]

In another embodiment is a compound of Formula (Id) wherein A is

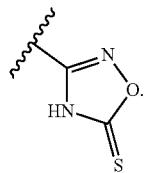

In another embodiment is a compound of Formula (Id) wherein A is

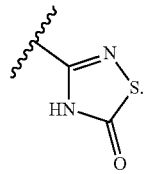

In another embodiment is a compound of Formula (Id) wherein A is

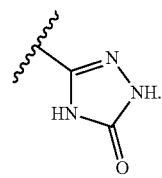 [SMILES: *c1n[nH]c(=O)[nH]1]

In another embodiment is a compound of Formula (Id) wherein A is

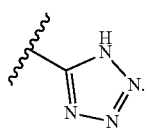 [SMILES: *c1nnn[nH]1]

In another embodiment is a compound of Formula (Id) wherein A is

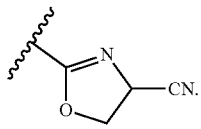

In another embodiment is a compound of Formula (Id) wherein A is

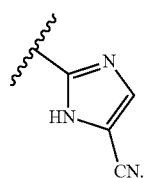

In another embodiment is a compound of Formula (Id) wherein A is

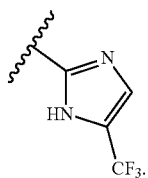

In another embodiment is a compound of Formula (Id) wherein X is optionally substituted aryl. In another embodiment is a compound of Formula (Id) wherein X is optionally substituted phenyl. In another embodiment is a compound of Formula (Id) wherein X is optionally substituted heteroaryl. In another embodiment is a compound of Formula (Id) wherein X is optionally substituted pyridine or optionally substituted pyrimidine. In another embodiment is a compound of Formula (Id) wherein X is optionally substituted —($C_1$-$C_6$)alkyl-. In another embodiment is a compound of Formula (Id) wherein Y is optionally substituted aryl. In another embodiment is a compound of Formula (Id) wherein Y is optionally substituted phenyl. In another embodiment is a compound of Formula (Id) wherein Y is optionally substituted heteroaryl. In another embodiment is a compound of Formula (Id) wherein Y is optionally substituted —($C_1$-$C_6$) alkyl-. In another embodiment is a compound of Formula (Id) wherein Y is —O—($C_1$-$C_6$)alkyl-. In another embodiment is a compound of Formula (Id) wherein Y is —N(H)—($C_1$-$C_6$)alkyl-. In another embodiment is a compound of Formula (Id) wherein Y is a bond. In another embodiment is a compound of Formula (Id) wherein Z is —($C_1$-$C_6$)alkyl. In another embodiment is a compound of Formula (Id) wherein Z is optionally substituted aryl. In another embodiment is a compound of Formula (Id) wherein Z is optionally substituted phenyl. In another embodiment is a compound of Formula (Id) wherein Z is optionally substituted heteroaryl. In another embodiment is a compound of Formula (Id) wherein Z is optionally substituted —($C_3$-$C_7$)cycloalkyl. In another embodiment is a compound of Formula (Id) wherein Z is halogen.

In another embodiment is a compound of Formula (Id) wherein —X—Y—Z is

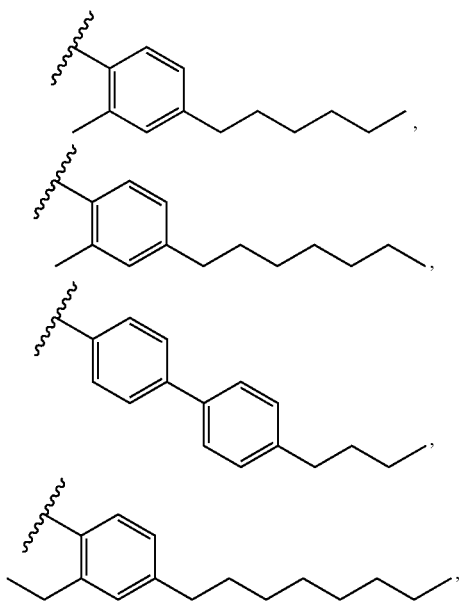

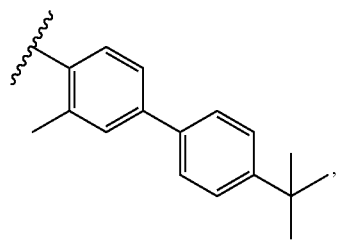

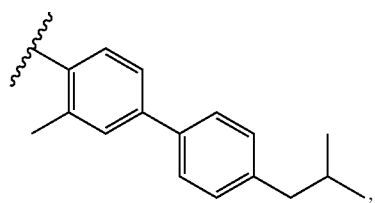

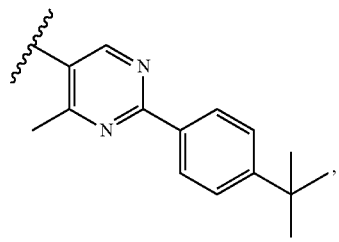

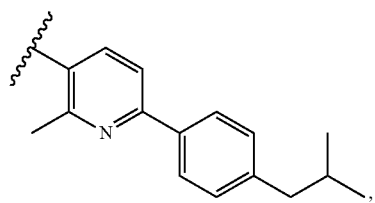

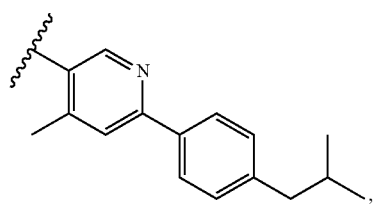

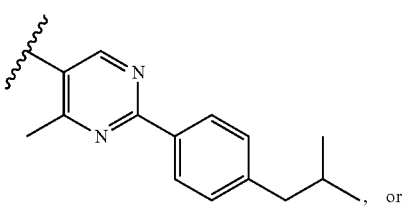, or

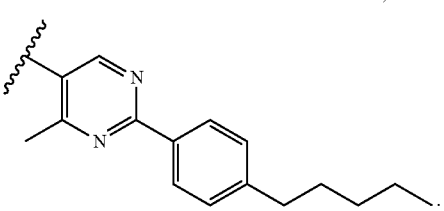

In one aspect described herein are compounds of Formula (II):

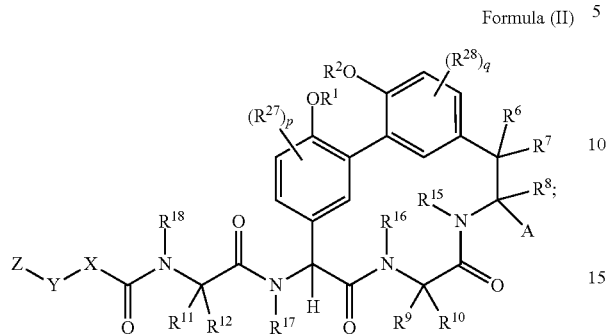

Formula (II)

wherein:
- R¹ and R² are each independently H, —(C₁-C₆)alkyl, —(C₁-C₆)alkyl-OR²³, —CH₂CH(OH)CH₂NH₂, —CH₂CH(heterocycloalkyl)CH₂NH₂, —CH₂C(O)NH₂, —CH₂C(O)N(H)CH₂CN, —(C₁-C₆)alkyl-C(O)OR²³, —(C₁-C₆)alkyl-NR²¹R²², —(C₁-C₆)alkyl-C(O)NR²⁵R²⁶, —(C₁-C₆)alkyl-N(R²³)C(O)(C₁-C₆)alkylNR²¹R²², or —(C₁-C₆)alkyl-C(O)N(R²³)(C₁-C₆)alkyl, or optionally substituted heterocycloalkyl;
- R⁶, R⁷, and R⁸ are each independently H, or —(C₁-C₆)alkyl;
- R⁹ is H, —(C₁-C₆)alkyl, —(C₁-C₆)haloalkyl, or —(C₃-C₆)cycloalkyl;
- R¹⁰ is H, or —(C₁-C₆)alkyl;
- R¹¹ and R¹² are each independently H, —NH₂, —(C₁-C₆)alkyl, —(C₁-C₆)alkyl-OR²³, —(C₁-C₆)alkyl-SR²³, —(C₁-C₆)alkyl-C(O)OR²³, —(C₁-C₆)alkyl-NR²¹R²², —(C₁-C₆)alkyl-CN, —(C₁-C₆)alkyl-C(O)NR²⁵R²⁶, —(C₁-C₆)alkyl-S(O)—(C₁-C₆)alkyl, —(C₁-C₆)alkyl-N(H)CH=NH, —(C₁-C₆)alkyl-C(NH₂)=NH, —(C₁-C₆)alkyl-N(H)C(NH)NH₂, —(C₁-C₆)alkyl-N(H)SO₂NR²¹R²², —(C₁-C₆)alkyl-NH—C(O)R²¹R²², —(C₁-C₆)alkyl-heterocycloalkyl, optionally substituted —(C₁-C₆)alkyl-N(H)heterocycloalkyl, or —(C₁-C₆)alkyl-heteroaryl; or R¹¹ and R¹⁸ are combined to form an optionally substituted heterocycloalkyl ring, and R¹² is H;
- R¹⁵, R¹⁶, R¹⁷, and R¹⁸ are each independently H, —(C₁-C₆)alkyl, —(C₃-C₆)cycloalkyl, —(C₁-C₆)alkyl-OR²³, —(C₁-C₆)alkyl-C(O)OR²³, or —(C₁-C₆)alkyl-NR²¹R²²;
- A is —CN, —CH₂CN, —CH=CHCN, —CH₂N(H)C(O)CH₂CN, —CH₂N(H)C(O)N(H)R²⁴, —C(O)N(H)R³⁴, —C(O)N(H)C(R²³)₂C(O)OR²⁹, —C(O)N(H)C(R²³)₂C(O)NR³²R³³, —C(O)N(H)C(R²³)₂C=NR³⁰, —C(O)N(H)SO₃H, —C(O)N(H)SO₂CH=CH₂, —C(O)N(H)SO₂CH₂Cl, —C(O)N(H)N(R²⁴)C(O)CH=CH₂, —C(O)N(H)N(R²⁴)C(O)CH₂Cl,

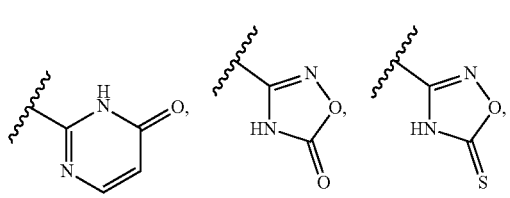

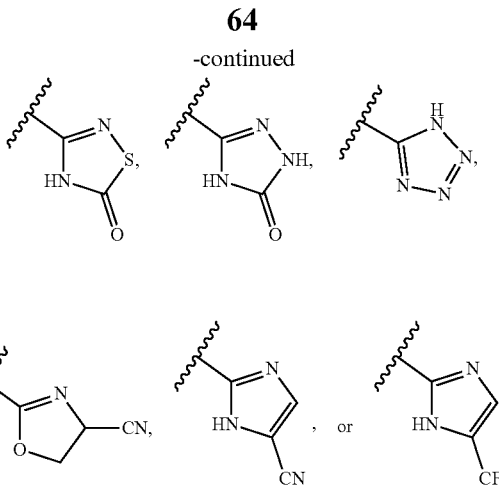

- X is optionally substituted —(C₁-C₆)alkyl-, —(C₂-C₆)alkenyl-, —(C₂-C₆)alkynyl, —(C₃-C₇)cycloalkyl-, optionally substituted heterocycloalkyl, optionally substituted aryl, optionally substituted heteroaryl, —O—(C₁-C₆)alkyl-, —N(R²⁴)(C₁-C₆)alkyl-, —N(R²⁴)(C₆-C₁₀)aryl-, or —SO₂(C₁-C₆)alkyl-;
- Y is a bond, optionally substituted —(C₁-C₆)alkyl-, —(C₂-C₆)alkenyl-, —(C₂-C₆)alkynyl, —(C₁-C₆)alkyl-N(R²⁴)(C₁-C₆)alkyl-, —O—(C₁-C₆)alkyl-, —O(C₆-C₁₀)aryl-, —N(R²⁴)(C₁-C₆)alkyl-, —N(R²⁴)SO₂(C₁-C₆)alkyl-, —N(R²⁴)C(O)(C₁-C₆)alkyl-, —C(O)(C₁-C₆)alkyl-, —S(C₁-C₆)alkyl-, —SO₂(C₁-C₆)alkyl-, —C(O)NH(C₁-C₆)alkyl-, —(C₃-C₇)cycloalkyl-, optionally substituted —C(O)N(R²⁴)aryl-, optionally substituted —N(R²⁴)C(O)aryl-, optionally substituted —N(R²⁴)SO₂aryl-, optionally substituted aryl, or optionally substituted heteroaryl;
- Z is H, halogen, —NH₂, —CN, —CF₃, —CO₂H, —(C₁-C₁₂)alkyl, —(C₂-C₁₂)alkenyl, —(C₂-C₁₂)alkynyl, —C(O)NR²⁵R²⁶, —N(R²⁴)(C₁-C₁₂)alkyl, —N(R²⁴)C(O)(C₁-C₁₂)alkyl, optionally substituted —(C₃-C₇)cycloalkyl, —(C₁-C₆)alkyl-heterocycloalkyl, optionally substituted aryl, or optionally substituted heteroaryl;
- each R²¹ and R²² is independently H, —(C₁-C₆)alkyl, —(C₁-C₆)heteroalkyl, —(C₁-C₆)alkyl-CO₂H, —C(O)(C₁-C₆)alkyl, —C(O)N(R³¹)₂, —SO₂N(R³¹)₂; or R²¹ and R²² and the nitrogen atom to which they are attached form a heterocycloalkyl ring;
- each R³¹ is independently H or —(C₁-C₆)alkyl; or two R³¹ and the nitrogen atom to which they are attached form a heterocycloalkyl ring;
- each R²³ is independently H or —(C₁-C₆)alkyl;
- each R²⁴ is independently H or —(C₁-C₆)alkyl;
- each R²⁵ and R²⁶ is independently H or optionally substituted —(C₁-C₆)alkyl; or R²⁵ and R²⁶ and the nitrogen atom to which they are attached form a heterocycloalkyl ring;
- each R²⁷ is independently halogen, —NR²³R²⁴, —NC(O)NR²³R²³), nitro, hydroxyl, (C₁-C₆)alkoxy, acyl, sulfonate, —(C₁-C₆)alkyl, or —(C₁-C₆)heteroalkyl;
- each R²⁸ is independently halogen, —NR²³R²³, —NC(O)R²³, —NC(O)NR²³R²³), nitro, hydroxyl, (C₁-C₆)alkoxy, acyl, sulfonate, —(C₁-C₆)alkyl, or —(C₁-C₆)heteroalkyl;
- R²⁹ is —CH₂C(O)NH₂ or optionally substituted aryl;

$R^{30}$ is

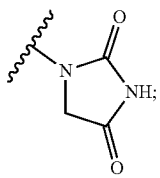 [SMILES: *N1CC(=O)NC1=O]

$R^{32}$ is H or —$(C_1-C_6)$alkyl;
$R^{33}$ is —$CH_2CN$, —$OC(O)(C_1-C_6)$alkyl, —$OC(O)NH_2$, or —$SO_2NH_2$;
$R^{34}$ is —OH, —$NH_2$, —CN, —$CH_2CH_2CN$, —$O(C_1-C_6)$alkyl, —$C(O)(C_1-C_6)$alkyl, —$SO_2N(R^{24})_2$,

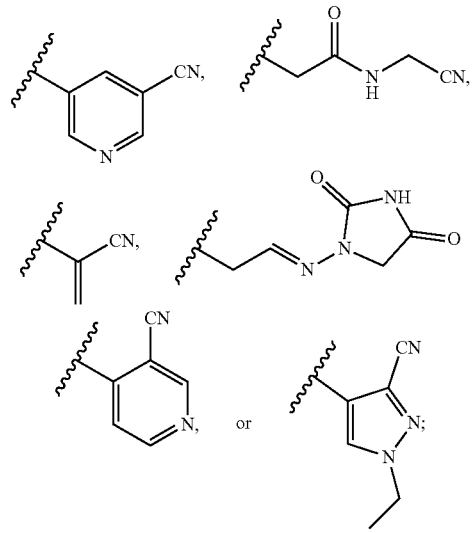

p is 0, 1, or 2; and
q is 0, 1, or 2;
or a pharmaceutically acceptable salt, solvate, or prodrug thereof.

In one embodiment is a compound of Formula (II) wherein $R^6$, $R^7$, and $R^8$ are H.

In another embodiment is a compound of Formula (II) wherein $R^{15}$ and $R^{16}$ are H.

In one embodiment is a compound of Formula (II) wherein $R^{17}$ is —$(C_1-C_6)$alkyl. In another embodiment is a compound of Formula (II) wherein $R^{17}$ is —$CH_3$. In another embodiment is a compound of Formula (II) wherein $R^{17}$ is —$CH_2CH_3$. In another embodiment is a compound of Formula (II) wherein $R^{17}$ is —$(C_3-C_6)$cycloalkyl. In another embodiment is a compound of Formula (II) wherein $R^{17}$ is cyclopropyl. In another embodiment is a compound of Formula (II) wherein $R^{17}$ is —$(C_1-C_6)$alkyl-$C(O)OR^{23}$. In another embodiment is a compound of Formula (II) wherein $R^{17}$ is —$CH_2CH_2OH$. In another embodiment is a compound of Formula (II) wherein $R^{17}$ is —$(C_1-C_6)$alkyl-$NR^{21}R^{22}$. In another embodiment is a compound of Formula (II) wherein $R^{17}$ is —$CH_2CH_2NH_2$. In another embodiment is a compound of Formula (II) wherein $R^{17}$ is H.

In another embodiment is a compound of Formula (II) wherein $R^{18}$ is H.

In another embodiment is a compound of Formula (II) wherein $R^{10}$ is H.

In another embodiment is a compound of Formula (II) wherein $R^{10}$ is H and $R^9$ is —$(C_1-C_6)$alkyl. In another embodiment is a compound of Formula (II) wherein $R^{10}$ is H and $R^9$ is —$CH_3$. In another embodiment is a compound of Formula (II) wherein $R^{10}$ is H and $R^9$ is —$CH_2CH_3$. In another embodiment is a compound of Formula (II) wherein $R^{10}$ is H and $R^9$ is —$(C_1-C_6)$haloalkyl. In another embodiment is a compound of Formula (II) wherein $R^{10}$ is H and $R^9$ is —$CH_2F$. In another embodiment is a compound of Formula (II) wherein $R^{10}$ is H and $R^9$ is —$CHF_2$. In another embodiment is a compound of Formula (II) wherein $R^{10}$ is H and $R^9$ is —$(C_3-C_6)$cycloalkyl. In another embodiment is a compound of Formula (II) wherein $R^{10}$ is H and $R^9$ is cyclopropyl. In another embodiment is a compound of Formula (II) wherein $R^{10}$ is H and $R^9$ is H.

In another embodiment is a compound of Formula (II) wherein $R^{12}$ is H.

In another embodiment is a compound of Formula (II) wherein $R^{12}$ is H and $R^{11}$ is —$(C_1-C_6)$alkyl. In another embodiment is a compound of Formula (II) wherein $R^{12}$ is H and $R^{11}$ is —$CH_3$. In another embodiment is a compound of Formula (II) wherein $R^{12}$ is H and $R^{11}$ is —$(C_1-C_6)$alkyl-$OR^{23}$. In another embodiment is a compound of Formula (II) wherein $R^{12}$ is H and $R^{11}$ is —$CH_2OH$. In another embodiment is a compound of Formula (II) wherein $R^{12}$ is H and $R^{11}$ is —$CH_2CH_2OH$. In another embodiment is a compound of Formula (II) wherein $R^{12}$ is H and $R^{11}$ is —$(C_1-C_6)$alkyl. In another embodiment is a compound of Formula (II) wherein $R^{12}$ is H and $R^{11}$ is —$(C_1-C_6)$alkyl-$NR^{21}R^{22}$. In another embodiment is a compound of Formula (II) wherein $R^{12}$ is H and $R^{11}$ is —$(C_1-C_6)$alkyl-$NH_2$. In another embodiment is a compound of Formula (II) wherein $R^{12}$ is H and $R^{11}$ is —$CH_2NH_2$. In another embodiment is a compound of Formula (II) wherein $R^{12}$ is H and $R^{11}$ is —$CH_2CH_2NH_2$. In another embodiment is a compound of Formula (II) wherein $R^{12}$ is H and $R^{11}$ is —$CH_2CH_2CH_2NH_2$. In another embodiment is a compound of Formula (II) wherein $R^{12}$ is H and $R^{11}$ is —$CH_2CH_2CH_2CH_2NH_2$. In another embodiment is a compound of Formula (II) wherein $R^{12}$ is H and $R^{11}$ is —$(C_1-C_6)$alkyl-CN. In another embodiment is a compound of Formula (II) wherein $R^{12}$ is H and $R^{11}$ is —$CH_2CN$. In another embodiment is a compound of Formula (II) wherein $R^{12}$ is H and $R^{11}$ is —$(C_1-C_6)$alkyl-$C(O)NR^{25}R^{26}$. In another embodiment is a compound of Formula (II) wherein $R^{12}$ is H and $R^{11}$ is —$CH_2C(O)NH_2$. In another embodiment is a compound of Formula (II) wherein $R^{12}$ is H and $R^{11}$ is —$CH_2CH_2C(O)NH_2$. In another embodiment is a compound of Formula (II) wherein $R^{12}$ is H and $R^{11}$ is —$(C_1-C_6)$alkyl-heteroaryl. In another embodiment is a compound of Formula (II) wherein $R^{12}$ is H and $R^{11}$ is H.

In another embodiment is a compound of Formula (II) wherein $R^{11}$ and $R^{18}$ are combined to form an optionally substituted heterocycloalkyl ring and $R^{12}$ is H.

In another embodiment is a compound of Formula (II) wherein p is 1 and $R^{27}$ is halogen. In another embodiment is a compound of Formula (II) wherein p is 1 and $R^{27}$ is optionally substituted —$(C_1-C_6)$alkyl. In another embodiment is a compound of Formula (II) wherein q is 0, p is 1 and $R^{27}$ is halogen. In another embodiment is a compound of Formula (II) wherein q is 0, p is 1 and $R^{27}$ is optionally substituted —$(C_1-C_6)$alkyl. In another embodiment is a compound of Formula (II) wherein q is 1 and $R^{28}$ is halogen. In another embodiment is a compound of Formula (II) wherein q is 1 and $R^{28}$ is optionally substituted —$(C_1-C_6)$alkyl. In another embodiment is a compound of Formula (II) wherein p is 0, q is 1 and $R^{28}$ is halogen. In another embodiment is a compound of Formula (II) wherein p is 0, q is 1 and $R^{28}$ is optionally substituted —$(C_1$-$C_6)$alkyl.

In another embodiment is a compound of Formula (II) wherein p is 0, and q is 0.

In another embodiment is a compound of Formula (II) wherein $R^1$ and $R^2$ are each independently H, or —$(C_1$-$C_6)$alkyl-$NR^{21}R^{22}$. In another embodiment is a compound of Formula (II) wherein $R^1$ and $R^2$ are each H. In another embodiment is a compound of Formula (II) wherein $R^1$ and $R^2$ are each independently —$(C_1$-$C_6)$alkyl-$NR^{21}R^{22}$. In another embodiment is a compound of Formula (II) wherein $R^1$ is H, and $R^2$ is —$(C_1$-$C_6)$alkyl-$NR^{21}R^{22}$. In another embodiment is a compound of Formula (II) wherein $R^1$ is —$(C_1$-$C_6)$alkyl-$NR^{21}R^{22}$, and $R^2$ is H. In another embodiment is a compound of Formula (II) wherein $R^1$ is H, and $R^2$ is —$CH_2CH_2NH_2$. In another embodiment is a compound of Formula (II) wherein $R^1$ is —$CH_2CH_2NH_2$, and $R^2$ is H. In another embodiment is a compound of Formula (II) wherein $R^1$ and $R^2$ are each —$CH_2CH_2NH_2$.

In another embodiment is a compound of Formula (II) wherein A is —CN. In another embodiment is a compound of Formula (II) wherein A is —$CH_2CN$. In another embodiment is a compound of Formula (II) wherein A is —CH=CHCN. In another embodiment is a compound of Formula (II) wherein A is —$CH_2N(H)C(O)CH_2CN$. In another embodiment is a compound of Formula (II) wherein A is —$CH_2N(H)C(O)N(H)R^{24}$. In another embodiment is a compound of Formula (II) wherein A is —$C(O)N(H)R^{34}$. In another embodiment is a compound of Formula (II) wherein A is —$C(O)N(H)C(R^{23})_2C(O)OR^{29}$. In another embodiment is a compound of Formula (II) wherein A is —$C(O)N(H)C(R^{23})_2C(O)NR^{32}R^{33}$. In another embodiment is a compound of Formula (II) wherein A is $C(O)N(H)C(R^{23})_2C=NR^{30}$. In another embodiment is a compound of Formula (II) wherein A is —$C(O)N(H)SO_3H$. In another embodiment is a compound of Formula (II) wherein A is —$C(O)N(H)SO_2CH=CH_2$. In another embodiment is a compound of Formula (II) wherein A is $C(O)N(H)N(R^{24})C(O)CH=CH_2$. In another embodiment is a compound of Formula (II) wherein A is —$C(O)N(H)N(R^{24})C(O)CH_2Cl$.

In another embodiment is a compound of Formula (II) wherein A is —$C(O)N(H)R^{34}$, wherein $R^{34}$ is —OH. In another embodiment is a compound of Formula (II) wherein A is —$C(O)N(H)R^{34}$, wherein $R^{34}$ is —$NH_2$. In another embodiment is a compound of Formula (II) wherein A is —$C(O)N(H)R^{34}$, wherein $R^{34}$ is —CN. In another embodiment is a compound of Formula (II) wherein A is —$C(O)N(H)R^{34}$, wherein $R^{34}$ is —$CH_2CH_2CN$. In another embodiment is a compound of Formula (II) wherein A is —$C(O)N(H)R^{34}$, wherein $R^{34}$ is —$O(C_1$-$C_6)$alkyl. In another embodiment is a compound of Formula (II) wherein A is —$C(O)N(H)R^{34}$, wherein $R^{34}$ is —$C(O)(C_1$-$C_6)$alkyl. In another embodiment is a compound of Formula (II) wherein A is —$C(O)N(H)R^{34}$, wherein $R^{34}$ is —$SO_2N(R^{24})_2$. In another embodiment is a compound of Formula (II) wherein A is —$C(O)N(H)R^{34}$, wherein $R^{34}$ is —$SO_2N(R^{24})_2$, and $R^{24}$ is —$(C_1$-$C_6)$alkyl. In another embodiment is a compound of Formula (II) wherein A is —$C(O)N(H)R^{34}$, wherein $R^{34}$ is —$SO_2NH_2$. In another embodiment is a compound of Formula (II) wherein A is —$C(O)N(H)R^{34}$, wherein $R^{34}$ is

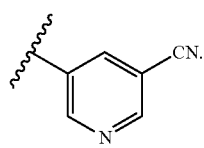 [SMILES: *c1cncc(C#N)c1]

In another embodiment is a compound of Formula (II) wherein A is —$C(O)N(H)R^{34}$, wherein $R^{34}$ is

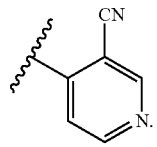 [SMILES: *c1ccncc1C#N]

In another embodiment is a compound of Formula (II) wherein A is —$C(O)N(H)R^{34}$, wherein $R^{34}$ is

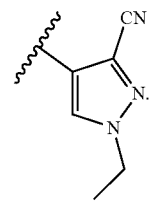 [SMILES: *c1cn(CC)nc1C#N]

In another embodiment is a compound of Formula (II) wherein A is

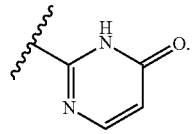 [SMILES: *c1nccc(=O)[nH]1]

In another embodiment is a compound of Formula (II) wherein A is

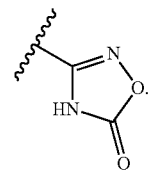 [SMILES: *c1noc(=O)[nH]1]

In another embodiment is a compound of Formula (II) wherein A is

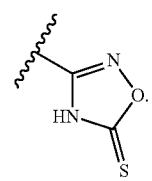 [SMILES: *c1noc(=S)[nH]1]

In another embodiment is a compound of Formula (II) wherein A is

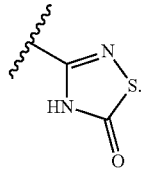 [SMILES: *c1nsc(=O)[nH]1]

In another embodiment is a compound of Formula (II) wherein A is

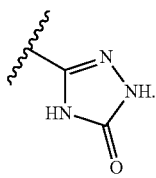 [SMILES: *c1n[nH]c(=O)[nH]1]

In another embodiment is a compound of Formula (II) wherein A is

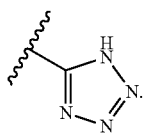

In another embodiment is a compound of Formula (II) wherein A is

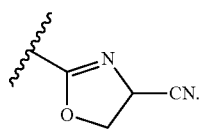 [SMILES: *C1=NC(C#N)CO1]

In another embodiment is a compound of Formula (II) wherein A is

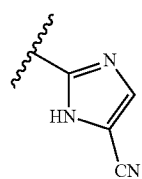 [SMILES: *c1ncc(C#N)[nH]1]

In another embodiment is a compound of Formula (II) wherein A is

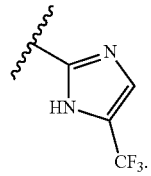 [SMILES: *c1ncc(C(F)(F)F)[nH]1]

In another embodiment is a compound of Formula (II) wherein X is optionally substituted aryl. In another embodiment is a compound of Formula (II) wherein X is optionally substituted phenyl. In another embodiment is a compound of Formula (II) wherein X is optionally substituted heteroaryl. In another embodiment is a compound of Formula (II) wherein X is optionally substituted pyridine or optionally substituted pyrimidine. In another embodiment is a compound of Formula (II) wherein X is optionally substituted —($C_1$-$C_6$)alkyl-. In another embodiment is a compound of Formula (II) wherein Y is optionally substituted aryl. In another embodiment is a compound of Formula (II) wherein Y is optionally substituted phenyl. In another embodiment is a compound of Formula (II) wherein Y is optionally substituted heteroaryl. In another embodiment is a compound of Formula (II) wherein Y is optionally substituted —($C_1$-$C_6$)alkyl-. In another embodiment is a compound of Formula (II) wherein Y is —O—($C_1$-$C_6$)alkyl-. In another embodiment is a compound of Formula (II) wherein Y is —N(H)—($C_1$-$C_6$)alkyl-. In another embodiment is a compound of Formula (II) wherein Y is a bond. In another embodiment is a compound of Formula (II) wherein Z is —($C_1$-$C_6$)alkyl. In another embodiment is a compound of Formula (II) wherein Z is optionally substituted aryl. In another embodiment is a compound of Formula (II) wherein Z is optionally substituted phenyl. In another embodiment is a compound of Formula (II) wherein Z is optionally substituted heteroaryl. In another embodiment is a compound of Formula (II) wherein Z is optionally substituted —($C_3$-$C_7$)cycloalkyl. In another embodiment is a compound of Formula (II) wherein Z is halogen.

In another embodiment is a compound of Formula (II) wherein —X—Y—Z is

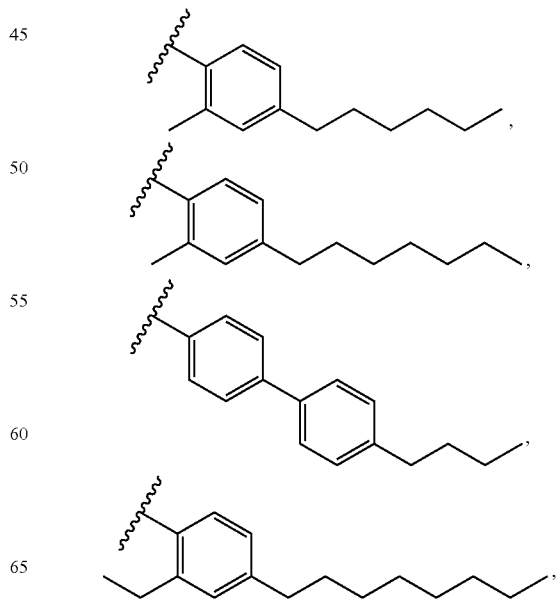

71
-continued
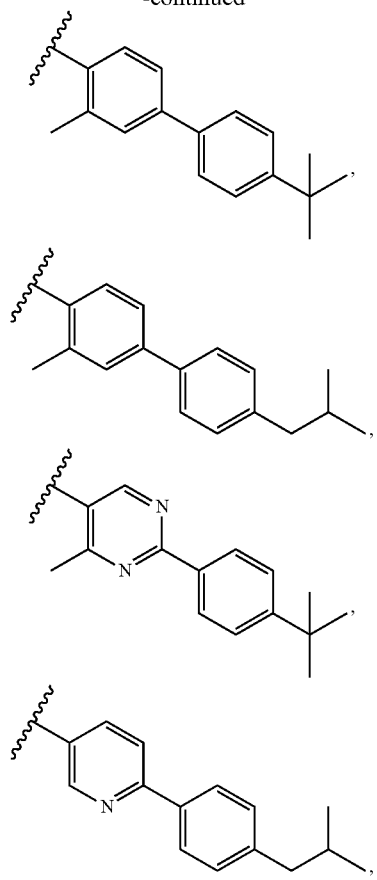
72
-continued
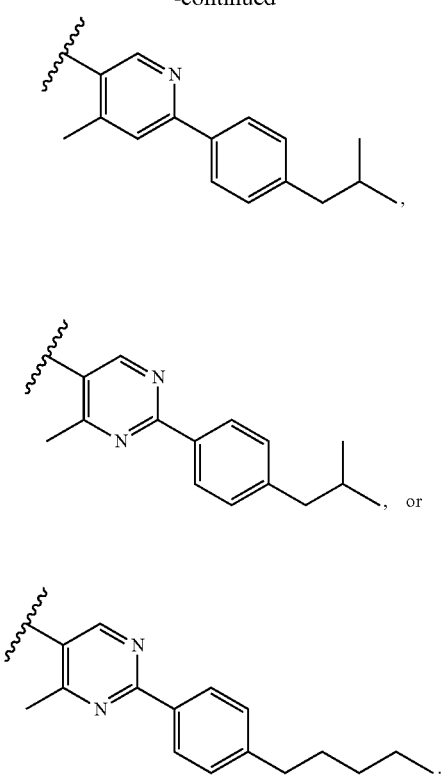
In another aspect, the compound disclosed herein has a structure provided in table 1 or a pharmaceutically acceptable salt, solvate, or prodrug thereof.
TABLE 1
| Compound | Structure |
| --- | --- |
| 101 | 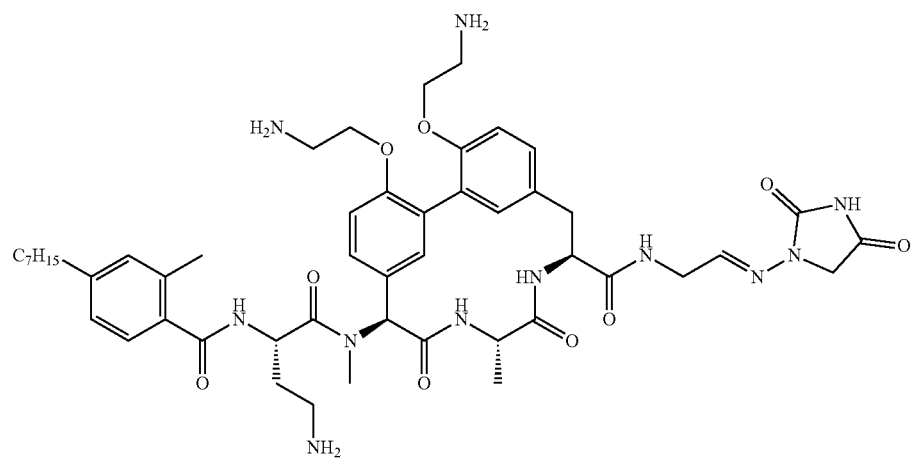 |

TABLE 1-continued
| Compound | Structure |
|---|---|
| 102 | 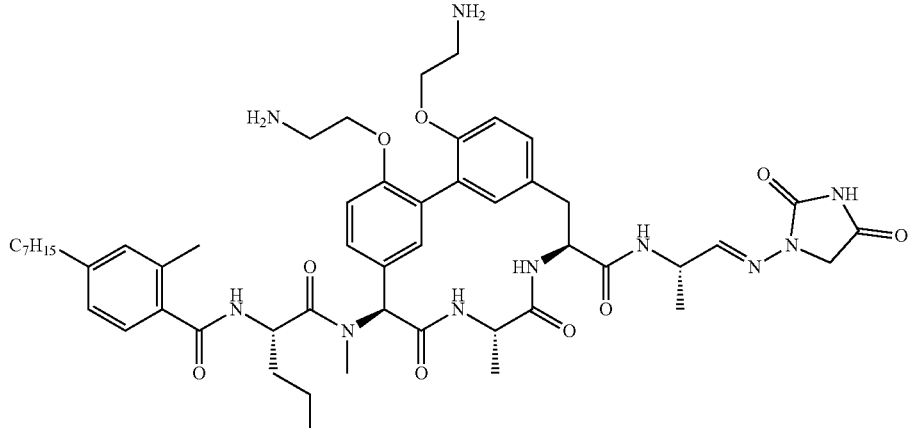 102 |
| 103 | 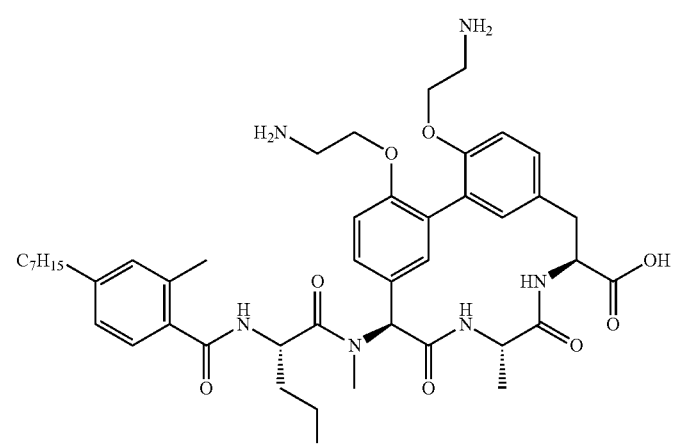 103 |
| 104 | 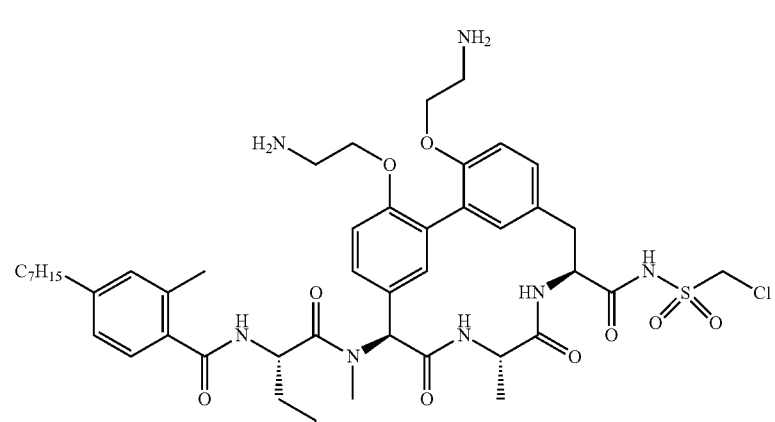 104 |

TABLE 1-continued
| Compound | Structure |
|---|---|
| 105 | 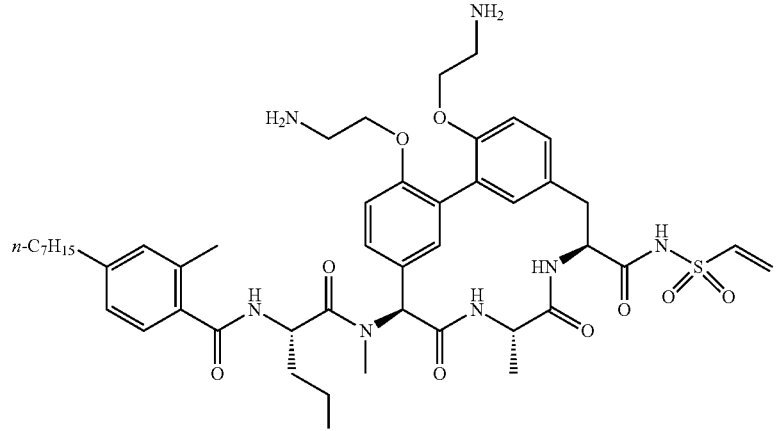 |
| 106 | 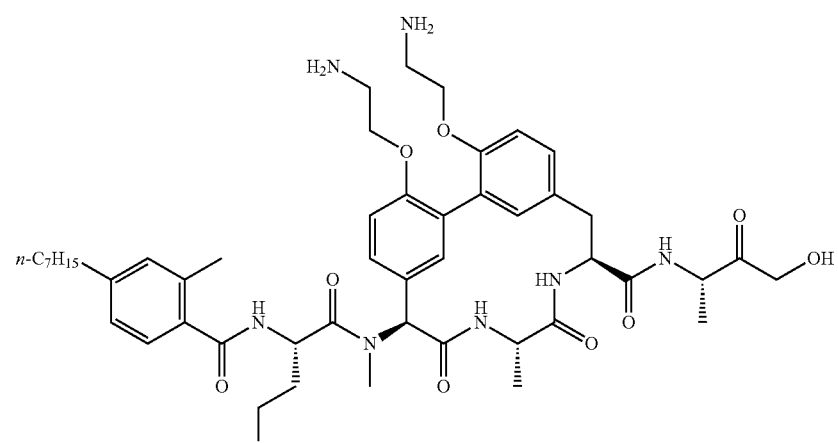 |
| 107 | 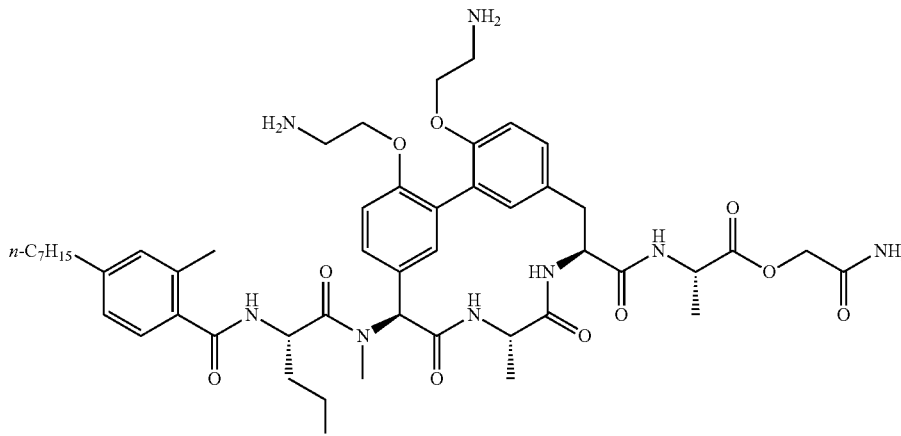 |

TABLE 1-continued
| Compound | Structure |
|---|---|
| 108 | 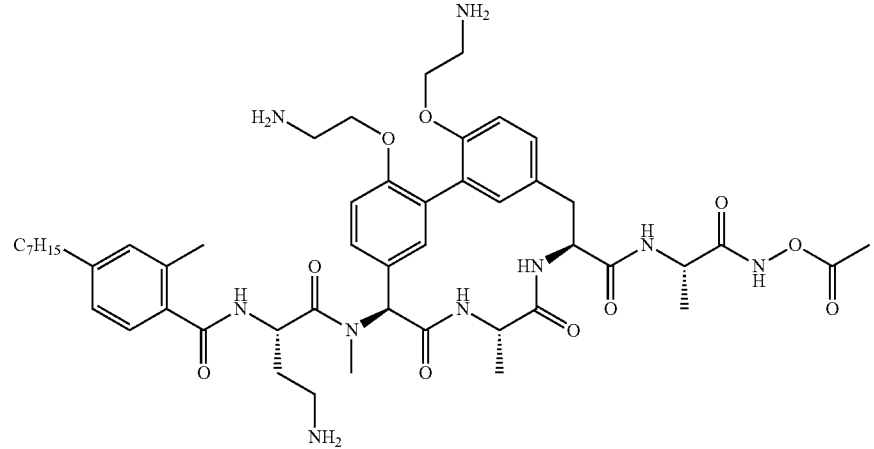<br>108 |
| 109 | 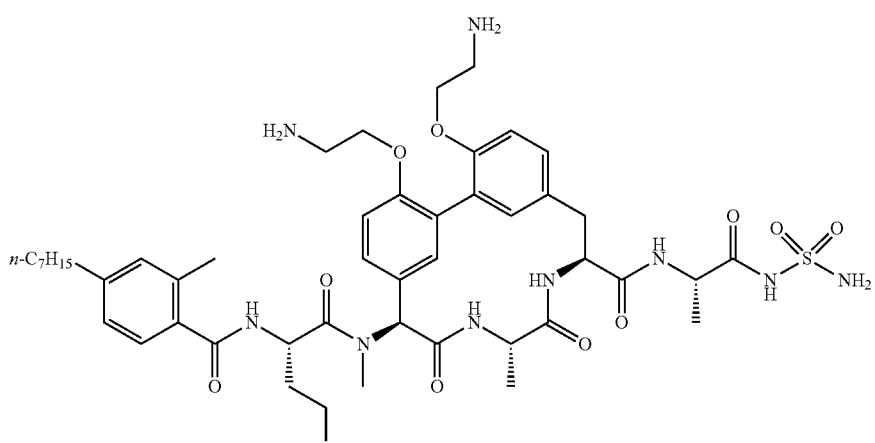<br>109 |
| 110 | 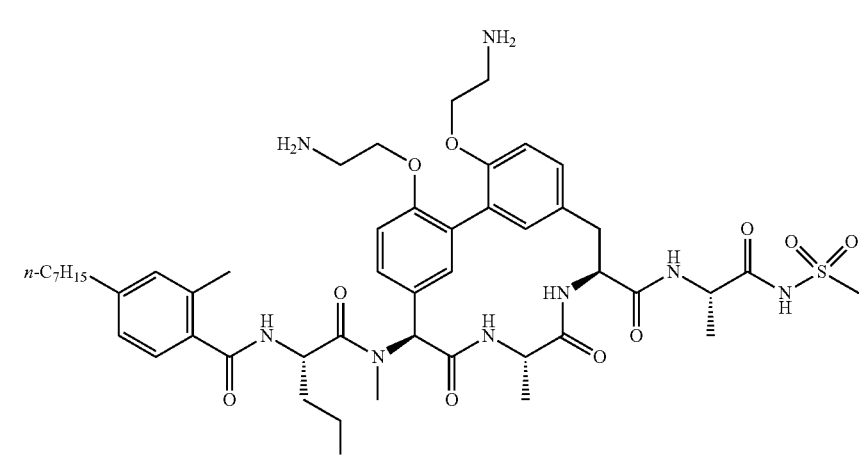<br>110 |

TABLE 1-continued

| Compound | Structure |
| --- | --- |
| 111 | 111 |
| 112 | 112 |
| 113 | 113 |

TABLE 1-continued
| Compound | Structure |
|---|---|
| 114 | 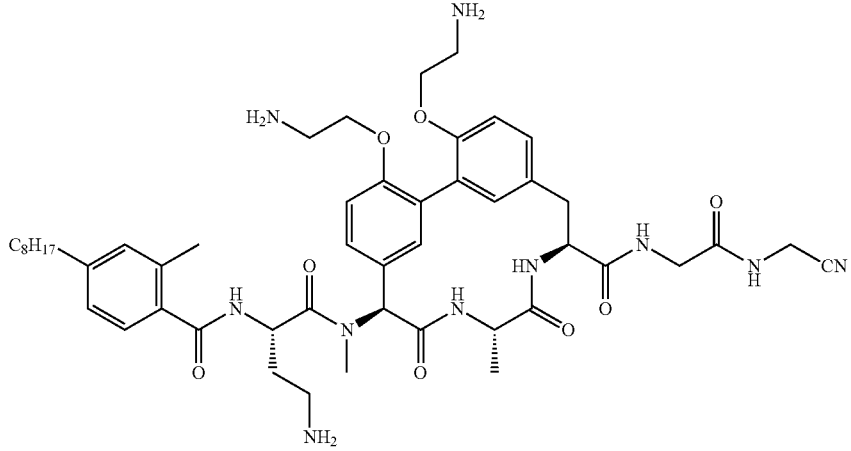<br>114 |
| 115 | 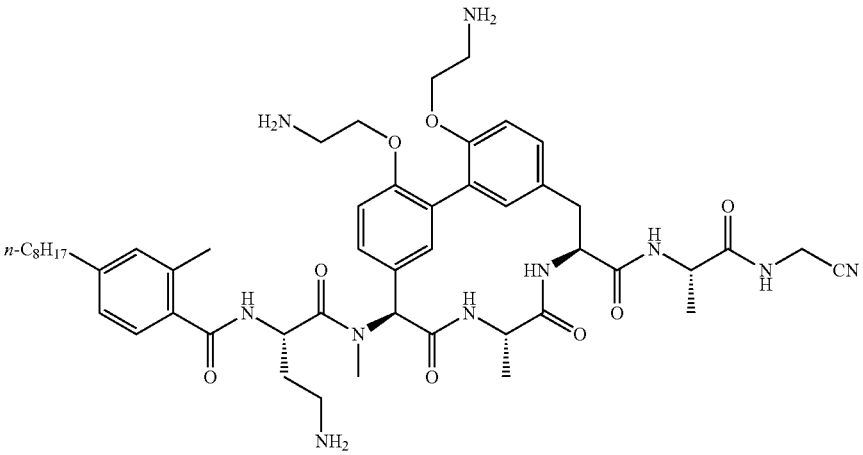<br>115 |
| 116 | 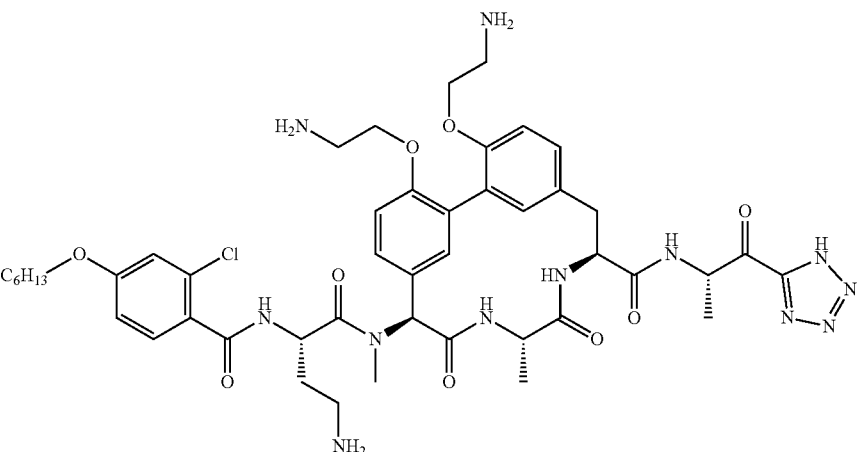<br>116 |

TABLE 1-continued
| Compound | Structure |
|---|---|
| 117 | 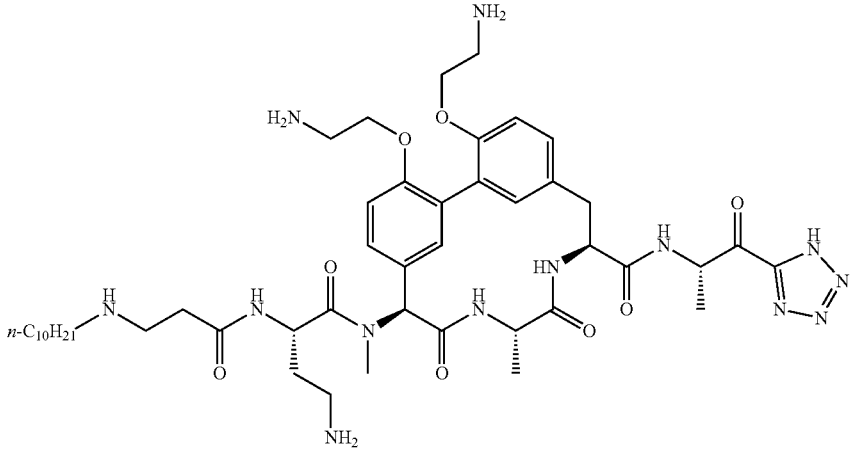 |
| 118 | 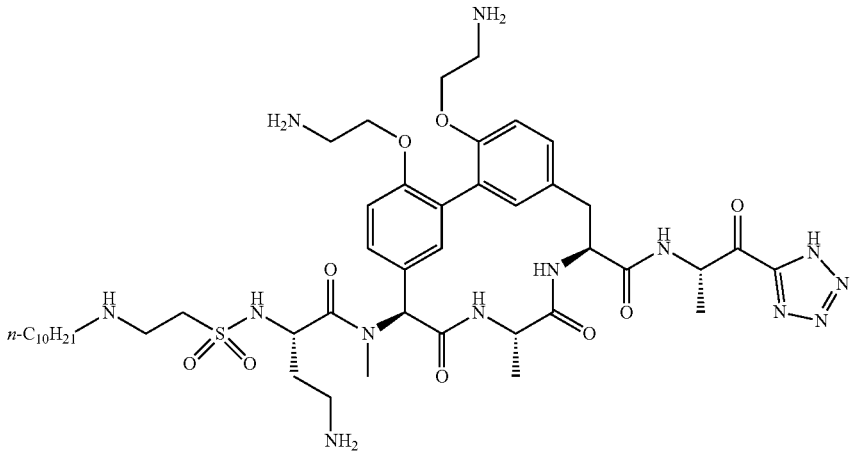 |
| 119 | 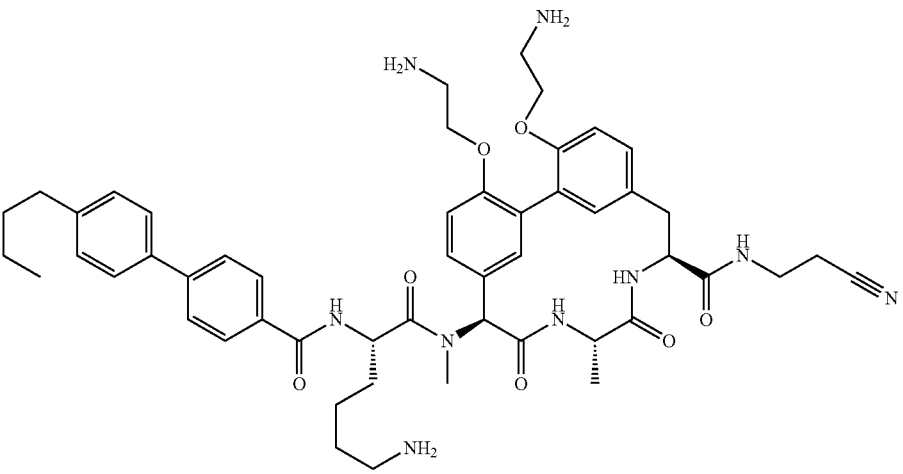 |

TABLE 1-continued
| Compound | Structure |
|---|---|
| 120 | 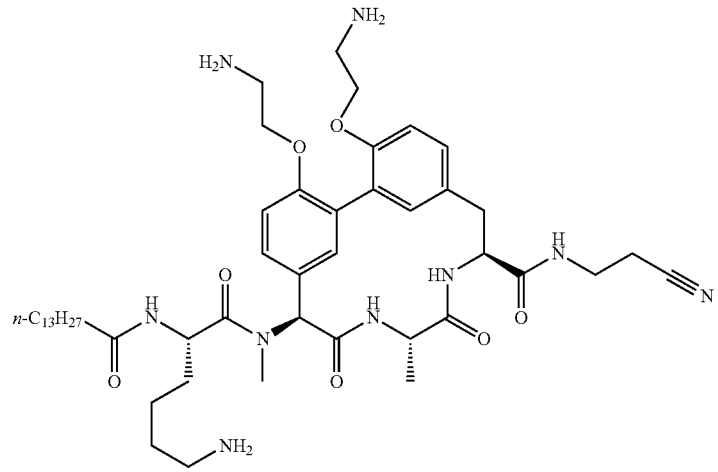 |
| 121 | 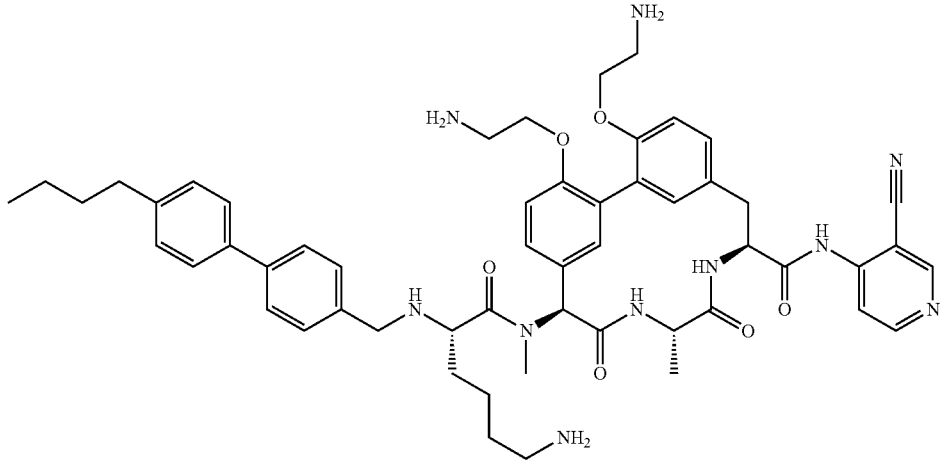 |
| 122 | 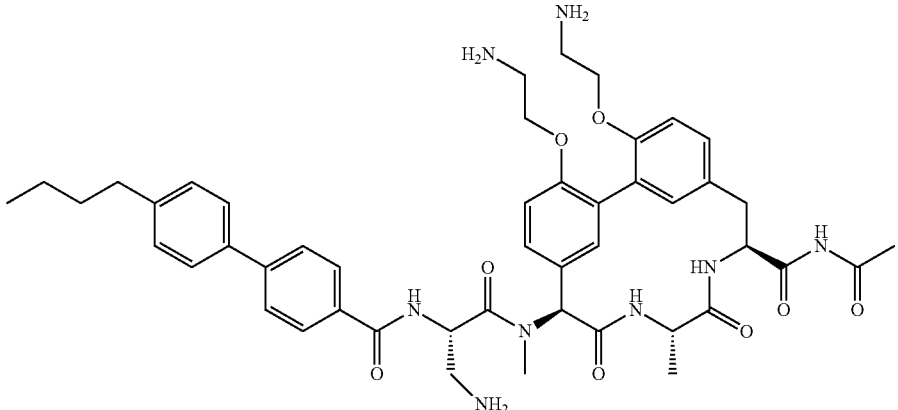 |

TABLE 1-continued
| Compound | Structure |
|---|---|
| 123 | 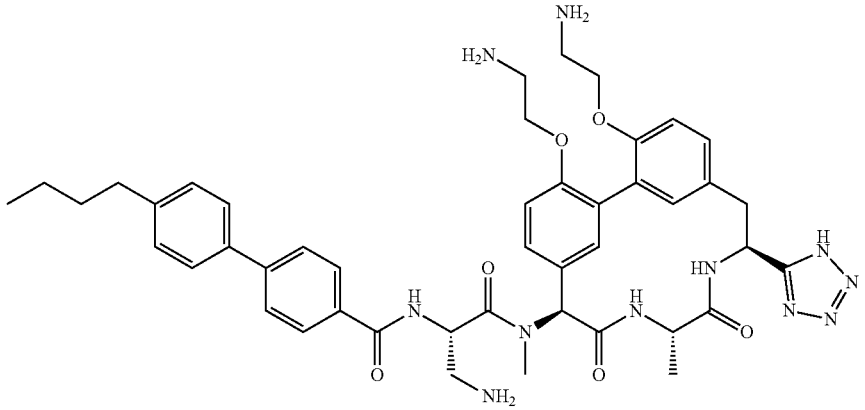 |
| 124 | 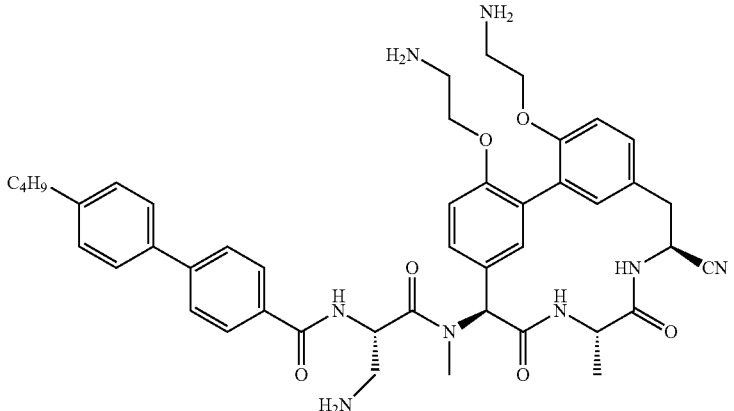 |
| 125 | 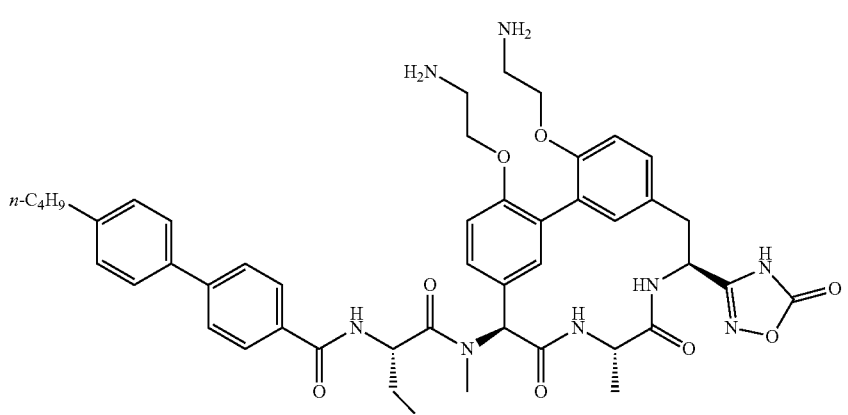 |

TABLE 1-continued
| Compound | Structure |
| --- | --- |
| 126 | 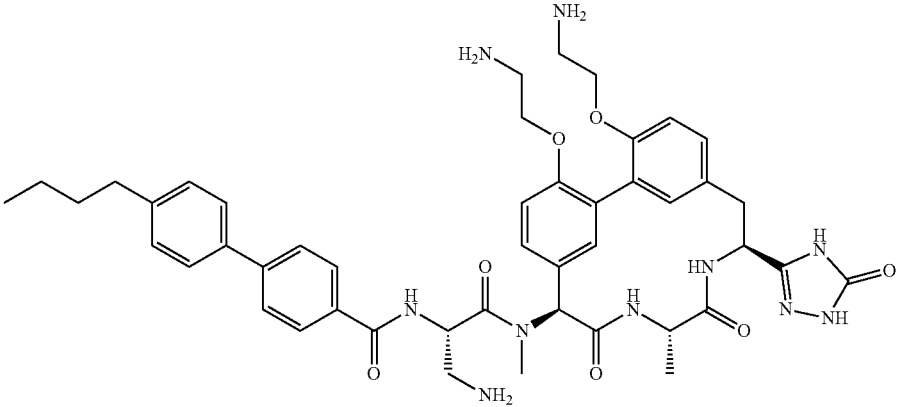 |
| 127 | 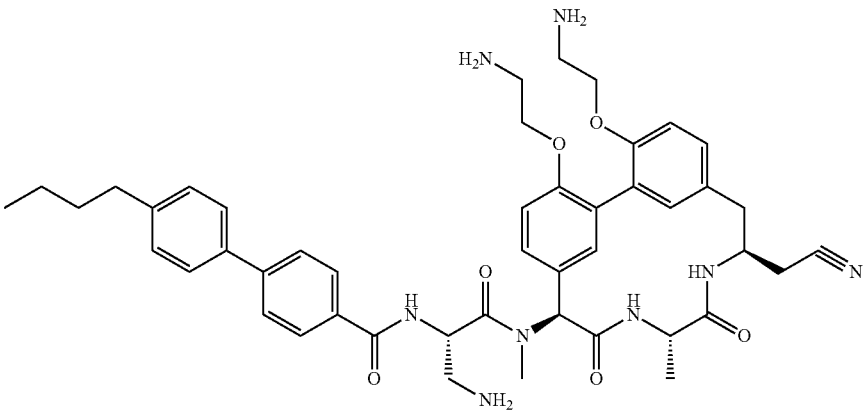 |
| 128 | 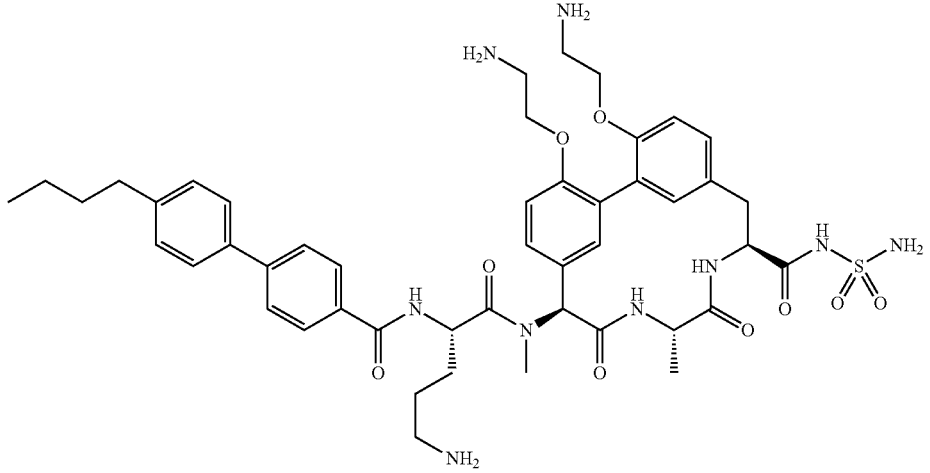 |

TABLE 1-continued
| Compound | Structure |
|---|---|
| 129 | 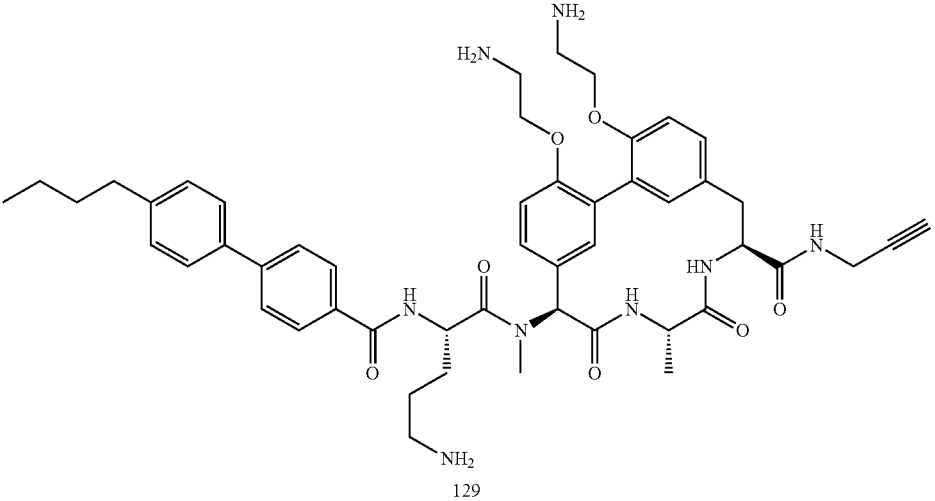 [SMILES: C#CCNC(=O)[C@@H]1Cc2ccc(OCCN)c(c2)-c2cc(ccc2OCCN)[C@H](N(C)C(=O)[C@H](CCCN)NC(=O)c2ccc(-c3ccc(CCCC)cc3)cc2)C(=O)N[C@@H](C)C(=O)N1] |
| 130 | 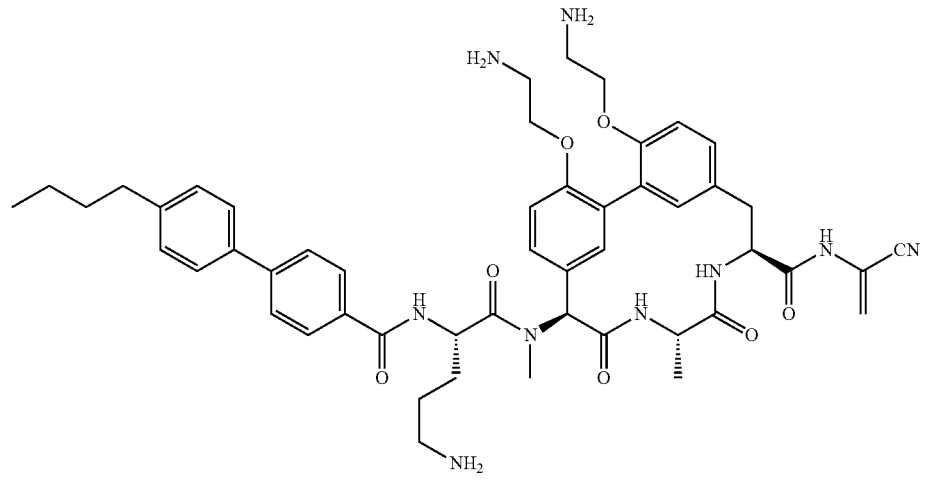 |
| 131 | 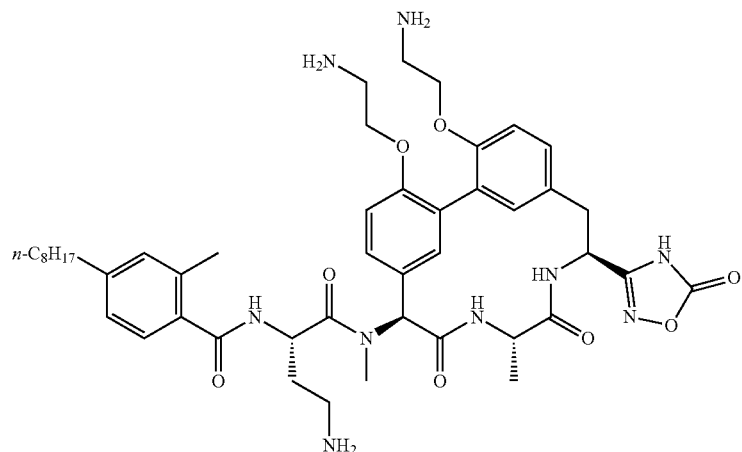 |

TABLE 1-continued
| Compound | Structure |
|---|---|
| 132 | 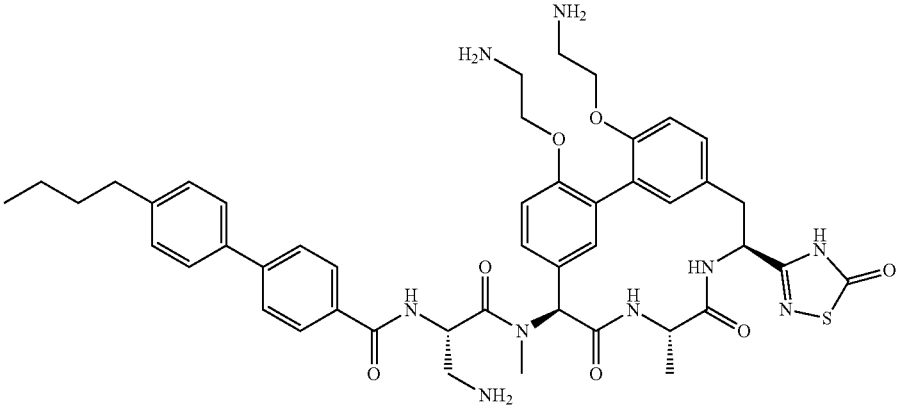 |
| 133 | 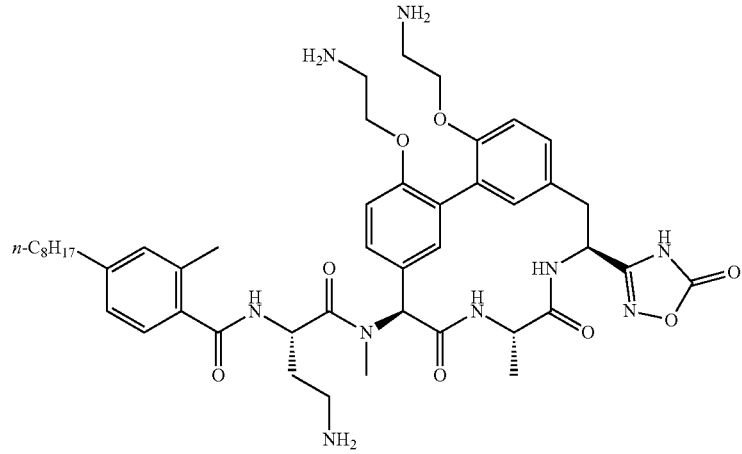 |
| 134 | 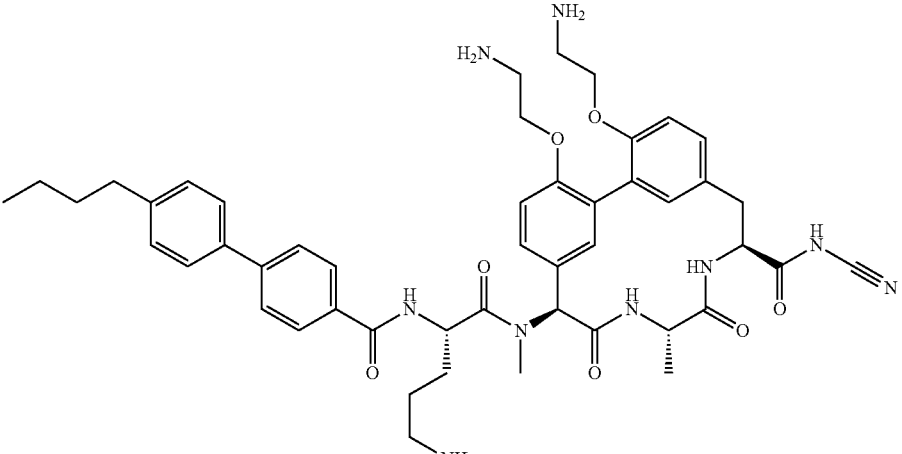 |

TABLE 1-continued

| Compound | Structure |
| --- | --- |
| 135 | 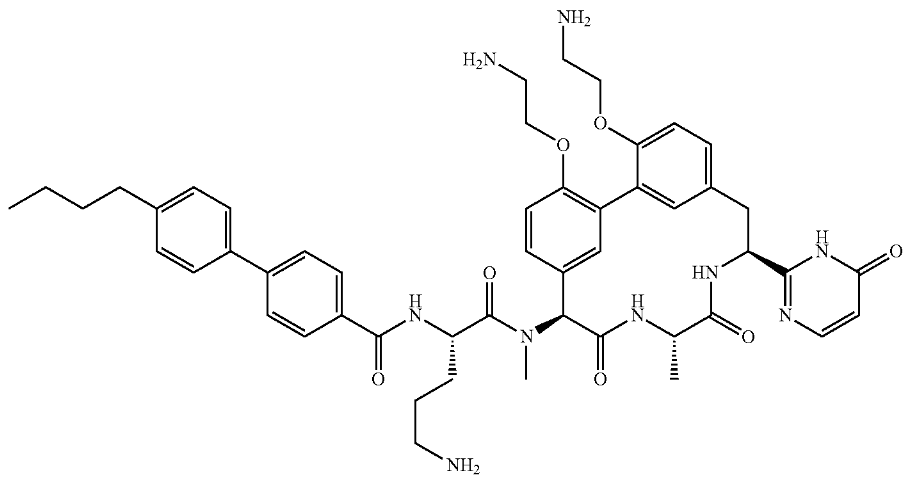 |
| 136 | 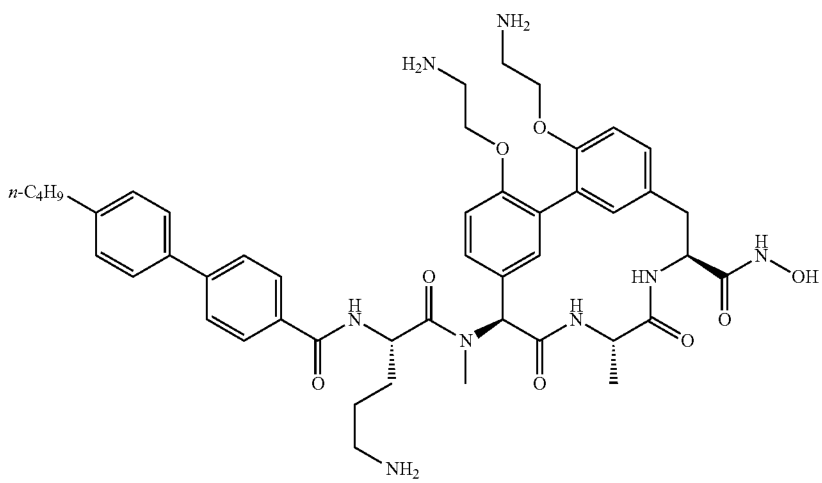 |
| 137 | 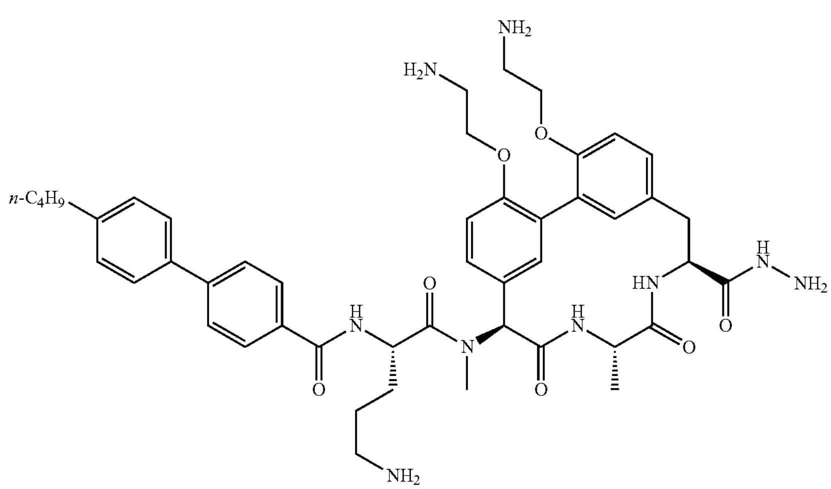 |

TABLE 1-continued
| Compound | Structure |
|---|---|
| 138 | 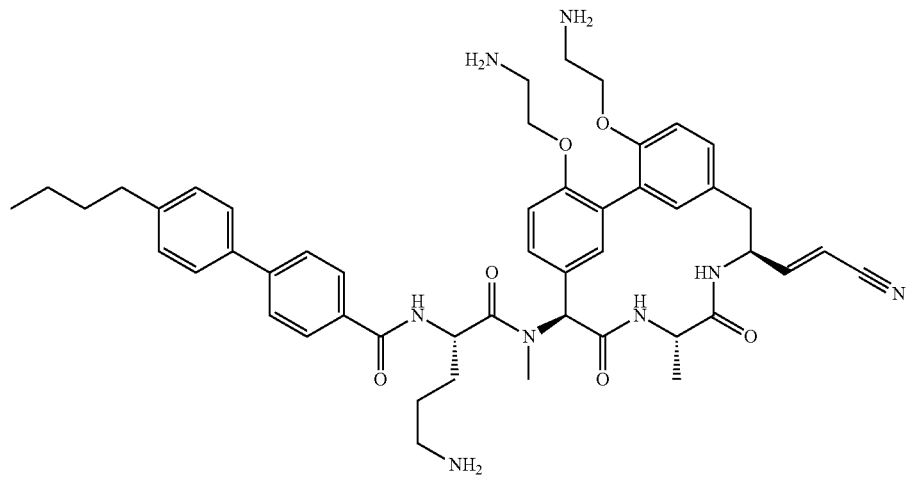 |
| 139 | 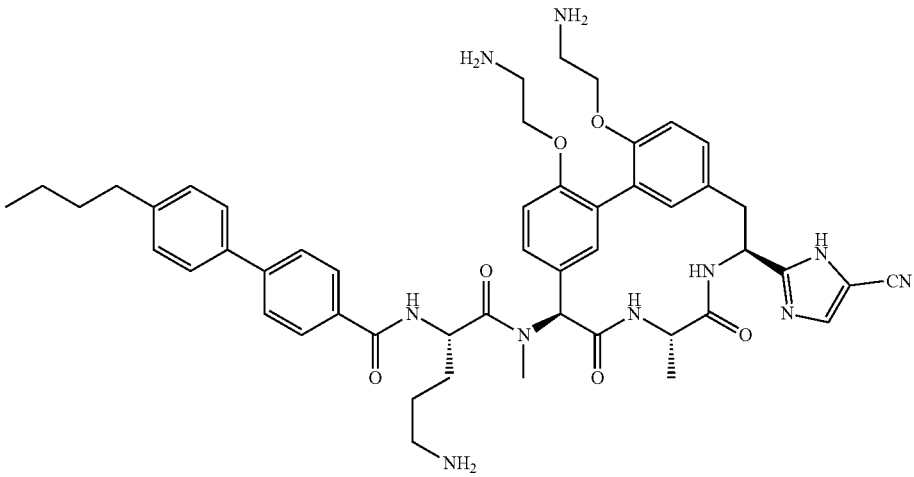 |
| 140 | 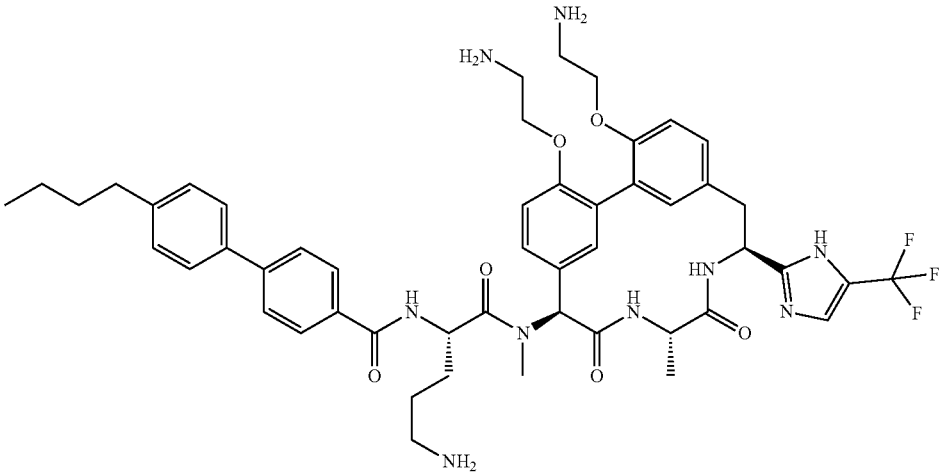 |

TABLE 1-continued
| Compound | Structure |
|---|---|
| 141 | 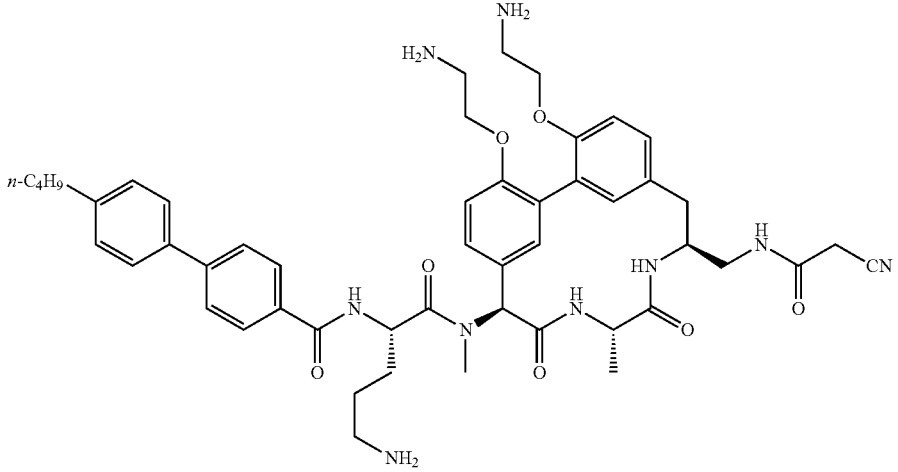<br>141 |
| 142 | 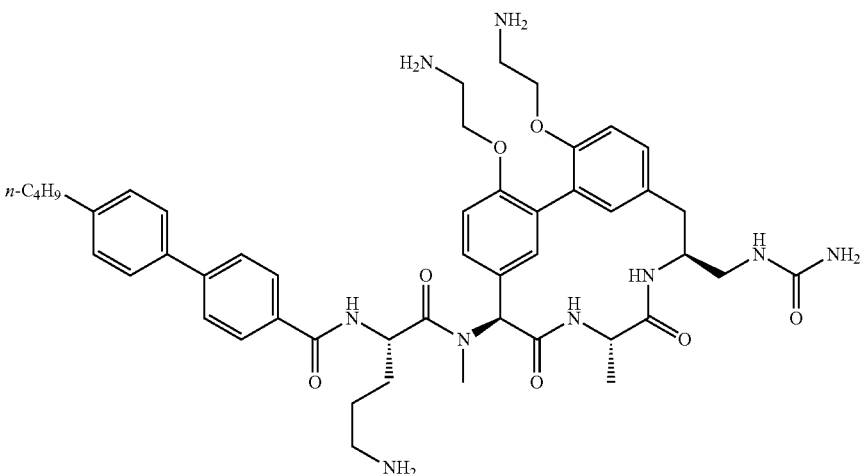<br>142 |
| 143 | 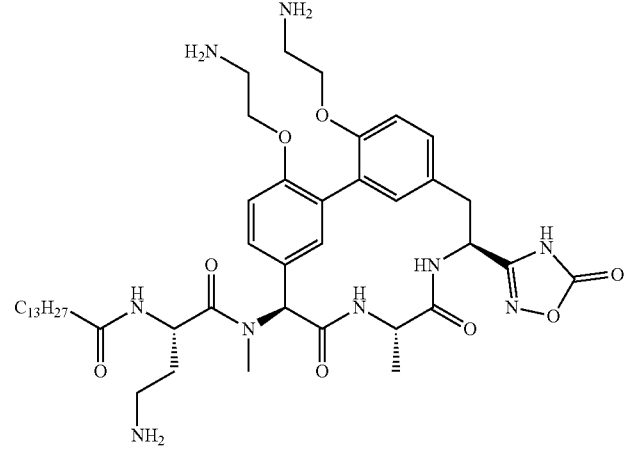<br>143 |

TABLE 1-continued

| Compound | Structure |
| --- | --- |
| 144 | 144 |
| 145 | 145 |
| 146 | 146 |

TABLE 1-continued
| Compound | Structure |
|---|---|
| 147 | 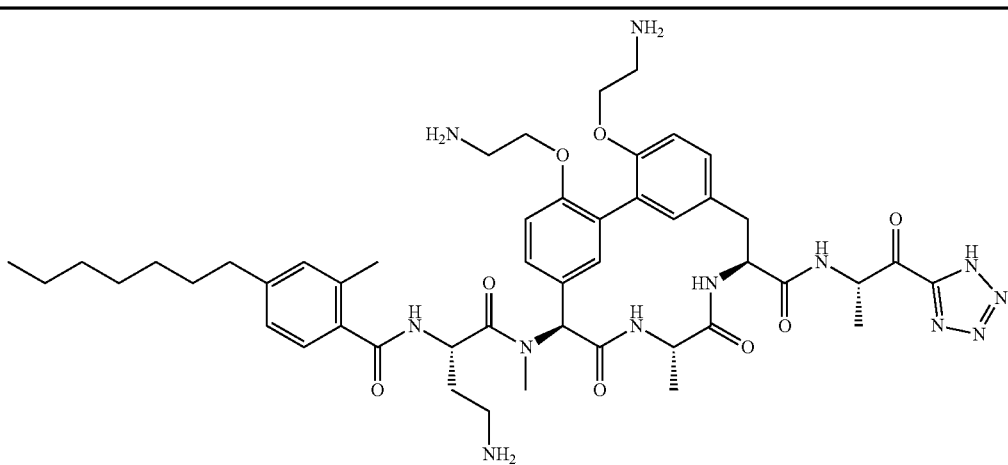 |
| 148 | 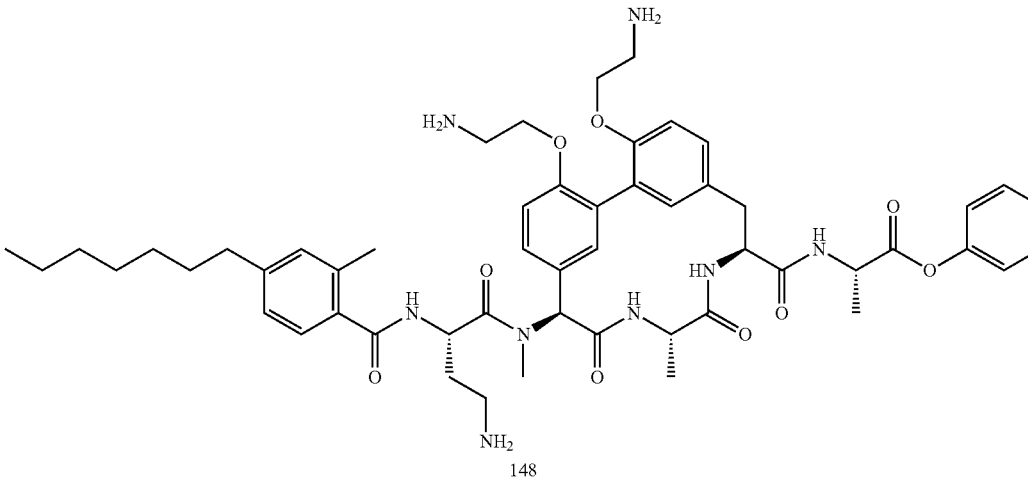 |
| 149 | 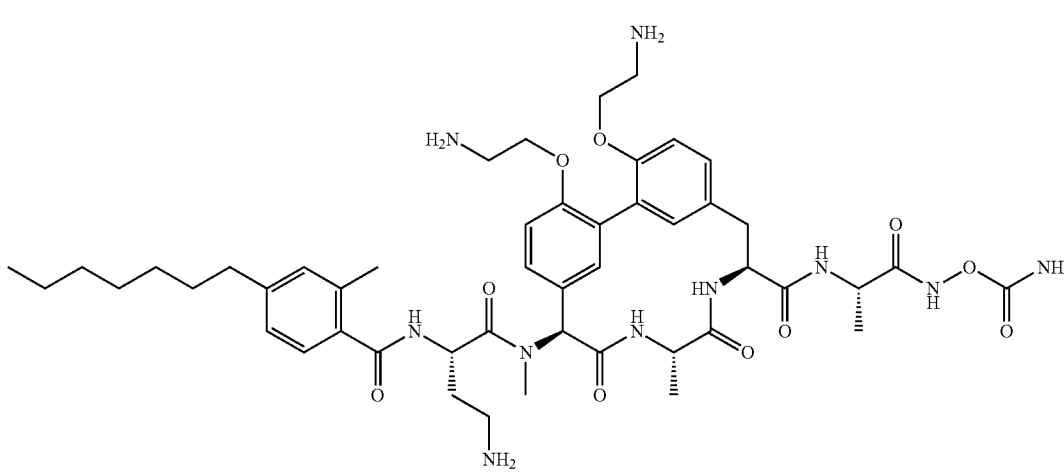 |

TABLE 1-continued

| Compound | Structure |
|---|---|
| 150 | 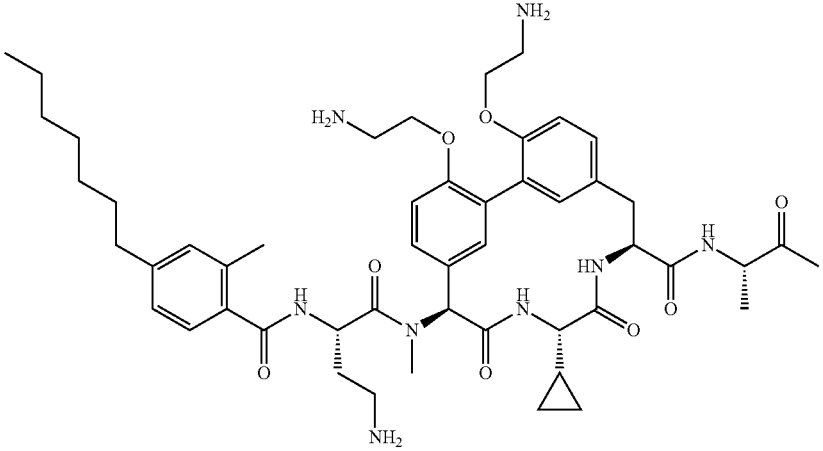 [SMILES: CCCCCCCc1ccc(C(=O)N[C@@H](CCN)C(=O)N(C)[C@@H]2C(=O)N[C@@H](C3CC3)C(=O)N[C@H](C(=O)N[C@@H](C)C(C)=O)Cc3ccc(OCCN)c(c3)-c3cc2ccc3OCCN)c(C)c1] |
| 151 | 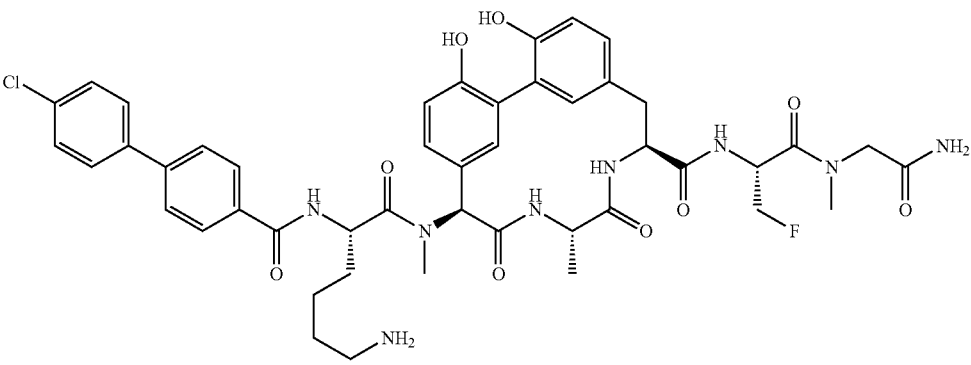 [SMILES: C[C@@H]1NC(=O)[C@@H](N(C)C(=O)[C@H](CCCCN)NC(=O)c2ccc(-c3ccc(Cl)cc3)cc2)c2ccc(O)c(c2)-c2cc(ccc2O)C[C@@H](C(=O)N[C@@H](CF)C(=O)N(C)CC(N)=O)NC1=O] |

In another aspect are hydrates or metabolites comprising any of the aforementioned compounds.

In another aspect are pharmaceutical compositions comprising any of the aforementioned compounds together with a pharmaceutically acceptable excipient.

In another aspect described herein is the use of a compound described herein in the manufacture of a medicament for treatment of a bacterial infection in a patient.

In another aspect are methods of treating a mammal in need of such treatment comprising administering to the mammal an antibacterial effective amount of any of the aforementioned compounds at a frequency and for a duration sufficient to provide a beneficial effect to the mammal. In one embodiment, the mammal has a bacteria-related infection that is resistant to treatment with arylomycin A2. In a further embodiment, the causative bacteria species of the bacteria infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus*. In another embodiment the bacterial infection is an infection involving a Gram-negative bacteria. In a further embodiment, the bacterial infection is an infection involving a Gram-positive bacteria.

In a further embodiment are methods of treating a mammal in need of such treatment comprising administering to the mammal a second therapeutic agent to any of the aforementioned methods of treatment. In another embodiment, the second therapeutic agent is a not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

In some embodiments is a method for treating a bacterial infection in a patient, preferably a human, where the treatment includes administering a therapeutically or pharmacologically effective amount of a combination of 1) a β-lactam antibiotic; and 2) a compound of Formula (I), (Ia), (Ib), (Ic), (Id), or (II), or a pharmaceutically acceptable salt thereof; and 3) a pharmaceutically acceptable carrier. In embodiments where a β-lactam antibiotic is used in combination with a compound of Formula (I), (Ia), (Ib), (Ic), (Id), or (II), the β-lactam antibiotic may be a carbapenem, cephalosporin, cephamycin, monobactam or penicillin. Exemplary carbapenem antibiotics useful in the methods of the invention include ertapenem, imipenem, biapenem, and meropenem. Exemplary cephalosporin antibiotics useful in the methods of the invention include, ceftobiprole, ceftaroline, Cefiprome, Cefozopran, cefepime, Cefotaxime, and ceftriazone. Exemplary penicillin antibiotics useful in the methods of the invention include ampicillin, amoxacillin, piperacillin, oxacillin, cloxacillin, methicillin, and nafcillin. In some embodiments of the invention, the β-lactam may be administered with a β-lactamase inhibitor. In some embodiments of the invention, the carbapenem may be administered with a DHP inhibitor, e.g., cilastatin.

In various embodiments of the invention where a compound of Formula (I), (Ia), (Ib), (Ic), (Id), or (II) and a β-lactam antibiotic are used in combination, the β-lactam antibiotic and compound of Formula (I), (Ia), (Ib), (Ic), (Id), or (II) are administered sequentially or concurrently. Preferably, the β-lactam antibiotic and compound of Formula (I), (Ia), (Ib), (Ic), (Id), or (II) are administered together. When administered concurrently, the β-lactam antibiotic and compound of Formula (I), (Ia), (Ib), (Ic), (Id), or (II) may be administered in the same formulation or in separate formulations. When administered sequentially, either the β-lactam or compound of Formula (I), (Ia), (Ib), (Ic), (Id), or (II) may be administered first. After administration of the first compound, the other compound is administered, for example, within from 1 to 60 minutes, e.g., within 1, 2, 3, 4, 5, 10, 15, 30, or 60 minutes. In one aspect of the invention, when a β-lactamase inhibitor is used, it may be administered separately, or in a formulation with the compound of Formula (I), (Ia), (Ib), (Ic), (Id), or (II) and/or β-lactam antibiotic. In one aspect of the invention, when a DHP inhibitor is used to improve the stability of a carbapenem, it may be administered separately, or in a formulation with the compound of Formula (I), (Ia), (Ib), (Ic), (Id), or (II) and/or carbapenem.

Further described herein are pharmaceutical compositions comprising a compound of Formula (I), (Ia), (Ib), (Ic), (Id), or (II), a pharmaceutically acceptable carrier, and optionally a β-lactam antibiotic. In embodiments where a combination is used, the β-lactam antibiotic and the compound of Formula (I), (Ia), (Ib), (Ic), (Id), or (II), are present in such amounts that their combination constitutes a therapeutically effective amount. Due to the potentiating effects of the compound of Formula (I), (Ia), (Ib), (Ic), (Id), or (II), the amount of β-lactam antibiotic present in a combination may be less that of a β-lactam antibiotic used alone. In certain embodiments, the composition further comprises a β-lactamase antibiotic.

In further embodiments where the β-lactam antibiotic is a carbapenem, is provided a pharmaceutical composition comprising a carbapenem antibiotic, a DHP inhibitor, a compound of Formula (I), (Ia), (Ib), (Ic), (Id), or (II), and a pharmaceutically acceptable carrier. In some embodiments where the β-lactara antibiotic is a carbepenem, the carbapenem antibiotic is preferably selected from the group consisting of ertapenem, imipenem, and meropenem. In some embodiments is a compound of Formula (I), (Ia), (Ib), (Ic), (Id), or (II) for use in treating a bacterial infection. In some embodiments is a compound of Formula (I), (Ia), (Ib), (Ic), (Id), or (II), in combination with one or more additional therapeutical agents including a β-lactam antibiotic, for use in treating a bacterial infection. In some embodiments is a compound of Formula (I), (Ia), (Ib), (Ic), (Id), or (II) for use as a medicament for treating a bacterial infection. In some embodiments is a compound of Formula (I), (Ia), (Ib), (Ic), (Id), or (II), in combination with one or more additional therapeutical agents including a β-lactam antibiotic, for use as a medicament for treating a bacterial infection. In some embodiments is a compound of Formula (I), (Ia), (Ib), (Ic), (Id), or (II) for use in the preparation of a medicament for treating a bacterial infection. In some embodiments is a compound of Formula (I), (Ia), (Ib), (Ic), (Id), or (II), in combination with one or more additional therapeutical agents including a β-lactam antibiotic, for use in the preparation of a medicament for treating a bacterial infection.

In some embodiments described herein, a compound of Formula (I), (Ia), (Ib), (Ic), (Id), or (II) can enhance the activity of a β-lactam antibacterial agent by inducing susceptibility to the antibacterial agent in a drug-resistant strain such as MRSA. In some embodiments, a compound of Formula (I), (Ia), (Ib), (Ic), (Id), or (II) can enhance the activity of a β-lactam antibacterial agent by reducing the dosage of the antibacterial agent need for a therapeutic effect in a drug-sensitive strain. For example, if a compound of Formula (I), (Ia), (Ib), (Ic), (Id), or (II) reduces the Minimum Inhibitory Concentration (MIC) of an antibacterial agent (where the MIC is the minimum concentration of antibacterial agent which will completely inhibit growth) in a susceptible strain, then such treatment may be advantageous to enable a reduction in the amount of antibacterial agent administered (could reduce side effects of an antibiotic), or to decrease the frequency of administration. In some embodiments, compounds of Formula (I), (Ia), (Ib), (Ic), (Id), or (II) can enhance the activity of an antibacterial agent such as a carbapenem to prevent the emergence of a resistant sub-population in a heterogeneous bacterial population with a resistant sub-population.

Potentiators can be used to enhance the activity of antibacterial agents whose clinical efficacy has been limited by the increasing prevalence of resistant strains. In some embodiments described herein, a compound of Formula (I), (Ia), (Ib), (Ic), (Id), or (II) is used as a potentiator wherein a compound of Formula (I), (Ia), (Ib), (Ic), (Id), or (II) can be administered together with a β-lactam antibiotic (either concurrently or sequentially) to allow effective treatment of an infection involving a resistant bacterium, or to reduce the amount of antibacterial agent necessary to treat an infection.

In one embodiment, is a compound described herein which displays antibiotic activity useful in the treatment of bacterial infections, such as by way of example only, various strains of S. aureus, S. pneumoniae, E. faecalis, E. faecium, B. subtilis and E. coli including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

Methicillin-Resistant *Staphylococcus aureus*

*Staphylococcus aureus* (*S. aureus*), a spherical bacterium, is the most common cause of staph infections. *S. aureus* has been known to cause a range of illnesses from minor skin infections, such as pimples, impetigo, boils, cellulitis folliculitis, furuncles, carbuncles, scalded skin syndrome, abscesses, to life-threatening diseases such as pneumonia, meningitis, osteomyelitis endocarditis, toxic shock syndrome, and septicemia. Further, *S. aureus* is one of the most common causes of nosocomial infections, often causing postsurgical wound infections.

Methicillin was introduced in the late 1950s to treat infections caused by penicillin-resistant *S. aureus*. It has been reported previously that *S. aureus* isolates had acquired resistance to methicillin (methicillin-resistant *S. aureus*, MRSA). The methicillin resistance gene (mecA) encodes a methicillin-resistant penicillin-binding protein that is not present in susceptible strains. mecA is carried on a mobile genetic element, the staphylococcal cassette chromosome mec (SCCmec), of which four forms have been described that differ in size and genetic composition. The methicillin-resistant penicillin-binding protein allows for resistance to β-lactam antibiotics and obviates their clinical use during MRSA infections.

In one aspect is a method for treating a subject having a resistant bacterium comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof. In one embodiment, the bacterium is a Gram-positive bacteria. In another embodiment, the Gram-positive bacterium is *S. aureus*. In further embodiment, the *S. aureus* is resistant or refractory to a beta-lactam antibiotic. In yet a further embodiment, the beta-lactam antibiotic belongs to the class of penicillins. In a further embodiment, the beta-lactam antibiotic is methicillin. In yet another embodiment, the subject has a methicillin-resistant *S. aureus* bacteria. In one embodiment the beta-lactam antibiotic is flucloxacillin. In another embodiment is a method for treating a subject having a dicloxacillin-resistant bacteria comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the subject is refractory to dicloxacillin. Also disclosed herein is a method for treating a subject having a methicillin-resistant bacteria comprising administering a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the subject has been determined to have a methicillin-resistant bacteria. In one embodiment the subject is screened for methicillin-resistant bacteria. In another embodiment, the subject screening is performed through a nasal culture. In a further embodiment the methicillin-resistant bacteria is detected by swabbing the nostril(s) of the subject and isolating the bacteria. In another embodiment, Real-time PCR and/or Quantitative PCR is employed to determine whether the subject has a methicillin-resistant bacteria.

In one embodiment is a method for treating a subject having a first-generation cephalosporin-resistant bacteria comprising administering a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the subject is refractory to a first-generation cephalosporin. In one embodiment, the bacteria is resistant to a first-generation cephalosporin. In a further embodiment, the bacteria is resistant to cefacetrile. In another embodiment, the bacteria is resistant to cefadroxil. In yet another embodiment, the bacteria is resistant to cefalexin. In one embodiment, the bacteria is resistant to cefaloglycin. In another embodiment, the bacteria is resistant to cefalonium. In another embodiment, the bacteria is resistant to cefaloridine. In yet another embodiment, the bacteria is resistant to cefalotin. In a further embodiment, the bacteria is resistant to cefapirin. In yet a further embodiment, the bacteria is resistant to cefatrizine. In one embodiment, the bacteria is resistant to cefazaflur. In another embodiment, the bacteria is resistant to cefazedone. In yet another embodiment, the bacteria is resistant to cefazolin. In a further embodiment, the bacteria is resistant to cefradine. In yet a further embodiment, the bacteria is resistant to cefroxadine. In one embodiment, the bacteria is resistant to ceftezole.

In one embodiment is a method for treating a subject having a second-generation cephalosporin-resistant bacteria comprising administering a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the subject is refractory to a second-generation cephalosporin. In another embodiment, the bacteria is resistant to a second-generation cephalosporin. In a further embodiment, the bacteria is resistant to cefaclor. In another embodiment, the bacteria is resistant to cefonicid. In yet another embodiment, the bacteria is resistant to cefprozil. In one embodiment, the bacteria is resistant to cefuroxime. In another embodiment, the bacteria is resistant to cefuzonam. In another embodiment, the bacteria is resistant to cefmetazole. In yet another embodiment, the bacteria is resistant to cefotetan. In a further embodiment, the bacteria is resistant to cefoxitin.

In one embodiment is a method for treating a subject having a third-generation cephalosporin-resistant bacteria comprising administering a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the subject is refractory to a third-generation cephalosporin. In another embodiment, the bacteria is resistant to a third-generation cephalosporin. In a further embodiment, the bacteria is resistant to cefcapene. In another embodiment, the bacteria is resistant to cefdaloxime. In yet another embodiment, the bacteria is resistant to cefdinir. In one embodiment, the bacteria is resistant to cefditoren. In another embodiment, the bacteria is resistant to cefixime. In another embodiment, the bacteria is resistant to cefmenoxime. In yet another embodiment, the bacteria is resistant to cefodizime. In a further embodiment, the bacteria is resistant to cefotaxime. In yet a further embodiment, the bacteria is resistant to cefpimizole. In one embodiment, the bacteria is resistant to cefpodoxime. In another embodiment, the bacteria is resistant to cefteram. In yet another embodiment, the bacteria is resistant to ceftibuten. In a further embodiment, the bacteria is resistant to ceftiofur. In yet a further embodiment, the bacteria is resistant to ceftiolene. In one embodiment, the bacteria is resistant to ceftizoxime. In another embodiment, the bacteria is resistant to ceftriaxone. In yet another embodiment, the bacteria is resistant to cefoperazone. In yet a further embodiment, the bacteria is resistant to ceftazidime.

In one embodiment is a method for treating a subject having a fourth-generation cephalosporin-resistant bacteria comprising administering a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the subject is refractory to a fourth-generation cephalosporin. In another embodiment, the bacteria is resistant to a fourth-generation cephalosporin. In a further embodiment, the bacteria is resistant to cefclidine. In another embodiment, the bacteria is resistant to cefepime. In yet another embodiment, the bacteria is resistant to cefluprenam. In one embodiment, the bacteria is resistant to cefoselis. In another embodiment, the bacteria is resistant to cefozopran. In another embodiment, the bacteria is resistant to cefpirome. In yet another embodiment, the bacteria is refractory to cefquinome.

In one embodiment is a method for treating a subject having a carbapenem-resistant bacteria comprising administering a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the subject is refractory to a carbapenem. In another embodiment, the bacteria is resistant to a carbapenem. In a further embodiment, the bacteria is resistant to imipenem. In another embodiment, the bacteria is resistant to meropenem. In yet another embodiment, the bacteria is resistant to ertapenem. In one embodiment, the bacteria is resistant to faropenem. In another embodiment, the bacteria is resistant to doripenem. In another embodiment, the bacteria is resistant to panipenem. In yet another embodiment, the bacteria is resistant to biapenem, Vancomycin-Intermediate and Vancomycin-Resistant *Staphylococcus aureus*

Vancomycin-intermediate *Staphylococcus aureus* and vancomycin-resistant *Staphylococcus aureus* are specific types of antimicrobial-resistant Staph bacteria that are refractory to vancomycin treatment. *S. aureus* isolates for which vancomycin MICS are 4-8 µg/mL are classified as vancomycin-intermediate and isolates for which vancomycin MICS are ≥16 µg/mL are classified as vancomycin-resistant (Clinical and Laboratory Standards Institute/NC-CLS. Performance Standards for Antimicrobial Susceptibility Testing. Sixteenth informational supplement. M100-S16. Wayne, Pa.: CLSI, 2006).

As used herein, the term "minimum inhibitory concentration" (MIC) refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic is determined from the tube with the lowest concentration that shows no turbidity (no growth).

In one aspect is a method of treating a subject having a bacterial infection comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the bacterial infection comprises a vancomycin-intermediate *Staphylococcus aureus* bacterium. In one embodiment, the vancomycin-intermediate *Staphylococcus aureus* bacterium has a MIC of between about 4 to about 8 □g/mL. In another embodiment, the vancomycin-intermediate *Staphylococcus aureus* bacterium has a MIC of about 4 □g/mL. In yet another embodiment, the vancomycin-intermediate *Staphylococcus aureus* bacterium has a MIC of about 5 µg/mL. In a further embodiment, the vancomycin-intermediate *Staphylococcus aureus* bacterium has a MIC of about 6 µg/mL. In yet a further embodiment, the vancomycin-intermediate *Staphylococcus aureus* bacterium has a MIC of about 7 µg/mL. In one embodiment, the vancomycin-intermediate *Staphylococcus aureus* bacterium has a MIC of about 8 µg/mL.

In another aspect is a method of treating a subject having a bacterial infection comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the bacterial infection comprises a vancomycin-resistant *Staphylococcus aureus* bacterium. In one embodiment, the vancomycin-resistant *Staphylococcus aureus* bacterium has a MIC of between about 16 µg/mL. In another embodiment, the vancomycin-resistant *Staphylococcus aureus* bacterium has a MIC of about ≥16 µg/mL. In yet another embodiment, the vancomycin-resistant *Staphylococcus aureus* bacterium has a MIC of about 20 µg/mL. In a further embodiment, the vancomycin-resistant *Staphylococcus aureus* bacterium has a MIC of about 25 µg/mL.

In one embodiment, conditions treated by the compounds described herein include, but are not limited to, endocarditis, osteomyelitis, meningitis, skin and skin structure infections, genitourinary tract infections, abscesses, and necrotizing infections. In another embodiment, the compounds disclosed herein are used to treat conditions, such as, but not limited to, diabetic foot infections, decubitus ulcers, burn infections, animal or human bite wound infections, synergistic-necrotizing gangrene, necrotizing fasciitis, intra-abdominal infection associated with breeching of the intestinal barrier, pelvic infection associated with breeching of the intestinal barrier, aspiration pneumonia, and post-operative wound infections. In another embodiment, the conditions listed herein are caused by, contain, or result in the presence of VISA and/or VRSA.

Vancomycin-Resistant Enterococci

Enterococci are bacteria that are normally present in the human intestines and in the female genital tract and are often found in the environment. These bacteria sometimes cause infections. In some cases, enterococci have become resistant to vancomycin (also known as vancomycin-resistant enterococci or VRE.) Common forms of resistance to vancomycin occur in enterococcal strains that involve the acquisition of a set of genes encoding proteins that direct peptidoglycan precursors to incorporate D-Ala-D-Lac instead of D-Ala-D-Ala. The six different types of vancomycin resistance shown by *Enterococcus* are: Van-A, Van-B, Van-C, Van-D, Van-E and Van-F. In some cases, Van-A VRE is resistant to both vancomycin and teicoplanin, while in other cases, Van-B VRE is resistant to vancomycin but sensitive to teicoplanin; in further cases Van-C is partly resistant to vancomycin, and sensitive to teicoplanin.

In one aspect, is a method of treating a subject having a vancomycin-resistant enterococci comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the enterococci has developed resistance to vancomycin. In one embodiment, the subject has been previously treated with vancomycin for a sustained period of time. In another embodiment, the subject has been hospitalized. In yet another embodiment, the subject has a weakened immune system such as patients in Intensive Care Units or in cancer or transplant wards. In a further embodiment, the subject has undergone surgical procedures such as, for example, abdominal or chest surgery. In yet a further embodiment, the subject has been colonized with VRE. In one embodiment, the subject has a medical device such that an infection has developed. In another embodiment, the medical device is a urinary catheter or central intravenous (IV) catheter.

In another embodiment, is a method of treating a subject having a vancomycin-resistant enterococci comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the *Enterococcus* has Van-A resistance.

In another embodiment, is a method of treating a subject having a vancomycin-resistant enterococci comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the *Enterococcus* has Van-B resistance.

In another embodiment, is a method of treating a subject having a vancomycin-resistant enterococci comprising administering to the subject a compound of Formula (I), (Ia), (Ib), (Ic), (Id), or (II) or a pharmaceutically acceptable salt, ester, solvate, alkylated quaternary ammonium salt, stereoisomer, tautomer or prodrug thereof wherein the *Enterococcus* has Van-C resistance.

Administration and Pharmaceutical Composition

Pharmaceutical compositions described herein comprise a therapeutically effective amount of a compound described herein (i.e., a compound of any of Formula (I), (Ia), (Ib), (Ic), (Id), or (II)) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This is optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound of any of Formula (I), (Ia), (Ib), (Ic), (Id), or (II)) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprise buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of a aerosol particles having with a mass medium average diameter predominantly between 1 to 5□. Further, the formulation preferably has balanced osmolarity ionic strength and chloride concentration, and the smallest aerosolizable volume able to deliver effective dose of the compounds described herein compound described herein (i.e., a compound of any of Formula (I), (Ia), (Ib), (Ic), (Id), or (II)) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

In some embodiments, compounds described herein compound described herein (i.e., a compound of any of Formula (I), (Ia), (Ib), (Ic), (Id), or (II)) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors known in the medical arts.

The total daily dose of the compounds described herein compound described herein (i.e., a compound of any of Formula (I), (Ia), (Ib), (Ic), (Id), or (II)) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound(s) described herein per day in single or multiple doses.

EXAMPLES

Compounds disclosed herein are made by the methods depicted in the reaction schemes shown below. Procedures are provided herein that, in combination with the knowledge of the synthetic organic chemist of ordinary skill in the art, are in some embodiments used to prepare the full range of compounds as disclosed and claimed herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds disclosed herein are in some embodiments synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data. Compounds are typically isolated as formic acid salts by reverse phase HPLC using AcCN/H$_2$O with formic acid as an additive. In some instances, purifications are conducted without formic acid, and the compounds are isolated as the free base.

The method of LCMS analysis is as follows: LCMS (Method 5-95 AB, ESI): ESI, 5% AcCN/H$_2$O, 0.7 min; to 95% AcCN/H$_2$O, 0.4 min; 1.5 mL/min, Merck RP-18e, 2×25 mm.

Method CRL: Experiments performed on a Waters Acquity UPLC system linked to a ZQ Mass Spectrometer with a PDA UV detector. The spectrometer has an electrospray source operating in positive and negative ion mode. This system uses an Acquity BEH C18 1.7 um 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minutes before returning to 95% solvent A and 5% solvent B over the next 0.2 minutes. Total run time was 8 minutes.

Some abbreviations used herein are as follows:

DIPEA: diisopropylethylamine

DMAP: 4-dimethylaminopyridine

DMF: dimethylformamide

DCM: dichloromethane

TFA: trifluoroacetic acid

EDC: 1-ethyl-3-(3-dimethylaminopropyl)carbodiimide

HATU: O-(7-azabenzotriazol-1-yl)-N,N,N',N'-tetramethyluronium hexafluorophosphate HCTU: O-(6-Chlorobenzotriazol-1-yl)-N,N,N,N'-tetramethyluronium hexafluorophosphate HOBt: hydroxybenzotriazole pyBOP: (Benzotriazol-1-yloxy)tripyrrolidinophosphonium hexafluorophosphate DMDO: 3,3-Dimethyldioxirane DMP: Dess-Martin periodinane THF: tetrahydrofuran MeOH: methanol EtOAc: ethyl acetate Trt resin: 2-Chlorotrityl chloride resin Rink amide resin: Rink amide (aminomethyl)polystyrene Boc: t-butoxycarbonyl CBz: benzyloxycarbonyl Fmoc: [(9H-fluoren-9-yl)methoxy]carbonyl Teoc: Trimethylsilylethoxycarbonyl CDI: 1,1'-Carbonyldiimidazole HFIP: 1,1,1,3,3,3-hexafluoropropan-2-ol TLC: thin-layer chromatography Example 1: Synthesis of (S)-methyl 2-amino-3-(4-methoxy-3-(4,4,5,5-tetramethyl-1,3,2-dioxaborolan-2-yl)phenyl)propanoate

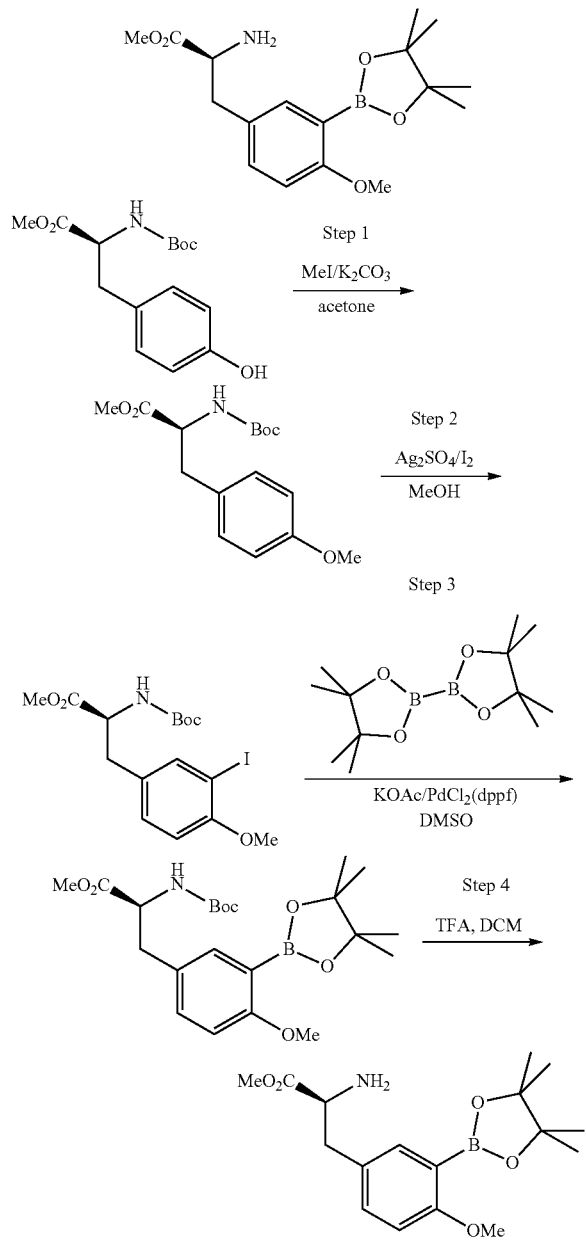

Step 1: To a solution of (S)-methyl 2-((tert-butoxycarbonyl)amino)-3-(4-hydroxyphenyl)propanoate (100 g, 0.323 mol) in acetone (2.0 L) was added $K_2CO_3$ (37 g, 0.34 mol). After the addition, MeI (32 mL, 0.97 mol) was added dropwise, and the reaction mixture was stirred at room temperature for 72 h and monitored by TLC. The reaction had not yet gone to completion, so NaOH (0.1 eq) was added to the reaction mixture. And after 2 h, the reaction was completed. The solid was filtered and the solvent was removed. The residue was taken up in ethyl acetate and washed with $H_2O$, extracted with ethyl acetate (300 mL×3). The combined organic layers were washed with brine, dried over $Na_2SO_4$ and concentrated to give (S)-methyl 2-((tert-butoxycarbonyl)amino)-3-(4-methoxyphenyl)propanoate (100 g, 95.4%).

Step 2: To a solution of (S)-methyl 2-((tert-butoxycarbonyl)amino)-3-(4-methoxyphenyl)propanoate (80 g, 40 g each ×2, run in two separate batches, 259 mmol overall) in methanol (1.5 L in each of the two flasks) was added sequentially $Ag_2SO_4$ (85 g, 272 mmol, ½-added to each flask) and $I_2$ (72 g, 283 mmol, ½-added to each flask). The reaction mixture was stirred at room temperature for 2 h. The reaction was monitored by LCMS. When all (S)-methyl 2-((tert-butoxycarbonyl)amino)-3-(4-methoxyphenyl)propanoate had been consumed, then a solution of 10% (w/w) sodium thiosulfate was added until the reaction turned pale yellow. The solid was filtered and most of the methanol was evaporated by rotary evaporation. Water and ethyl acetate were added to each batch. The aqueous layer was extracted with ethyl acetate (3×200 mL). The combined organic layers were washed with brine, dried over sodium sulfate and concentrated. The crude material was combined for the two batches and they were purified together by flash column chromatography on silica gel (25% then 35% then 40% ethyl acetate in hexanes) to give (S)-methyl 2-((tert-butoxycarbonyl)amino)-3-(3-iodo-4-methoxyphenyl)propanoate (97 g, 89%).

Step 3: (S)-Methyl 2-((tert-butoxycarbonyl)amino)-3-(3-iodo-4-methoxyphenyl)propanoate (92 g, 46 g each run in two separate batches, 211 mmol) was dissolved in anhydrous DMSO (1.5 L, ½-added for each batch) under argon and to the solution was added bis(pinacolato) diboron (80.5 g, 317 mmol, ½-added for each batch) and KOAc (103 g, 1.05 mol, ½-added for each batch). This mixture was degassed with argon for twenty minutes, then $Pd(dppf)Cl_2$ (4.6 g, 6 mmol, ½-added for each batch) was added. The mixture was degassed with argon five times, then kept under argon and heated to 80° C. for 3 h. TLC showed that the reaction was complete, and the reaction mixture was cooled to room temperature and filtered. The reaction mixture was dissolved in EA and washed with $H_2O$. The aqueous layer was extracted ethyl acetate (3×200 mL). The combined organic layers were dried over sodium sulfate, filtered and concentrated to give the crude product. The batches were then combined and purified together by flash column chromatography on silica gel (3% ethyl acetate in hexanes, then 20% to 25% ethyl acetate in hexanes to give (S)-methyl 2-((tert-butoxycarbonyl)amino)-3-(4-methoxy-3-(4,4,5,5-tetramethyl-1,3,2-dioxaborolan-2-yl)phenyl)propanoate (70 g, 76%).

Step 4: (S)-Methyl 2-((tert-butoxycarbonyl)amino)-3-(4-methoxy-3-(4,4,5,5-tetramethyl-1,3,2-dioxaborolan-2-yl)phenyl)propanoate (22 g, 50.6 mmol) was dissolved in dichloromethane (150 mL) and treated with trifluoroacetic acid (50 mL). The reaction mixture was stirred at room temperature and the reaction was monitored by HPLC. When all of the starting material had been consumed, the solvents were evaporated, DCM was added and $Na_2CO_3$ was added to neutralize the TFA. The mixture was filtered, and the solution was concentrated. DCM was added to the concentrated oil, and the mixture was cooled at 0° C. for 1 hr, whereupon the solid precipitates that formed were filtered. The filtrate was concentrated to give (S)-methyl 2-amino-3-(4-methoxy-3-(4,4,5,5-tetramethyl-1,3,2-dioxaborolan-2-yl)phenyl)propanoate. The material was used without further purification.

Example 2: Synthesis of (S)-2-((tert-butoxycarbonyl)amino)-2-(4-hydroxyphenyl)acetic acid

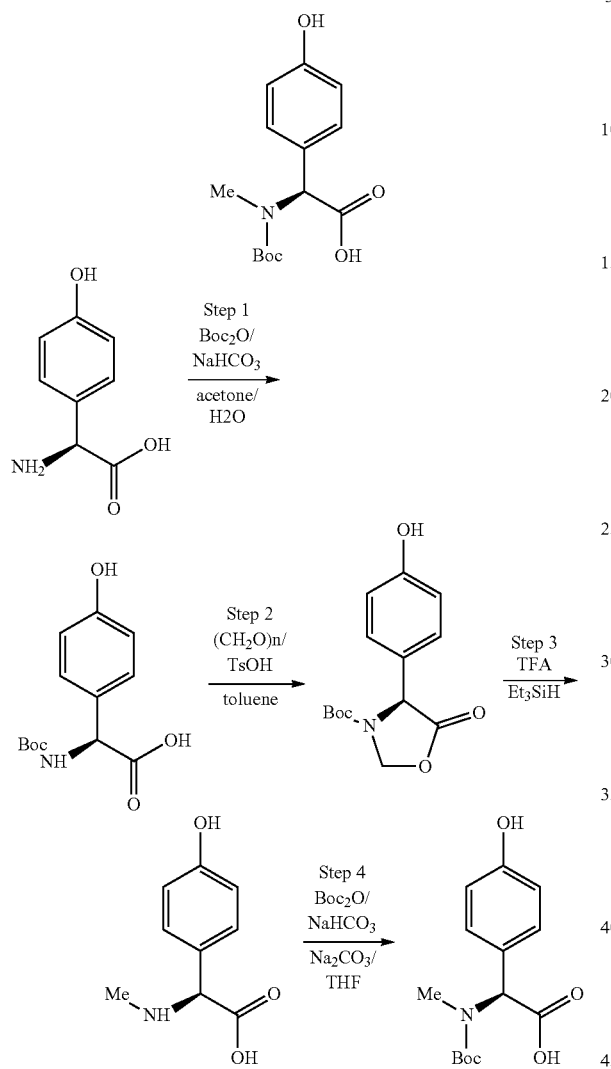

Step 1: To a stirred mixture of (S)-2-amino-2-(4-hydroxyphenyl)acetic acid (100 g, 0.6 mol, 1 eq) in a mixture of acetone (400 mL) and water (400 mL) was added di-tert-butyl dicarbonate (130.5 g, 0.6 mol, 1 eq) and NaHCO$_3$ (75.4 g, 0.9 mol, 1.5 eq). The mixture was allowed to stir at 25° C. overnight. After HPLC showed the reaction was complete, the mixture was acidified with 5% citric acid (pH ~3). The mixture was filtered and the filter cake was washed with water, then dried to give (S)-2-((tert-butoxycarbonyl)amino)-2-(4-hydroxyphenyl)acetic acid (140 g, 87.5%). The crude product was used directly without further purification.

Step 2: To a solution of (S)-2-((tert-butoxycarbonyl)amino)-2-(4-hydroxyphenyl)acetic acid (45 g, 0.17 mol) in dry benzene (500 mL) was added paraformaldehyde (75.6 g, 0.84 mol, 5 eq) and p-toluenesulfonic acid (1.6 g, 8.5 mmol, 0.05 eq). A Dean-Stark apparatus with an attached condenser was then fit to the top of the flask and the mixture was heated at approximately 120° C. until LC-MS showed the reaction was complete. The reaction was then cooled and the benzene was evaporated. The residue was taken up in ethyl acetate, washed with saturated NaHCO$_3$ (2×150 mL), then dried over sodium sulfate, and filtered. The solvent was removed to give (5)-tert-butyl 4-(4-hydroxyphenyl)-5-oxooxazolidine-3-carboxylate (36 g, 76.5%).

Step 3: (5)-tert-Butyl 4-(4-hydroxyphenyl)-5-oxooxazolidine-3-carboxylate (36 g, 0.13 mol, 1 eq) was dissolved in trifluoroacetic acid (75 mL) at 0° C. then treated with triethylsilane (80 mL, 4 eq). The mixture was stirred at room temperature overnight. After LC-MS showed the reaction was complete, TFA was then evaporated to afford (S)-2-(4-hydroxyphenyl)-2-(methylamino)acetic acid, which was used without further purification.

Step 4: The resultant (S)-2-(4-hydroxyphenyl)-2-(methylamino)acetic acid was dissolved in water (85 mL), and to this solution was added solid NaHCO$_3$ until the pH reached 7. The solution was cooled to 0° C., then Na$_2$CO$_3$ was added until pH reached 9. A solution of di-tert-butyldicarbonate (28.3 g, 1.0 eq) in THF (75 mL) was added to the mixture. The mixture was allowed to warm to room temperature then stirred overnight. After HPLC showed the reaction was complete, THF was then evaporated. The aqueous solution was extracted 2× with hexanes and then acidified with citric acid to pH ~3-4. The acidified solution was then extracted with ethyl acetate (200 mL×3). The combined organic layers were washed with brine, dried over sodium sulfate, filtered and concentrated to give (S)-2-((tert-butoxycarbonyl)(methyl)amino)-2-(4-hydroxyphenyl)acetic acid (35 g, 97% via 2 steps).

Example 3: Synthesis of Compound 101-B

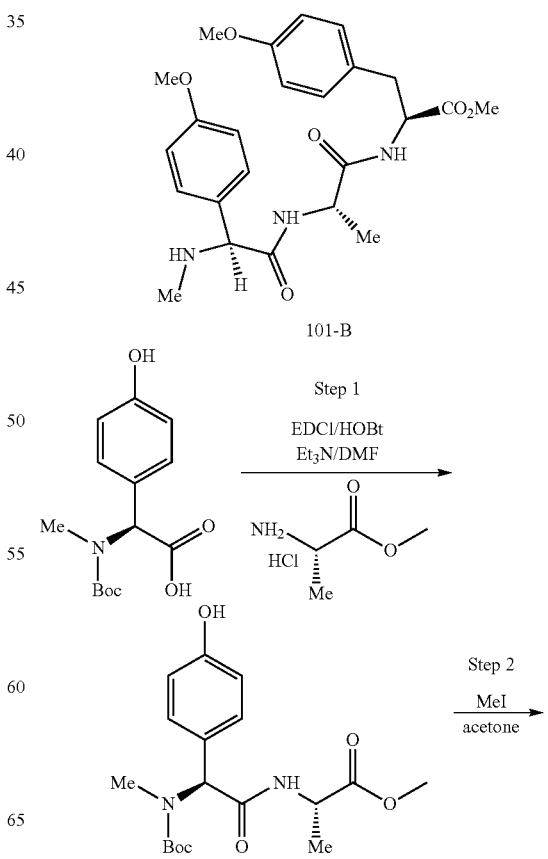

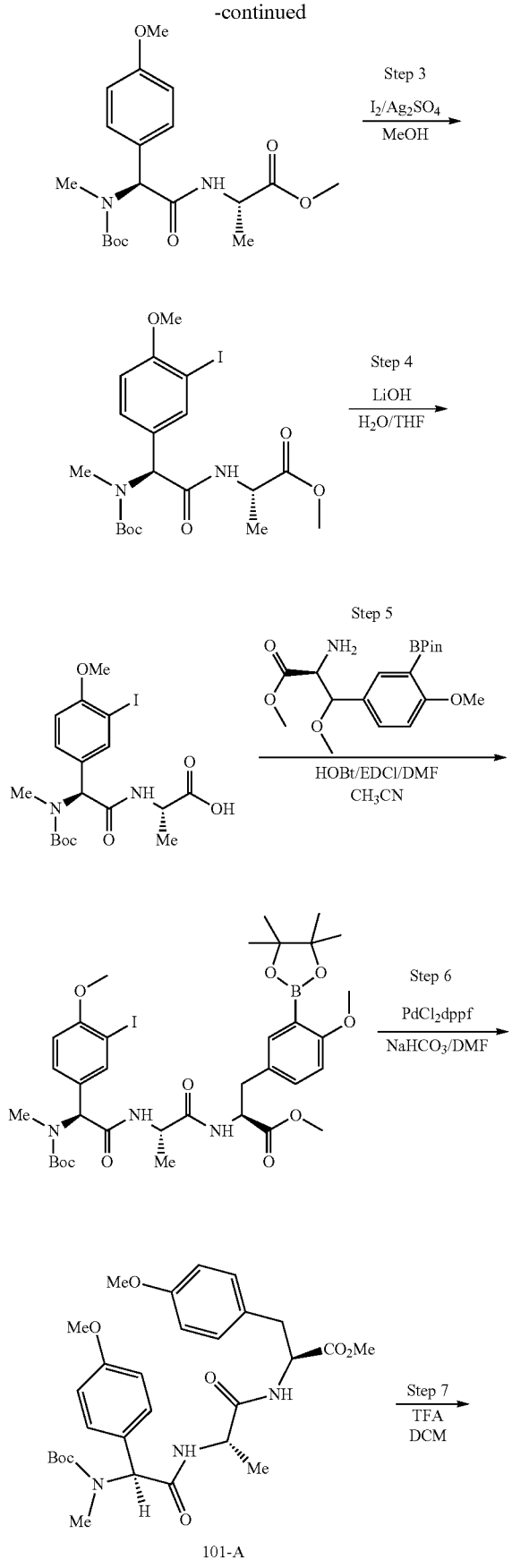

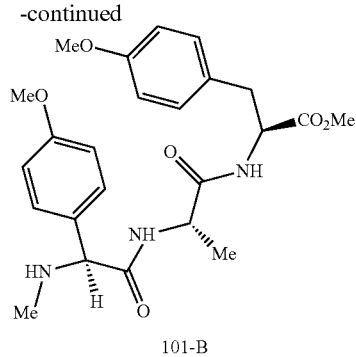

101-B

Step 1: To a solution of (S)-2-((tert-butoxycarbonyl)(methyl)amino)-2-(4-hydroxyphenyl)acetic acid (35 g, 0.12 mol) in DMF (300 mL) was added triethylamine (18.4 mL, 0.14 mol, 1.1 eq), HOBt (16.2 g, 0.12 mol, 1 eq), Ala-OMe HCl (19.5 g, 0.14 mol, 1.1 eq) and EDC (26.7 g, 0.14 mol, 1.1 eq) and the reaction was stirred overnight. After LC-MS showed the reaction was complete, water and EtOAc were added. The aqueous layer was extracted with EtOAc (3×150 mL), and the combined organic layers were washed with 5% citric acid (pH ~3), saturated NaHCO$_3$ (aq), water and brine. The combined organic layers were then dried over sodium sulfate, filtered and concentrated to give (S)-methyl 2-((S)-2-((tert-butoxycarbonyl)(methyl)amino)-2-(4-hydroxyphenyl)acetamido)propanoate (30 g, 65.8%) as a white foam. The crude product was taken on to the next step directly without further purification.

Step 2: To a solution of (S)-methyl 2-((S)-2-((tert-butoxycarbonyl)(methyl)amino)-2-(4-hydroxyphenyl)acetamido)propanoate (30 g, 82 mmol) in acetone (400 mL) was added K$_2$CO$_3$ (56.6 g, 0.41 mol, 5 eq) and iodomethane (20.8 mL, 0.41 mol, 5 eq) and the reaction was stirred at reflux overnight. After LC-MS showed the reaction was complete, the reaction was then cooled to room temperature and the mixture was filtered. The filtrate was concentrated and the residue was taken up in water and ethyl acetate. The aqueous phase was extracted with EtOAc (3×150 mL). The combined organic layers were dried over sodium sulfate, filtered and concentrated to give (S)-methyl 2-((S)-2-((tert-butoxycarbonyl)(methyl)amino)-2-(4-methoxyphenyl)acetamido)propanoate (28 g, 90%), as a white foam.

Step 3: To a solution of (S)-methyl 2-((S)-2-((tert-butoxycarbonyl)(methyl)amino)-2-(4-methoxyphenyl)acetamido)propanoate (85 g, 0.22 mol, 1 eq) in methanol (1000 mL) was added sequentially Ag$_2$SO$_4$ (72.6 g, 0.23 mol, 1.05 eq) and I$_2$ (59.6 g, 1.05 eq). After LC-MS showed the reaction was complete, a solution of 10% (w/w) sodium thiosulfate was added until the reaction turned pale yellow. Most of the methanol was evaporated by rotary evaporation and then water and ethyl acetate were added. The aqueous layer was extracted with ethyl acetate (3×300 mL). The combined organic layers were washed with brine, dried over sodium sulfate and concentrated to give (S)-methyl 2-((S)-2-((tert-butoxycarbonyl)(methyl)amino)-2-(3-iodo-4-methoxyphenyl)acetamido)propanoate (100 g, 88.5%).

Step 4: To (S)-methyl 2-((S)-2-((tert-butoxycarbonyl)(methyl)amino)-2-(3-iodo-4-methoxyphenyl)acetamido)propanoate (25 g, 49.4 mmol, 1 eq) in THF (300 mL) was added 0.2 M LiOH (500 mL, 98.8 mmol, 2 eq). The solution was stirred until TLC showed all starting material had been consumed. 5% citric acid (pH ~3) was added to pH ~3 and then the THF was evaporated by rotary evaporation. The aqueous layer was extracted with EtOAc (3×100 mL). The combined organic layers were washed with brine, dried over sodium sulfate, filtered and concentrated to give (S)-2-((S)-2-((tert-butoxycarbonyl)(methyl)amino)-2-(3-iodo-4-methoxyphenyl)acetamido)propanoic acid (23 g, 94.6%), which was used directly without further purification.

Step 5: To a solution of (S)-methyl 2-amino-3-(4-methoxy-3-(4,4,5,5-tetramethyl-1,3,2-dioxaborolan-2-yl)phenyl)propanoate (6.5 g, 19.4 mmol, 1 eq) and (S)-2-((S)-2-((tert-butoxycarbonyl)(methyl)amino)-2-(3-iodo-4-methoxyphenyl)acetamido)propanoic acid (10 g, 20.3 mmol, 1.05 eq) in acetonitrile:DMF (2.2:1, 168 mL) was added HOBt (6.5 g, 48.5 mmol, 2.5 eq) and EDC (8.1 g, 42.7 mmol, 2.2 eq). The reaction was stirred at room temperature overnight. After LC-MS showed the reaction was complete, diluted citric acid (pH ~3) was added and the aqueous was extracted with EtOAc (3×150 mL). The combined organic layers were then washed with saturated NaHCO₃ solution, brine and dried over sodium sulfate. The mixture was filtered and the filtrate was concentrated to give the crude product (6S,9S,12S)-methyl 6-(3-iodo-4-methoxyphenyl)-12-(4-methoxy-3-(4,4,5,5-tetramethyl-1,3,2-dioxaborolan-2-yl)benzyl)-2,2,5,9-tetramethyl-4,7,10-trioxo-3-oxa-5,8,11-triazatridecan-13-oate, which was used directly without further purification.

Step 6: (6S,9S,12S)-Methyl 6-(3-iodo-4-methoxyphenyl)-12-(4-methoxy-3-(4,4,5,5-tetramethyl-1,3,2-dioxaborolan-2-yl)benzyl)-2,2,5,9-tetramethyl-4,7,10-trioxo-3-oxa-5,8,11-triazatridecan-13-oate (16 g, 19.4 mmol, 1 eq) and NaHCO₃ (16.3 g, 0.19 mol) were sealed in a flask with a condenser and put under an atmosphere of argon. DMF (600 mL) in a round bottle flask was purged several times via cycling with vacuum and Ar. PdCl₂(dppf) (3.3 g, 4.5 mmol) was then added to the DMF. The DMF solution was then degassed with Ar for 15 minutes. The solution of PdCl₂(dppf) dissolved in DMF was then transferred via syringe to the flask containing the substrate and NaHCO₃. The resulting mixture was submitted to several more cycles of vacuum and Ar then heated to 120° C. overnight. After LCMS showed the reaction was completed, DMF was evaporated under vacuum. The crude material was subjected to abbreviated column chromatography (40% EA in PE) to remove most of the Pd species and then purified by prep HPLC to give Compound 101-A (2.1 g, 19.5% over two steps).

Step 7: To a stirred solution of Compound 101-A (2.1 g, 3.78 mmol) in DCM (25 mL) was added TFA (2 mL). The reaction was monitored via TLC and when starting material was consumed, the solvent was evaporated under vacuum. The residue was then dissolved in EtOAc and the organic layer was washed with saturated NaHCO₃ (10 mL), dried over sodium sulfate and concentrated to give Compound 101-B (1.7 g, 98.8%). MS (ESI) m/z 456.2 (M+H)⁺.

Example 4: Synthesis of Compound 101-G

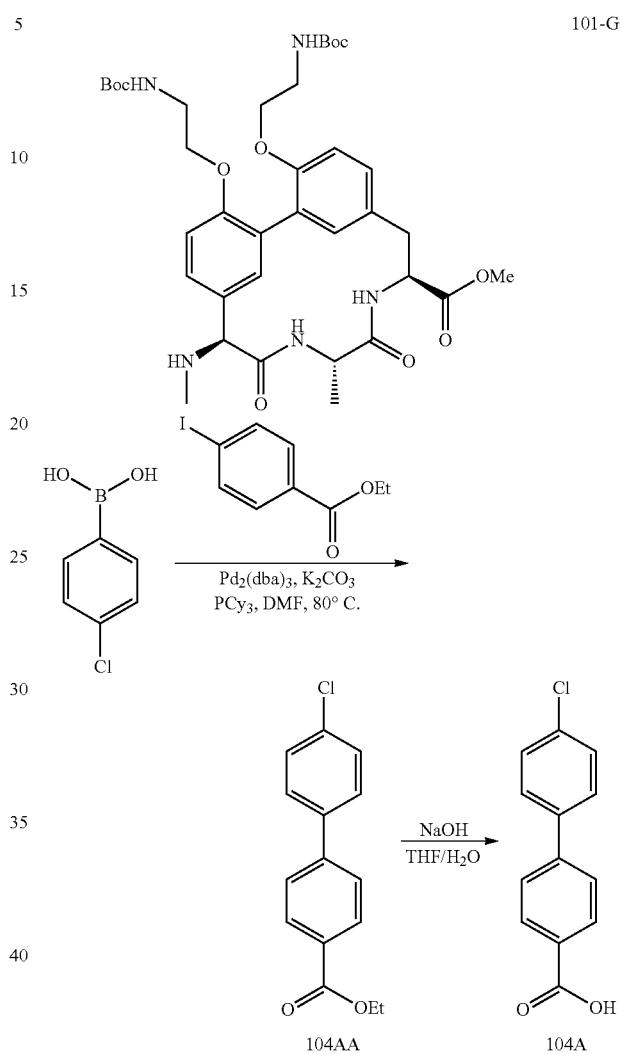

Step 1: The removal of the methoxy protecting groups is described and is referred to as General Method 1. To a solution of Compound 101-B (5.0 g, 11.0 mmol) in EtSH (116 mL, 1.61 mol), AlBr₃ (165 mL, 165 mmol) was added slowly at 0° C. under N₂. The mixture was stirred for 18 h. The volatiles were removed under reduced pressure and the residue was quenched by water (50 mL), which was further washed by DCM (20 mL×3). The aqueous layer was purified by prep-HPLC (acetonitrile 1-20%/0.1% TFA in water) to give Compound 101-C (4.5 g, 99.2% yield) as a white solid.

Step 2: To a solution of Compound 101-C (4.7 g, 8.9 mmol) in 1,4-dioxane/H₂O (9:1, 165 mL) was added 1 N NaOH dropwise until pH ~11. A solution of Cbz-OSu (6.66 g, 26.7 mmol) dissolved in 1,4-dioxane (50 mL) was then added. After stirring for 1 h, NaOH (1.07 g, 26.7 mmol) was then added to the reaction followed by MeOH (60 mL). This resulting mixture was allowed to stir for 20 mins. To the reaction was then added dilute citric acid (10% v/v, 50 mL), the aqueous layer was extracted with EtOAc (3×150 mL) and the combined organic layers were washed with brine (3×100 mL), dried over Na₂SO₄ and concentrated to give the crude product. The residue was diluted with DCM (50 mL)

and the suspension was filtered to give desired compound (3.2 g). The DCM phase was concentrated and the residue was purified by silica gel column (eluting 10~20% methanol in EtOAc) to give the desired compound (1.0 g). The combined batches gave Compound 101-D (4.2 g, 86.1% yield) as a white solid.

Step 3: To Compound 101-D (4.3 g, 7.85 mmol) was added a solution of 1.25M HCl in MeOH (128 mL) and the reaction was stirred at 0° C. The volatiles were removed to afford Compound 101E (4.15 g, 94.1% yield) as a white solid, which was used directly in the next step.

Step 4: The bis-alkylation of phenol groups is described and is referred to as General Method 2. To a solution of Compound 101-E (3.9 g, 6.94 mmol) and K$_2$CO$_3$ (14.4 g, 104 mmol) in DMF (50 mL) was added tert-butyl 2-bromoethylcarbamate (15.6 g, 69.5 mmol) at 0° C. The mixture was stirred at room temperature for 48 h. The mixture was filtered and the filtrate was diluted with EtOAc (500 mL). The EtOAc layer was washed with brine (2×400 mL), dried over Na$_2$SO$_4$, concentrated and purified by chromatography on silica (solvent gradient: 0-60% EtOAc in petroleum ether) to afford Compound 101-F (4.8 g, 81.5% yield) as a white solid.

Step 5: The hydrogenation of Cbz protecting groups is described and is referred to as General Method 3. To a solution of Compound 101-F (4.8 g, 5.7 mmol) in MeOH (100 mL), 10% Pd/C (1.26 g, 1.18 mmol) on carbon was added at room temperature. The reaction mixture was stirred for 1 h at the same temperature under hydrogen atmosphere (15 psi). The filtrate was then concentrated to afford Compound 101-G (4.0 g, 99% yield) as a white solid.

Example 5: Synthesis of Compounds 101-I, 101-J, 101-K, and 101-L

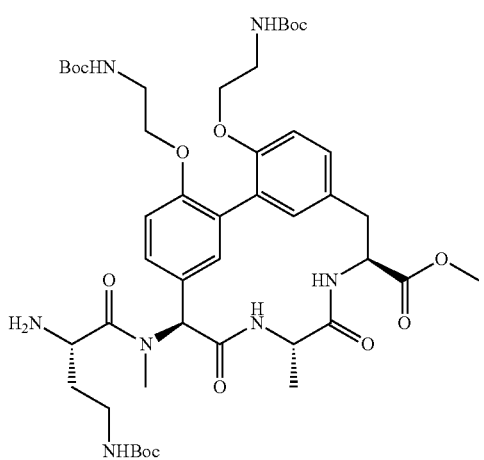

101-I

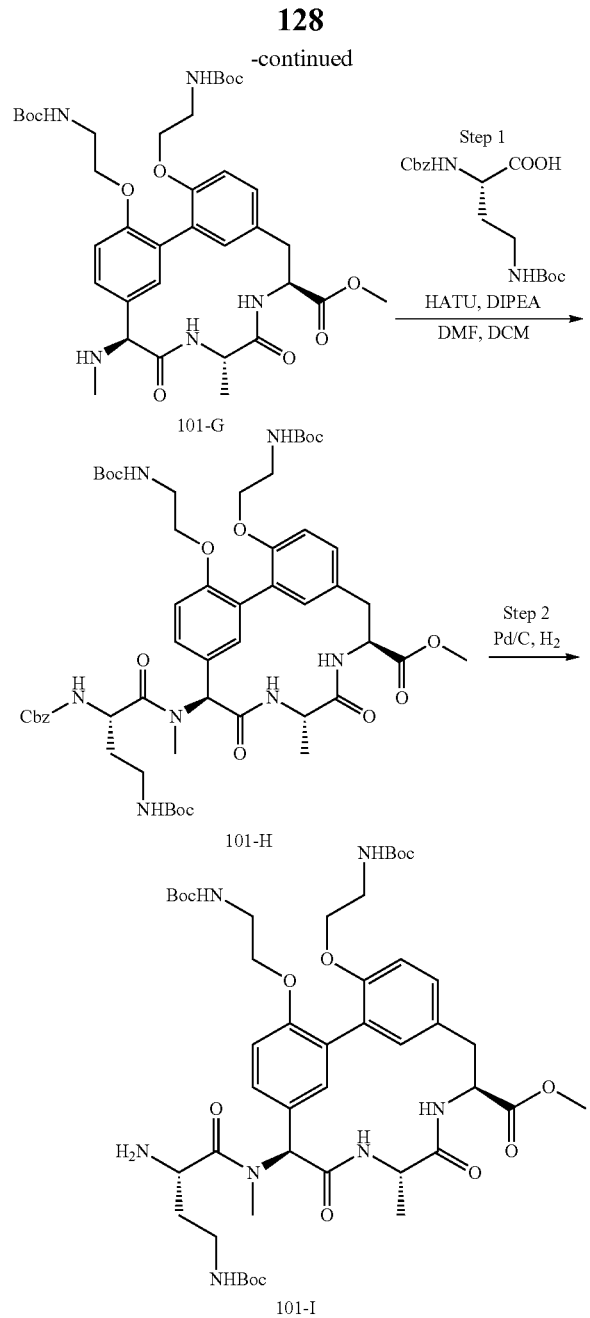

Step 1: The coupling of a Cbz-protected amino acid to an amine is described and is referred to as General Method 4. To a solution of Compound 101-G (7.56 g, 10.6 mmol) and (S)-2-(((benzyloxy)carbonyl)amino)-4-((tert-butoxycarbonyl)amino)butanoic acid (4.48 g, 12.7 mmol) in DCM/DMF (100 mL, v/v=4/1) at 0° C., HATU (8.05 g, 21.2 mmol) and DIPEA (4.11 g, 31.8 mmol) was added. The resulting mixture was allowed to gradually warm up to room temperature and stirred for 2 h. The reaction mixture was diluted with DCM (300 mL), which was washed with brine (300 mL×3). The organic layer was dried over Na$_2$SO$_4$, concentrated and the residue was purified by silica column chromatography to afford Compound 101-H (9.83 g, 88.5% yield) as a white solid.

Step 2: The hydrogenation step was performed using General Method 3 (Example 4) using Compound 101-H (8.83 g, 8.4 mmol) to afford Compound 101-I (7.5 g, 97.4% yield) as a white solid. LCMS (Method 5-95 AB, ESI): t$_R$=0.838, [M+H]$^+$=914.5.

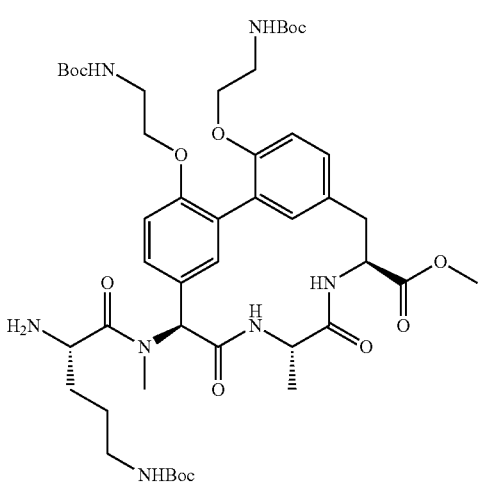

101-J

Compound 101-J was prepared from Compound 101-G and (S)-2-(((benzyloxy)carbonyl)amino)-5-((tert-butoxycarbonyl)amino)pentanoic acid using the conditions in Example 5. LCMS (Method 5-95 AB, ESI): $t_R$=0.841, $[M+H]^+$=928.4.

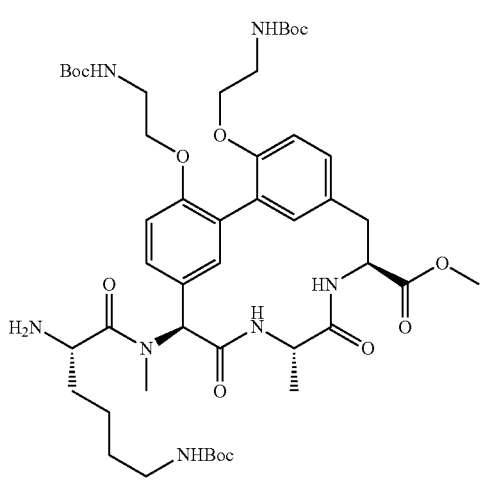

101-K

Compound 101-K was prepared from Compound 101G and (S)-2-(((benzyloxy)carbonyl)amino)-6-((tert-butoxycarbonyl)amino)hexanoic acid using the conditions in Example 5. LCMS (Method 5-95 AB, ESI): $t_R$=0.711, $[M+H]^+$=942.6.

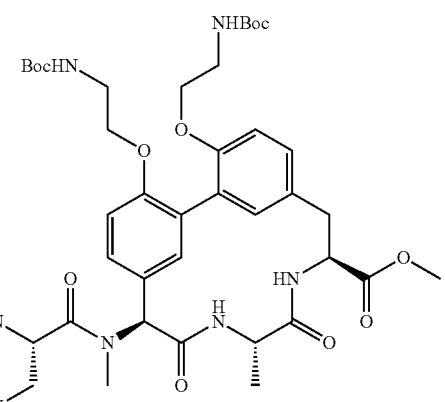

101-L

Compound 101-L was prepared from Compound 101G and (S)-2-(((benzyloxy)carbonyl)amino)-3-((tert-butoxycarbonyl)amino)propanoic acid using the conditions in Example 5. LCMS (Method 5-95 AB, ESI): $t_R$=0.833, $[M+H]^+$=900.5.

Example 6: Synthesis of Compound 101

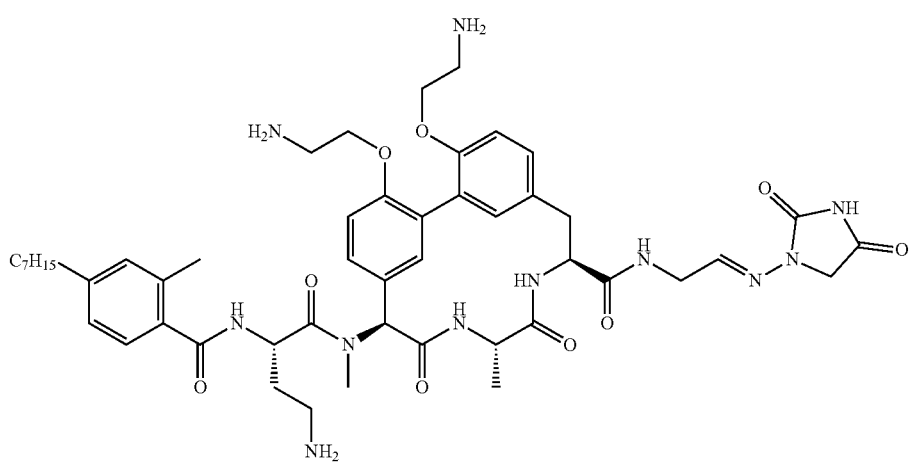

101

-continued

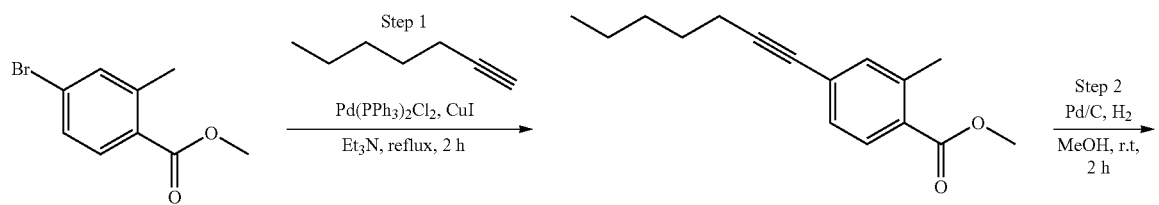

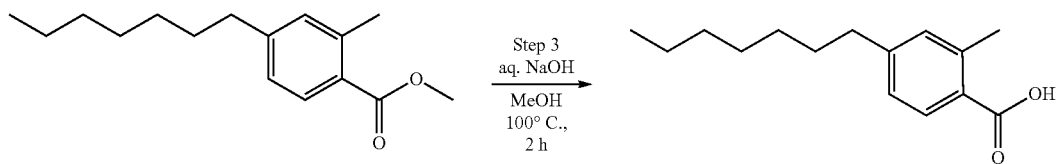

Synthesis of 4-heptyl-2-methylbenzoic acid

Step 1: 4-heptyl-2-methylbenzoic acid was synthesized using a Sonogashira coupling method. A mixture of methyl 4-bromo-2-methylbenzoate (51 g, 223 mmol), hept-1-yne (42.8 g, 446 mmol), Pd(PPh$_3$)$_2$Cl$_2$ (15.6 g, 22.3 mmol) and CuI (4.2 g, 22.3 mmol) in triethylamine (600 mL) was stirred at 100° C. for 16 h under nitrogen atmosphere. The volatiles were removed and the residue was purified by column chromatography on silica gel (100% petroleum ether) to afford methyl 4-(hept-1-yn-1-yl)-2-methylbenzoate (34 g, 62.5%) as a yellow oil.

Step 2: A mixture of methyl 4-(hept-1-yn-1-yl)-2-methylbenzoate (34 g, 139 mmol) and 10% Pd/C (14.8 g) in methanol (200 mL) was stirred at 25° C. for 16 h under hydrogen atmosphere. The catalyst was filtered off and the solvent was evaporated to afford methyl 4-heptyl-2-methylbenzoate (30 g, 86.8%) as a yellow oil.

Step 3: To a solution of methyl 4-heptyl-2-methylbenzoate (30 g, 121 mmol) in MeOH/H$_2$O (300 mL, v/v=1:1) was added sodium hydroxide (14.5 g, 363 mmol). The reaction mixture was stirred at 80° C. for 2 h. The reaction was cooled at 20° C. and hydrochloric acid (1.0 M) was added until pH=3-4. The mixture was extracted with ethyl acetate (3×200 mL). The combined extracts were washed with brine (2×500 mL), dried over sodium sulfate and filtered. The filtrate was concentrated to give 4-heptyl-2-methylbenzoic acid (24 g, 84.8%) as a yellow oil. LCMS (Method 5-95 AB, ESI): t$_R$=1.030 min, [M+H]$^+$=235.0.

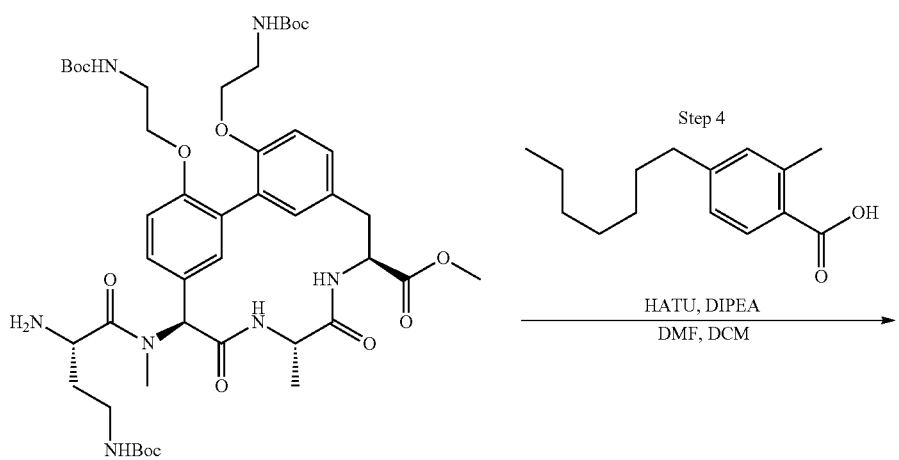

101-I

-continued
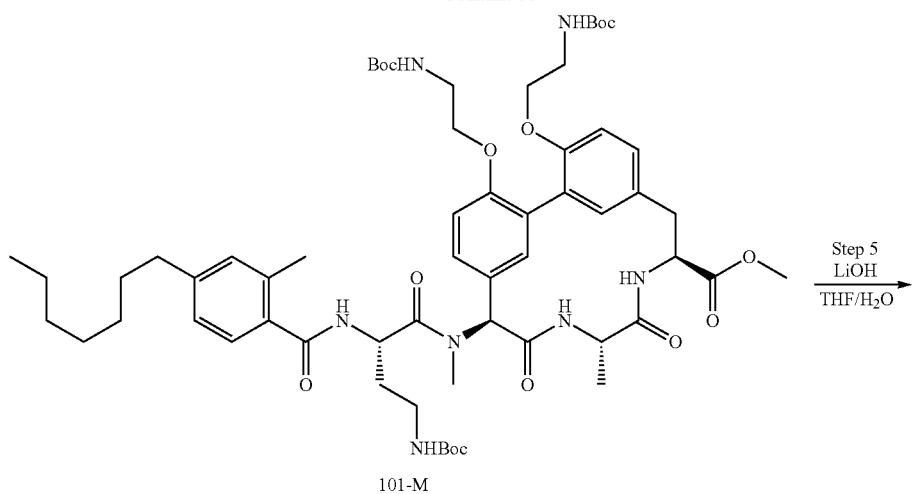
101-M
Step 5
LiOH
THF/H₂O
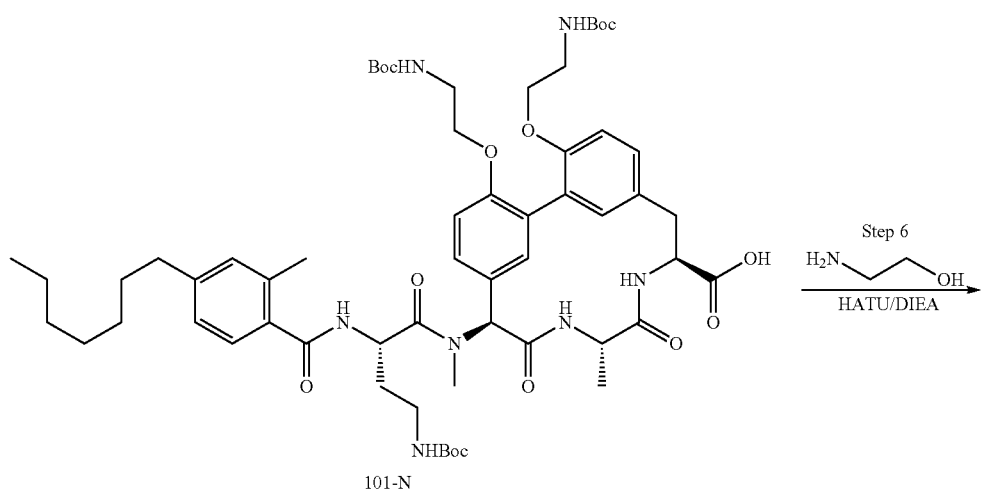
101-N
Step 6
H₂N-CH₂CH₂-OH
HATU/DIEA
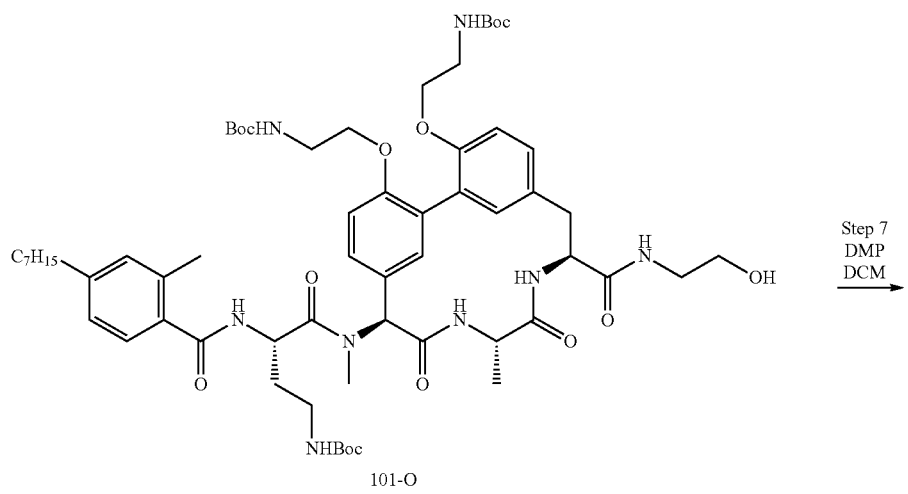
101-O
Step 7
DMP
DCM

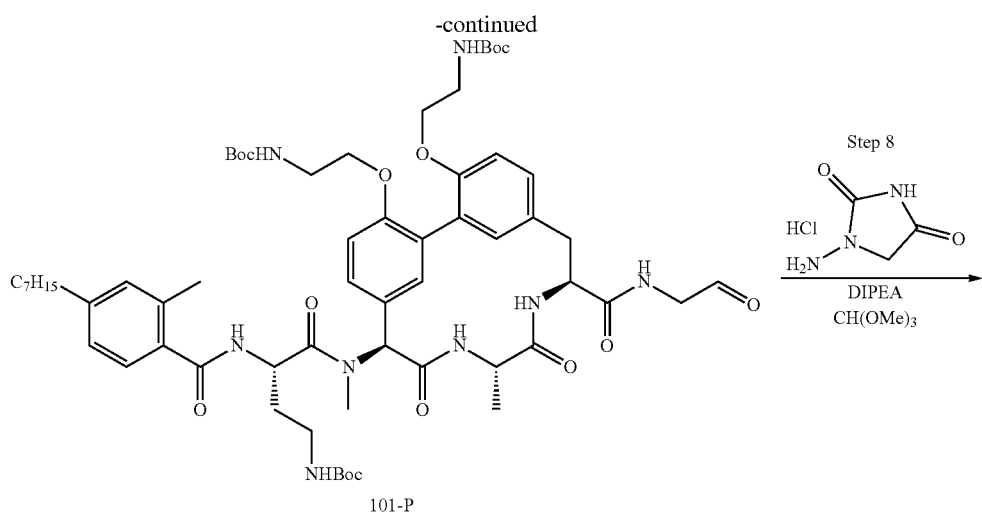
101-P
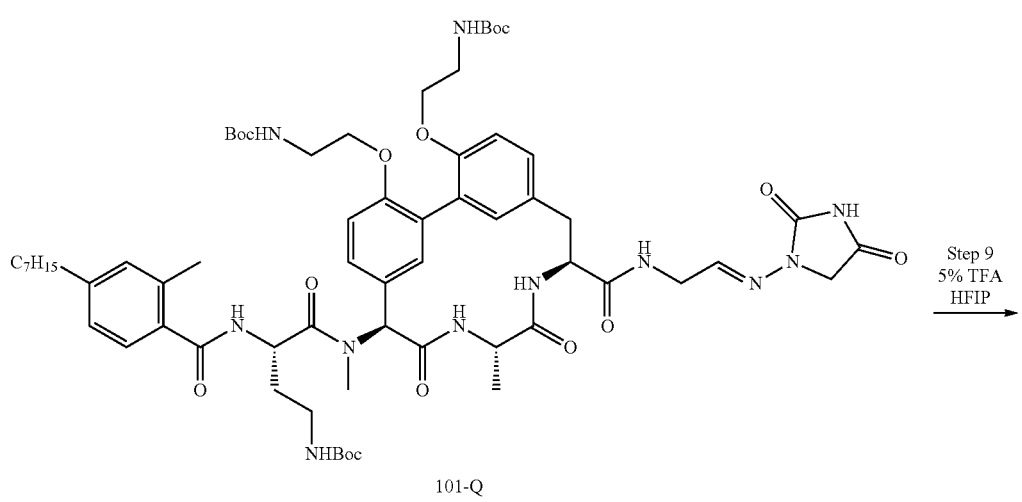
101-Q
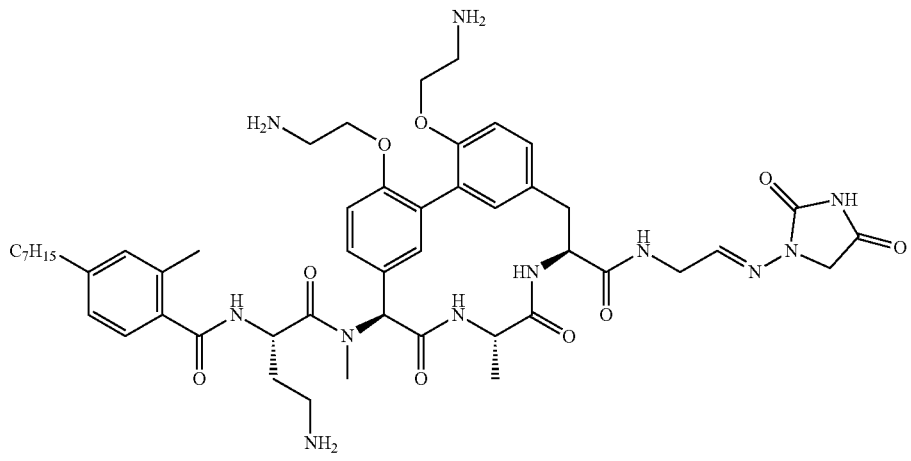
101

Synthesis of Compound 101

Step 4: The HATU coupling method (Example 5) was applied to Compound 101-I (9.0 g, 9.9 mmol) and 4'-butyl-[1,1'-biphenyl]-4-carboxylic acid (2.42 g, 10.4 mmol) to afford Compound 101-M (9.1 g, 82% yield) as a white solid.

Step 5: The lithium hydroxide hydrolysis of an ester to an acid is described and is referred to as General Method 5. To a solution of Compound 101-M (17.5 g, 15.5 mmol) in THF/H$_2$O (40 mL, 1:1) was added LiOH monohydrate (13 mg, 31 mmol) at 0° C. The mixture was allowed to gradually warm up to room temperature and stirred for 1 h. Most THF was removed under reduced pressure and the resulting mixture was adjusted pH=2 with saturated citric acid, which was further extracted by DCM (50 mL×3). The combined organic layers were washed with brine (100 mL), dried over Na$_2$SO$_4$ and concentrated to give Compound 101-N (17 g, 98.4% yield) as a white solid. LCMS (Method 5-95 AB, ESI): $t_R$=0.989 min, [M+H]$^+$=1116.7.

Step 6: The HATU coupling (Example 4) was applied to Compound 101-N (100 mg, 0.09 mmol) amino ethanol (16.4 mg, 0.27 mmol) to afford Compound 101-O (75 mg, 72.2% yield) as a white solid.

Step 7: Dess-Martin Periodinane oxidation. To a solution of Compound 101-O (75 mg, 0.06 mmol) in DCM (5 mL) was added DMP (276 mg, 0.65 mmol) in several portions and the mixture was stirred at room temperature for 30 h. The volatiles were removed and the residue was taken up by EtOAc (50 mL), which was washed with by brine (50 mL×2). The organic layer was dried over MgSO$_4$, concentrated and the crude was purified by prep-TLC to give Compound 101-P (50 mg, 66.8% yield) as a white solid. LCMS (Method 5-95 AB, ESI): $t_R$=1.098, [M+H]$^+$=1158.2

Step 8: To a solution of Compound 101-P (40 mg, 0.03 mmol) in trimethylorthoformate (2 mL) was added 1-aminohydantoin.HCl (6.3 mg, 0.04 mmol) and DIPEA (4.9 mg, 0.04 mmol) and the mixture was stirred at room temperature for 30 h. The volatiles were concentrated and the residue was taken up by EtOAc (10 ml), which was washed with brine (10 mL×2). The organic layer was dried over MgSO$_4$, concentrated and the residue was purified by prep-TLC to give Compound 101-Q (20 mg, 46.1% yield) as a white solid. LCMS (Method 5-95 AB, ESI): $t_R$=1.078, [M+H]$^+$=1255.1.

Step 9: A solution of Compound 101-Q (18 mg, 0.014 mmol) in a 5% TFA in 1,1,1,3,3,3-hexafluoro-2-propanol (HFIP) (1 mL) was stirred until complete removal of the Boc protecting groups. HPLC purification afforded Compound 101 (8 mg, 52% yield) as the formic acid salt. LCMS (Method 5-95 AB, ESI): $t_R$=0.748, [M+H]$^+$=955.0.

Example 7: Synthesis of Compound 102

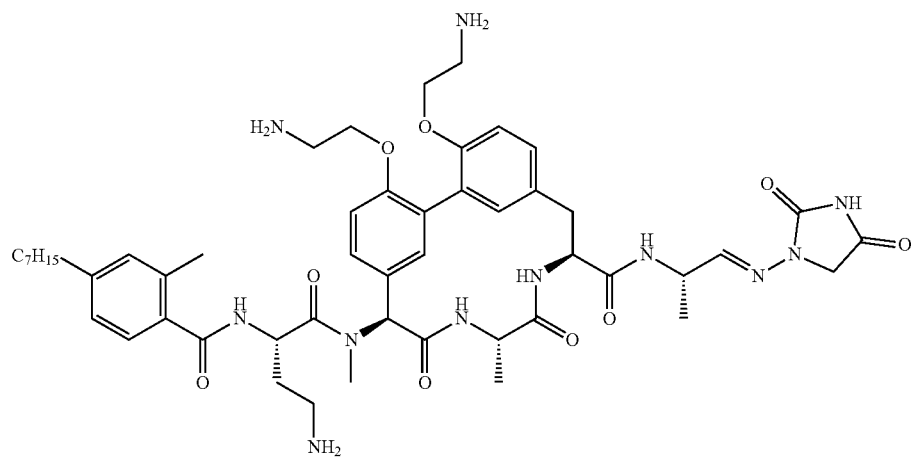

Compound 102 was prepared using the methods in Example 6 from Compound 101-N and (S)-2-aminopropan-1-ol. LCMS (Method 5-95 AB, ESI): $t_R$=0.748, [M+H]$^+$= 968.7; $^1$H NMR (400 MHz, MeOH-d$_4$) δ 8.49 (brs, 1H, HCOOH), 7.36-7.34 (m, 3H), 7.21-7.11 (m, 5H), 6.94-6.92 (m, 2H), 6.35 (s, 1H), 5.17-5.14 (m, 2H), 4.82-4.68 (m, 3H), 4.30-4.20 (m, 4H), 3.48-3.44 (m, 2H), 3.20-3.12 (m, 6H), 2.95 (s, 3H), 2.64 (t, J=7.6 Hz, 2H), 2.44 (s, 3H), 2.35-2.14 (m, 3H), 1.65-1.63 (m, 2H), 1.40-1.32 (m, 13H), 0.94 (t, J=6.8 Hz, 3H).

Example 8: Synthesis of Compound 103

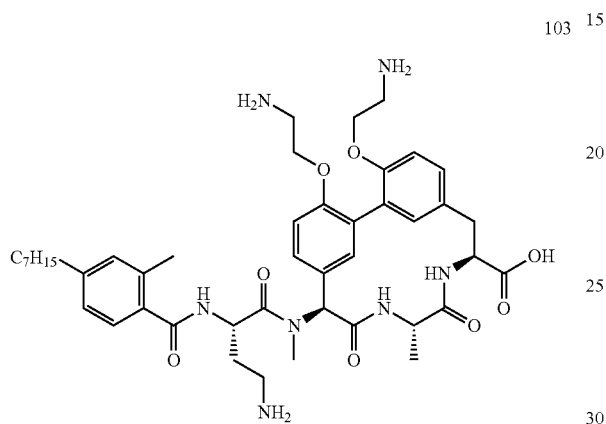

Compound 103 (formic acid salt) was prepared utilizing the TFA/HFIP hydrolysis method in Example 6 from Compound 101-N. LCMS (Method 5-95 AB, ESI): $t_R$=0.742, [M+H]$^+$=816.5; $^1$H NMR (400 MHz, MeOH-d$_4$) δ 7.31-7.16 (m, 2H), 7.12 (d, J=8.0 Hz, 1H), 7.06 (d, J=8.0 Hz, 1H), 6.99 (brs, 1H), 6.98-6.92 (m, 2H), 6.74 (brs, 2H), 6.43 (s, 1H), 5.15-5.11 (m, 1H), 4.80-4.78 (m, 1H), 4.46-4.44 (m, 1H), 4.10-4.00 (m, 4H), 3.39-3.13 (m, 2H), 3.06-2.90 (m, 4H), 2.95 (s, 3H), 2.70-2.53 (m, 4H), 2.37 (s, 3H), 2.28-2.06 (m, 4H), 1.59-1.50 (m, 2H), 1.45-1.31 (m, 11H), 0.92 (t, J=6.8 Hz, 3H).

Example 9: Synthesis of Compound 104

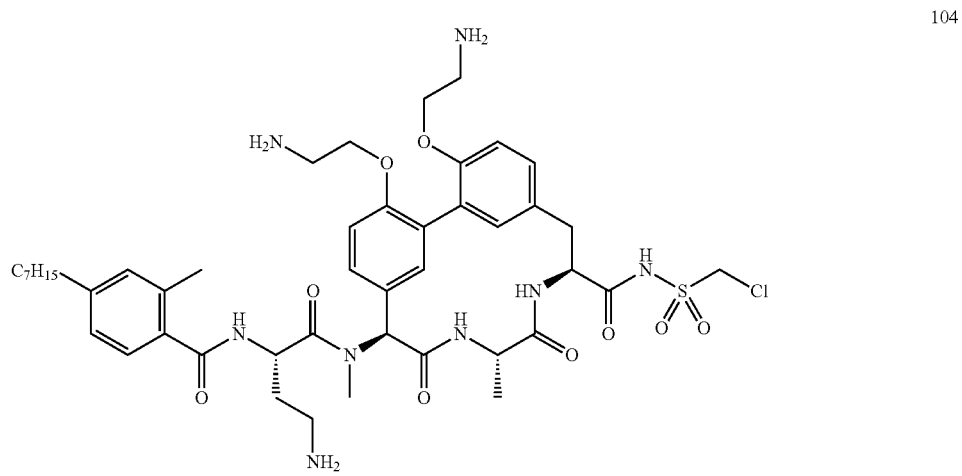

-continued
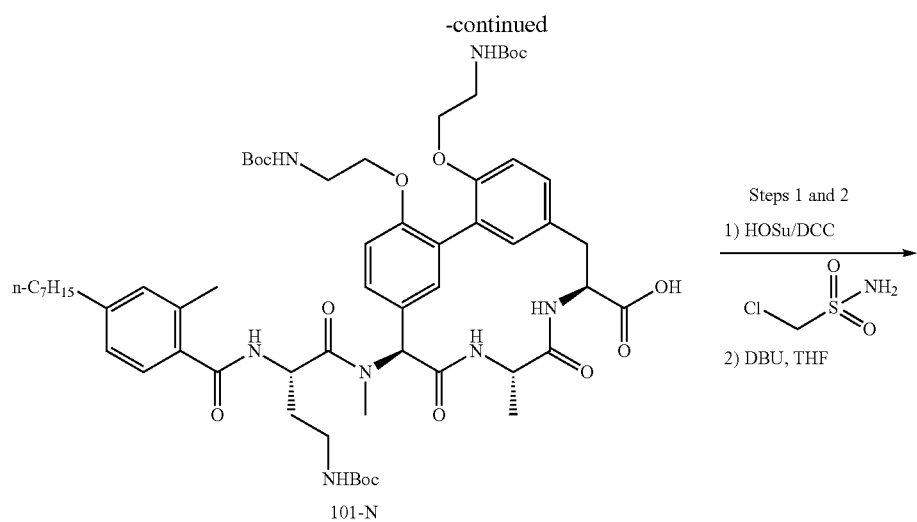
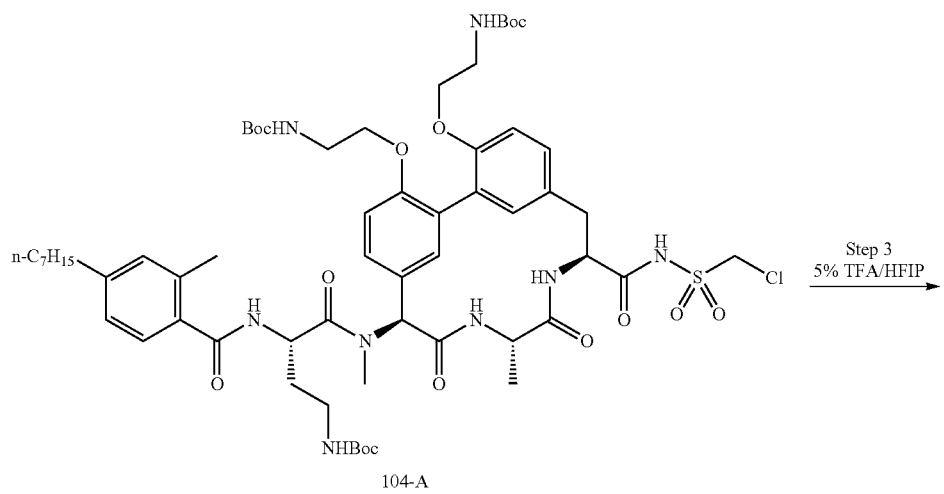
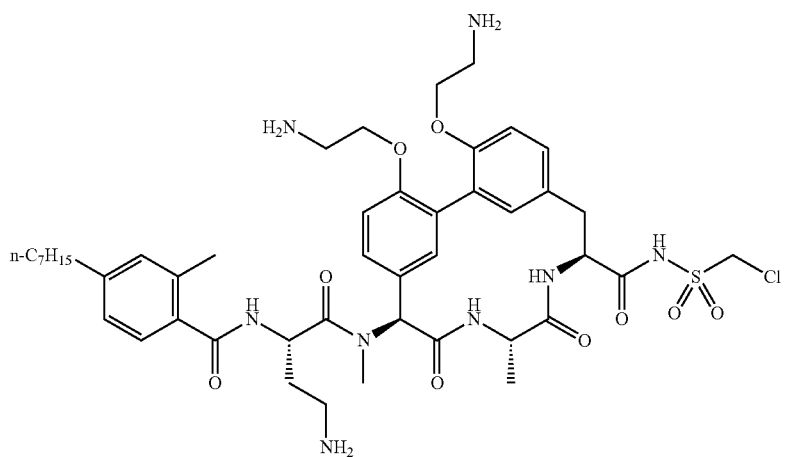

Step 1: To a stirred solution of Compound 101-N (50 mg, 0.04 mmol) in THF (5 mL) was added N-hydroxysuccinimide (HOSu) (15.5 mg, 0.13 mmol) and DCC (27.7 mg, 0.13 mmol) and the mixture was stirred at room temperature for 2 h. LCMS showed the completion of the reaction. The volatiles were removed to give the crude, which was used directly.

Step 2: To a stirred solution of chloromethanesulfonamide (12.8 mg, 0.10 mmol) in THF (3 mL) was added DBU (25.1 mg, 0.16 mmol) and the mixture was stirred at room temperature for 0.5 h, followed by the addition of the compound from the previous reaction. The resulting mixture was stirred at room temperature for another 1 h. After that, the volatiles were removed and the residue was taken up by EtOAc (5 mL), which was washed with brine (5 mL×3). The organic layer was concentrated and the residue was purified by Prep-TLC to afford Compound 104-A (17 mg, 36% yield) as a white solid. LCMS (Method 5-95 AB, ESI): $t_R$=1.127, $[M+H]^+$=1249.5.

Compound 104 (formic acid salt) was prepared as a white solid in 38% yield utilizing the TFA/HFIP method in Example 6. LCMS (Method 5-95 AB, ESI): $t_R$=0.761, $[M+H]^+$=927.9.

Example 10: Synthesis of Compound 105

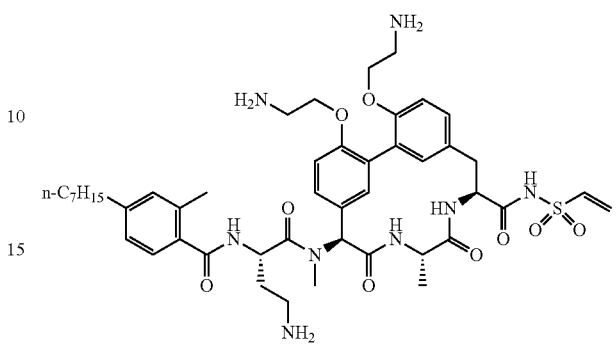

Compound 105 (formic acid salt) was prepared as a white solid utilizing the methods in Example 9. LCMS (Method 5-95 AB, ESI): $t_R$=0.754, $[M+H]^+$=905.4.

Example 11: Synthesis of Compound 106

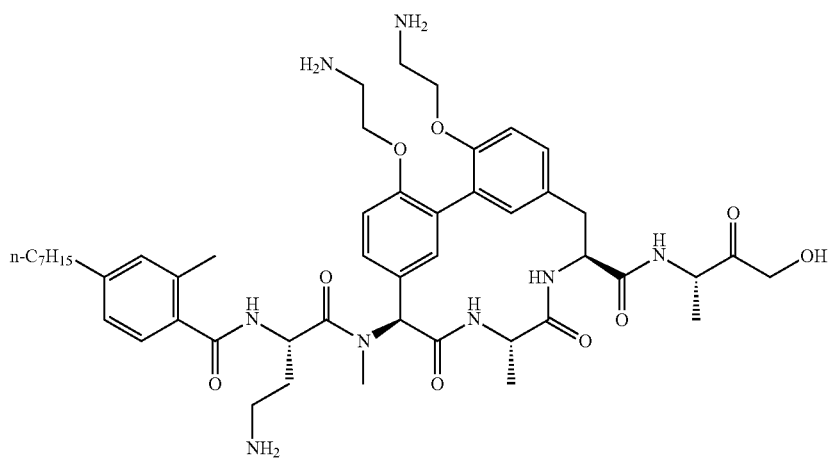

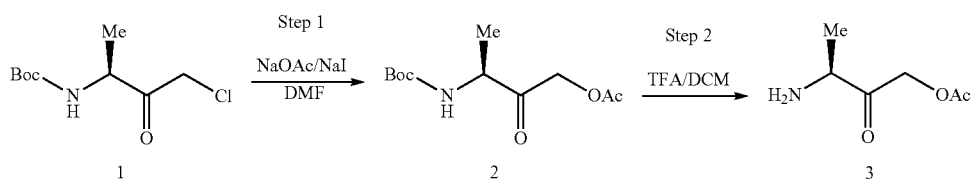

-continued
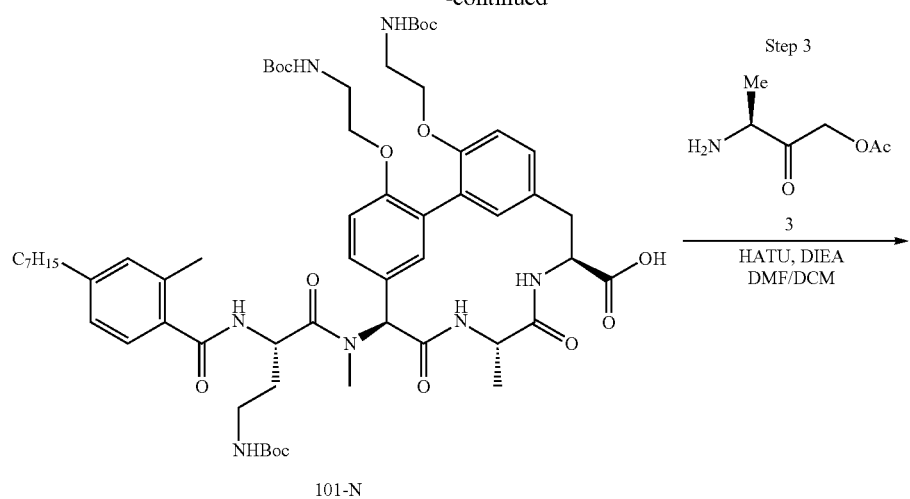
101-N
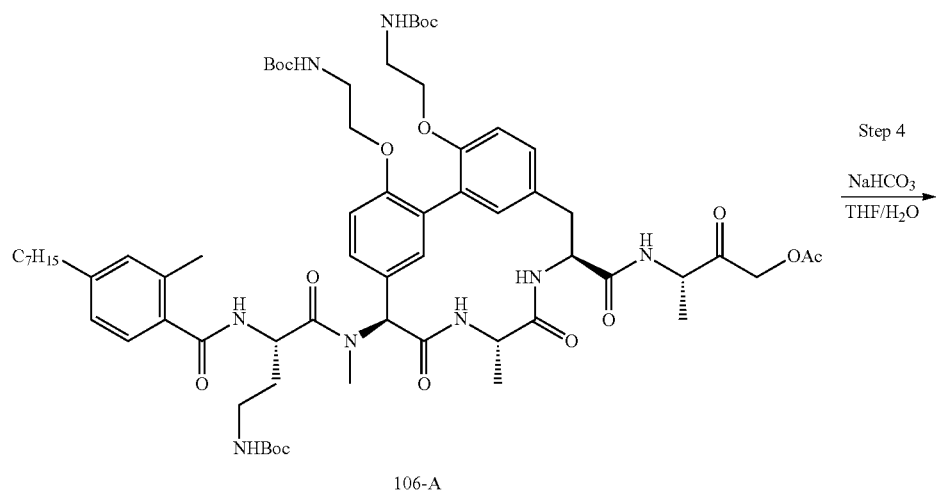
106-A
7
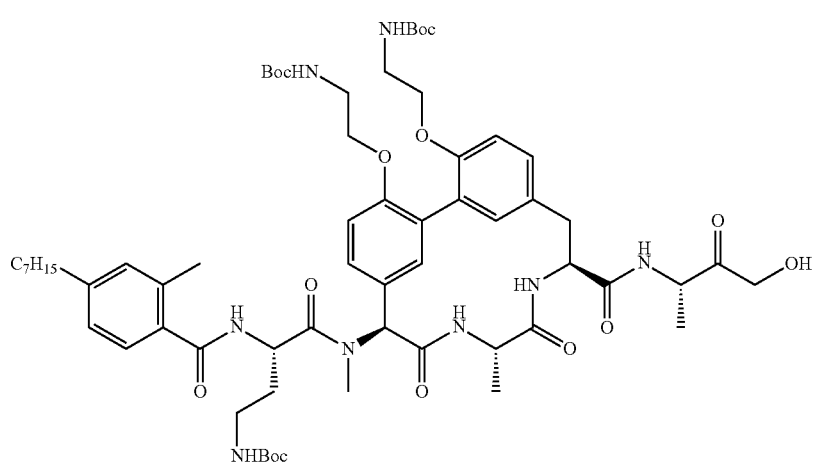
106-B
8

Step 1: To a solution of tert-butyl (S)-(4-chloro-3-oxobutan-2-yl)carbamate (500.0 mg, 2.26 mmol) in N,N-dimethylformamide (4 mL) were added sodium acetate (277.5 mg, 3.38 mmol) and sodium iodide (405.7 mg, 2.71 mmol) and stirred at 30° C. for 16 h. Crushed ice was added and the resulting white solid was collected by filtration and dried under vacuum to afford (S)-3-((tert-butoxycarbonyl)amino)-2-oxobutyl acetate (240 mg, 43.4% yield) as a white solid.

Step 2: To a solution of (S)-3-((tert-butoxycarbonyl)amino)-2-oxobutyl acetate (240 mg, 0.98 mmol) in dichloromethane (1.5 mL) was added trifluoroacetic acid (0.46 mL, 6.17 mmol). The reaction was stirred at 30° C. for 2 h and concentrated to afford crude compound 3 (140 mg, 98.6% yield) as a colorless oil, which was used directly in the next step without purification.

Step 3: Treatment of Compound 101-N using the standard HATU method (Example 5) afforded Compound 106-A.

Step 4: To a solution of Compound 106-A (270.0 mg, 0.22 mmol) in tetrahydrofuran (3 mL) was added a solution of sodium bicarbonate (54.7 mg, 0.65 mmol) in water (1 mL) and stirred at 30° C. for 16 h. The reaction was quenched with water (10 mL) and extracted with EtOAc (50 mL×3). The combined organic layers were washed with brine (30 mL×3), dried over $Na_2SO_4$ and concentrated to give Compound 106-B (240 mg, 92% yield) as a white solid. LCMS (Method 5-95 AB, ESI): $t_R$=1.090 min, $[M+Na]^+$=1223.7.

Compound 106 (formic acid salt) was prepared as a white solid utilizing the TFA/HFIP hydrolysis method in Example 6. LCMS (Method 5-95 AB, ESI): $t_R$=0.743 min, $[M+H]^+$= 901.5.

Example 12: Synthesis of Compound 107

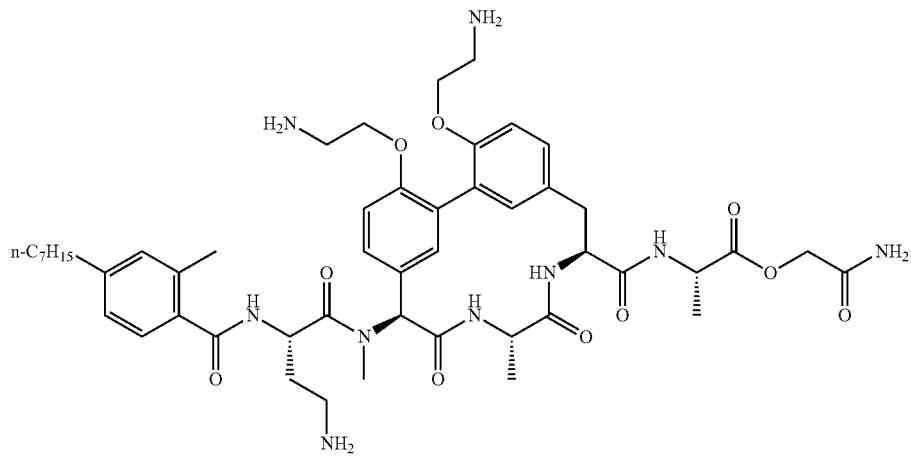

107

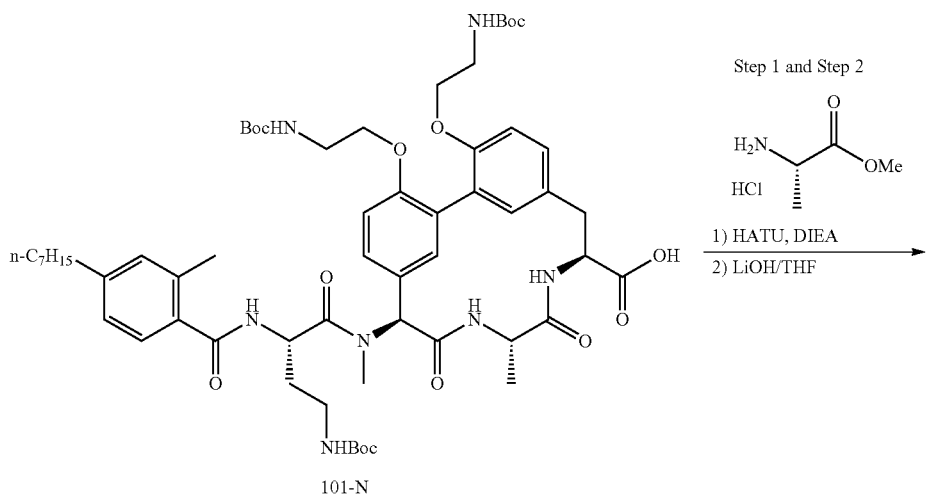

101-N

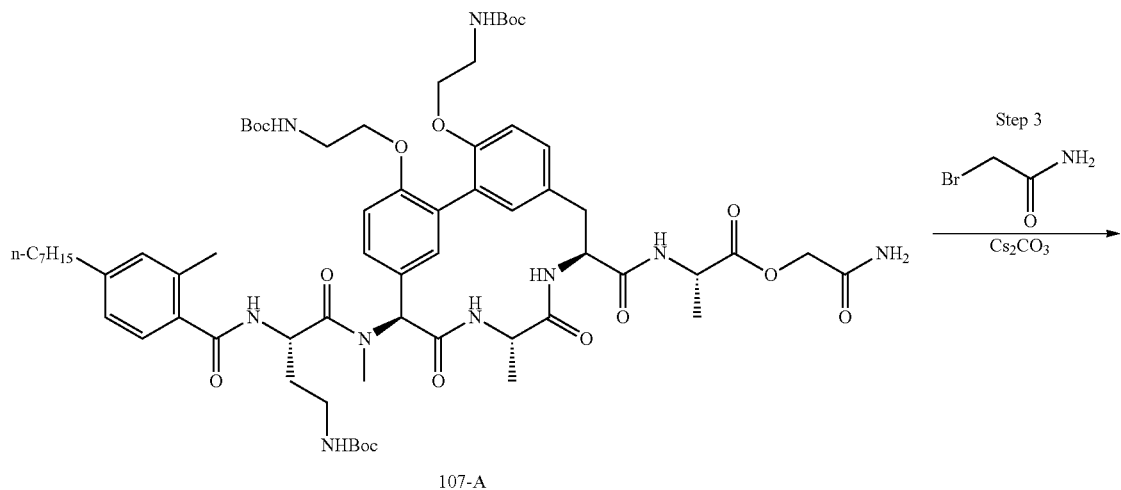

107-A

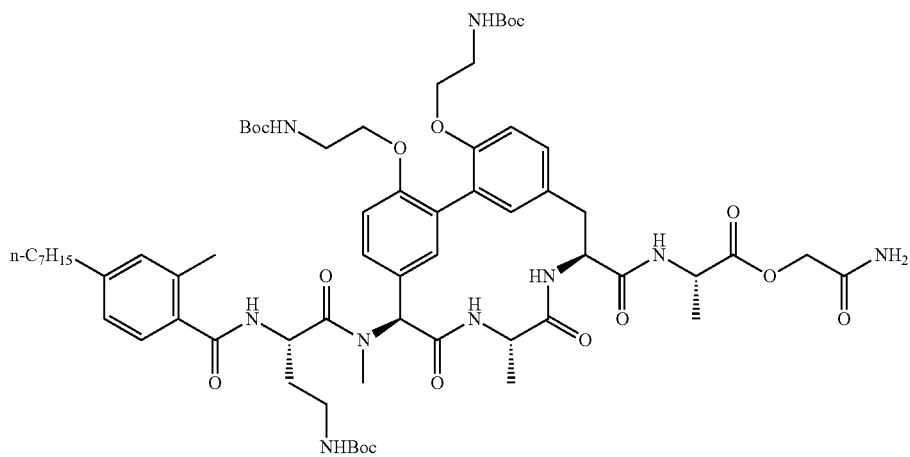

107-B

Steps 1 and 2: Starting from Compound 101-N, HATU coupling with (S)-methyl 2-aminopropanoate hydrochloride (Example 5) and LiOH ester hydrolysis (Example 6) afforded Compound 107-A.

Step 3: To a stirred solution of Compound 107-A (40 mg, 0.03 mmol) in DMF (1 mL) was added 2-bromoacetamide (9.3 mg, 0.07 mmol) and $Cs_2CO_3$ (22 mg, 0.07 mmol). The mixture was stirred at room temperature for 16 h. The reaction was added with EtOAc (10 mL), which was washed with $H_2O$ and brine sequentially (10 mL each). The organic layer was dried over $MgSO_4$, concentrated and the residue was purified by prep-TLC to give Compound 107-B (18 mg, 42.9% yield) as a white solid. LCMS (Method 5-95 AB, ESI): $t_R$=0.954, M+H$^+$=1245.7.

Starting from Compound 107-B (18 mg, 0.01 mmol), typical Boc removal (TFA/HFIP, Example 6) procedure was followed to afford Compound 107 (8.0 mg, 58% yield) as a white solid. LCMS (Method 5-95 AB, ESI): $t_R$=0.748, M+H$^+$=944.7.

Example 13: Synthesis of Compound 108
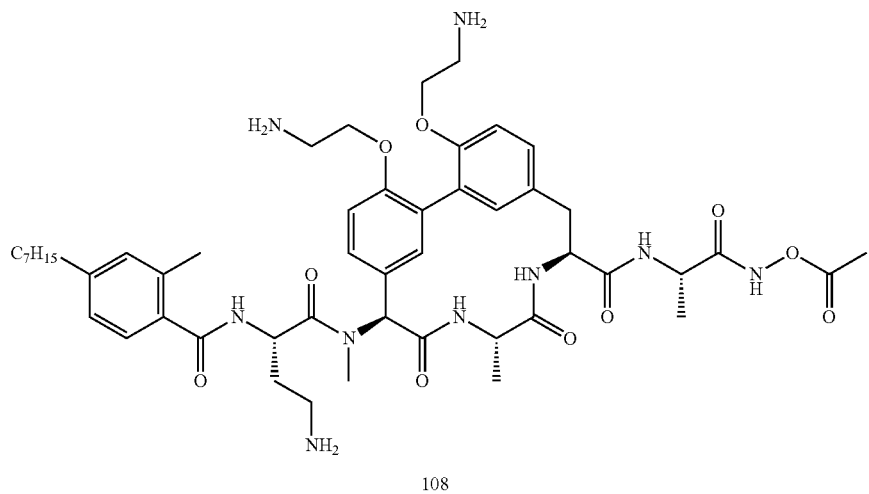
108
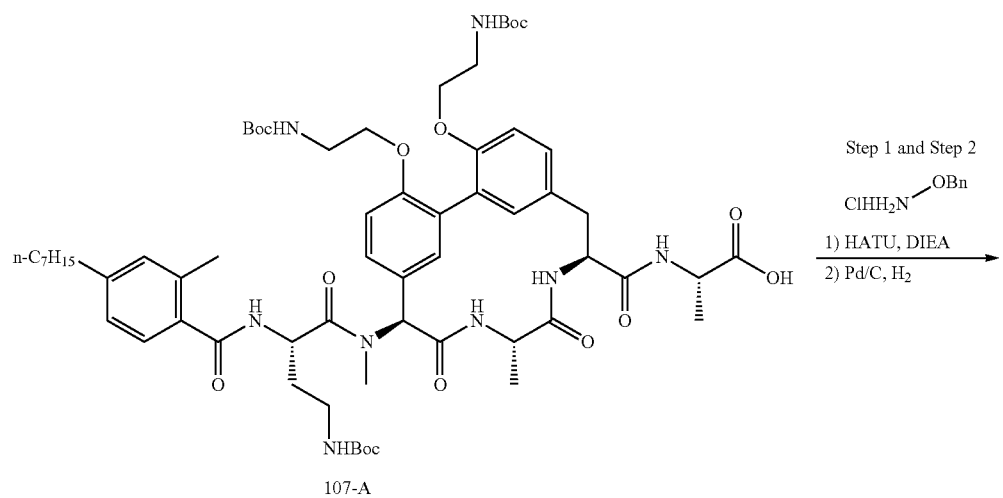
107-A
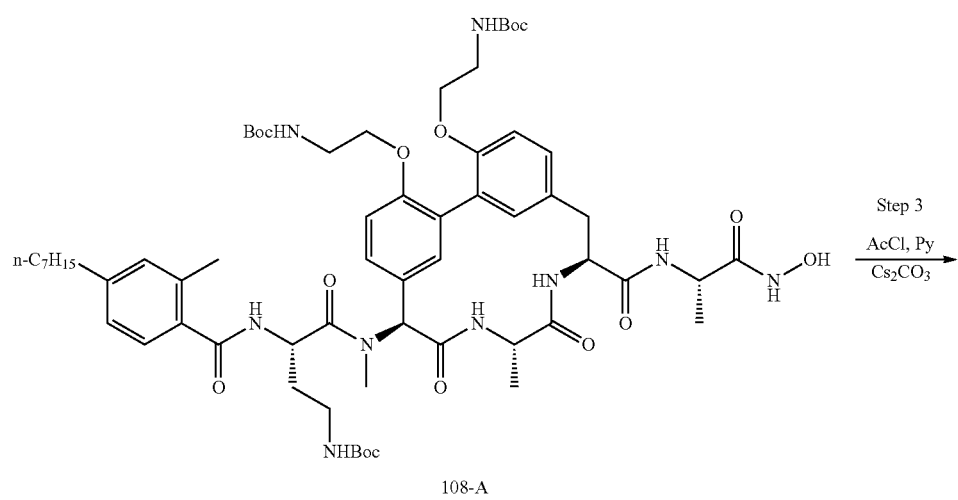
108-A

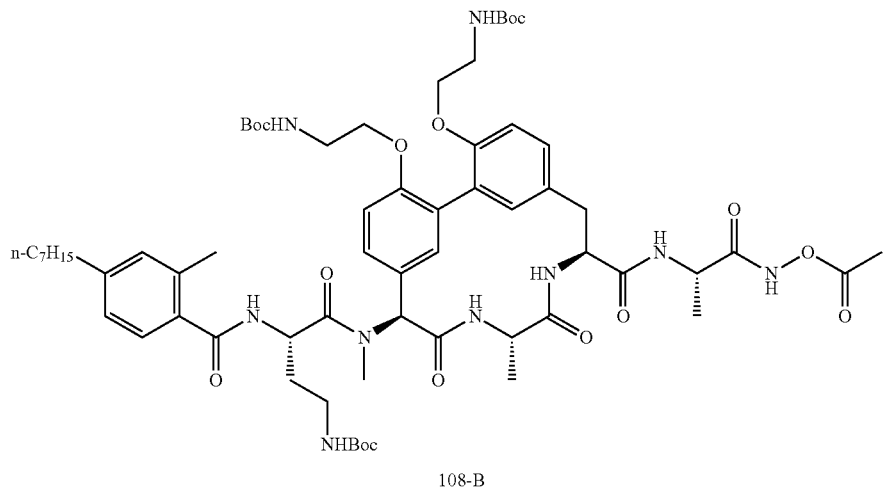

108-B

Steps 1 and 2: Starting from Compound 107-A (Example 12), typical HATU amide coupling (Example 5) and Pd hydrogenation (Example 4) procedure was followed to afford Compound 108-A (45 mg) as a white solid. LCMS (Method 5-95 AB, ESI): $t_R$=1.079, M+Na$^+$=1224.8.

Step 3: To a solution of Compound 108-A (30 mg, 0.02 mmol), pyridine (7.9 mg, 0.10 mmol) in DCM (2 mL) was added acetyl chloride (5.3 uL, 0.07 mmol) at 0° C. and the mixture was gradually warmed up to room temperature while stirring and stirred at the same temperature for 1 h. The volatiles were removed and the residue was taken up by EtOAc (30 mL), which was washed with H$_2$O and brine sequentially (30 mL each). The organic layer was dried over MgSO$_4$, concentrated and the residue was purified by prep-TLC to afford Compound 108-B (25 mg, 80.5% yield) as a white solid. LCMS (Method 5-95 AB, ESI): $t_R$=1.091, M+Na$^+$=1267.6.

Starting from Compound 108-B (25 mg, 0.02 mmol), the TFA/HFIP Boc removal (Example 12) procedure was followed to afford Compound 108 (4.3 mg, 25% yield) as a white solid. LCMS (Method 5-95 AB, ESI): $t_R$=0.762, M+H$^+$=944.7.

Example 14: Synthesis of Compound 109

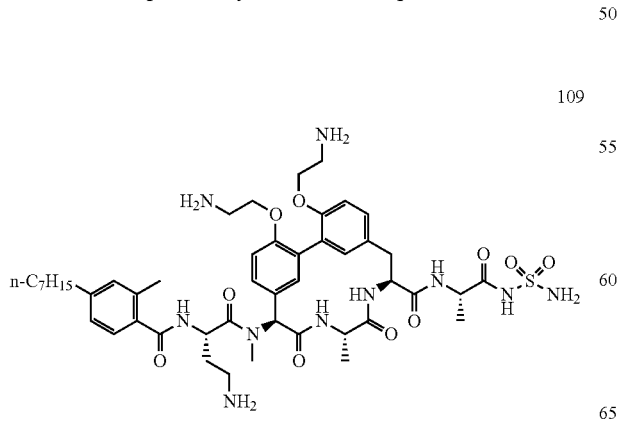

109

Compound 109 (formic acid salt) was prepared as a white solid utilizing the coupling and Boc-hydrolysis methods in Example 9 from Compound 107-A. LCMS (Method 5-95 AB, ESI): $t_R$=0.748, M+H$^+$=965.5.

Example 15: Synthesis of Compound 110

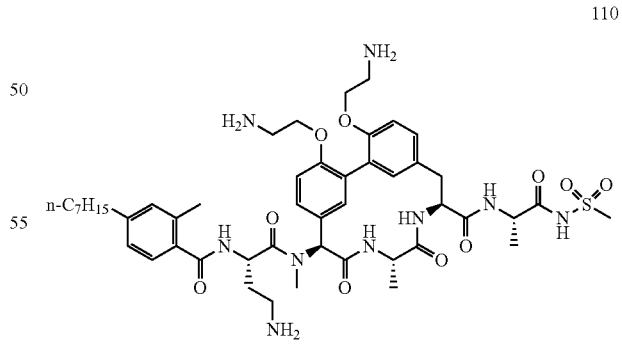

110

Compound 110 (formic acid salt) was prepared as a white solid utilizing the coupling and Boc-hydrolysis methods in Example 9 from Compound 107-A. LCMS (Method 5-95 AB, ESI): $t_R$=0.745, M+H$^+$=964.6.

Example 16: Synthesis of Compound 111
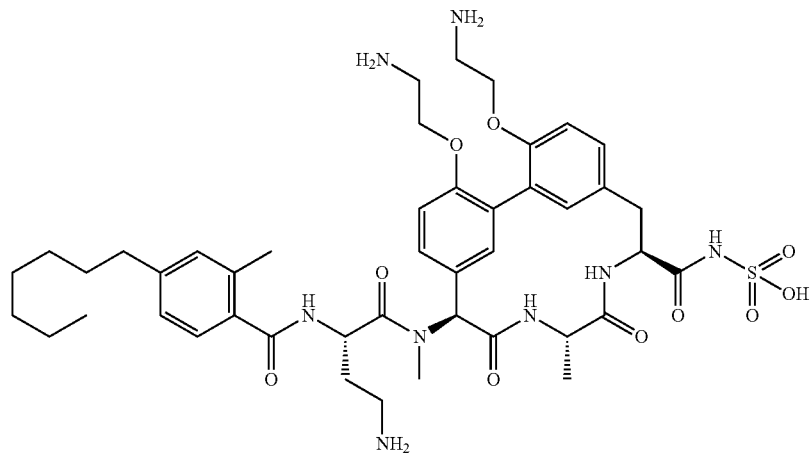
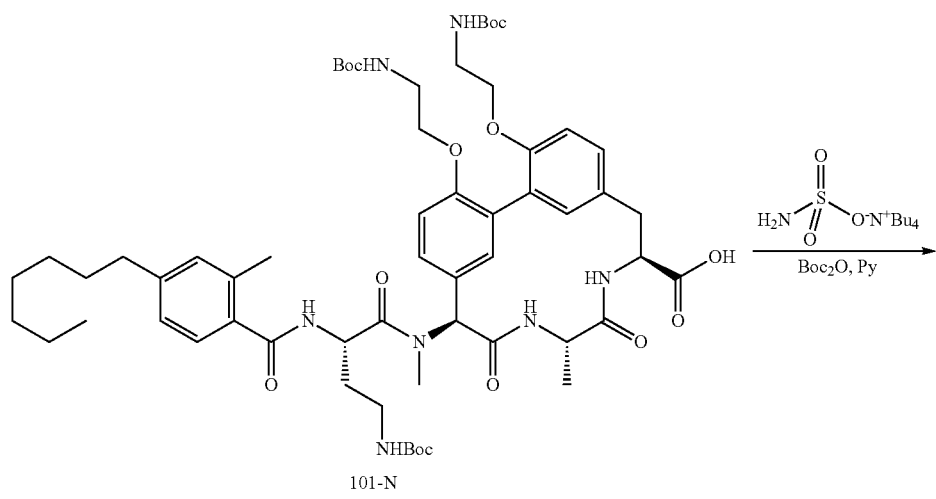
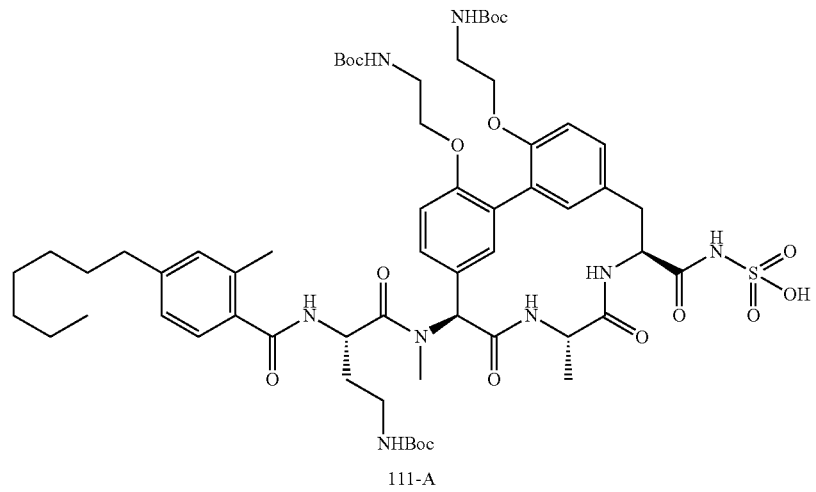

To a mixture of tetrabutylammonium hydroxide (29.3 mg, 0.11 mmol) and sulfamic acid (11.0 mg, 0.11 mmol) in pyridine (0.2 mL) was added Compound 101-N (70.0 mg, 0.06 mmol). The mixture was stirred at 25° C. for 10 min and more tetrabutylammonium hydroxide (29.3 mg, 0.11 mmol) in pyridine (0.3 mL) was added slowly. The mixture was stirred at 25° C. for 16 h and concentrated in vacuo. The residue was purified by prep-TLC (9% methanol in DCM, Rf=0.35) to afford Compound 111-A (25 mg, 33.4% yield) as a light yellow oil. LCMS (Method 5-95 AB, ESI): $t_R$=0.933 min, $[M+H]^+$=1194.7.

Compound 111 (formic acid salt) was prepared as a white solid utilizing the TFA/TFIP Boc-hydrolysis methods in Example 9. LCMS (Method 5-95 AB, ESI): $t_R$=0.768 min, $[M+H]^+$=895.8.

Example 17: Synthesis of Compound 112

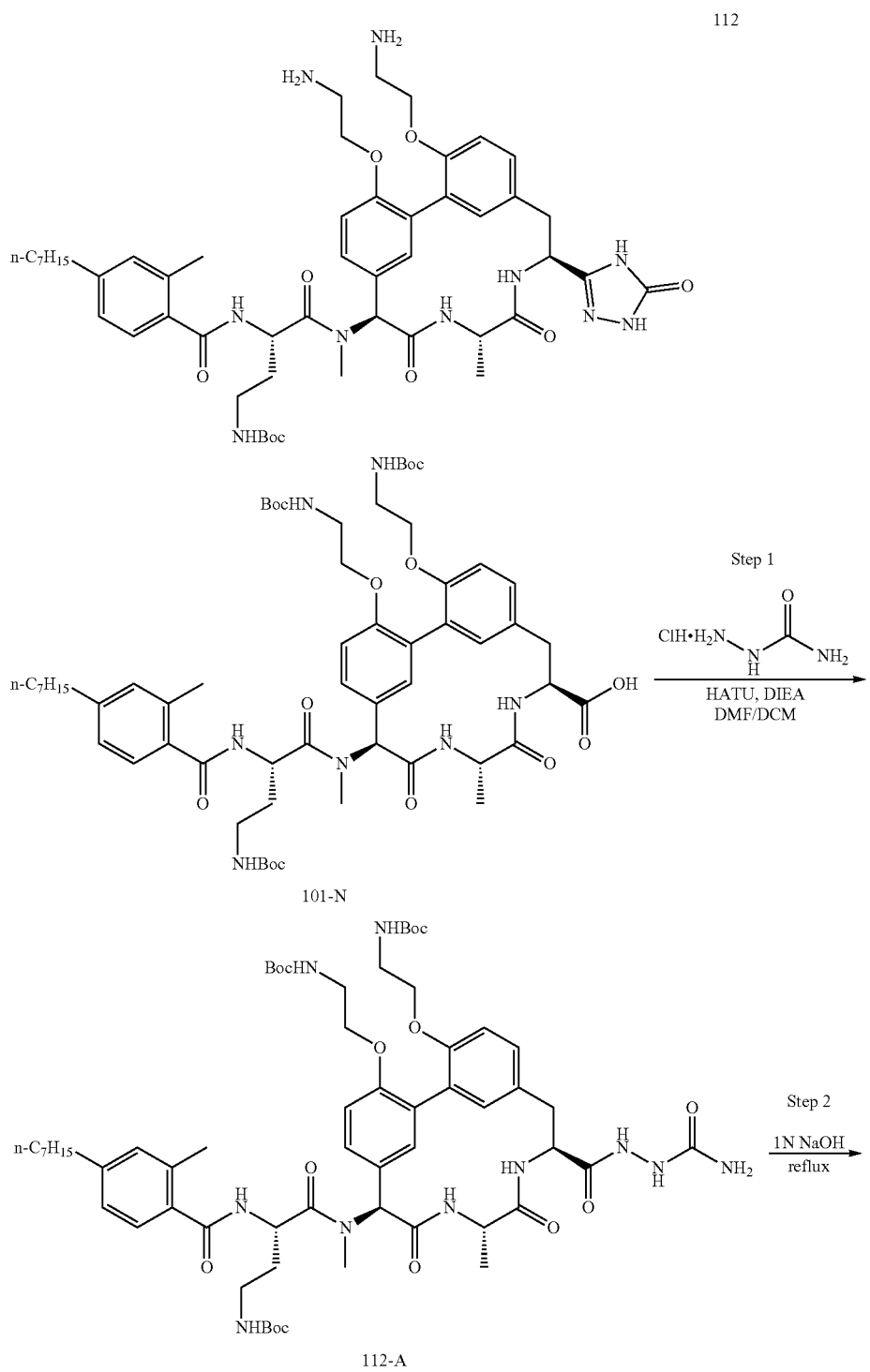

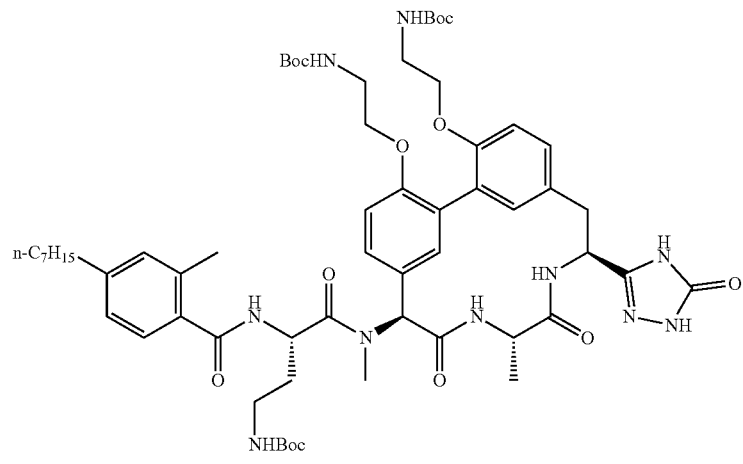

112-B

Step 1: To a stirred solution of Compound 101-N (300.0 mg, 0.26 mmol), hydrazinecarboxamide hydrochloride (60.0 mg, 0.54 mmol) and HATU (153.28 mg, 0.40 mmol) in DCM (6 mL) and N,N-dimethylformamide (2 mL) at 0° C. was added N,N-diisopropylethylamine (104.2 mg, 0.81 mmol). The reaction was stirred at 0° C. to room temperature for 12 h and DCM was removed under reduced pressure. The residue was poured into water (10 mL) and extracted with EtOAc (40 mL×3). The combined organic layers were washed with brine (10 mL×3), dried over $Na_2SO_4$ and concentrated. The residue was purified by prep-TLC (12% MeOH in DCM, Rf=0.5) to give Compound 112-A (230 mg, 72.9% yield) as a white solid. LCMS (Method 5-95 AB, ESI): $t_R$=0.955 min, $[M+H]^+$=1173.8.

Step 2: A mixture of Compound 112-A (180.0 mg, 0.15 mmol) in 1N NaOH (36 mL, 36 mmol) was stirred at 100° C. for 4 h. upon reaction completion, the mixture was cooled to room temperature and extracted with EtOAc (50 mL×3). The combined organic layers were washed with brine (25 mL×3), dried over $Na_2SO_4$ and concentrated. The residue was purified by prep-TLC (10% methanol in DCM, Rf=0.22) to give Compound 112-B (75 mg, 42.3% yield) as a white solid. LCMS (Method 5-95 AB, ESI): $t_R$=0.953 min, $[M+H]^+$=1155.7.

Compound 112 (formic acid salt) was prepared as a white solid utilizing the TFA/TFIP Boc-hydrolysis methods in Example 9. LCMS (Method 5-95 AB, ESI): $t_R$=0.742 min, $[M+H]^+$=855.6.

Example 18: Synthesis of Compound 113

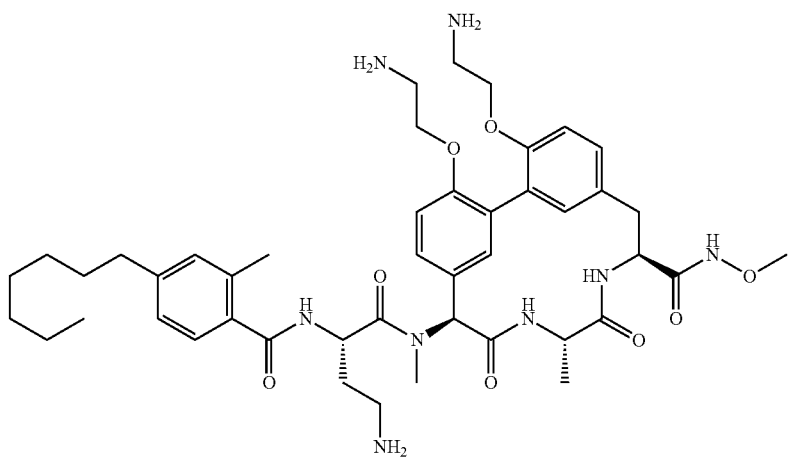

113

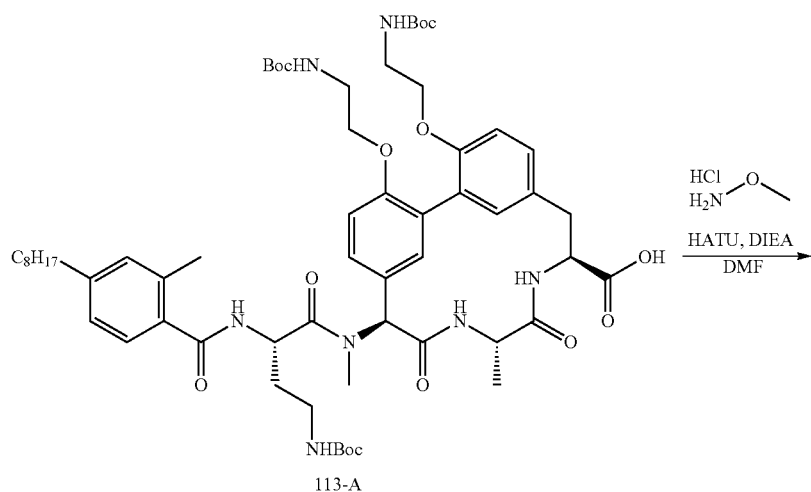

113-A

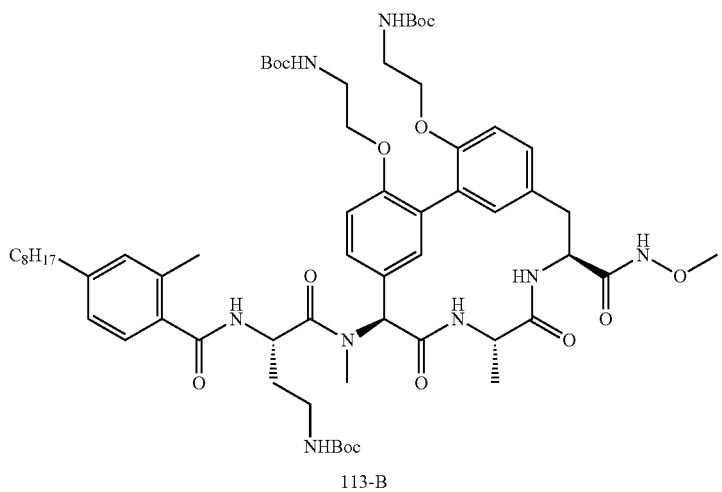

113-B

Compound 113-A was prepared utilizing the methods in Example 6 except 2-methyl-4-octylbenzoic acid was used in the amide coupling step.

To a solution of Compound 113-A (120 mg, 0.11 mmol) in N,N-dimethylformamide (3 mL) and N,N-diisopropylethylamine (0.19 mL, 1.06 mmol) was added HATU (403.6 mg, 1.06 mmol). The reaction mixture was stirred at 0° C. for 1 h and diluted with water (10 mL). The mixture was filtered and the filter cake was dissolved in methanol (10 mL). The solution was concentrated and the residue was purified by prep-TLC (5% methanol in dichloromethane) to give Compound 113-B (70 mg, 0.06 mmol, 56.9% yield) as a white solid. LCMS (5-95AB_1.5 min_ELSD): $t_R$=1.152 min, [M+Na]⁺1181.7.

Compound 113 (formic acid salt) was prepared in 25% yield as a white solid utilizing the TFA/TFIP Boc-hydrolysis methods in Example 9. LCMS (5-95AB_1.5 min_ELSD): $t_R$=0.782 min, [M+H]⁺=859.4. ¹H NMR (400 MHz, CD₃OD) δ 8.95 (d, J=8.0 Hz, 1H), 8.38 (d, J=8.8 Hz, 1H), 7.40-7.30 (m, 2H), 7.30-7.16 (m, 2H), 7.16-7.05 (m, 3H), 6.90-6.75 (m, 2H), 6.33 (s, 1H), 5.15-5.10 (m, 1H), 4.85-4.70 (m, 2H), 4.40-4.20 (m, 4H), 3.71 (s, 3H), 3.45-3.30 (m, 2H), 3.25-3.10 (m, 6H), 2.91 (s, 3H), 2.65-2.55 (m, 2H), 2.42 (s, 3H), 2.35-2.20 (m, 1H), 2.20-2.05 (m, 1H), 1.65-1.55 (m, 2H), 1.40-1.20 (m, 13H), 0.95-0.85 (m, 3H).

Example 19: Synthesis of Compound 114
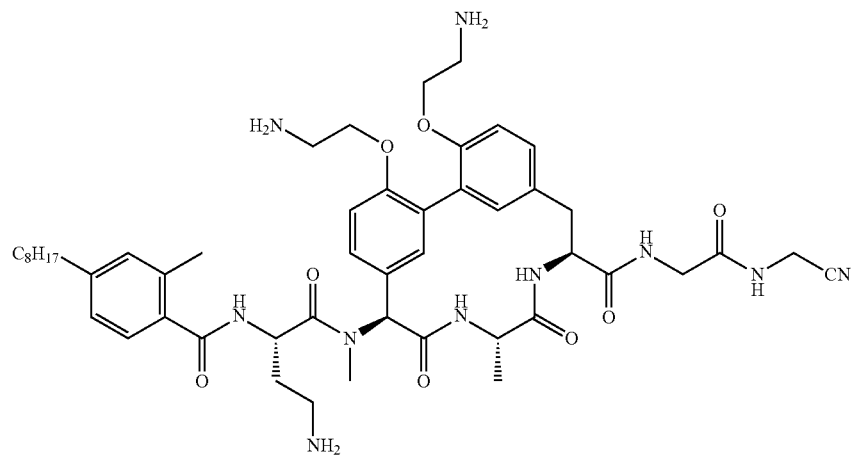
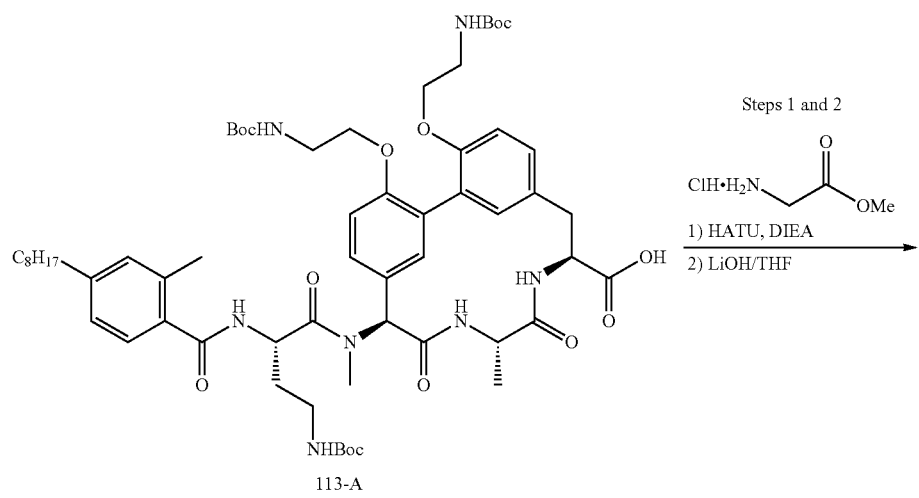

-continued
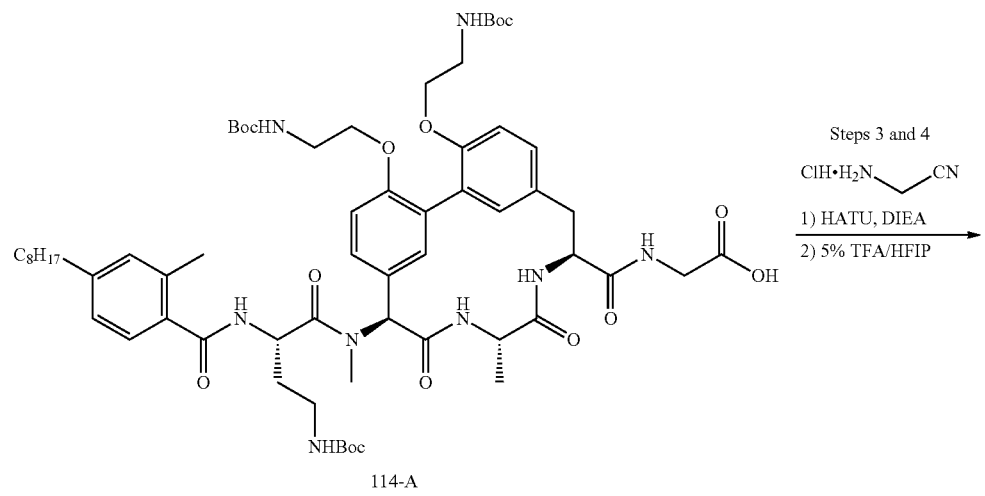
114-A
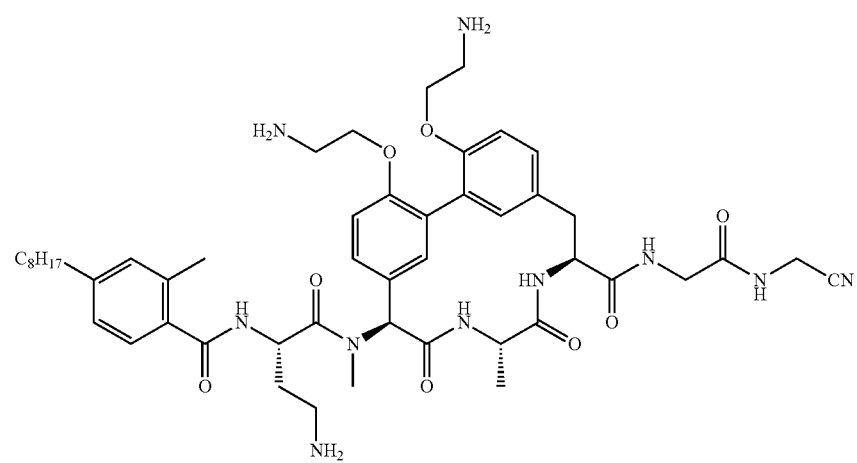
114-A

Steps 1 and 2: Starting from Compound 113-A (Example 18), HATU coupling with methyl 2-aminoacetate (Example 5) and LiOH ester hydrolysis (Example 6) afforded Compound 114-A.

Steps 3 and 4: Starting from Compound 114-A, HATU coupling with 2-aminoacetonitrile hydrochloride (Example 5) and global Boc de-protection with TFA/HFIP (Example 6) afforded Compound 114 (formic acid salt) as a white solid. LCMS (Method 5-95 AB, ESI): $t_R$=0.651, $[M+H]^+$=925.5.

Example 20: Synthesis of Compound 115

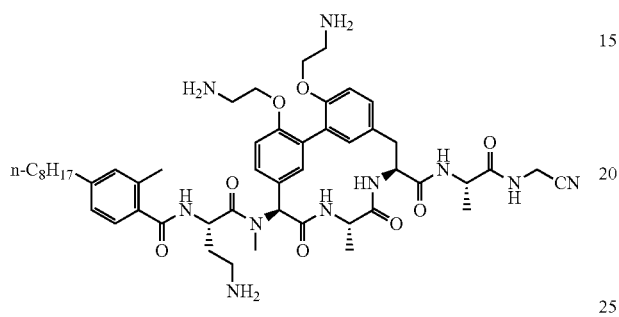

115

Compound 115 (formic acid salt) was prepared as a white solid utilizing the methods in Example 19 from Compound 107-A and 2-aminoacetonitrile hydrochloride. LCMS (Method 5-95 AB, ESI): $t_R$=0.649, $[M+H]^+$=939.6.

Example 21: Synthesis of Compound 116

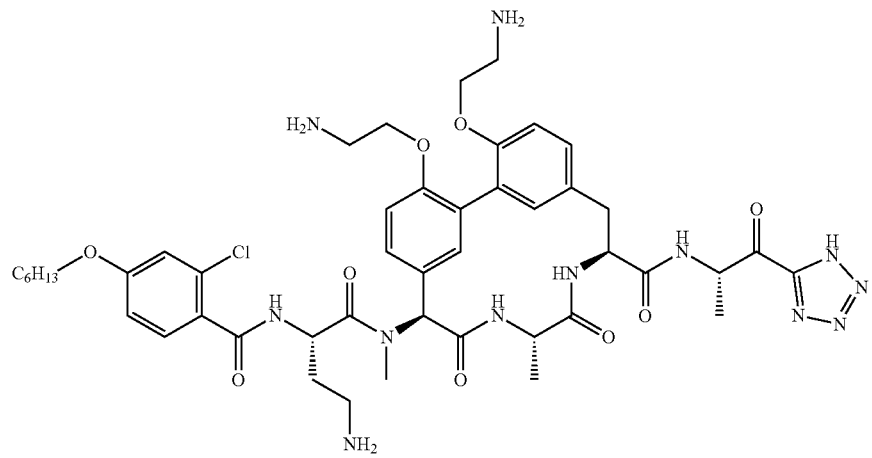

116

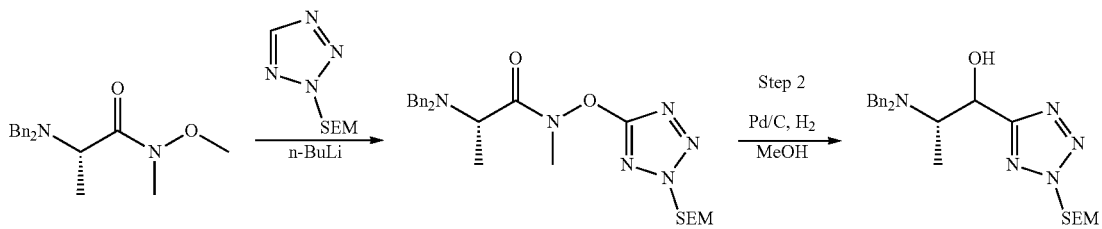

Synthesis of (2S)-2-amino-1-(2-((2-(trimethylsilyl)ethoxy)methyl)-2H-tetrazol-5-yl)propan-1-ol Step 1: To a stirred solution of 2-((2-(trimethylsilyl)ethoxy)methyl)-2H-tetrazole (10 g, 50.1 mmol) in THF (200 mL) was added 2.5M n-BuLi in hexane (21.7 mL) dropwise at −78° C. The mixture was stirred at the same temperature for 30 min. To a stirred solution of (S)-2-(dibenzylamino)-N-methoxy-N-methylpropanamide (13 g, 41.8 mmol) in 100 mL THF was added to the above-mentioned solution at −78° C., and the resulting mixture was slowly allowed to reach room temperature over a period of 2 h. The mixture was then quenched by addition of saturated NH$_4$Cl solution (100 mL), which was extracted with EtOAc (3×100 mL). The combined organic extracts were washed with brine, dried over MgSO$_4$, and concentrated. The residue was purified by flash column (0-25% EtOAc in petroleum ether) to afford (S)-2-(dibenzylamino)-1-(2-((2-(trimethylsilyl)ethoxy)methyl)-2H-tetrazol-5-yl)propan-1-one (18.1 g, 95.9% yield) as a light yellow oil.

Step 2: Standard hydrogenation condition (Pd/C, 1 atm H$_2$, Example 4) was applied to (S)-2-(dibenzylamino)-1-(2-((2-(trimethylsilyl)ethoxy)methyl)-2H-tetrazol-5-yl)propan-1-one (18.1, 40.1 mmol) to afford (2S)-2-amino-1-(2-((2-(trimethylsilyl)ethoxy)methyl)-2H-tetrazol-5-yl)propan-1-ol (6.5 g, 59.3% yield) as colorless oil after HPLC purification.

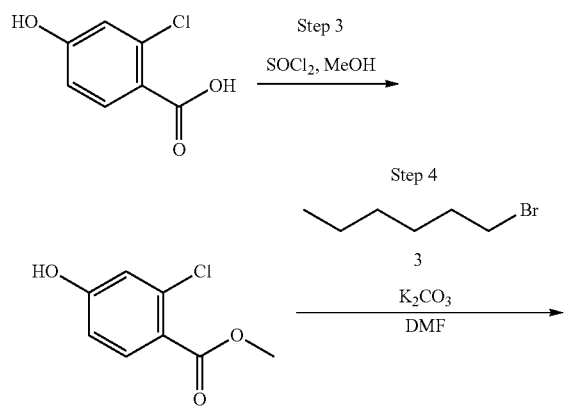

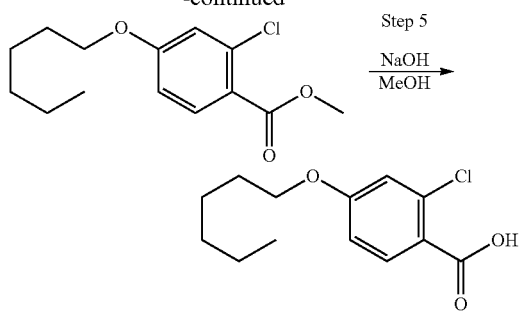

Synthesis of 2-chloro-4-(hexyloxy)benzoic acid

Step 3: To a solution of 2-chloro-4-hydroxybenzoic acid (200.0 mg, 1.16 mmol) in methanol (5 mL) was added thionyl chloride (413.6 mg, 3.48 mmol) dropwise at 0° C. The reaction mixture was stirred at 70° C. for 2 h and concentrated. The residue was diluted with water (15 mL) and extracted with EtOAc (15 mL×2). The organic layers were combined and washed with water (30 mL×2) and brine (20 mL). The organic layers were separated, dried over Na$_2$SO$_4$ and concentrated to obtain methyl 2-chloro-4-hydroxy-benzoate (200 mg, 92.5% yield) as a yellow solid which was used directly without further purification.

Step 4: To a solution of methyl 2-chloro-4-hydroxybenzoate (730 mg, 3.91 mmol) in N,N-dimethylformamide (10 mL) was added 1-bromohexane (6.46 g, 39.1 mmol) and potassium carbonate (5.41 g, 39.12 mmol). The mixture was stirred at 20° C. for 4 h, diluted with water (20 mL) and extracted with EtOAc (20 mL×2). The organic layers were combined and washed with water (40 mL×4) and brine (20 mL). The organic layers were separated, dried over Na$_2$SO$_4$ and concentrated. The residue was purified by preparative TLC (5% EtOAc in petroleum ether) to obtain methyl 2-chloro-4-(hexyloxy)benzoate (800 mg, 75.5% yield) as a yellow oil.

Step 5: Methyl 2-chloro-4-(hexyloxy)benzoate (800 mg, 2.95 mmol) was hydrolyzed previously described (General Method NaOH) to give crude 2-chloro-4-(hexyloxy)benzoic acid (670 mg, 88.3% yield) as a yellow solid. LCMS (Method 5-95 AB, ESI): $t_R$=0.926 min, [M+H]$^+$=256.9.

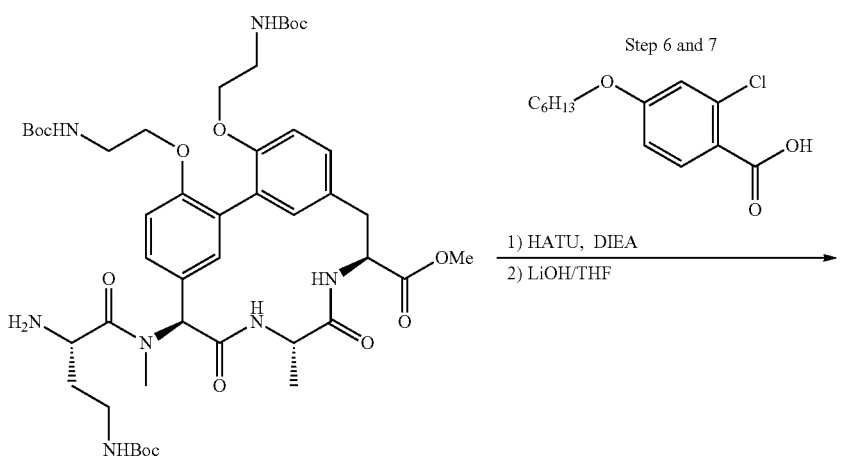

101-I

-continued
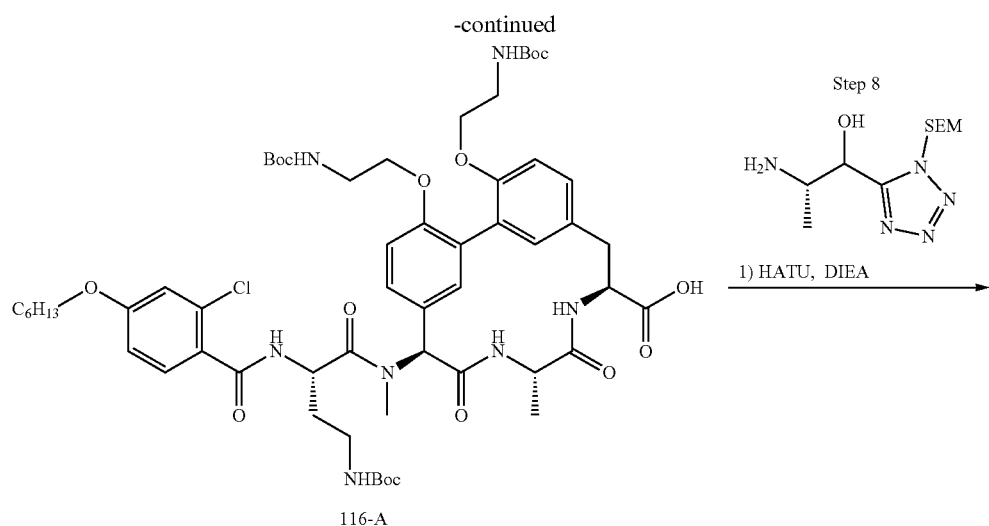
116-A
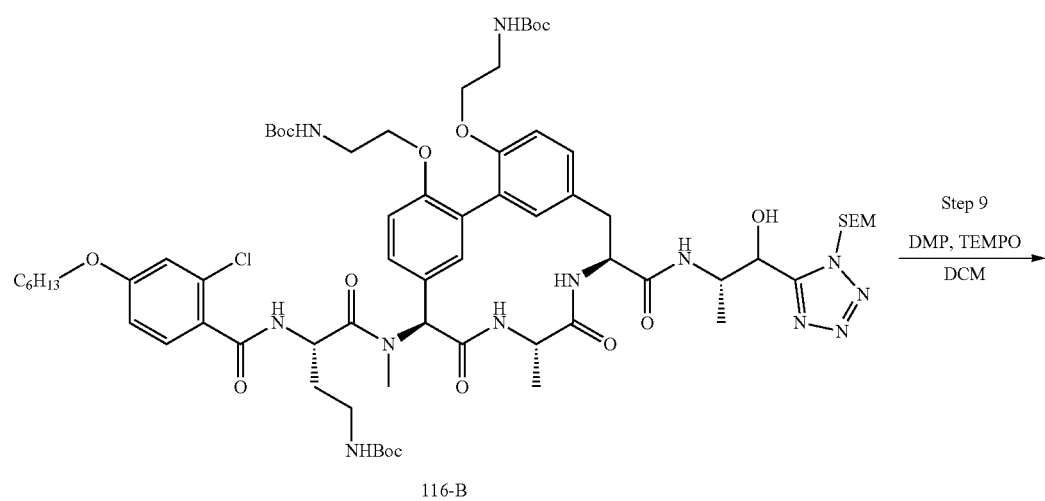
116-B
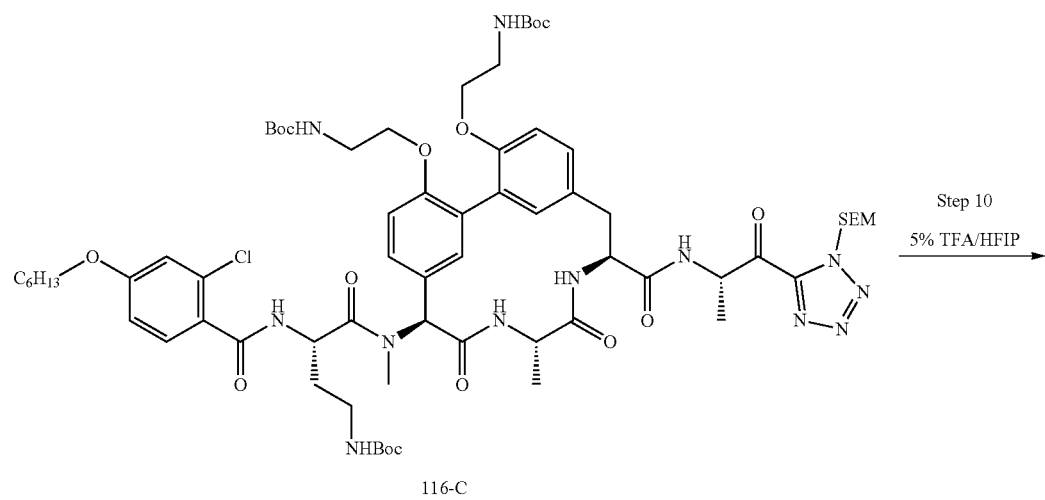
116-C

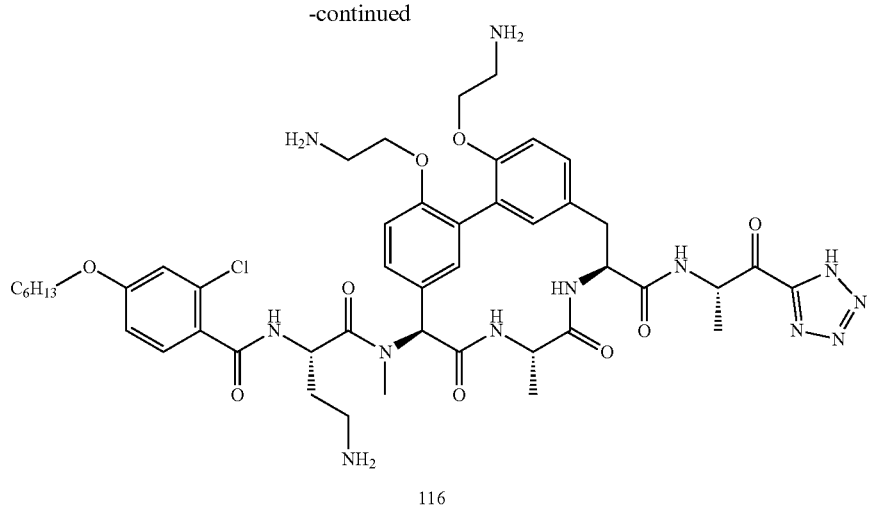

116

Steps 6 and 7: Compound 116-A was prepared utilizing the HATU coupling method (Example 5) from Compound 101-I (Example 5) and 2-chloro-4-(hexyloxy)benzoic acid followed by the LiOH ester hydrolysis method (Example 6). LCMS (Method 5-95 AB, ESI): $t_R$=0.938 min, $[M+Na]^+$= 1161.5.

Step 8: To a solution of Compound 116-A (330 mg, 0.29 mmol) in DCM (10 mL) was added (2S)-2-amino-1-(2-((2-(trimethylsilyl)ethoxy)methyl)-2H-tetrazol-5-yl)propan-1-ol (317 mg, 1.16 mmol), HATU (220 mg, 0.58 mmol) and DIPEA (201 µL, 1.16 mmol) at 0° C. The mixture was warmed up to room temperature while stirring and stirred at the same temperature for 1 h. The volatiles were removed and the residue was taken up by EtOAc (50 mL), which was washed with brine (50 mL×3). The organic layer was dried over $Na_2SO_4$, concentrated and the residue was purified by Prep-TLC to afford Compound 116-B (300 mg, 74.3% yield) as a white solid. LCMS (Method 5-95 AB, ESI): $t_R$=1.027 min, $[M+H]^+$=1393.6.

Step 9: To a solution of Compound 116-B (270 mg, 0.19 mmol) in DCM (5 mL) was added DMP (246 mg, 0.58 mmol) and TEMPO (30 mg, 0.19 mmol) at 0° C. The mixture was warmed to room temperature while stirring and stirred at the same temperature for 16 h. The mixture was added with aq. $Na_2S_2O_3$ (2M, 20 mL), which was extracted with DCM (25 mL×3). The organic layers were dried over $MgSO_4$, concentrated and the residue was purified by prep-TLC to give Compound 116-C (250 mg 92.7% yield) as a white solid. LCMS (Method 5-95 AB, ESI): $t_R$=1.037 min, $[M+H]^+$=1391.8.

Step 10: A solution of 5% TFA in HFIP (2.0 mL) and Compound 116-C (230 mg, 0.17 mmol) was stirred at room temperature for 16 h. The volatiles were removed and the residue was dissolved in acetonitrile, which was neutralized with solid $NaHCO_3$. The filtrate was concentrated and purified by Prep-HPLC to afford Compound 116 (55 mg, 33% yield) as a white solid. LCMS (Method 5-95 AB, ESI): $t_R$=0.619 min, $[M+H]^+$=963.5.

Example 22: Synthesis of Compound 117

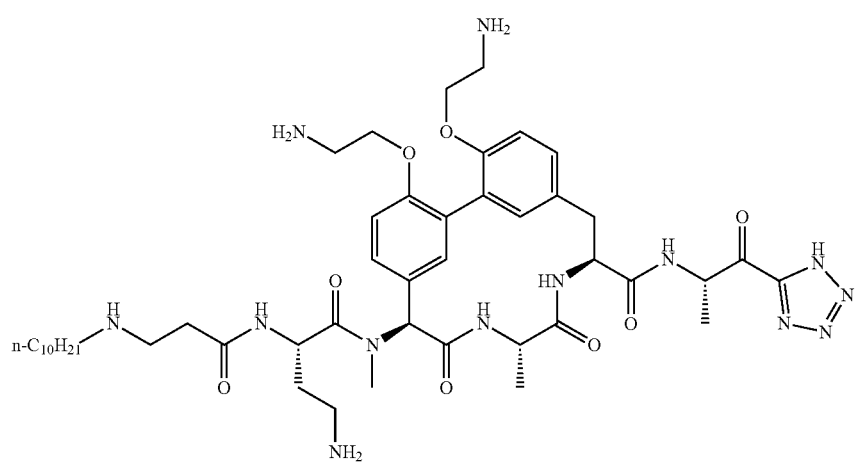

117

-continued

Step 1

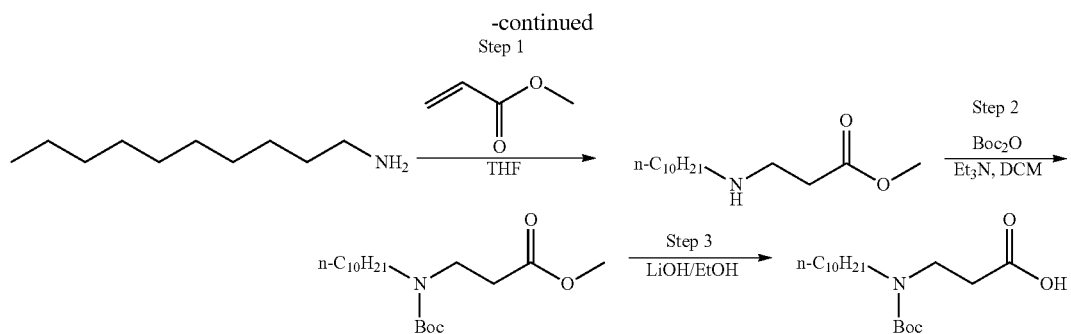

Step 1: To a solution of methyl acrylate (2.2 g, 26 mmol) in THF (20 mL) was added a solution of decan-1-amine (6 g, 38 mmol) in THF (20 mL) at 0° C. The reaction mixture was stirred at 30° C. for 48 h. The resulting solution was concentrated to obtain methyl 3-(decylamino)propanoate (6.4 g).

Step 2: The boc-protection of an amine is described. To a solution of crude methyl 3-(decylamino)propanoate (6.4 g, 15 mmol) and $Et_3N$ (4 g, 40 mmol) in DCM (30 mL) was added dropwise a solution of $Boc_2O$ (5.7 g, 26 mmol) in DCM (20 mL) at 0° C. The reaction mixture was then allowed to warm to 30° C. gradually and stirred for 18 h. After the reaction was completed, $H_2O$ (50 mL) was added and the resulting aqueous layer was further extracted with DCM (50 mL×2). The combined organic layers were concentrated and the residue was purified by silica gel column (PE/EtOAc=50/1~20/1) to give methyl 3-((tert-butoxycarbonyl)(decyl)amino)propanoate (6.5 g, 73%) as a colorless oil.

Step 3: To a solution of methyl 3-((tert-butoxycarbonyl)(decyl)amino)propanoate (8.2 g, 23.9 mmol, crude) in EtOH (40 mL) was added a solution of LiOH (1.15 g, 48 mmol) in $H_2O$ (20 mL) at 0° C. The reaction mixture was then allowed to warm to 30° C. gradually and stirred for 18 h. After the reaction was complete, EtOH was removed under reduced pressure. The remaining aqueous solution was then adjusted to pH=2~3 with 6 N HCl, followed by the extraction with EtOAc (50 mL×3). The combined EtOAc layers were dried over $Na_2SO_4$, and concentrated to give 3-((tert-butoxycarbonyl)(decyl)amino)propanoic acid (7 g, 88.6%) as a colorless oil. $^1H$ NMR (400 MHz, $CDCl_3$) δ 3.47-3.43 (t, J=6.8 Hz, 2H), 3.19-3.15 (t, J=7.2 Hz, 2H), 2.61 (brs, 2H), 1.51-1.39 (m, 11H), 1.24-1.22 (m, 14H), 0.88-0.84 (t, J=6.8 Hz, 3H).

Compound 117 (formic acid salt) was prepared utilizing the methods in Example 6 using 3-((tert-butoxycarbonyl)(decyl)amino)propanoic acid and Example 21 using (2S)-2-amino-1-(2-((2-(trimethylsilyl)ethoxy)methyl)-2H-tetrazol-5-yl)propan-1-ol. LCMS (Method 5-95 AB, ESI): $t_R$=0.696, $[M+H]^+$=934.6; $^1H$ NMR (400 MHz, MeOH-$d_4$) δ 8.45 (brs, 2H), 7.29-7.15 (m, 2H), 7.13-7.00 (m, 2H), 6.86-6.76 (m, 1H), 6.65 (brs, 1H), 6.31 (s, 1H), 5.51-5.35 (m, 2H), 4.82-4.76 (m, 2H), 4.31-3.99 (m, 4H), 3.51-3.42 (m, 1H), 3.28-3.14 (m, 4H), 3.13-2.96 (m, 5H), 2.87-2.72 (m, 1H), 2.82 (s, 3H), 2.71-2.62 (m, 1H), 2.18-2.00 (m, 2H), 2.00-1.88 (m, 2H), 1.79-1.64 (m, 3H), 1.55-1.46 (m, 3H), 1.45-1.18 (m, 16H), 0.89 (t, J=6.4 Hz, 3H).

Example 23: Synthesis of Compound 118

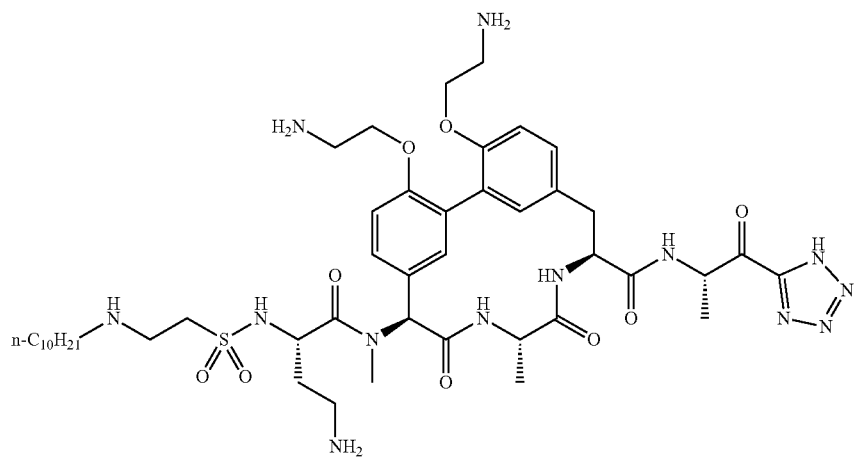

118

-continued
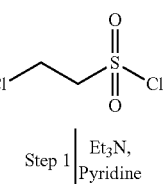
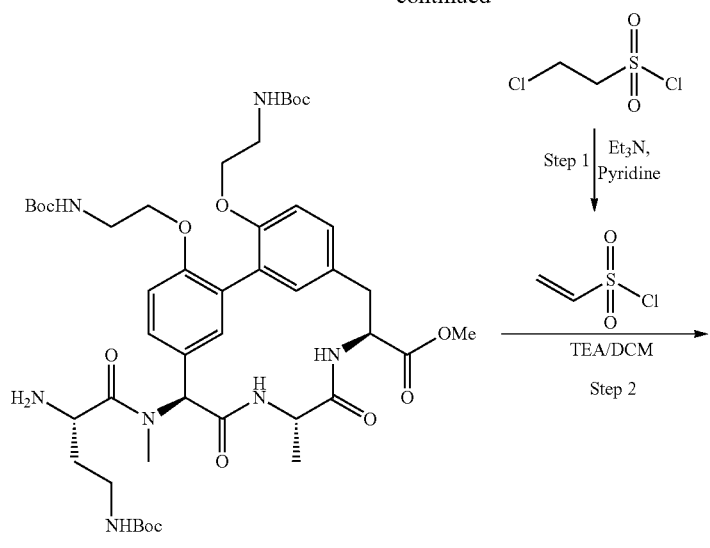
101-I
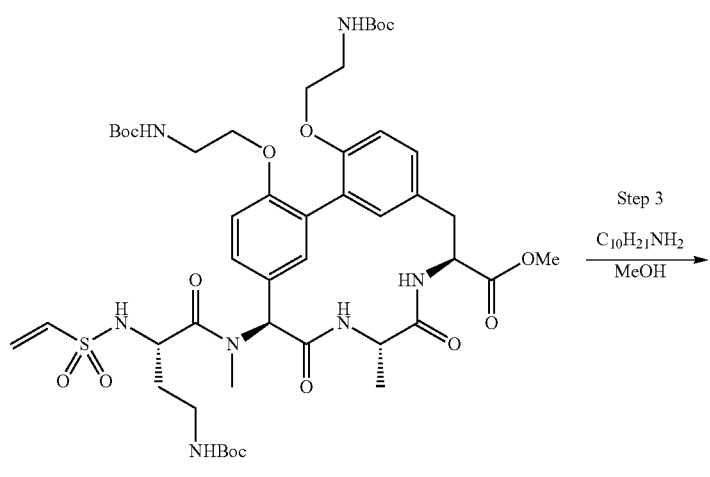
118A
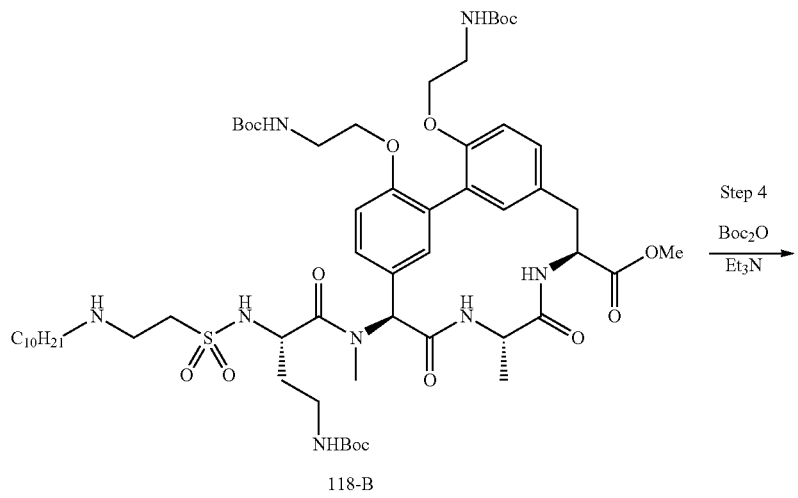
118-B

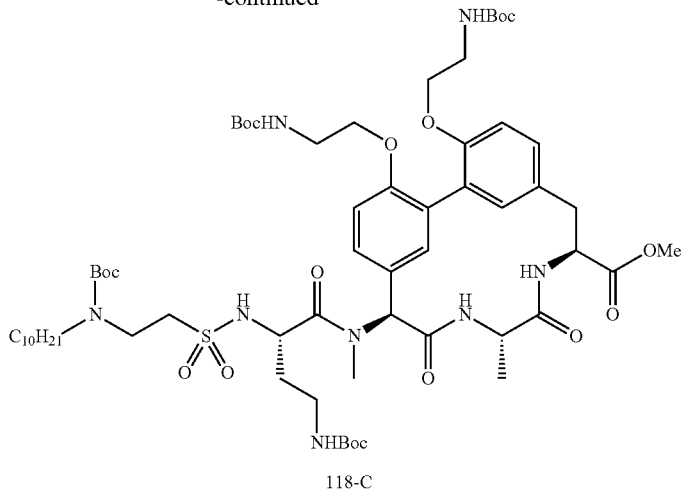

118-C

Step 1: To a solution of 2-chloroethanesulfonyl chloride (0.64 mL, 6.1 mmol) in DCM (10 mL) was added pyridine (0.97 g, 12.2 mmol) at −78° C. and the resulting mixture was stirred at the same temperature for 20 min. After that, the reaction was warmed to room temperature while stirring and stirred for another 20 min at the same temperature.

Step 3: To a solution of Compound 101-I (Example 5) (300 mg, 0.33 mmol) and Et$_3$N (332 mg, 3.28 mmol) in DCM (5 mL) was added the above solution at 0° C. The resulting mixture was warmed to room temperature and stirred for 1 h at the same temperature. After that, the reaction was added with DCM (50 mL), which was washed with saturated citric acid, saturated NaHCO$_3$ and brine (50 mL each). The organic layer was dried over anhydrous Na$_2$SO$_4$, concentrated and the residue was purified by pre-TLC to afford Compound 118-A (250 mg, 76% yield) as a yellow solid. LCMS (5-95 AB, ESI): t$_R$=0.926, M+Na$^+$=1026.7.

To a solution of Compound 118-A (250 mg, 0.25 mmol) in MeOH (6 mL) was added 1-aminodecane (78 mg, 0.50 mmol) at 0° C. and the mixture was warmed and stirred at room temperature for 16 h. The volatiles were removed to afford Compound 117-B.

Typical Boc protection condition (Boc$_2$O, Et$_3$N, DCM, Example 22) was applied to Compound 118-B to afford Compound 118-B (230 mg, 73.3% yield) as a white solid. LCMS (Method 5-95 AB, ESI): t$_R$=1.059 min, [M+Na]$^+$= 1283.3.

Compound 118 (formic acid salt) was prepared as a white solid utilizing the methods in Example 21. LCMS (Method 5-95 AB, ESI): t$_R$=0.658, [M+H]$^+$=970.6; $^1$H NMR (400 MHz, MeOH-d$_4$) δ 8.45 (brs, 2H), 7.20-7.00 (m, 3H), 6.80-6.60 (m, 3H), 6.34 (s, 1H), 5.40-5.30 (m, 1H), 4.80-4.75 (m, 1H), 4.65-4.50 (m, 2H), 4.30-4.10 (m, 4H), 3.60-3.35 (m, 5H), 3.30-3.20 (m, 3H), 3.15-2.95 (m, 5H), 2.80-2.70 (m, 3H), 2.60-2.56 (m, 1H), 2.20-1.80 (m, 4H), 1.70-1.60 (m, 3H), 1.50-1.20 (m, 17H), 0.88 (t, J=5.2 Hz, 3H).

Example 24: Synthesis of Compound 119-H

119-H

-continued
Step 1
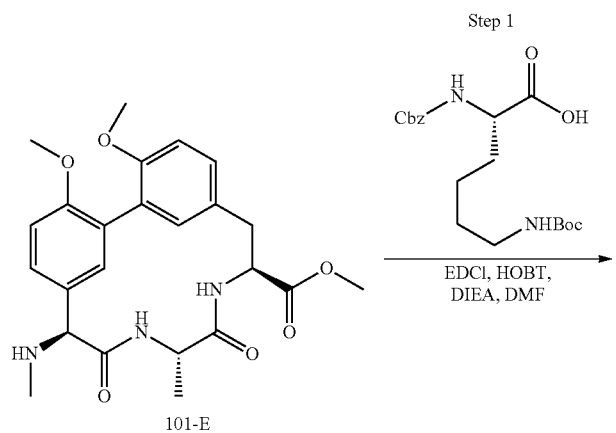
Step 2
Pd/C, H$_2$
THF
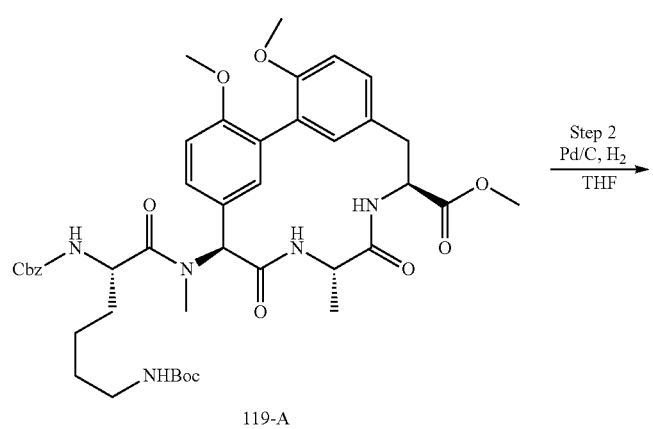
Step 3
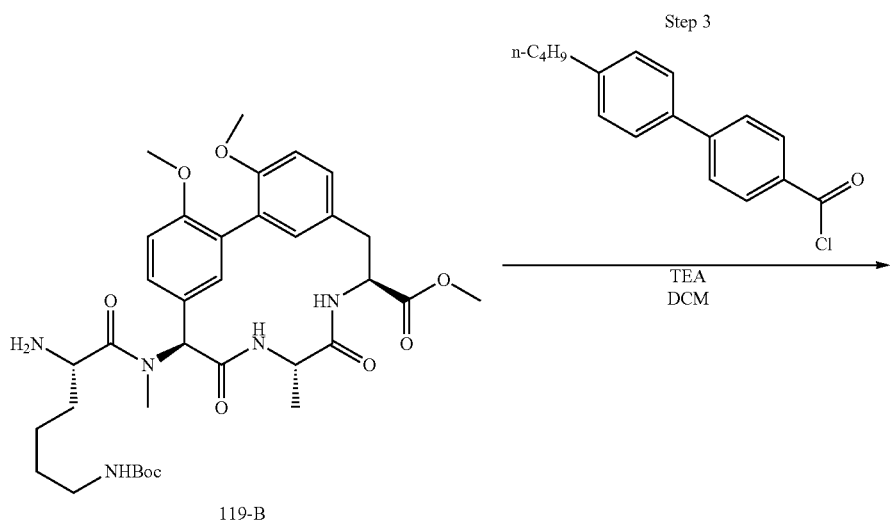

-continued
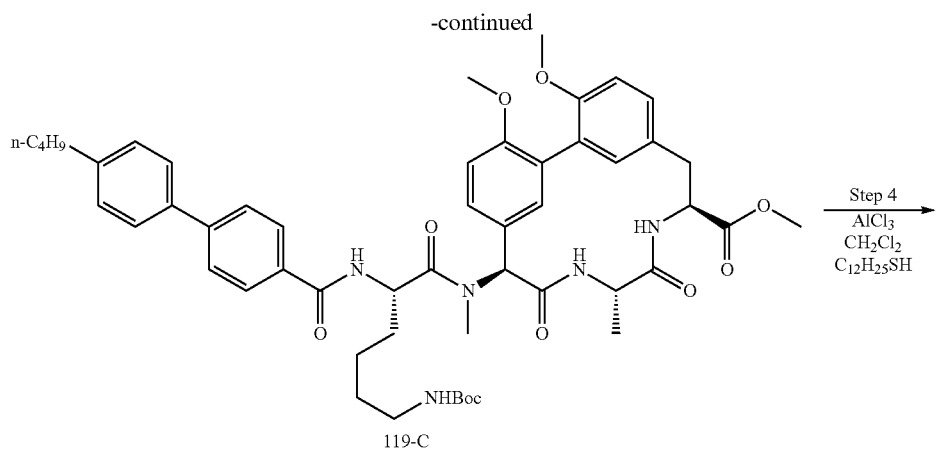
119-C
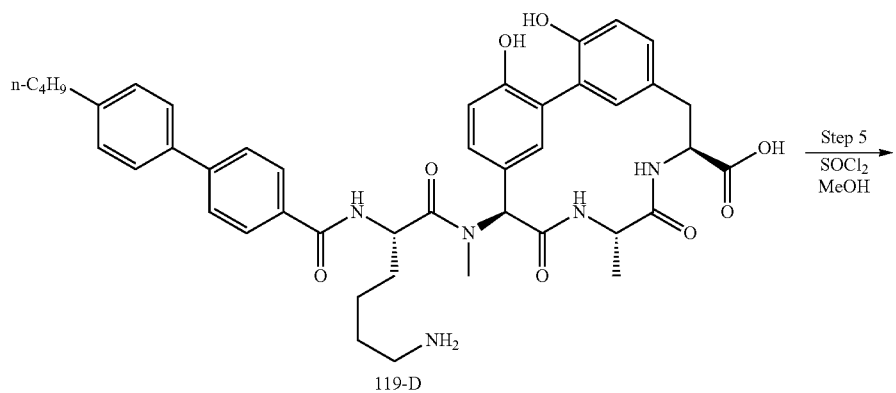
119-D
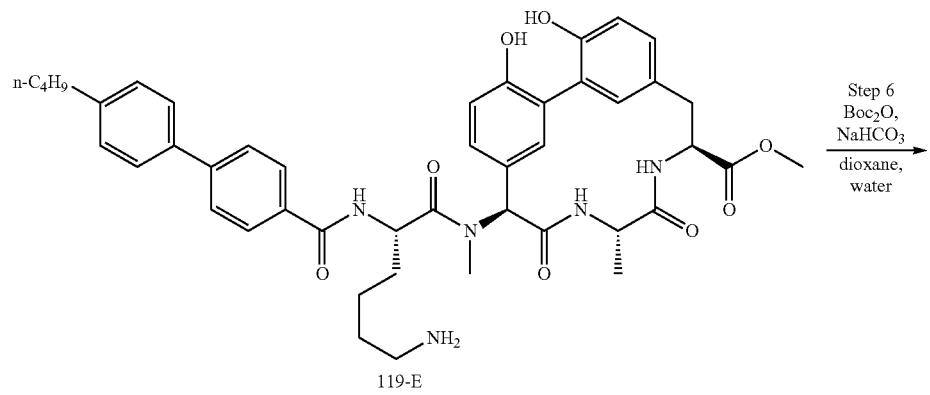
119-E
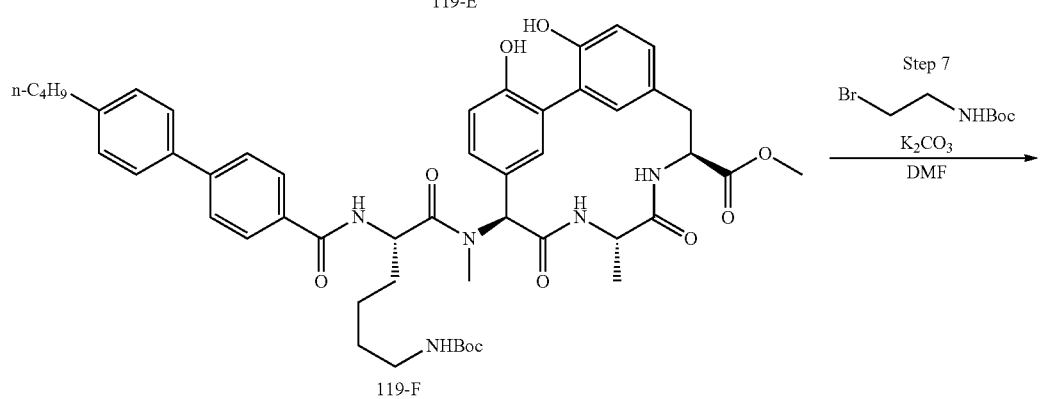
119-F

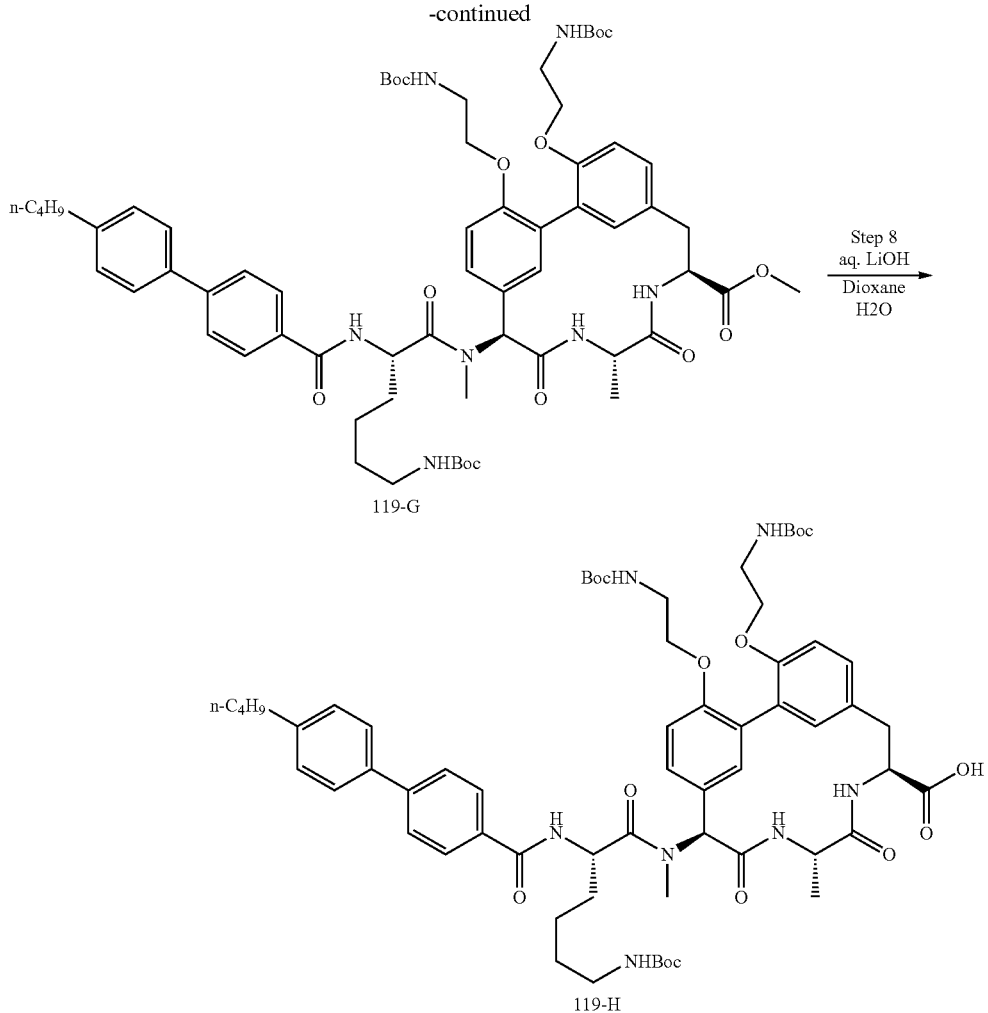

Step 1: To a solution of Compound 101-E (800 mg, 1.76 mmol) in DMF (15 mL) was added (S)-2-(((benzyloxy) carbonyl)amino)-6-((tert-butoxycarbonyl)amino)hexanoic acid (735 mg, 1.93 mmol), 3-[(E)-ethylazo]-N,N-dimethylpropan-1-amine hydrochloride (946.8 mg, 5.27 mmol), 1-hydroxybenzotriazole (711.9 mg, 5.27 mmol), and N,N-diisopropylethylamine (681 mg, 5.27 mmol). The mixture was stirred at 30° C. for 16 h. The mixture was poured into water (30 mL). The precipitate was filtered, washed with water, re-dissolved in methanol, and concentrated to give Compound 119-A (1200 mg, 1.45 mmol, 83.5% yield) as a yellow solid.

Step 2: To a solution of Compound 119-A (1200 mg, 1.47 mmol) in methanol (15 mL) was added Pd/C (200.0 mg, 1.47 mmol), and the mixture was stirred at 30° C. under hydrogen (50 psi) for 16 h. The catalyst was filtered off and the filtrate was concentrated to give Compound 119-B (900 mg, 81.6% yield) as a white solid. LCMS (5-95AB_1.5 min_1500): $t_R$=0.782 min, [M+H]$^+$684.4.

Step 3: The coupling of an acid chloride to an amine is described for this example. A mixture of 4-(4-butylphenyl) benzoic acid (200 mg, 0.79 mmol) in thionyl chloride (5.0 mL) was stirred at 60° C. for 16 h. The solution was concentrated and dissolved in dichloromethane (2 mL). To the solution of Compound 119-B (500 mg, 0.73 mmol) and triethylamine (74 mg, 0.73 mmol) in dichloromethane (15 mL) was added the above solution of 4-(4-butylphenyl) benzoyl chloride in dichloromethane. The reaction mixture was stirred at 25° C. for 3 h. The reaction was concentrated to dryness and the residue was purified by flash column chromatography (eluted with 5% dichloromethane in methanol). The desired fractions were concentrated to afford Compound 119-C (650 mg, 96.6% yield) as a white solid. LCMS (5-95AB/1.5 min): $t_R$=0.951 min, [M+H]$^+$921.4. Alternatively, this coupling reaction can be performed using 4'-butyl-[1,1'-biphenyl]-4-carboxylic acid using General Method HATU conditions in Example 4.

Step 4: A mixture of aluminium chloride (2.8 g, 21.19 mmol) and 1-dodecanethiol (4.3 g, 21.19 mmol) in dichloromethane (12 mL) was stirred at 26° C. for 5 min, and then cooled to 0° C. Then Compound 119-C (650 mg, 0.71 mmol) was added slowly. The solution was stirred at 26° C. for 2 h. The solution was quenched by 1N hydrochloride acid, and filtered. The filter cake was dried to afford crude Compound 119-D as a white solid. LCMS (5-95AB/1.5 min): $t_R$=0.828 min, [M+H]$^+$=778.4.

Step 5: A solution of Compound 119-D (500 mg, 0.64 mmol) and thionyl chloride (229 mg, 1.93 mmol) in methanol (10 mL) was stirred at 60° C. for 1 h. The solution was concentrated to afford Compound 119-E (500 mg, 98.2% yield) as a yellow solid. LCMS (5-95AB/1.5 min): $t_R$=0.856 min, [M+H]$^+$=792.8.

Step 6: To the solution of Compound 119-E (500 mg, 0.63 mmol) and sodium bicarbonate (10.6 mg, 0.13 mmol) in 1,4-dioxane (6 mL) and water (2 mL) was added di-tert-butyl dicarbonate (138 mg, 0.63 mmol). The reaction was concentrated to dryness and the residue was taken up in ethyl acetate (50 mL), washed with water (20 mL×2), brine (10 mL), dried (sodium sulfate) and concentrated. The crude product was purified by flash column chromatography (eluted with 5% dichloromethane in methanol) to afford Compound 119-F (500 mg, 88.8% yield) as a white solid. LCMS (5-95AB/1.5 min): $t_R$=1.048 min, [M+H]$^+$=892.4.

Step 7: A mixture of Compound 119-F (500 mg, 0.56 mmol), tert-butyl 2-bromoethylcarbamate (1.25 g, 5.61 mmol) and potassium carbonate (2.32 g, 16.82 mmol) in N,N-dimethylformamide (20 mL) was stirred at 26° C. for 96 h. The reaction was quenched with ice-water (5 mL), and the mixture was taken up in ethyl acetate (20 mL). The organic layer was washed with water (20 mL×2) and brine (10 mL), dried (sodium sulfate), and concentrated. The crude was purified by flash column chromatography (eluted with ethyl acetate). The desired fractions were concentrated to afford Compound 119-G (450 mg, 68.1% yield) as a colorless oil. LCMS (5-95AB/1.5 min): $t_R$=0.995 min, [M+H]$^+$ 1179.0.

Step 8: A mixture of Compound 119-G (80 mg, 0.07 mmol) and aqueous lithium hydroxide hydrate (0.41 mL, 0.2 mmol, 0.5 M) in 1,4-dioxane (2 mL) and water (1 mL) was stirred at 26° C. for 2 h. The solution was quenched with 5% aqueous potassium bisulfate solution to pH=6, and the mixture was taken up in ethyl acetate (20 mL). The organic solution was washed with water (20 mL×2) and brine (10 mL), dried (sodium sulfate) and concentrated to afford Compound 119-H (50 mg, 63.2% yield) as a white solid. LCMS (5-95AB/1.5 min): $t_R$=1.103 min, [M+H]$^+$ 1164.9.

Step 9

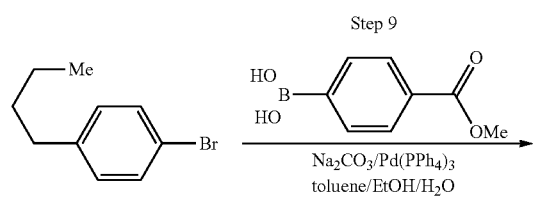

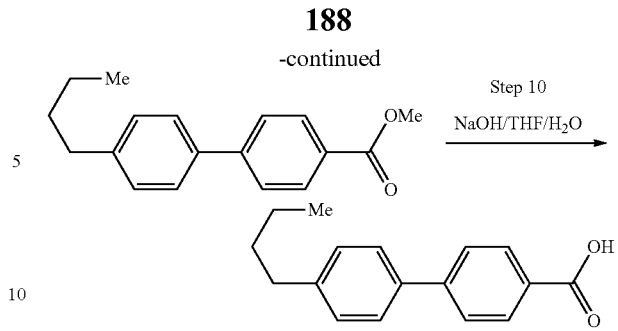

Synthesis of 4'-butyl-[1,1'-biphenyl]-4-carboxylic acid

Step 9: A solution of 1-bromo-4-n-butylbenzene (100 g, 0.472 mol), 4-(methoxycarbonyl)benzeneboronic acid (82.0 g, 0.46 mol), 2 M Na$_2$CO$_3$ (150 g, 1.42 mol) in toluene/EtOH (900 mL/300 mL) was degassed with N$_2$ three times, then Pd(PPh$_3$)$_4$ (27.2 g, 23.6 mmol) was added. The resulting mixture was degassed with N$_2$ three times and then heated to reflux for 5 h. After TLC showed the reaction was complete, toluene and EtOH was removed under vacuum. The residue was extracted with EA (3×). The combined organic layers were washed with brine and dried with Na$_2$SO$_4$. The solvent was removed to give the crude product. The crude product was purified by column chromatography on silica gel eluted with PE:EA (150:1). The solvent was removed to give methyl 4'-butyl-[1,1'-biphenyl]-4-carboxylate (105 g, 86.0%) as a white solid.

Step 10: A mixture of methyl 4'-butyl-[1,1'-biphenyl]-4-carboxylate (89.0 g, 0.332 mol), NaOH (26.6 g, 0.664 mol) in THF/H$_2$O (500 mL/100 mL) was heated to reflux overnight. After TLC showed the reaction was complete, THF was removed. The residue was adjusted pH=3~4 with 2 N HCl solution. The resulting mixture was filtered and the cake was washed with water, and dried to give 4'-butyl-[1,1'-biphenyl]-4-carboxylic acid (60.0 g, 71.1%) as a white solid.

Example 25: Synthesis of Compound 119

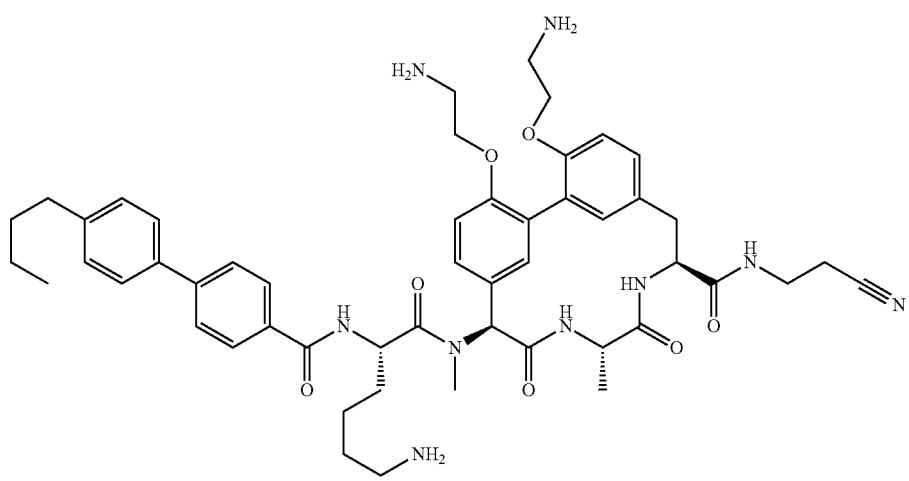

119

189
190
-continued
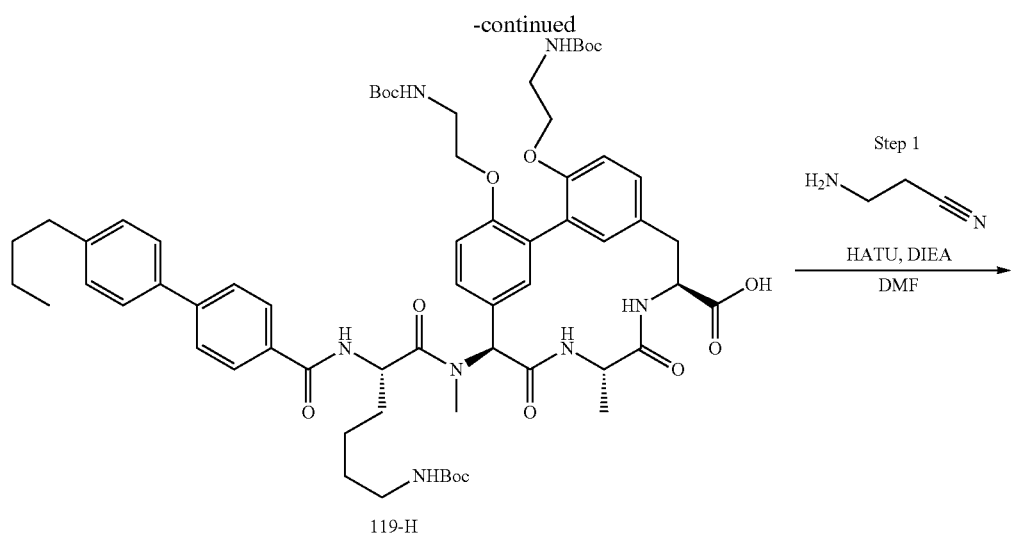
119-H
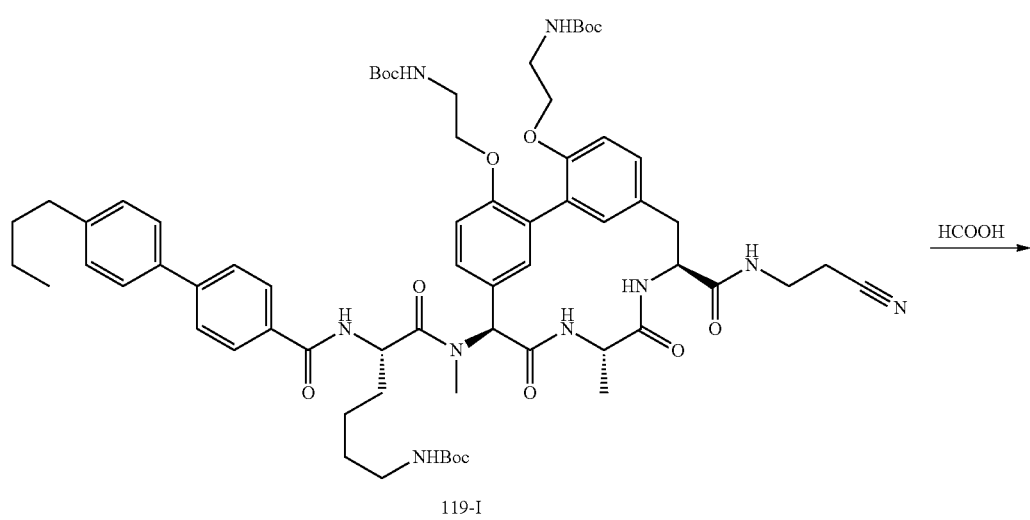
119-I
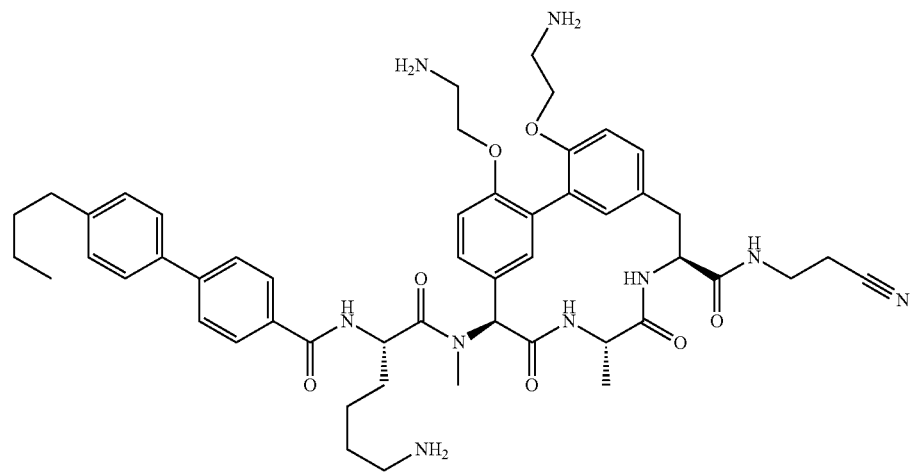
119

To a solution of Compound 119-H (40.0 mg, 0.03 mmol) in DMF (3 mL) were added 3-aminopropionitrile (3.6 mg, 0.05 mmol), HATU (39.2 mg, 0.1000 mmol) and N,N-diisopropylethylamine (13.3 mg, 0.10 mmol). The reaction was stirred at 26° C. for 1 h and poured into water (3 mL). The precipitate was filtered and purified by prep-TLC (5% methanol in DCM, Rf=0.5) to afford Compound 119-1 (28 mg, 0.023 mmol, 66.9% yield) as a white solid. LCMS (Method 5-95 AB, ESI): $t_R$=1.111 min, $[M-Boc+H]^+$= 1117.6.

A solution of Compound 119-I (28.0 mg, 0.0230 mmol) in formic acid (1 mL) was stirred at 26° C. for 1 h and lyophilized. The residue was purified by pre-HPLC (acetonitrile 10-40%/0.2% formic acid in water) to afford Compound 119 (7 mg, 32.6% yield) as a white solid. LCMS (Method 5-95 AB, ESI): $t_R$=0.754 min, $[M+H]^+$=916.5.

Example 26: Synthesis of Compound 120

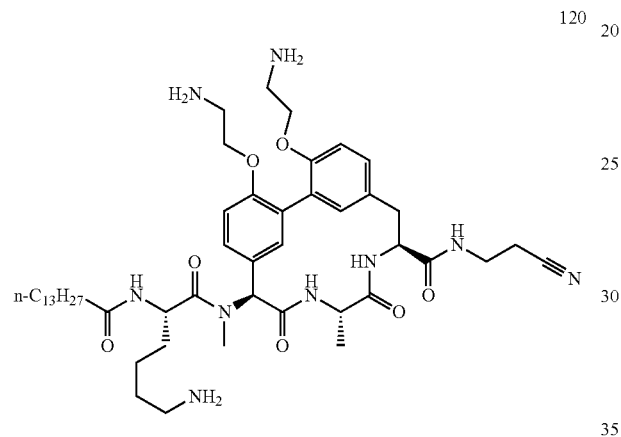

120

Compound 120 (formic acid salt) was prepared as a white solid utilizing the methods in Example 24 and Example 25 from 3-aminopropanenitrile. LCMS (Method 5-95 AB, ESI): $t_R$=0.775 min, $[M+H]^+$=890.6.

Example 27: Synthesis of Compound 121

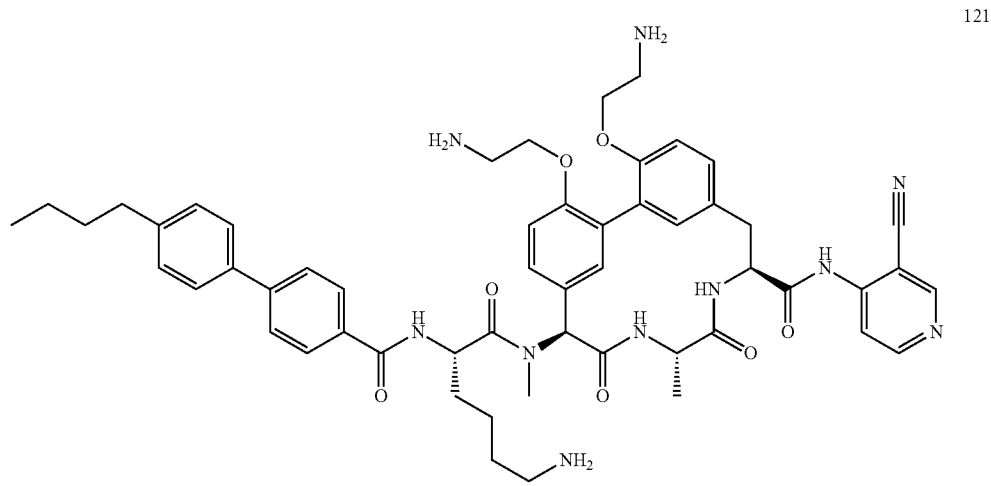 [SMILES: CCCCc1ccc(-c2ccc(C(=O)N[C@@H](CCCCN)C(=O)N(C)[C@@H]3C(=O)N[C@@H](C)C(=O)N[C@H](C(=O)Nc4ccncc4C#N)Cc4ccc(OCCN)c(c4)-c4cc3ccc4OCCN)cc2)cc1]

121

Compound 121 (formic acid salt) was prepared using the HATU coupling (Example 5) and TFA/HFIP deprotection (Example 6) from Compound 119-H (Example 24) and 4-aminopyridine-3-carbonitrile. LC-MS: m/z=965 [M+H]$^+$.
Example 28: Synthesis of Compound 122
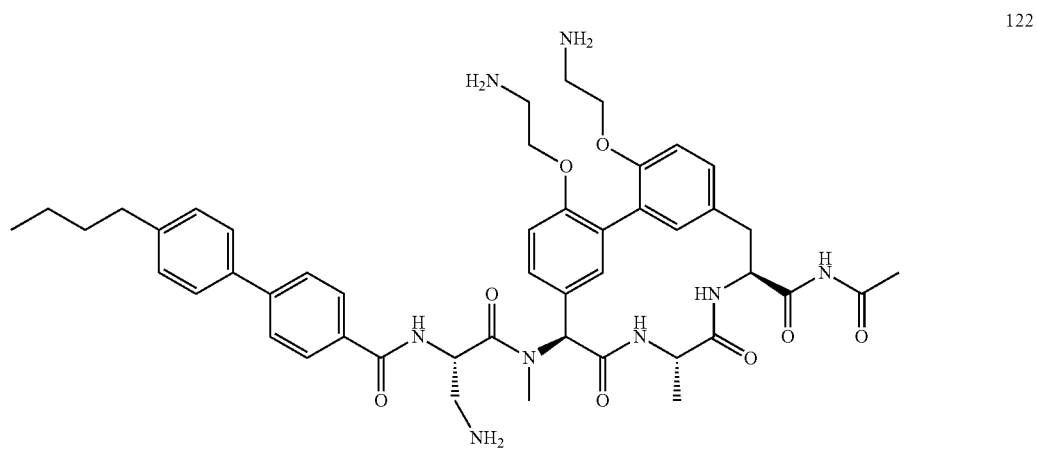
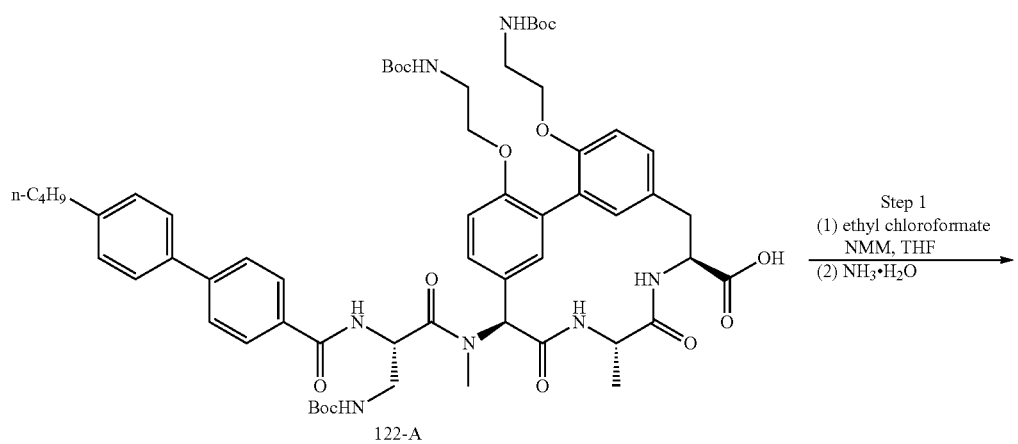
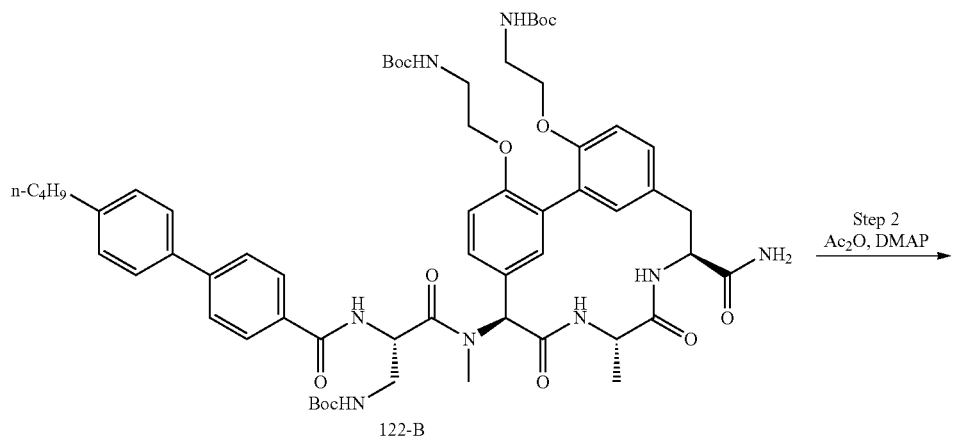

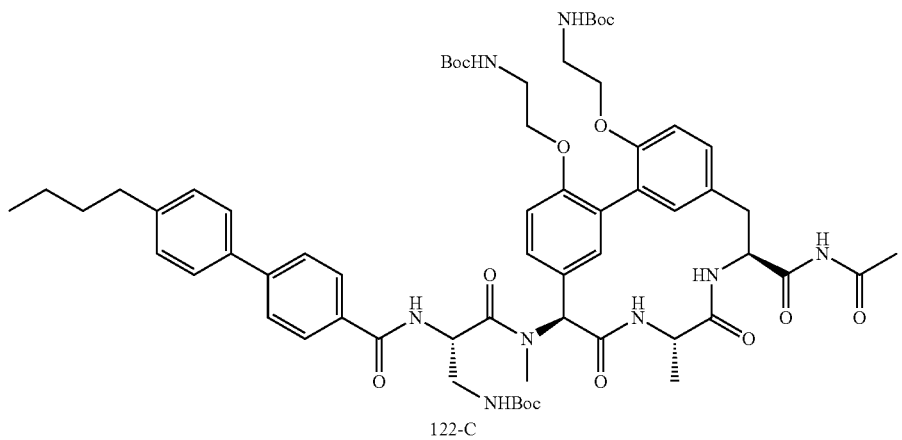

122-C

Compound 122-A was prepared utilizing the methods in Example 24 from (S)-2-(((benzyloxy)carbonyl)amino)-3-((tert-butoxycarbonyl)amino)propanoic acid. LCMS (Method 5-95 AB, ESI): $t_R$=0.941 min, [M+H]$^+$=1123.4

Step 1: To the solution of Compound 122-A (100 mg, 0.09 mmol) and N-methylmorpholine (54.1 mg, 0.53 mmol) in tetrahydrofuran (5 mL) was added isobutyl chloroformate (36.5 mg, 0.27 mmol) at 0° C. The solution was stirred at 0° C. for 30 min. Then ammonium hydroxide (867.5 mg, 8.91 mmol) was added. The solution was stirred at 0° C. for 30 min and quenched with saturated aqueous ammonium chloride solution (10 mL) and brine (10 mL). The resulting mixture was extracted with ethyl acetate (30 mL). The organic layer was washed with water (30 mL) and concentrated. The residue was purified by prep-TLC (5% methanol in dichloromethane) to afford Compound 122-B (80 mg, 80.1% yield) as a white solid.

Step 2: A mixture of Compound 122-B (50 mg, 0.04 mmol), acetic anhydride (9.1 mg, 0.09 mmol) and 4-dimethylaminopyridine (10.9 mg, 0.09 mmol) in acetonitrile (3 mL) was stirred at 60° C. for 16 h and concentrated. The residue was taken up in ethyl acetate (10 mL) and the organic solution was washed with water (10 mL×2) then brine (10 mL). The organic layer was separated and dried (sodium sulfate) before concentration to dryness. The crude product was then purified by prep-TLC (5% methanol in dichloromethane) to afford Compound 122-C (20 mg, 38.5% yield) as a white solid.

Compound 122 (formic acid salt) was prepared in 10% yield as a white solid using the TFA/HFIP deprotection method (Example 6). LCMS (Method 5-95 AB, ESI): $t_R$=0.655 min, [M+Na$^+$]=885.6. $^1$H NMR (400 MHz, CD$_3$OD) δ 8.49 (s, 3H), 7.97 (d, J=8.4 Hz, 2H), 7.76 (d, J=8.4 Hz, 2H), 7.60 (d, J=8.0 Hz, 2H), 7.32-7.23 (m, 4H), 7.21-7.06 (m, 2H), 6.87 (m, 2H), 6.27 (s, 1H), 5.33-5.27 (m, 2H), 4.82 (m, 1H), 4.22-4.18 (m, 4H), 3.47-3.31 (m, 2H), 3.18-3.15 (m, 4H), 3.14-3.08 (m, 2H), 2.83-2.69 (m, 3H), 2.68-2.66 (m, 2H), 2.22 (m, 3H), 1.69-1.63 (m, 2H), 1.43-1.33 (m, 5H), 0.97 (t, J=7.2 Hz, 3H).

Example 29: Synthesis of Compound 123

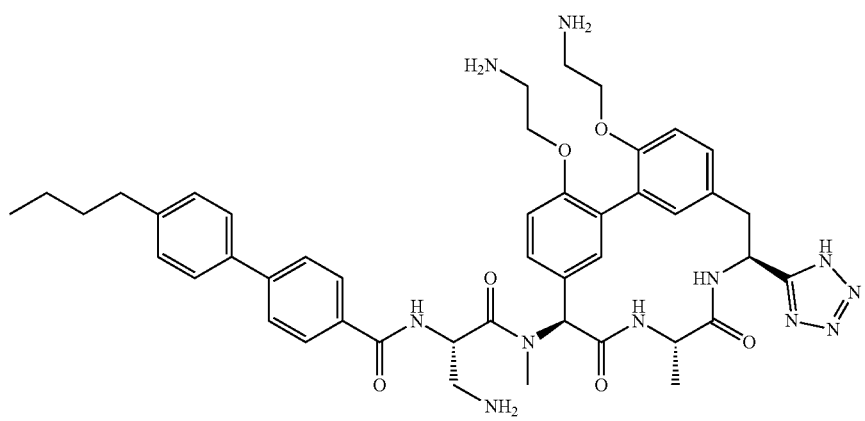

123

-continued
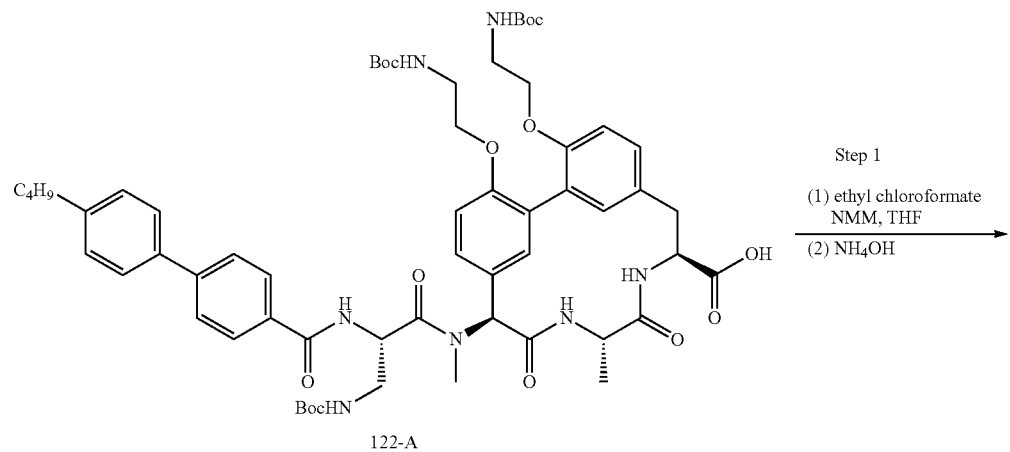
122-A
Step 1
(1) ethyl chloroformate NMM, THF
(2) NH$_4$OH
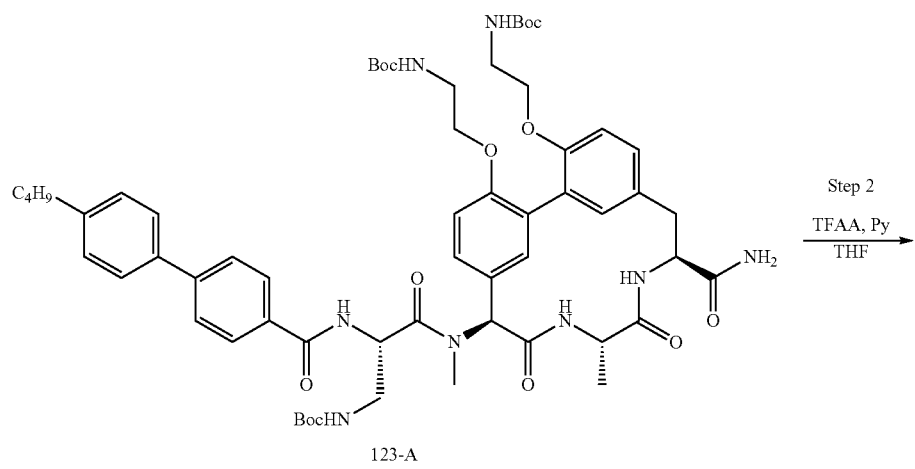
123-A
Step 2
TFAA, Py
THF

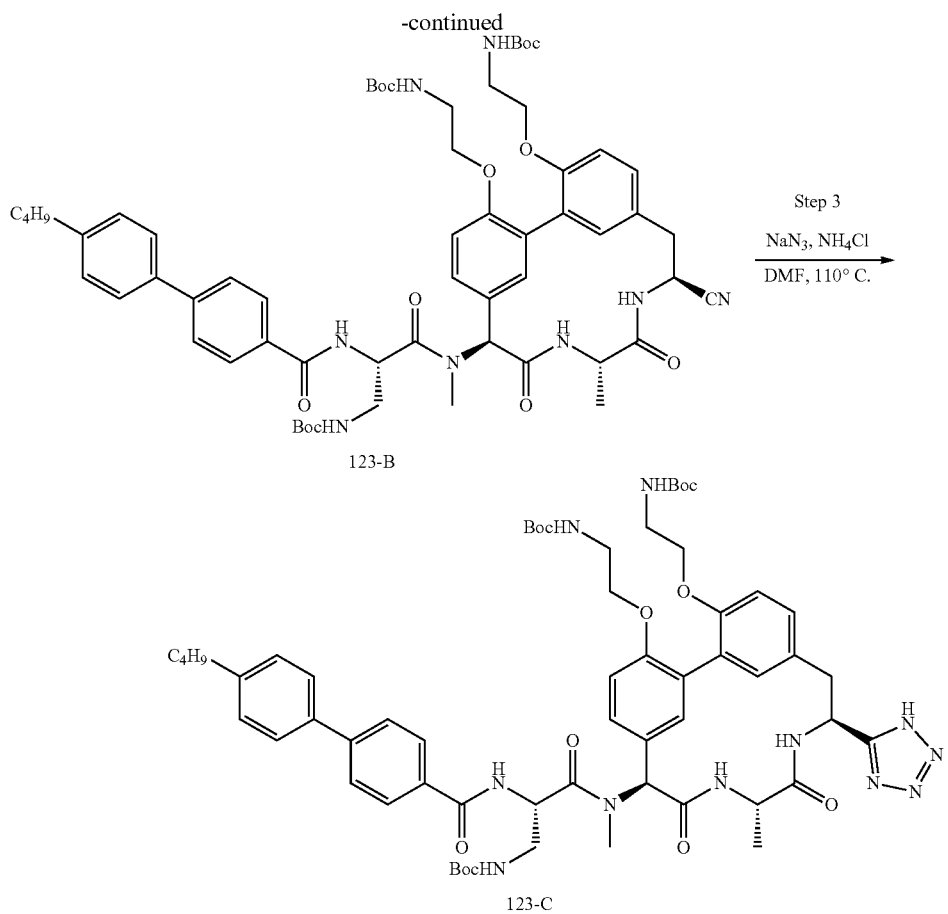

Step 1: A solution of Compound 122-A (Example 28) (200.0 mg, 0.18 mmol) and ethyl chloroformate (0.02 mL, 0.21 mmol) in THF (10 mL) was treated with N-methylmorpholine (27.0 mg, 0.27 mmol) at −10° C. under nitrogen. The resulting mixture was stirred at −10° C. for 30 min. Ammonium hydroxide (62.6 mg, 1.78 mmol) was added to the above solution and warmed to 20° C. for 1 hour. The reaction mixture was diluted with water (10 mL) and extracted with ethyl acetate (20 mL×3). The combined organic layers were washed with brine (15 mL), dried on sodium sulfate and concentrated to afford crude Compound 123-A (200 mg, 0.18 mmol). Compound 123-A was used in the next step without further purification. LCMS (Method 5-95 AB, ESI_1.5 min): $t_R$=1.081 min, [M+H]$^+$=1121.5

Step 2: To a mixture of Compound 123-A (200.0 mg, 0.18 mmol) and pyridine (42.3 mg, 0.54 mmol) in THF (10 mL) was added trifluoroacetic anhydride (56.2 mg, 0.27 mmol) at −10° C. The resulting mixture was stirred at −10° C. for 2 hours. The reaction mixture was quenched with 5% potassium bisulfate (0.5 mL) and water (5 mL), and extracted with ethyl acetate (15 mL×3). The combined organic layers were dried over sodium sulfate and concentrated. The residue was purified by prep-TLC (10% methanol in dichloromethane, Rf=0.5) to afford Compound 123-B (120 mg, 61% yield) as a white solid. LCMS (5-95AB_1.5 min): $t_R$=1.111 min, [M+H]$^+$=1103.7.

Step 3: A mixture of Compound 123-B (120.0 mg, 0.11 mmol), sodium azide (141.7 mg, 2.18 mmol) and ammonium chloride (116.4 mg, 2.18 mmol) in DMF (1 mL) was heated at 110° C. for 10 hours under nitrogen. The reaction mixture was poured into water (20 mL) and extracted with ethyl acetate (20 mL×3). The combined organic layers were washed with brine (20 mL), dried over sodium sulfate and concentrated to afford the crude Compound 123-C (80 mg, 64.2% yield) as a brown solid, which was used in the next step without further purification.

Compound 123 (formic acid salt) was prepared as a white solid in 59% yield using the formic acid Boc-deprotection method (Example 25). LCMS (Method 5-95 AB, ESI): $t_R$=0.752 min, [M+H]$^+$=846.6.

Example 30: Synthesis of Compound 124

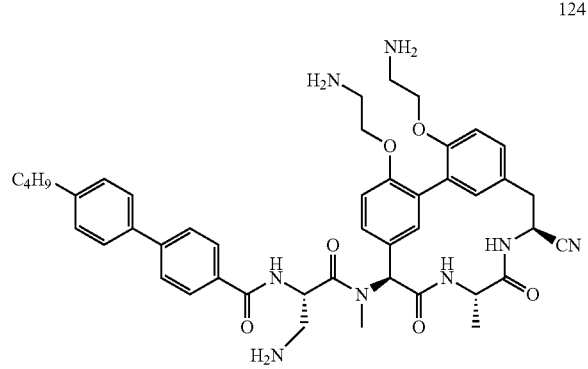

Compound 124 (formic acid salt) was prepared as a white solid in 42% yield using the formic acid Boc-deprotection method (Example 25) from Compound 123-B (Example 29). LCMS (Method 5-95 AB, ESI): $t_R$=0.767 min, [M+H]$^+$= 803.9.
Example 31: Synthesis of Compound 125
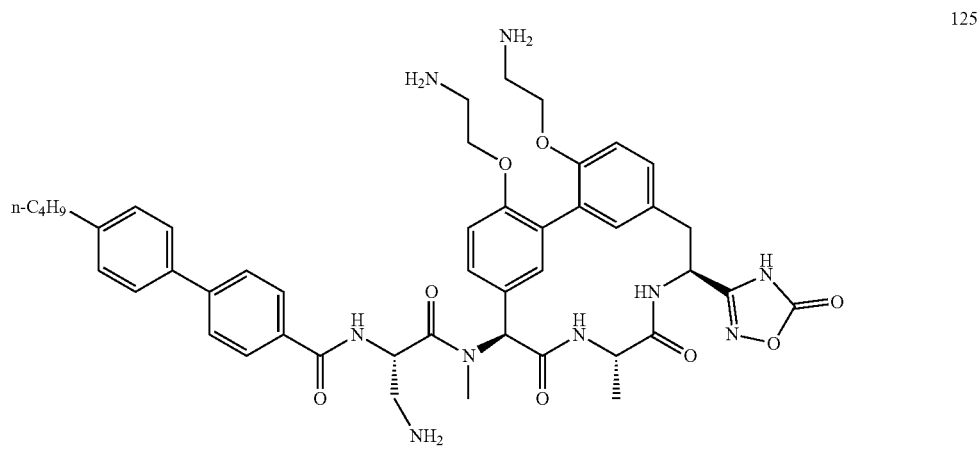
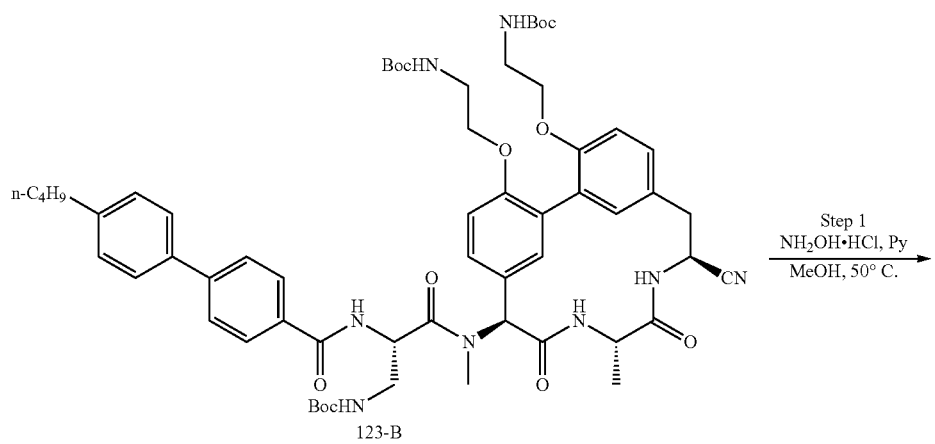
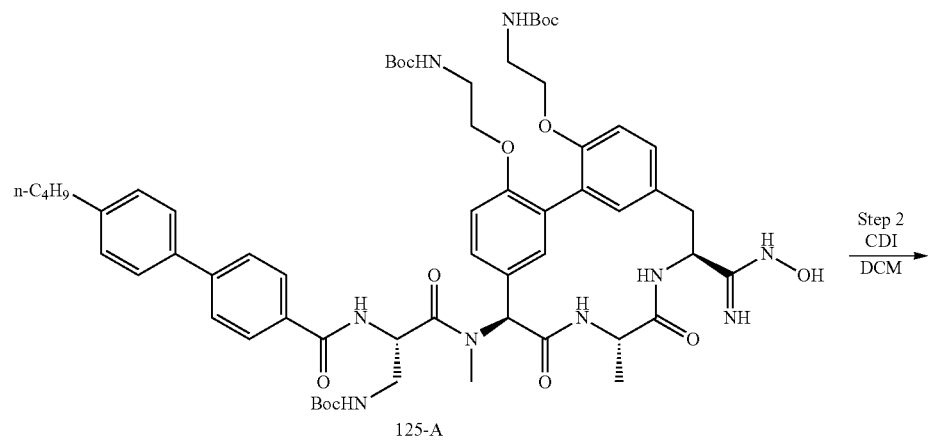

-continued

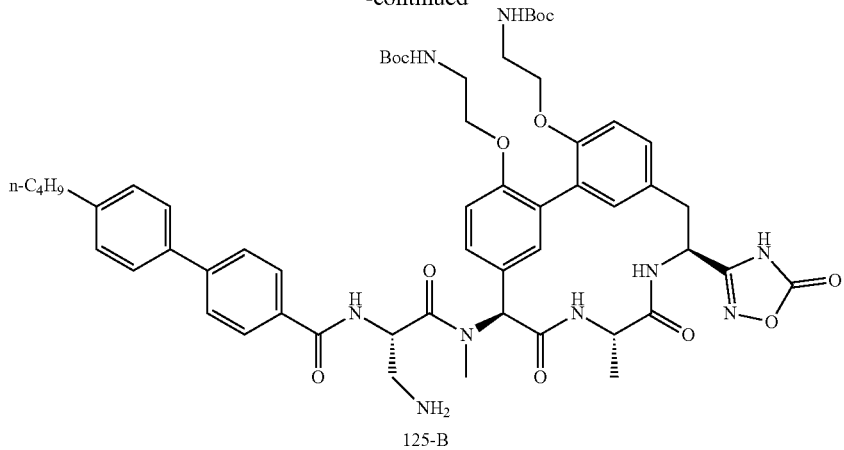

125-B

To a mixture of Compound 123-B (150.0 mg, 0.14 mmol) and sodium bicarbonate (34.3 mg, 0.41 mmol) in methanol (8 mL) was added hydroxylamine hydrochloride (14.2 mg, 0.20 mmol) at 50° C. The resulting mixture was stirred at 50° C. for 10 hours under nitrogen. The reaction mixture was concentrated. The residue was diluted with water (10 mL) and extracted with ethyl acetate (20 mL×3). The combined organic layers were dried over sodium sulfate and filtered. The filtrate was concentrated to afford the crude Compound 125-A (160 mg), which was used in the next step without further purification. LCMS (5-95AB_1.5 min): $t_R$=1.006 min, $[M+H]^+$=1137.8.

A mixture of Compound 125-A (160.0 mg, 0.14 mmol), 1,8-diazabicyclo[5.4.0]undec-7-ene (42.9 mg, 0.28 mmol) and 1,1-carbonyldiimidazole (45.7 mg, 0.28 mmol) in 1,4-dioxane (10 mL) was heated at 60° C. for 10 hours under nitrogen. The reaction mixture was diluted with water (10 mL) and extracted with ethyl acetate (20 mL×3). The combined organic layers were dried over sodium sulfate and filtered. The filtrate was concentrated. The residue was purified by prep-TLC (10% methanol in dichloromethane) to afford Compound 125-B (50 mg, 30.6% yield) as a white solid. LCMS (5-95AB_1.5 min): $t_R$=1.107 min, $[M+Na]^+$=1185.0.

Compound 125 (formic acid salt) was prepared as a white solid in 30% yield using the formic acid Boc-deprotection method (Example 25). LCMS (Method 5-95 AB, ESI): $t_R$=0.760 min, $[M+H]^+$=862.5. $^1$H NMR (400 MHz, CD$_3$OD) δ 8.38 (s, 2H), 7.97-7.95 (m, 2H), 7.76-7.73 (m, 2H), 7.58-7.56 (m, 2H), 7.31-7.21 (m, 4H), 7.09-7.05 (m, 2H), 6.83 (s, 1H), 6.31 (s, 1H), 5.33-5.25 (m, 2H), 4.79-4.76 (m, 2H), 4.18-4.14 (m, 3H), 3.47-3.33 (m, 4H), 3.22-3.14 (m, 4H), 2.73-2.65 (m, 5H), 1.66-1.62 (m, 2H), 1.42-1.27 (m, 5H), 0.96 (t, J=7.6 Hz, 3H).

Example 32: Synthesis of Compound 126

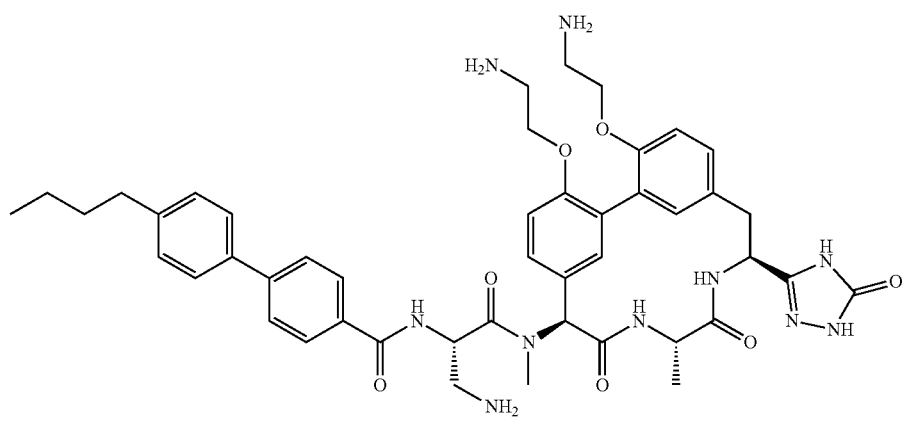

126

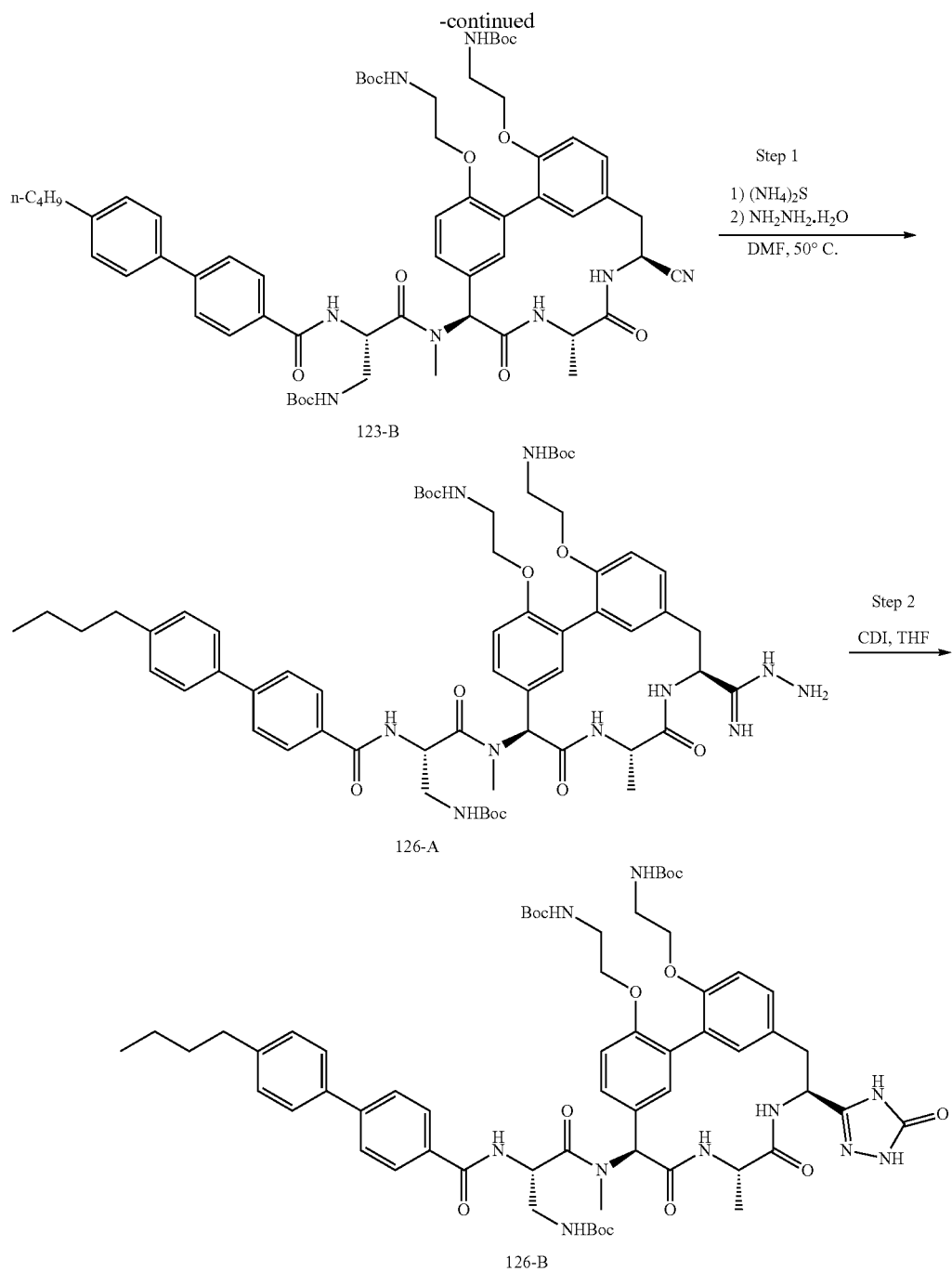

A mixture of Compound 123-B (Example 29) (80.0 mg, 0.07 mmol) and ammonium sulfide (0.5 mL, 0.7 mmol) in N,N-dimethylformamide (10 mL) was stirred at 100° C. for 1 h. Hydrazine (23.24 mg, 0.7 mmol) was added and the solution was stirred at 20° C. for 1 h. The reaction was evaporated to dryness. The residue was taken up in EtOAc (10 mL) and washed with water (10 mL×2) and brine (10 mL). The combined organic layers were dried over MgSO$_4$ and concentrated. The residue was purified by prep-TLC (5% methanol in DCM, Rf=0.1) to afford Compound 126-A (60 mg, 72.4% yield) as a white solid.

A solution of Compound 126-A (60.0 mg, 0.05 mmol) and 1,1'-carbonyldiimidazole (25.7 mg, 0.16 mmol) in tetrahydrofuran (5 mL) was stirred at 20° C. for 2 h. The reaction was evaporated to dryness. The residue was taken up in EtOAc (20 mL) and washed with water (20 mL×2) and brine (20 mL). The combined organic layers were dried over MgSO$_4$ and concentrated. The residue was purified by prep-TLC (5% methanol in DCM, Rf=0.6) to afford Compound 126-B (40 mg, 65.2% yield) as a white solid. LCMS (Method 5-95 AB, ESI): t$_R$=0.934 min, [M+H]$^+$=1162.3.

Compound 126 (formic acid salt) was prepared as a white solid in 21% yield using the TFA/HFIP deprotection method (Example 6). LCMS (Method 5-95 AB, ESI): t$_R$=0.629 min, [M+H]$^+$=862.4.

Example 33: Synthesis of Compound 127
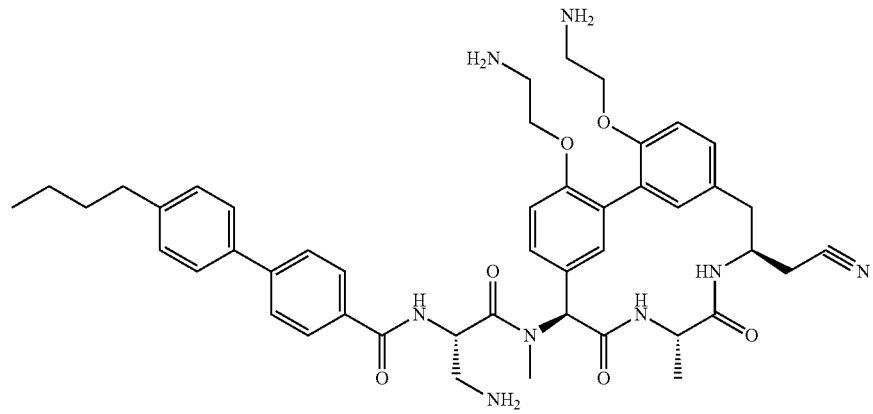
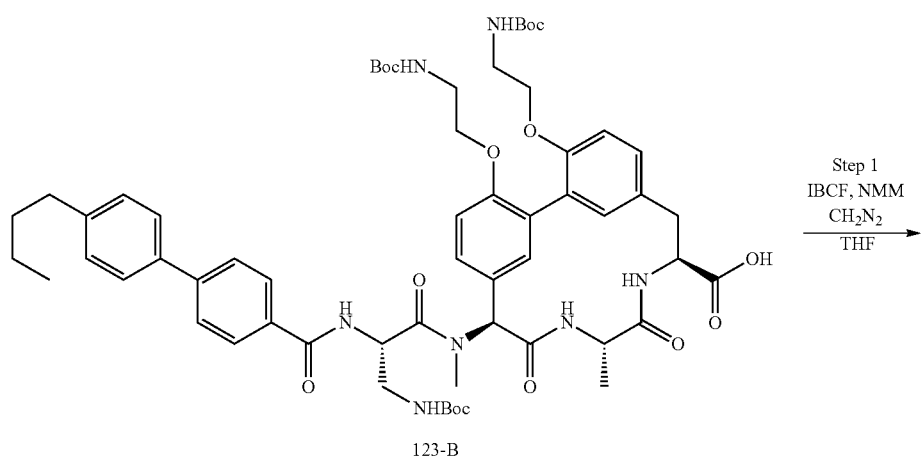
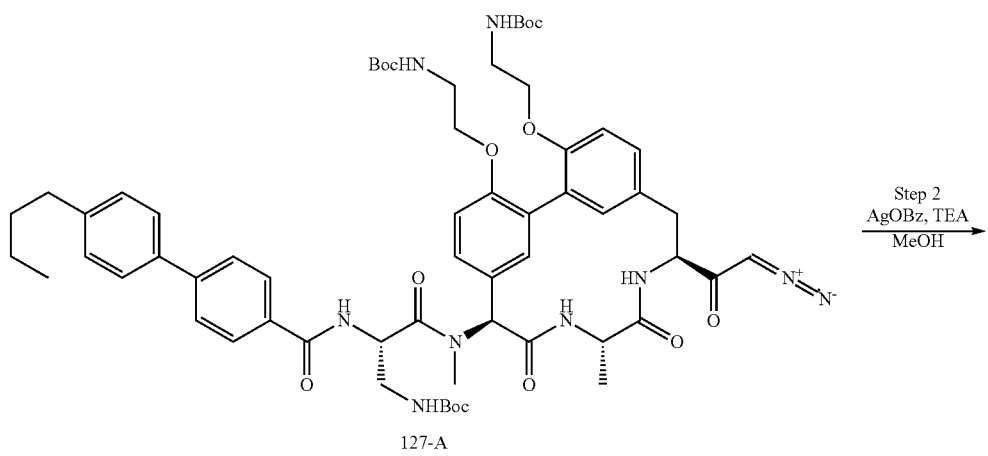

-continued
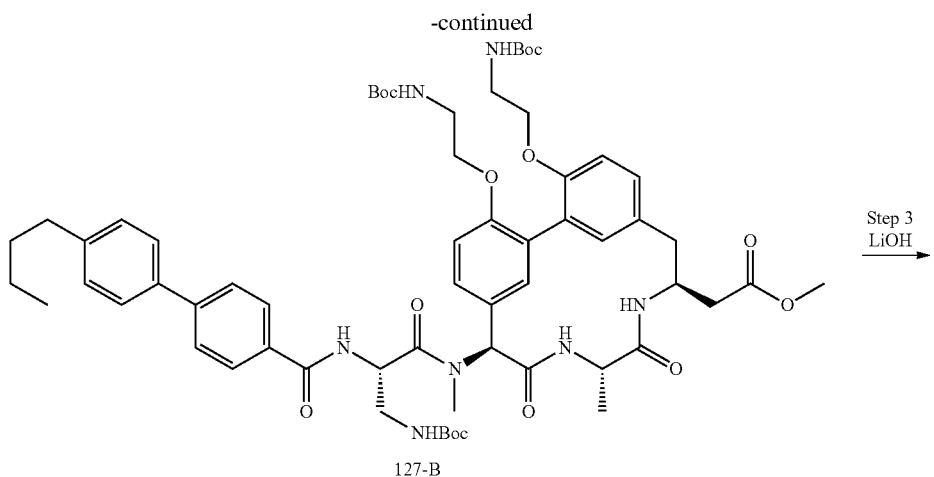
127-B
Step 3
LiOH
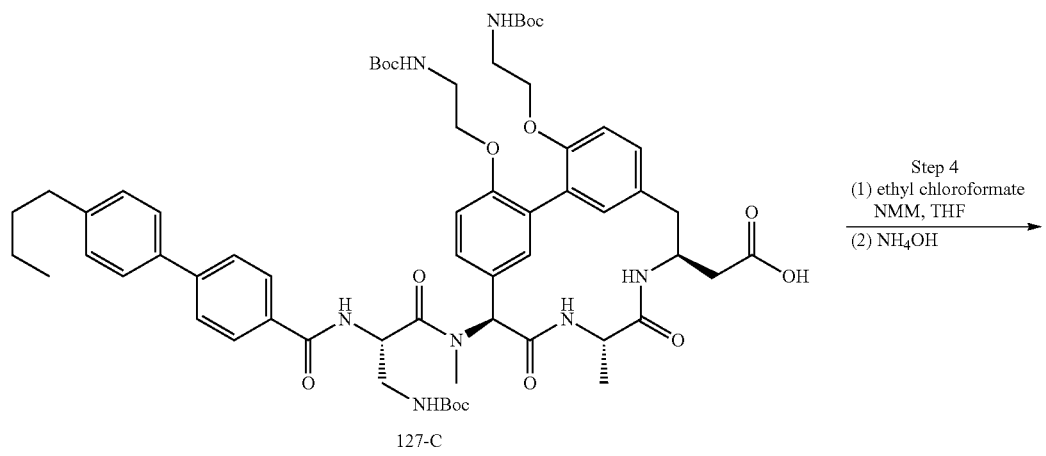
127-C
Step 4
(1) ethyl chloroformate NMM, THF
(2) NH₄OH
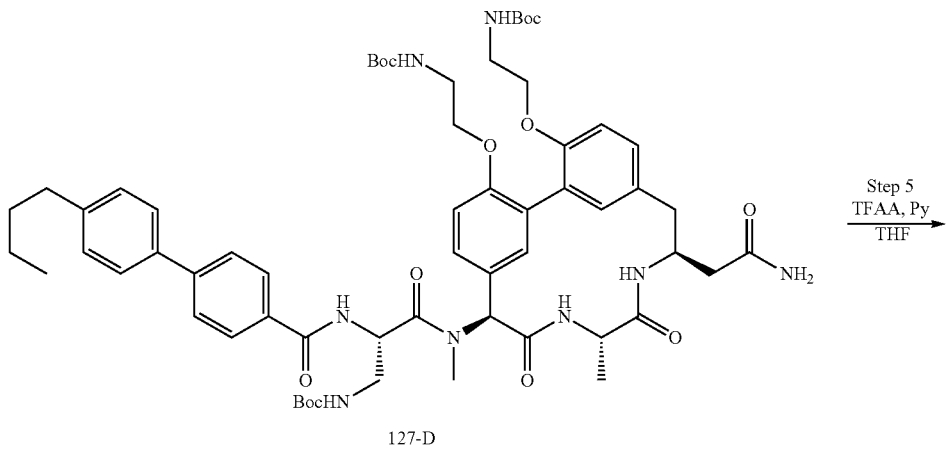
127-D
Step 5
TFAA, Py
THF

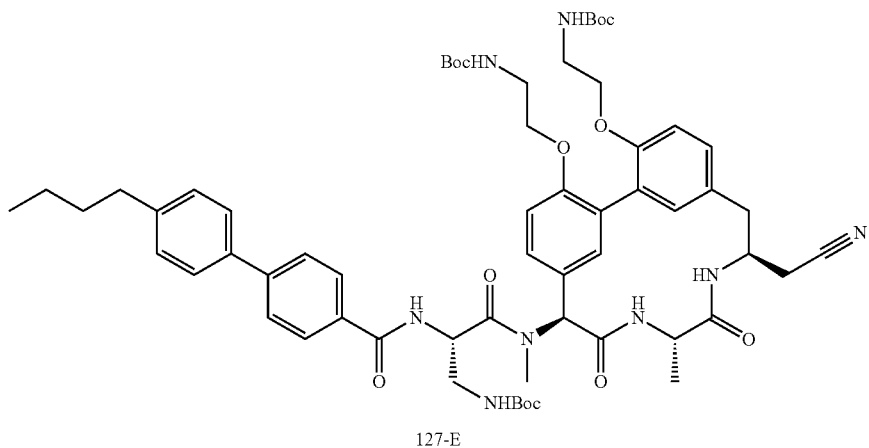

127-E

Step 1: To a solution of Compound 123-B (Example 29) (420.0 mg, 0.37 mmol) in tetrahydrofuran (80 mL) at 0° C. were added N-methylmorpholine (189.3 mg, 1.87 mmol) and isobutyl chloroformate (255.6 mg, 1.87 mmol) and stirred at 15° C. for 1 h. Diazomethane (9.36 mL, 18.71 mmol) was added and the solution was stirred at 15° C. for 3 h. The reaction was quenched with water (10 mL), and extracted with DCM (20 mL). The combined organic layers were washed with water (20 mL×2) and brine (10 mL), dried over $MgSO_4$ and concentrated. The residue was purified by prep-TLC (10% methanol in DCM, Rf=0.6) to afford Compound 127-A (400 mg, 93.2% yield) as a white solid.

Step 2: A mixture of Compound 127-A (400.0 mg, 0.35 mmol), silver benzoate (79.9 mg, 0.35 mmol) and triethylamine (35.3 mg, 0.35 mmol) in methanol (10 mL) was stirred at 20° C. for 30 min and filtered. The filtrate was diluted with EtOAc (40 mL) and washed with water (40 mL×2) and brine (20 mL), dried over $MgSO_4$ and concentrated. The residue was purified by flash column chromatography (5% methanol in DCM) to afford Compound 127-B (390 mg, 97.2% yield) as a white solid. LCMS (Method 5-95 AB, ESI): $t_R$=1.112 min, $[M+H]^+$=1150.6.

Steps 3-5: Starting from Compound 127-B, LiOH ester hydrolysis (Example 6), followed by amide and nitrile formation (Example 29) afforded Compound 127-E.

Compound 127 (formic acid salt) was prepared as a white solid in 42% yield using the TFA/HFIP deprotection method (Example 6). LCMS (Method 5-95 AB, ESI): $t_R$=0.629 min, $[M+H]^+$=817.3.

Example 34: Synthesis of Compound 128

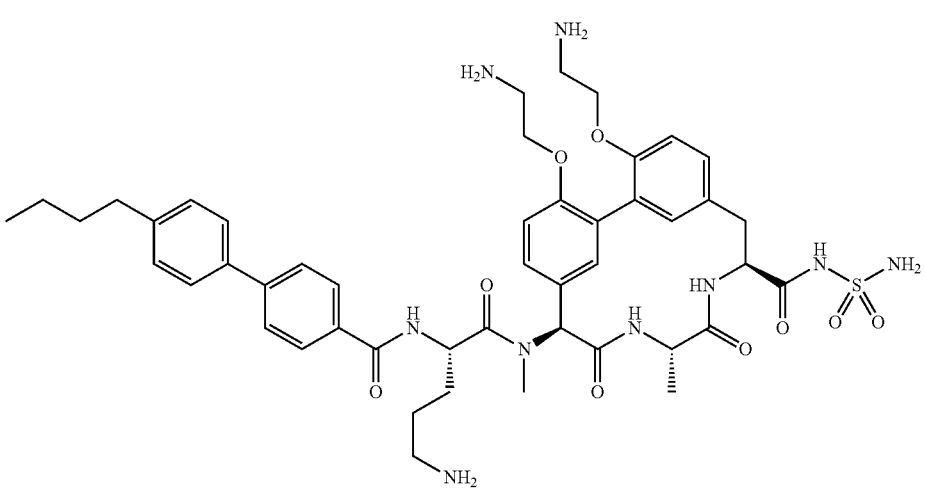

128

-continued
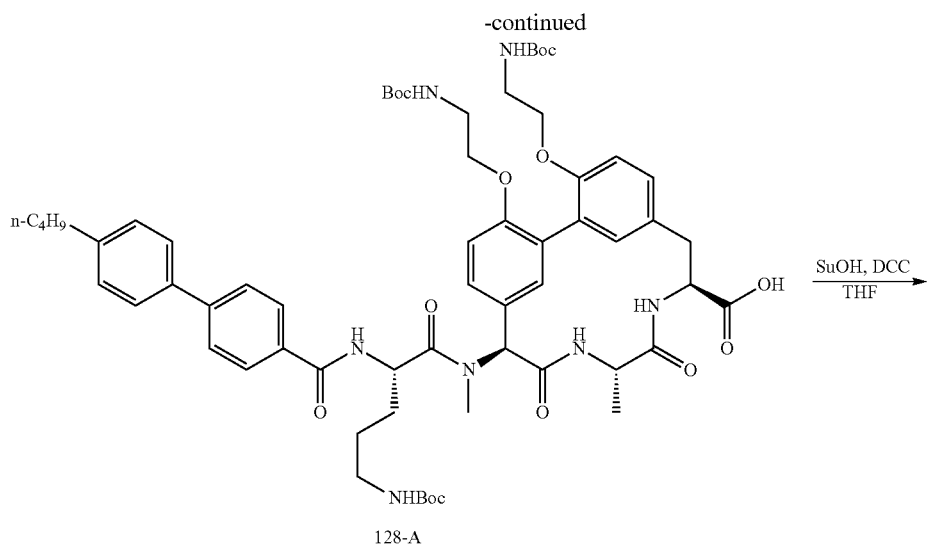
128-A
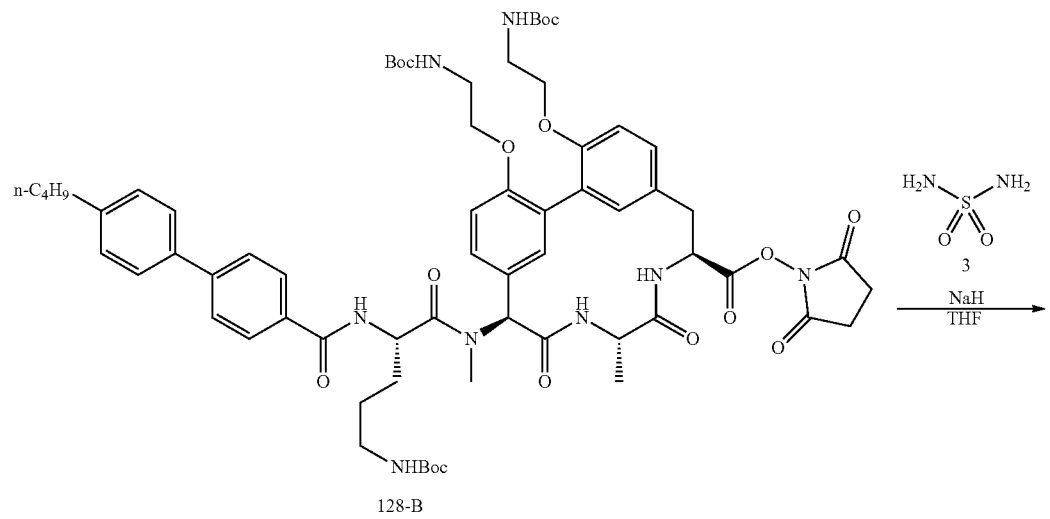
128-B
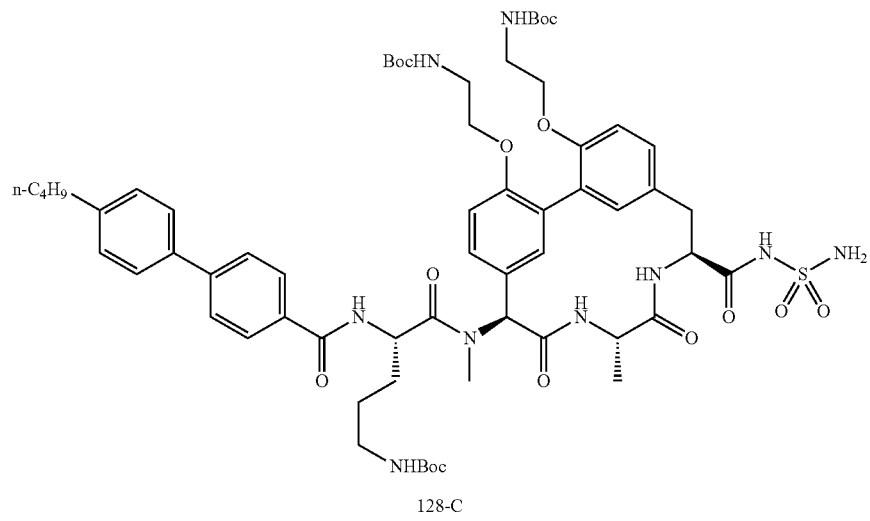
128-C

Compound 128-A was prepared utilizing the methods in Example 24 from (S)-2-(((benzyloxy)carbonyl)amino)-5-((tert-butoxycarbonyl)amino)pentanoic acid. LCMS (Method 5-95 AB, ESI): $t_R$=1.106 min, [M+H]$^+$=1151.9.

A mixture of Compound 128-A (100 mg, 0.09 mmol) and N-hydroxysuccinimide (11 mg, 0.1 mmol) in tetrahydrofuran (3 mL) was treated with N,N'-dicyclohexylcarbodiimide (19.73 mg, 0.1 mmol). The resulting mixture was stirred at 15° C. for 1 h under nitrogen and filtered. The filtrate, Compound 128-B, was used in the next step without purification. LCMS (5-95AB/1.5 min): $t_R$=0.998 min, [M+Na]$^+$= 1269.9.

To a solution of sulfamide (11.6 mg, 0.12 mmol) in tetrahydrofuran (3 mL) was added sodium hydride (2.9 mg, 0.12 mmol) at 0° C., and the mixture was stirred at 0° C. for 1 h. Then to the mixture was added the Compound 128-B solution, and the reaction mixture was stirred at 0° C. for 1 h. LCMS showed desired product was major peak. The mixture was quenched with saturated aqueous ammonium chloride (5 mL), and the mixture was extracted with ethyl acetate (20 mL×3). The organics were dried over sodium sulfate and concentrated. The residue was purified by prep-TLC (10% methanol in dichlormethane) to give Compound 128-C (70 mg, 71.1% yield) as a white solid. LCMS (5-95AB_1.5 min_220&254_1500): $t_R$=0.944 min, [M+H]$^+$= 1229.9.

Compound 128 (formic acid salt) was prepared as a white solid in 54% yield using the TFA/HFIP deprotection method (Example 6). LCMS (5-95AB_1.5 min_220&254_1500): $t_R$=0.757 min, [M+H]$^+$=928.2. $^1$H NMR (400 MHz, CD$_3$OD) δ 7.99-7.89 (m, 2H), 7.77-7.68 (m, 2H), 7.59-7.51 (m, 2H), 7.35-7.22 (m, 4H), 7.15-7.03 (m, 2H), 6.95-6.81 (m, 2H), 6.48 (s, 1H), 5.15-5.07 (m, 1H), 4.83-4.77 (m, 2H), 4.71-4.64 (m, 1H), 4.30-4.14 (m, 3H), 3.49-3.36 (m, 3H), 3.27-3.92 (m, 8H), 2.75-2.64 (m, 2H), 2.12-2.01 (m, 1H), 2.00-1.78 (m, 3H), 1.70-1.60 (m, 2H), 1.50-1.28 (m, 5H), 1.01-0.92 (m, 3H).

Example 35: Synthesis of Compound 129

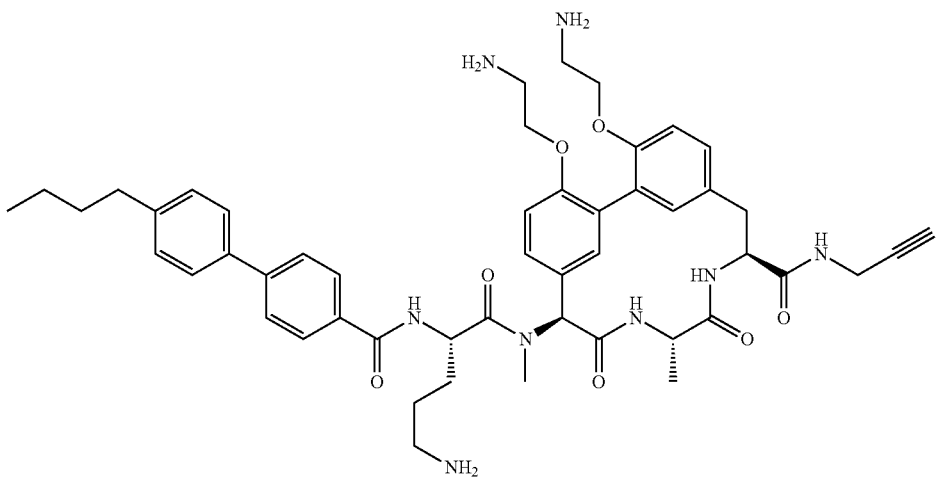

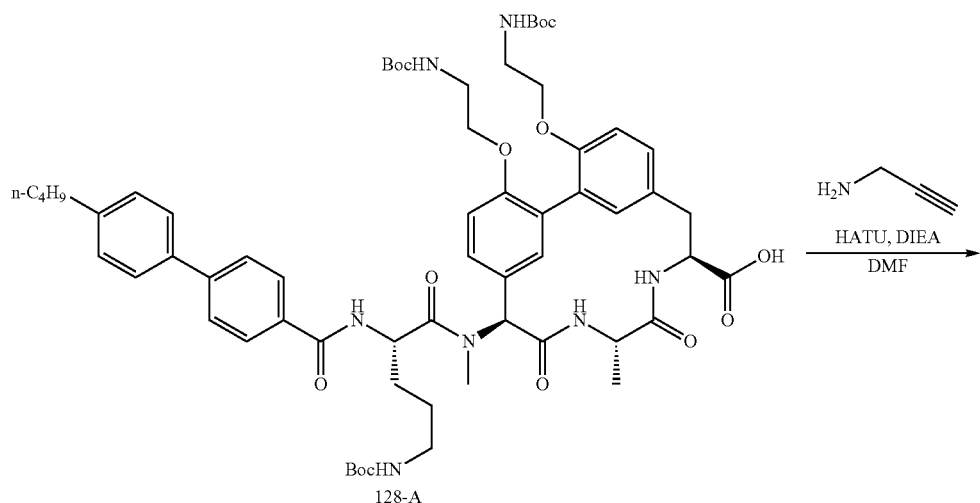

128-A

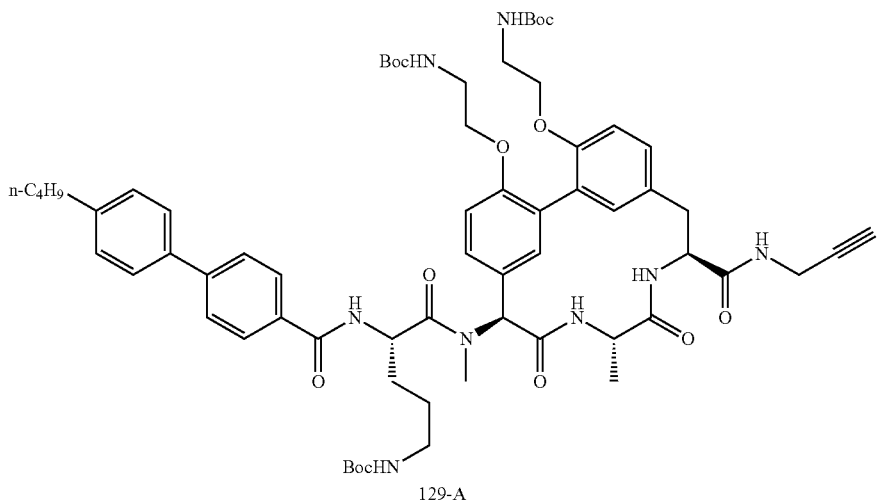

129-A

A mixture of Compound 128-A (70 mg, 0.06 mmol), prop-2-yn-1-amine (33.5 mg, 0.61 mmol), N,N-diisopropylethylamine (31.5 mg, 0.24 mmol) and HATU (92.6 mg, 0.24 mmol) in N,N-dimethylformamide (3 mL) was stirred at 0° C. for 20 min. LCMS showed starting material was consumed. The reaction was quenched with water (10 mL) and the mixture was filtered. The filter cake was dissolved in methanol (10 mL) and concentrated. The residue was purified by prep-TLC (10% methanol in dichloromethane) to give Compound 129-A (50 mg, 69.1% yield) as a yellow solid. LCMS (5-95AB_1.5 min_1500): $t_R$=0.996 min, [M+H]$^+$=1188.8.

Compound 129 (formic acid salt) was prepared as a white solid in 60% yield using the formic acid Boc-deprotection method (Example 25). LCMS (5-95AB_1.5 min_220&254_1500): $t_R$=0.757 min, [M+H]$^+$=887.5. $^1$H NMR (400 MHz, CD$_3$OD) δ 8.35 (s, 3H), 8.03-7.91 (m, 2H), 7.80-7.70 (m, 2H), 7.64-7.56 (m, 2H), 7.38-7.22 (m, 4H), 7.20-7.05 (m, 2H), 6.92-6.73 (m, 2H), 6.41 (s, 1H), 5.15-5.05 (m, 1H), 4.82-4.76 (m, 2H), 4.35-4.16 (m, 4H), 4.05-3.93 (m, 2H), 3.27-2.90 (m, 1H), 2.76-2.59 (m, 3H), 2.10-2.00 (m, 1H), 1.97-1.75 (m, 3H), 1.70-1.60 (m, 2H), 1.47-1.28 (m, 5H), 1.01-0.92 (m, 3H).

Example 36: Synthesis of Compound 130

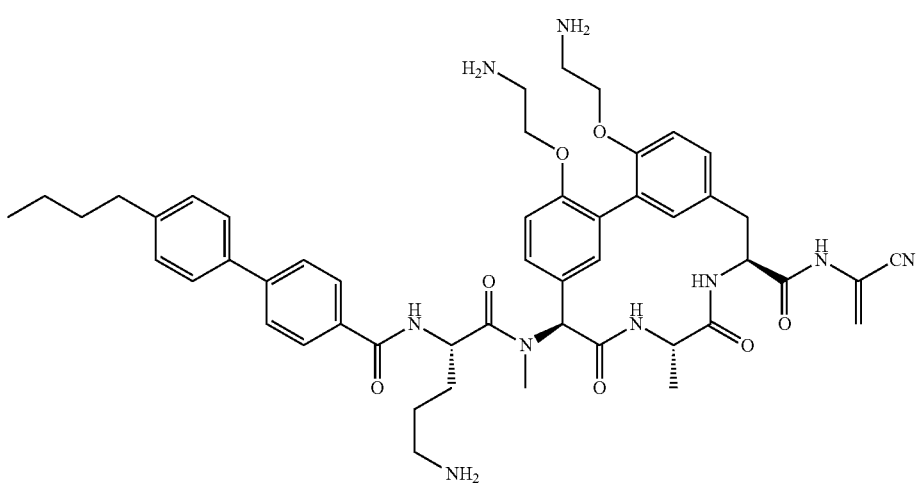

130

219                                    220
-continued
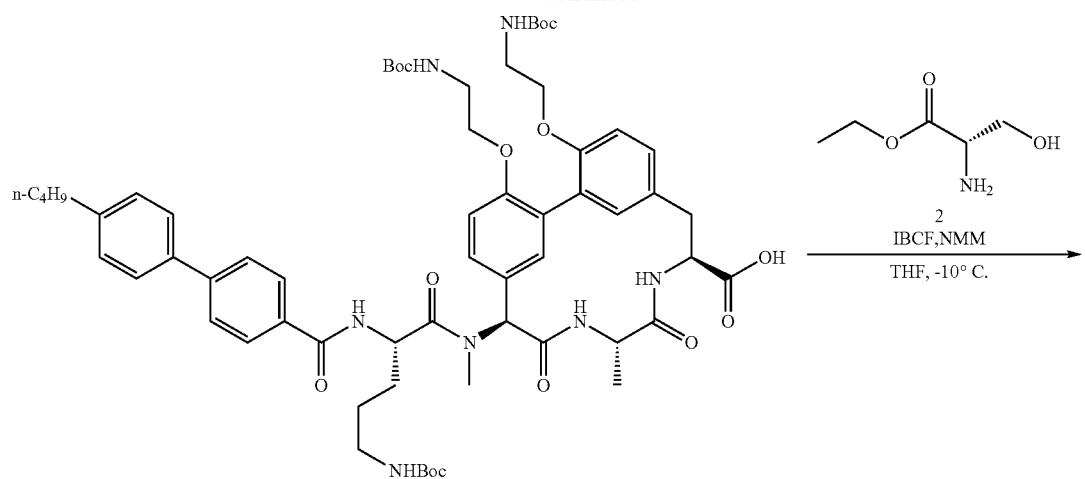
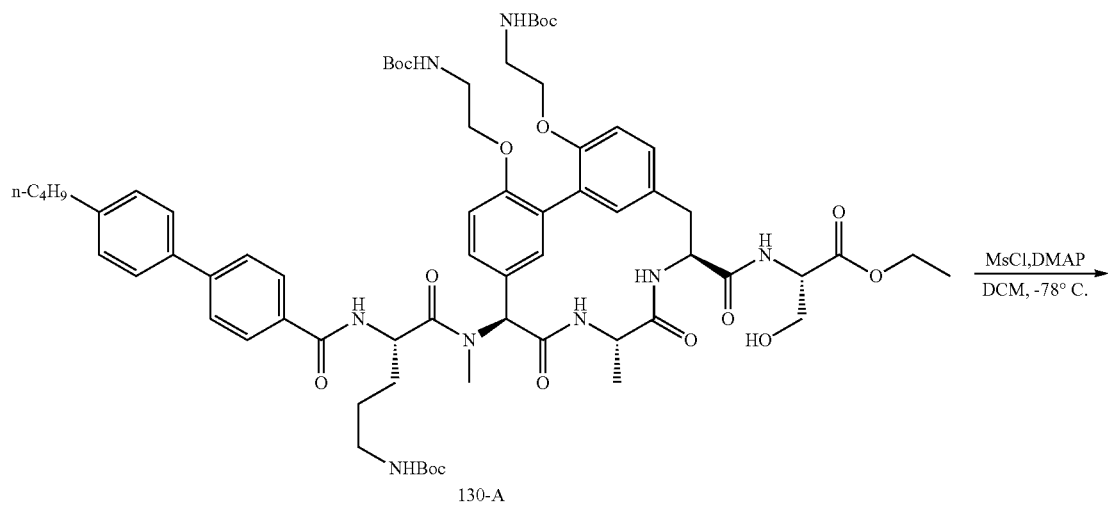
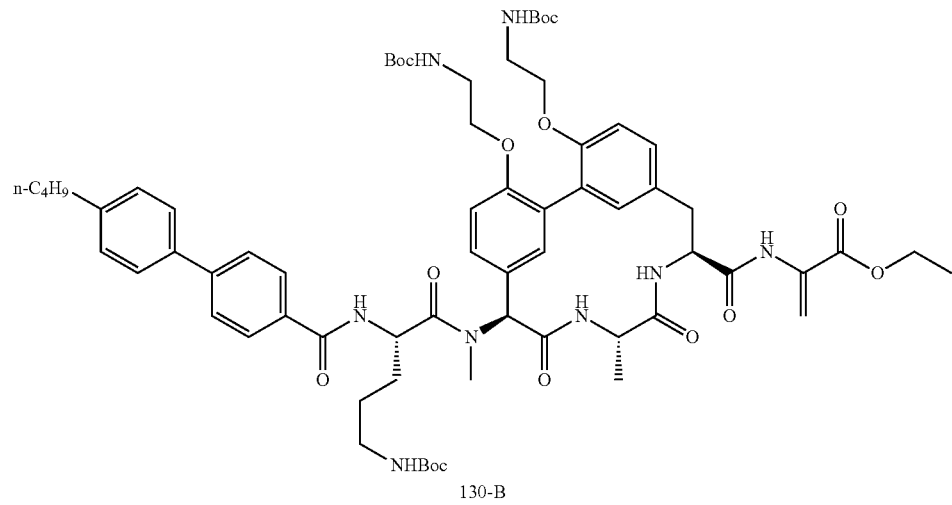

Step 1: To a solution of isobutyl chloroformate (13.1 mg, 0.10 mmol) in tetrahydrofuran (10 mL) cooled at −10° C. were added Compound 128-A (Example 34) (100 mg, 0.09 mmol) and ethyl 2-amino-3-hydroxy-propanoate (12.7 mg, 0.1 mmol) and stirred at −10° C. for 30 min. N-methylmorpholine (18.5 mg, 0.18 mmol) was added and the mixture was stirred at 15° C. for 16 h. The reaction mixture was diluted with DCM (30 mL), washed with water (50 mL×3), dried over anhydrous sodium sulfate, and concentrated in vacuo to afford Compound 130-A (100 mg, 90.9% yield) as a white solid. LCMS (Method 5-95 AB, ESI): $t_R$=1.088 min, $[M+H]^+$=1266.0.

Step 2: To a solution of Compound 130-A (100 mg, 0.08 mmol) in DCM (2 mL) cooled to 0° C. were added triethylamine (9.1 mg, 0.09 mmol) and methanesulfonyl chloride (7.8 mg, 0.07 mmol) and stirred at 0° C. for 1 h. The reaction mixture was diluted with DCM (20 mL), washed with water (20 mL×3), dried over anhydrous sodium sulfate, and concentrated in vacuo. The residue was purified by prep-TLC (5% methanol in DCM, Rf=0.5) to afford Compound 130-B (70 mg, 71% yield) as a white solid. LCMS (Method 5-95 AB, ESI): $t_R$=1.147 min, $[M+H]^+$=1249.0.

Compound 130 (formic acid salt) was prepared as a white solid in utilizing the LiOH ester hydrolysis, amide formation, nitrile formation, and TFA/HFIP procedures from Compound 127 (Example 33). LCMS (Method 5-95 AB, ESI): $t_R$=0.646 min, $[M+H]^+$=900.8. $^1$H NMR (400 MHz, CD$_3$OD) δ 8.50 (br s, 3H), 7.96 (d, J=8.4 Hz, 2H), 7.76 (d, J=8.4 Hz, 2H), 7.60 (d, J=8.0 Hz, 2H), 7.31 (d, J=7.2 Hz, 2H), 7.25-7.08 (m, 4H), 6.90-6.86 (m, 2H), 6.39 (s, 1H), 6.04 (s, 1H), 5.62 (s, 1H), 5.10-5.08 (m, 1H), 4.89-4.80 (m, 1H), 4.24-4.22 (m, 4H), 3.35-3.24 (m, 2H), 3.24-3.17 (m, 4H), 3.15-2.99 (m, 2H), 2.94 (s, 2H), 2.68 (t, J=7.8 Hz, 2H), 2.20-1.84 (m, 7H), 1.69-1.63 (m, 3H), 1.43-1.35 (m, 4H), 0.97 (t, J=7.4 Hz, 3H).

Example 37: Synthesis of Compound 131

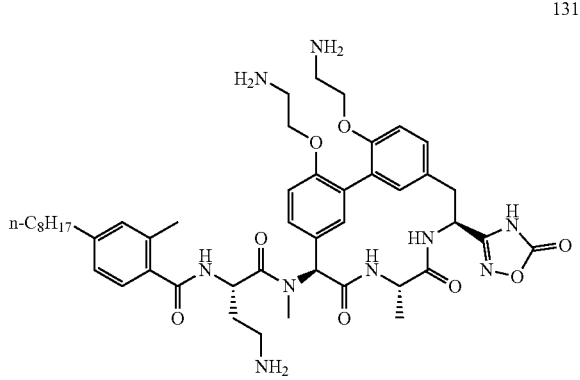

131

Compound 131 (formic acid salt) was prepared as a white solid in utilizing the methods from Compound 125 (Example 31) from Compound 101-N (Example 6). LCMS (Method 5-95 AB, ESI): $t_R$=0.631 min, $[M+H]^+$=870.4.

Example 38: Synthesis of Compound 132

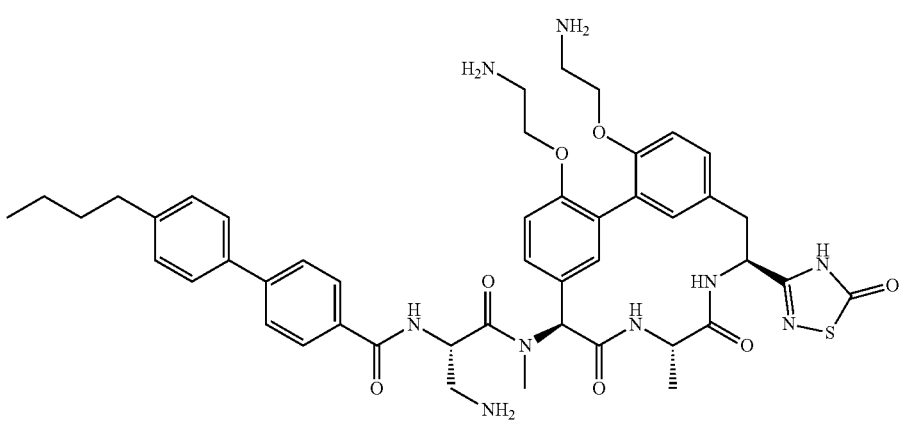

132

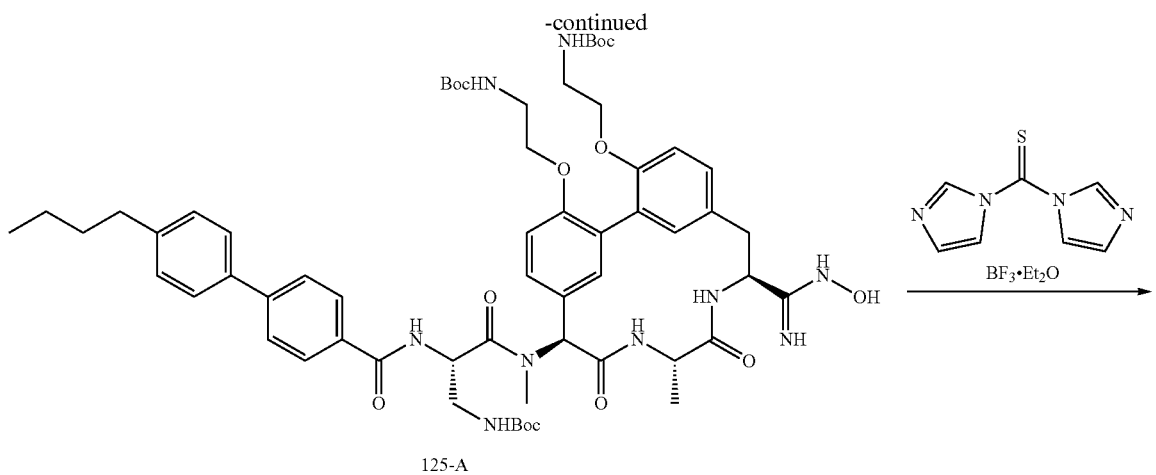

125-A

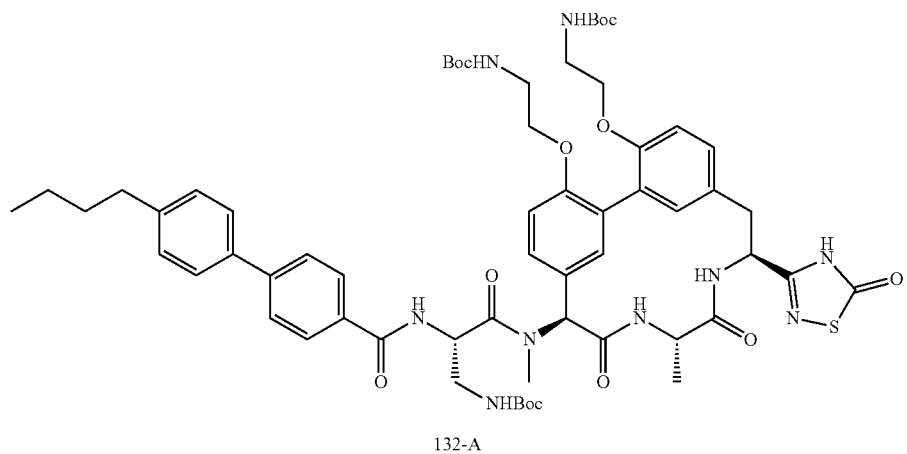

132-A

To a solution of Compound 125-A (Example 31) (100 mg, 0.09 mmol) in tetrahydrofuran (5 mL) were added 1,1'-thiocarbonyldiimidazole (31.3 mg, 0.18 mmol) and boron trifluoride diethyl etherate (12.5 mg, 0.09 mmol). The resulting mixture was stirred at 15° C. for 10 hours. The reaction was quenched with saturated sodium bicarbonate (10 mL) and extracted with ethyl acetate (15 mL×3). The combined organic layers were dried over sodium sulfate, filtered and concentrated. The residue was purified by prep-TLC (10% methanol in dichloromethane, Rf=0.4) to afford Compound 132-A (40 mg, 38.5% yield) as a white solid.

Compound 132 (formic acid salt) was prepared as a white solid in 36% yield using the TFA/HFIP deprotection method (Example 6). LCMS (Method 5-95 AB, ESI): $t_R$=0.779 min, $[M+H]^+$=878.3.

Example 39: Synthesis of Compound 133

133

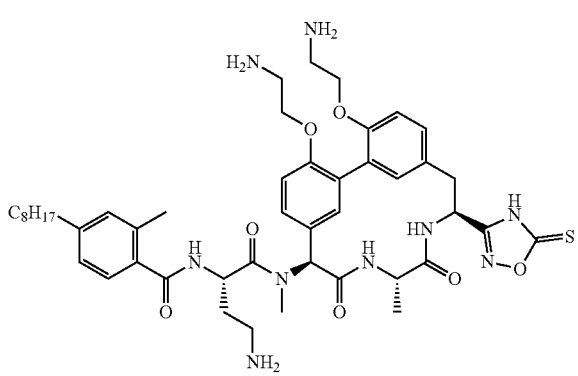

Compound 133 (formic acid salt) was prepared as a white solid in utilizing the methods from Compound 132 (Example 38) from Compound 101-N (Example 6). LCMS (Method 5-95 AB, ESI): $t_R$=0.783 min, [M+H]$^+$=886.6.

Example 40: Synthesis of Compound 134

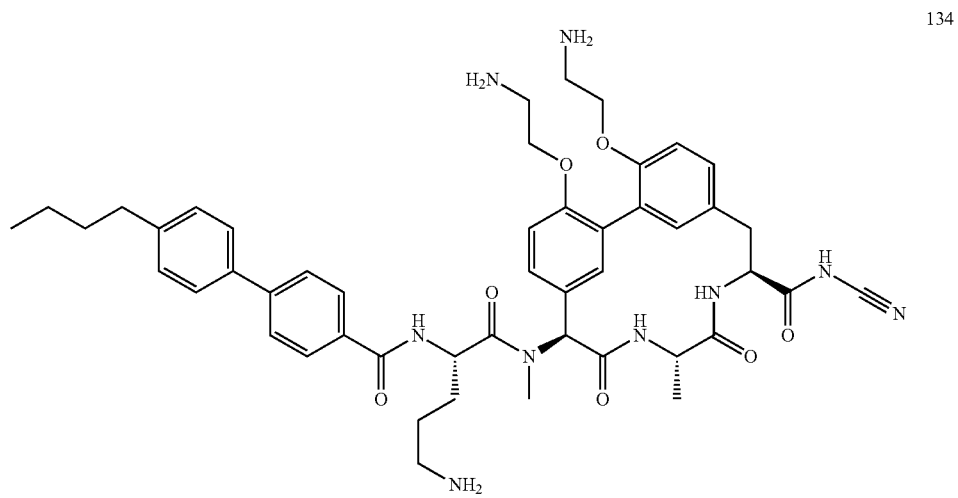 [SMILES: CCCCc1ccc(-c2ccc(C(=O)N[C@@H](CCCN)C(=O)N(C)[C@@H]3C(=O)N[C@@H](C)C(=O)N[C@H](C(=O)NC#N)Cc4ccc(OCCN)c(c4)-c4cc3ccc4OCCN)cc2)cc1]

Compound 134 (formic acid salt) was prepared as a white solid in utilizing the HATU coupling (Example 5) and TFA/HFIP deprotection (Example 6) methods starting from Compound 128-A and the sodium salt of cyanamide. LCMS (Method 5-95 AB, ESI): $t_R$=0.759 min, [M+H]$^+$=874.7.

Example 41: Synthesis of Compound 135

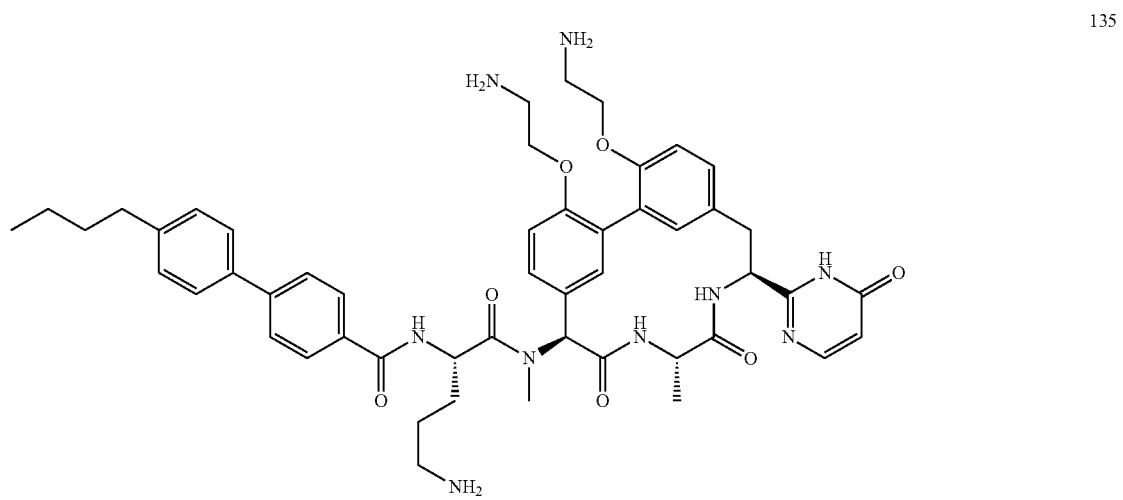

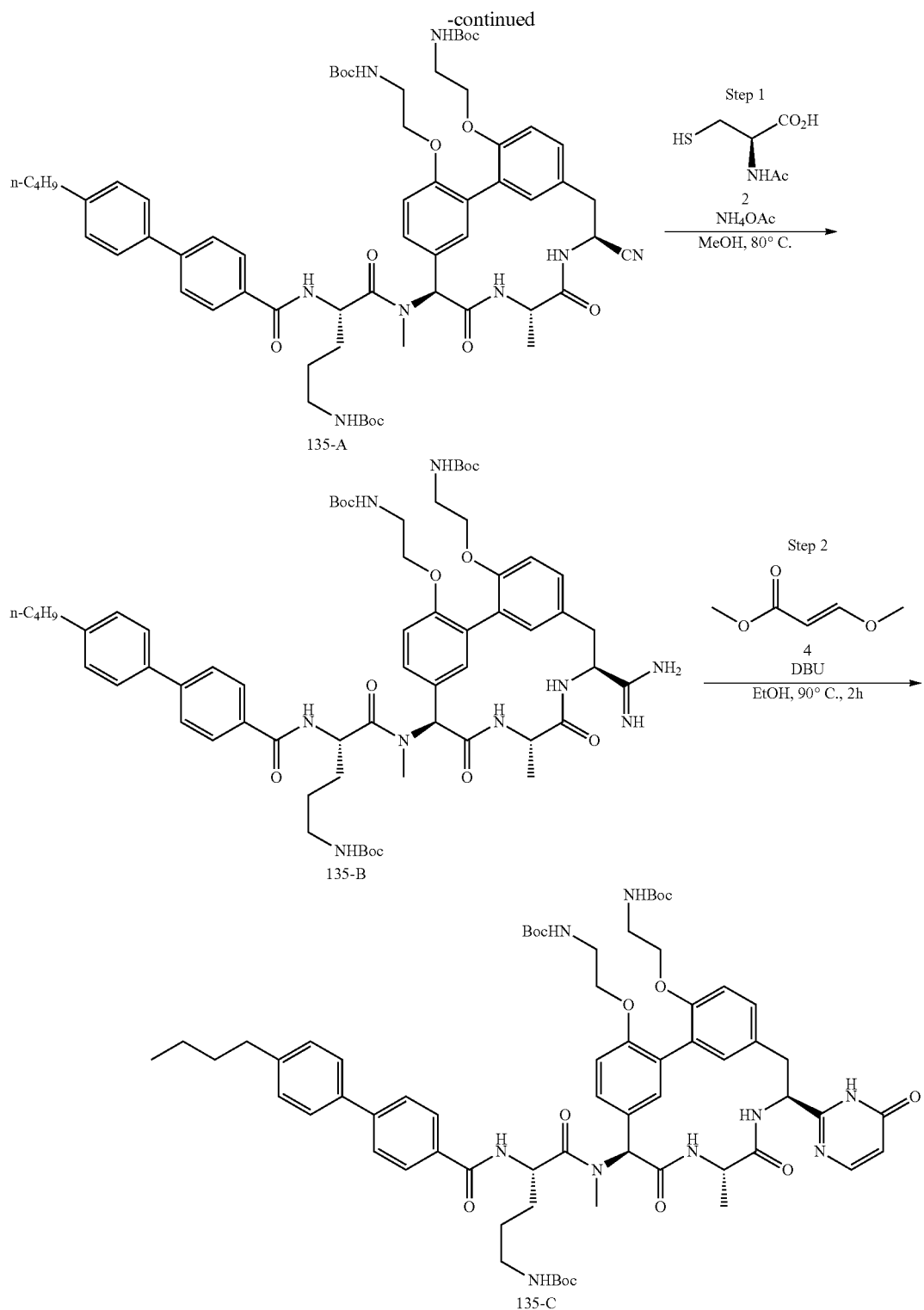

Compound 135-A was prepared utilizing the methods in Example 29 starting from Compound 128-A.

A mixture of Compound 135-A (400 mg, 0.35 mmol), (2R)-2-(acetylamino)-3-sulfanylpropanoic acid (577 mg, 3.54 mmol), and ammonium acetate (272 mg, 3.54 mmol) in methanol (10 mL) was stirred at 60° C. for 24 h. The reaction mixture was diluted with water (20 mL) and extracted with EtOAc (30 mL×3). The combined organic layers were washed with water (20 mL×2) and brine (20 mL), dried over MgSO$_4$ and concentrated. The residue was purified by prep-TLC (10% methanol in dichloromethane, Rf=0.4) to obtain Compound 135-B (160 mg, 39.4% yield) as a white solid. LCMS (Method 5-95 AB, ESI): t$_R$=1.003 min, [M+H]$^+$=1148.7.

A mixture of Compound 135-B (60 mg, 0.05 mmol), methyl 3-methoxyacetate (9.1 mg, 0.08 mmol), and DBU (15.9 mg, 0.10 mmol) in ethanol (10 mL) was stirred at 90° C. for 2 h. LCMS (5-95AB/1.5 min): $t_R$=1.093 min, [M-Boc+H]$^+$=1100.7 showed desired product was major. The reaction was concentrated and purified by prep-TLC (6.3% methanol in dichloromethane, Rf=0.4) to obtain Compound 135-C (40 mg, 0.03 mmol, 63.8% yield) as a white solid.

Compound 135 (formic acid salt) was prepared as a white solid in 20% yield using the TFA/HFIP deprotection method (Example 6). LCMS (Method 5-95 AB, ESI): $t_R$=0.750 min, [M+H]$^+$=900.5.

Example 42: Synthesis of Compound 136

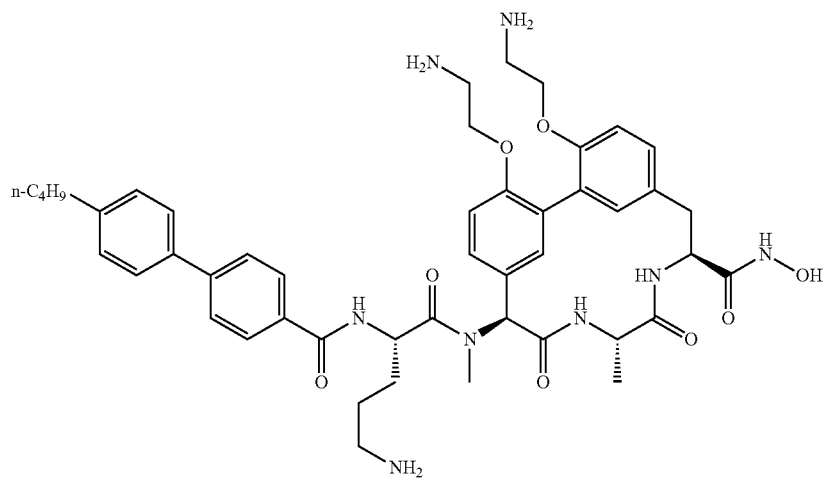

136

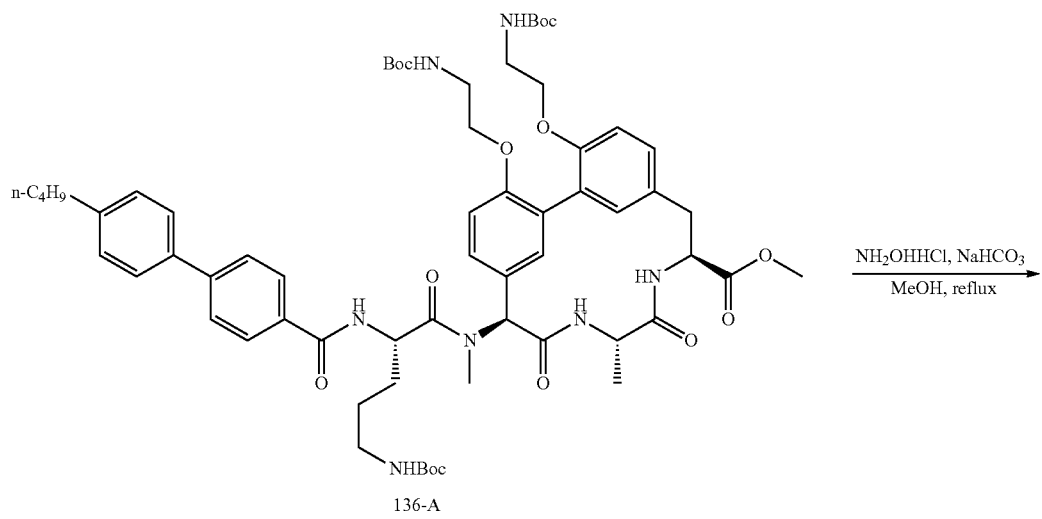

136-A

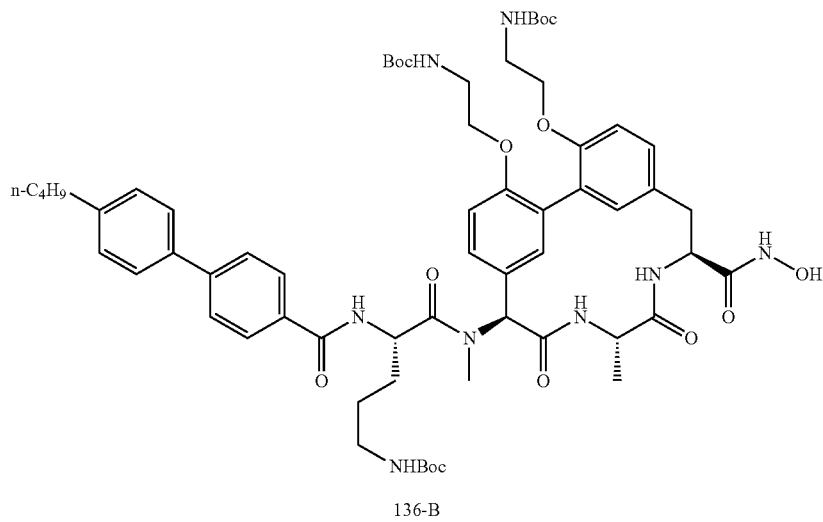

136-B

Compound 136-A is an intermediate in the preparation of Compound 128-A (Example 34).

A mixture of Compound 136-A (100 mg, 0.09 mmol), hydroxylamine hydrochloride (60 mg, 0.86 mmol) and sodium bicarbonate (72 mg, 0.86 mmol) in methanol (10 mL) was stirred at 60° C. for 2 h. The reaction mixture was diluted with water (20 mL), and the mixture was extracted with ethyl acetate (30 mL×3). The organics were washed with water (20 mL×2) then brine (20 mL). The organics were concentrated to give Compound 136-B (100 mg, 99.9% yield) as a white solid. LCMS (5-95AB/1.5 min): $t_R$=1.090 min, $[M+H]^+$=1165.9.

Compound 136 (formic acid salt) was prepared as a white solid in 18% yield using the formic acid Boc-deprotection method (Example 25). LCMS (Method 5-95 AB, ESI): $t_R$=0.737 min, $[M+H^+]$=865.5. $^1$H NMR (400 MHz, CD$_3$OD) δ 7.94 (d, J=7.6 Hz, 2H), 7.74 (d, J=7.6 Hz, 2H), 7.58 (d, J=8.0 Hz, 2H), 7.30-7.22 (m, 4H), 7.16-7.08 (m, 2H), 6.84 (d, J=11.6 Hz, 2H), 6.42 (s, 1H), 5.09 (s, 1H), 4.81-4.76 (m, 2H), 4.22-4.21 (m, 4H), 3.30-3.19 (m, 5H), 3.00-2.92 (m, 5H), 2.69-2.65 (m, 3H), 1.90-1.70 (m, 5H), 1.66-1.62 (m, 2H), 1.42-1.32 (m, 4H), 0.98-0.94 (t, J=4.0 Hz, 3H).

Example 43: Synthesis of Compound 137

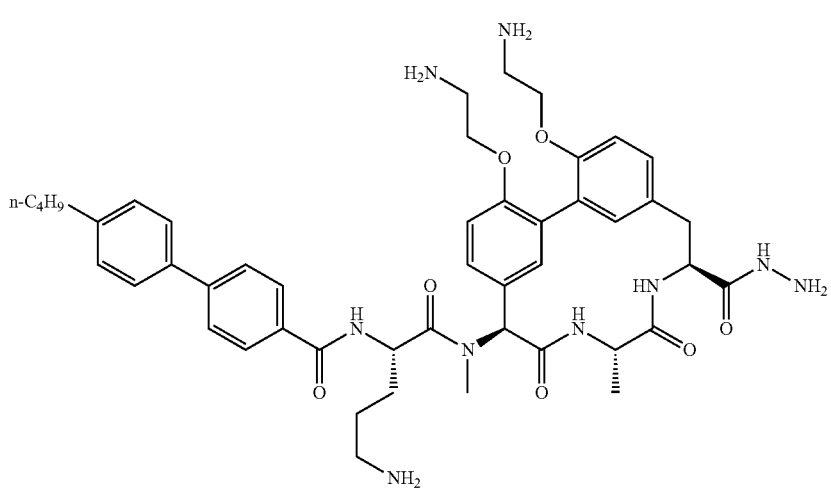

137

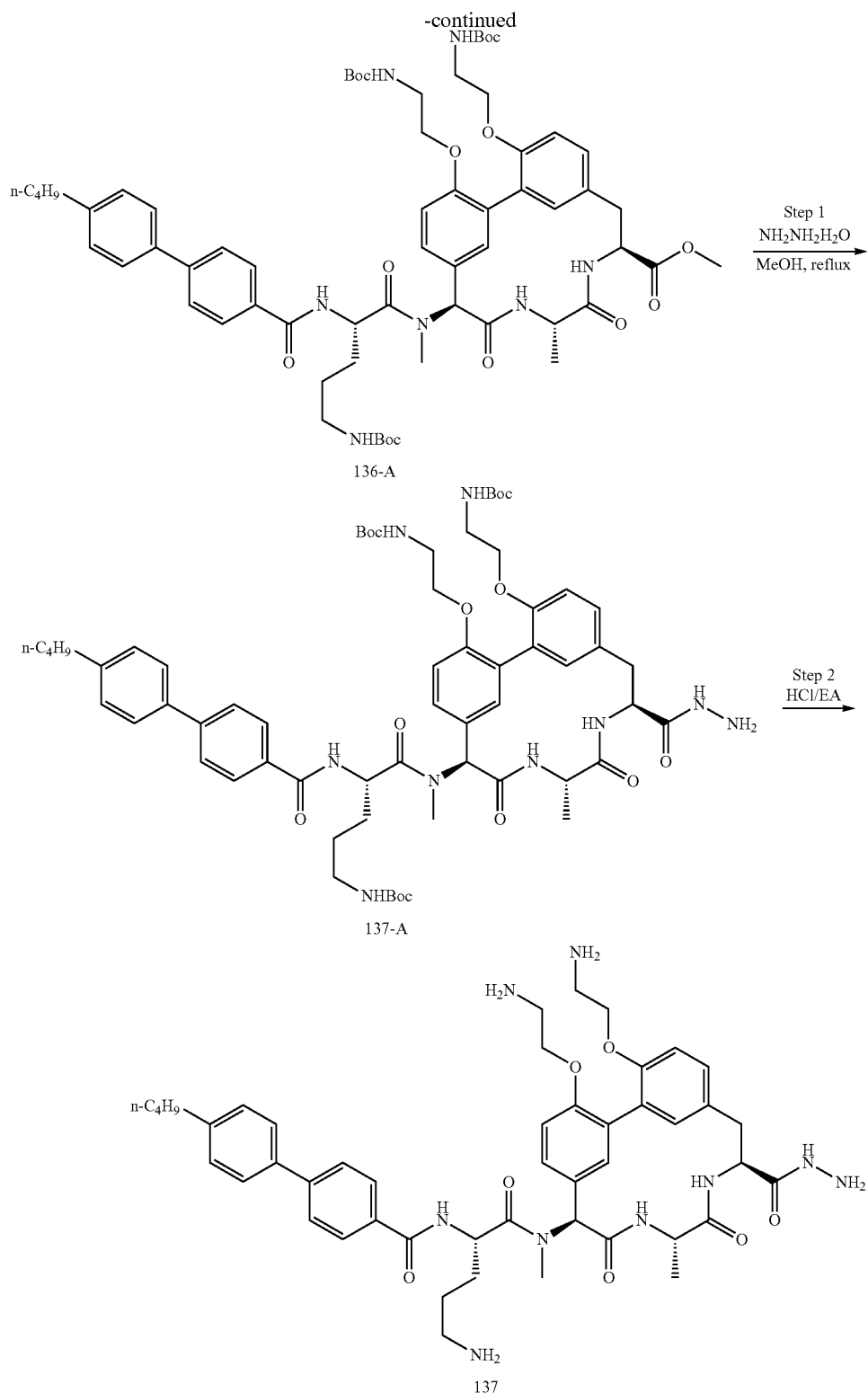

Step 1: A mixture of Compound 136-A (Example 42) (60 mg, 0.05 mmol) and hydrazine hydrate (26 mg, 0.52 mmol) in methanol (10 mL) was stirred at 60° C. for 2 h. The reaction mixture was diluted with water (20 mL), and extracted with ethyl acetate (30 mL×3). The organics were washed with water (20 mL×2) then brine (20 mL). The organics were concentrated to give Compound 137-A (60 mg, 100% yield) as a white solid.

Step 2: A mixture of Compound 137-A (60 mg, 0.05 mmol) in ethyl acetate (5 mL) was treated with 4.0 M HCl (5 mL, 20 mmol) in ethyl acetate at 0° C. The reaction was stirred at this temperature for 1 h and evaporated under reduced pressure. The residue was purified by prep-HPLC (acetonitrile 12-42%/0.05% HCl in water) to give Compound 137 (7.5 mg, 16.3% yield) as a white solid. LCMS (Method 5-95 AB, ESI): $t_R$=0.596 min, [M+H]$^+$=864.4. $^1$H NMR (400 MHz, CD$_3$OD) δ 9.17 (d, J=7.6 Hz, 1H), 8.47 (d, J=8.8 Hz, 1H), 7.97 (d, J=8.4 Hz, 2H), 7.61 (d, J=8.0 Hz, 2H), 7.60 (d, J=8.0 Hz, 2H), 7.32-7.12 (m, 6H), 6.85 (d, J=12.0 Hz, 2H), 6.37 (s, 1H), 5.09-5.06 (m, 1H), 4.81-4.77 (m, 2H), 4.32-4.28 (m, 4H), 3.23-3.10 (m, 5H), 3.01-2.71 (m, 5H), 2.69-2.65 (m, 3H), 1.94-1.80 (m, 5H), 1.66-1.62 (m, 2H), 1.42-1.32 (m, 4H), 0.98-0.94 (t, J=8.0 Hz, 3H).
Example 44: Synthesis of Compound 138
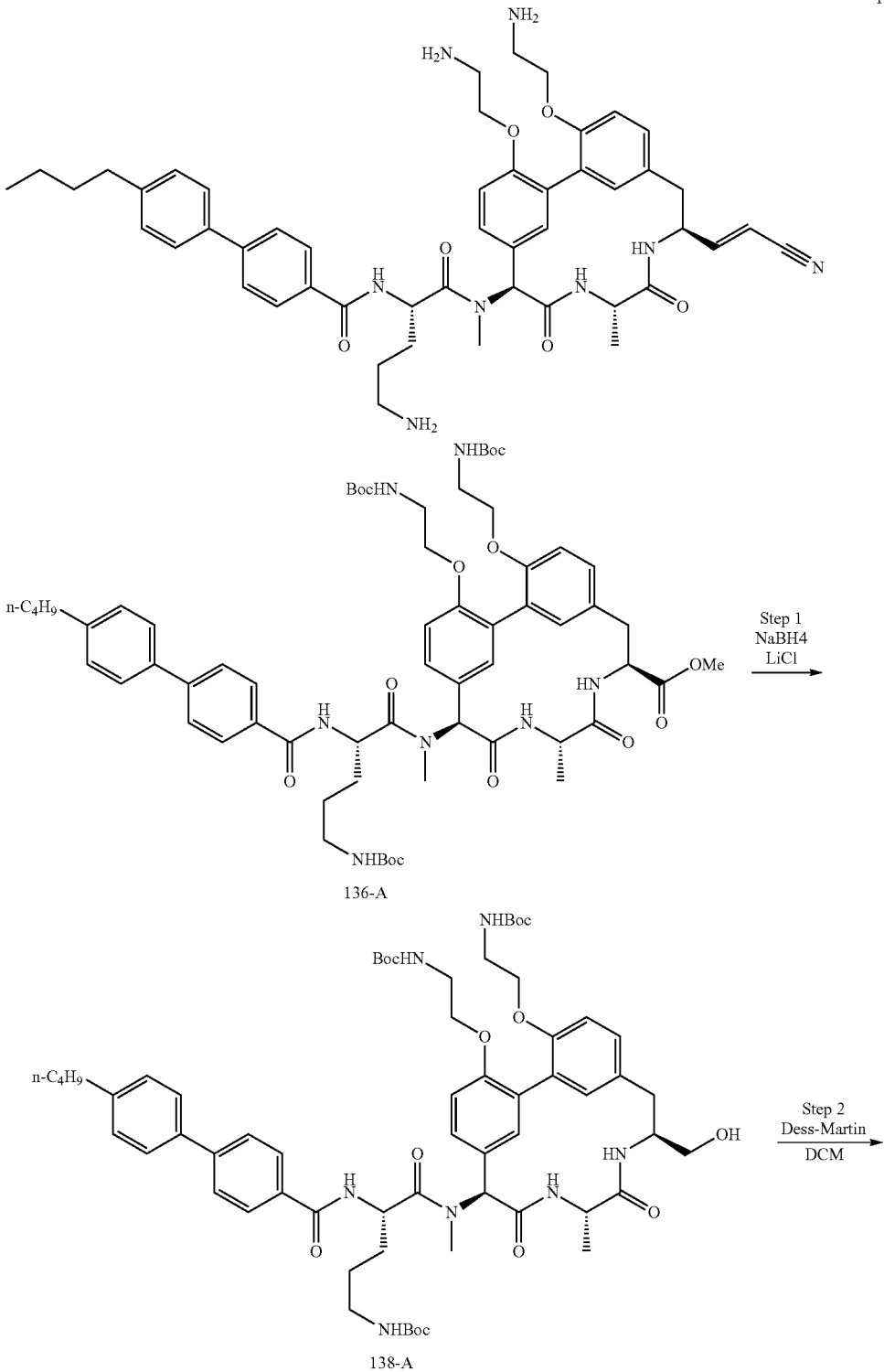

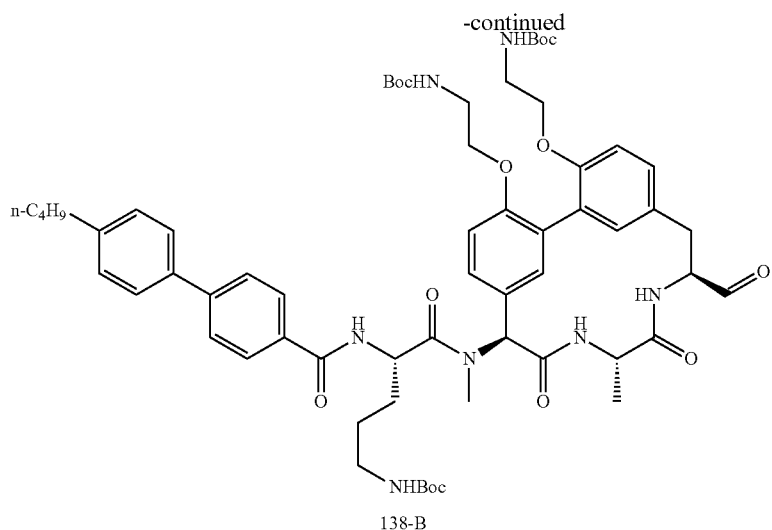
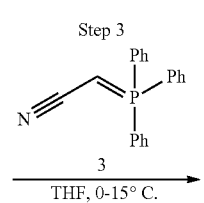

138-B

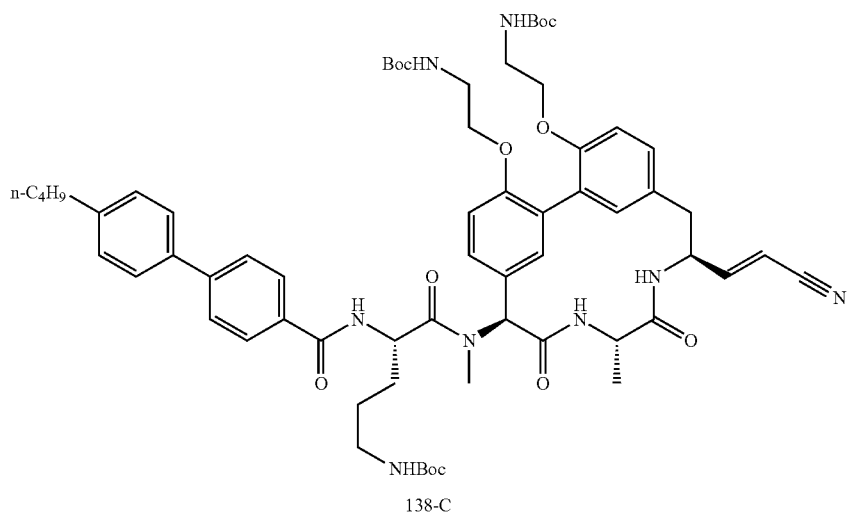

138-C

Step 1: To a solution of Compound 136-A (Example 42) (450 mg, 0.39 mmol) in tetrahydrofuran (20 mL) was added sodium borohydride (146.2 mg, 3.87 mmol) and lithium chloride (163.8 mg, 3.87 mmol). The reaction mixture was stirred at 15° C. for 1 h, quenched with saturated aqueous ammonium chloride (20 mL) and water (20 mL), and extracted with ethyl acetate (30 mL×3). The combined organic layers were washed with water (50 mL×2) and brine (50 mL), dried (sodium sulfate) and concentrated to give Compound 138-A (400 mg, yield 91%) as a white solid. LCMS (5-95AB/1.5 min): $t_R$=1.107 min, [M-Boc+H]$^+$ 1037.0.

Step 2: To a solution of Compound 138-A (90.0 mg, 0.08 mmol) in dichloromethane (10 mL) was added Dess-Martin periodane (67.2 mg, 0.16 mmol) at 0° C. and stirred at 15° C. for 1 h. The reaction mixture was diluted with water (10 mL) and extracted with EtOAc (30 mL×3). The combined organic layers were washed with water (20 mL×2) and brine (20 mL), dried over MgSO$_4$ and concentrated to obtain crude Compound 138-B (100 mg) as a white solid. LCMS (Method 5-95 AB, ESI): $t_R$=1.100 min, [M-Boc+H]$^+$= 1034.6.

To a solution of Compound 138-B (90.0 mg, 0.08 mmol) in tetrahydrofuran (10 mL) was added (triphenylphosphoranylidene)acetonitrile (47.8 mg, 0.16 mmol). The reaction mixture was stirred at 15° C. for 12 h, diluted with water (20 mL) and extracted with EtOAc (30 mL×3). The combined organic layers were washed with water (20 mL×2) and brine (20 mL), dried over MgSO$_4$ and concentrated. The residue was purified by prep-TLC (5% methanol in DCM, Rf=0.4) to obtain Compound 138-C (80 mg, 87.2% yield) as a white solid. LCMS (Method 5-95 AB, ESI): $t_R$=1.121 min, [M+H]$^+$=1158.0.

Compound 138 (formic acid salt) was prepared as a white solid in 11% yield using the TFA/HFIP deprotection method (Example 6). LCMS (Method 5-95 AB, ESI): $t_R$=0.629 min, $[M+H]^+$=857.4.
Example 45: Synthesis of Compound 139
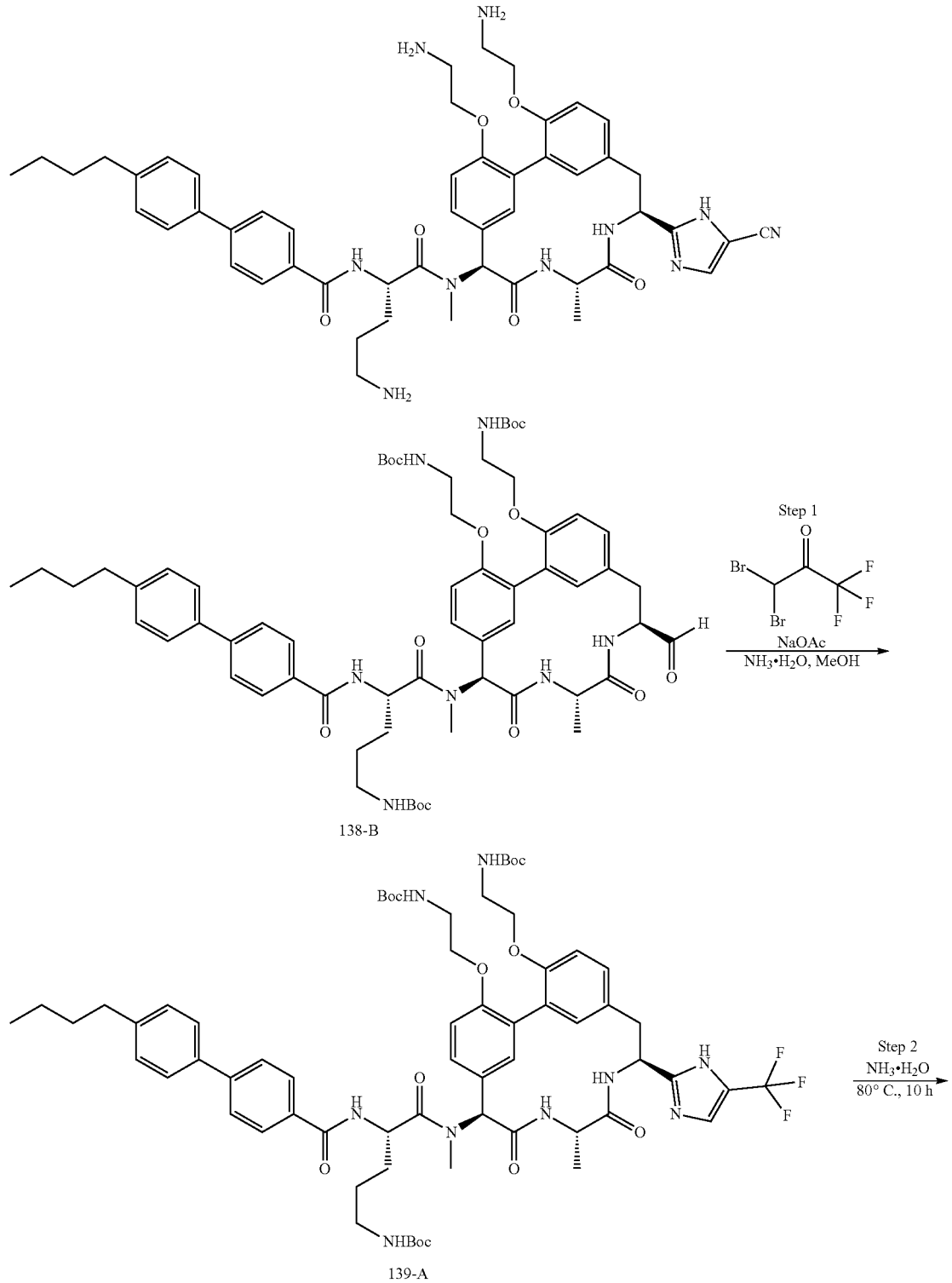

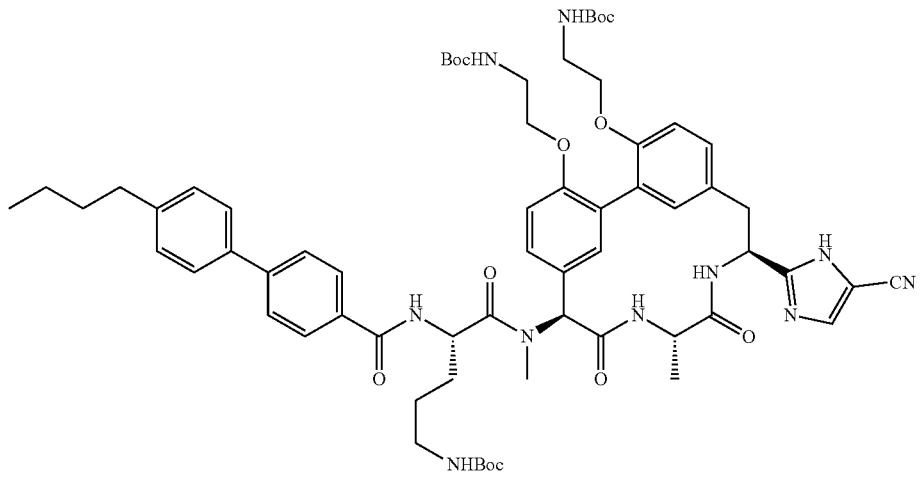

139-B

Step 1: A solution of 1,1-dibromo-3,3,3-trifluoroacetone (237.8 mg, 0.88 mmol) in 15% aq. sodium acetate (4.5 mL, 0.18 mmol) was stirred at 90° C. for 30 min and cooled to 15° C. Compound 138-B (Example 42) (100 mg, 0.09 mmol) in methanol (20 mL) and ammonia (6 mL) were added. The solution was stirred at 15° C. for 16 h and concentrated. The residue was taken up in EtOAc (10 mL), washed with water (10 mL×2) and brine (10 mL), dried over MgSO$_4$ and concentrated. The residue was purified by prep-TLC (5% methanol in DCM, Rf=0.4) to afford Compound 139-A (70 mg, 64% yield) as a white solid.

Step 2: A mixture of Compound 139-A (60.0 mg, 0.05 mmol) in ammonium hydroxide (20 mL) was stirred at 80° C. for 10 hours and extracted with ethyl acetate (15 mL×3). The combined organic layers were dried over sodium sulfate and concentrated. The residue was purified by prep-TLC (10% methanol in DCM, Rf=0.5) to afford Compound 139-B (30 mg, 51.8% yield) as a white solid. LCMS (Method 5-95 AB, ESI): $t_R$=1.092 min, [M-Boc+H]$^+$= 1097.9.

Compound 139 (formic acid salt) was prepared as a white solid in 25% yield using the TFA/HFIP deprotection method (Example 6). LCMS (Method 5-95 AB, ESI): $t_R$=0.608 min, [M+H]$^+$=898.3.

Example 46: Synthesis of Compound 140

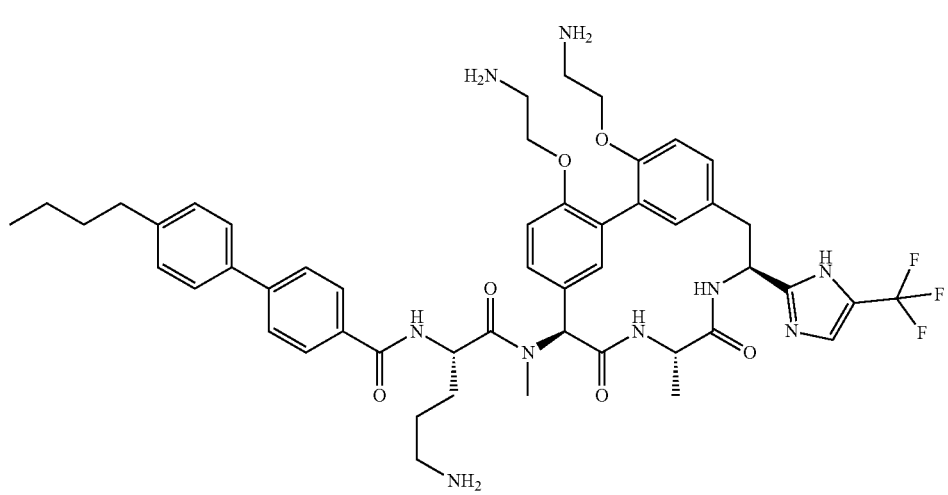

140

Compound 140 (formic acid salt) was prepared as a white solid in 19% yield using the TFA/HFIP deprotection method (Example 6) from Compound 139-A (Example 45). LCMS (Method 5-95 AB, ESI): $t_R$=0.772 min, [M+H]$^+$=940.6.
Example 47: Synthesis of Compound 141
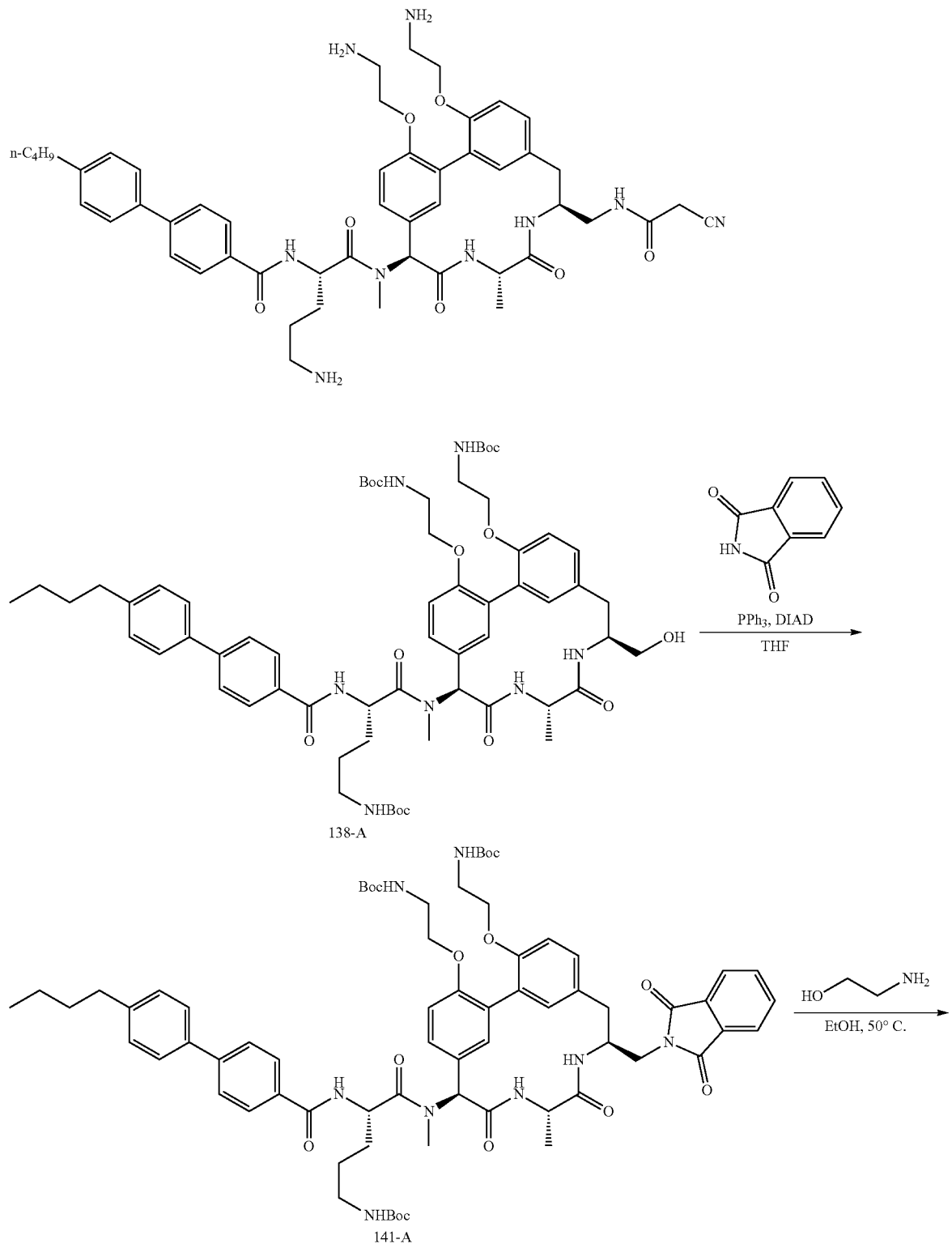

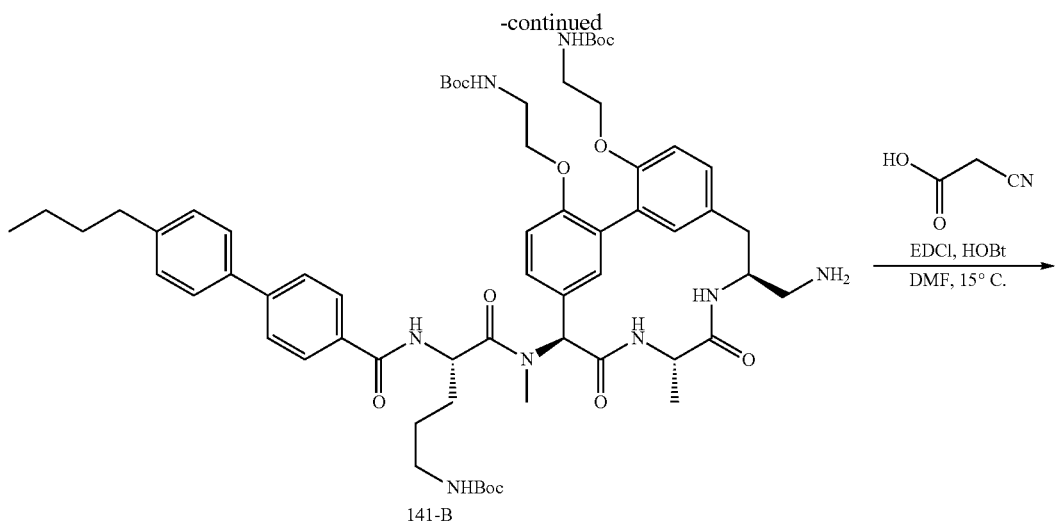

141-B

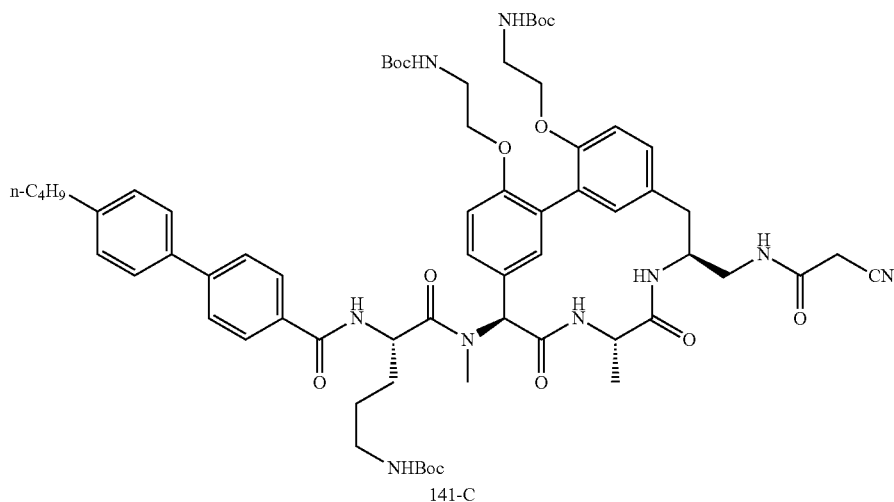

141-C

Step 1: Compound 138-A (Example 44) (200.0 mg, 0.18 mmol) was dissolved in dry tetrahydrofuran (10 mL) and triphenylphosphine (138.5 mg, 0.53 mmol) was added at 0° C. The solution was stirred under nitrogen and 1H-isoindole-1,3(2H)-dione (38.8 mg, 0.26 mmol) was added followed by diisopropyl azodicarboxylate (89.0 mg, 0.44 mmol). The mixture was stirred at room temperature for 12 h and concentrated in vacuo. The residue was purified by prep-TLC (5% methanol in DCM, Rf=0.5) to obtain Compound 141-A (200 mg, 89.8% yield) as a white solid.

Step 2: To a solution of Compound 141-A (200.0 mg, 0.16 mmol) in ethanol (10 mL) was added 2-aminoethanol (96.5 mg, 1.58 mmol). The reaction mixture was stirred at 50° C. for 12 h, diluted with water (20 mL) and extracted with EtOAc (30 mL×3). The combined organic layers were washed with water (20 mL×2) and brine (20 mL), dried over MgSO$_4$ and concentrated to obtain crude Compound 141-B (179.4 mg) as a white solid.

Step 3: A mixture of Compound 141-B (30.0 mg, 0.03 mmol), 1-(3-dimethylaminopropyl)-3-ethylcarbodiimide hydrochloride (10.1 mg, 0.05 mmol), 1-hydroxybenzotriazole (7.1 mg, 0.05 mmol), cyanoacetic acid (4.5 mg, 0.05 mmol), N,N-diisopropylethylamine (13.6 mg, 0.11 mmol) in N,N-dimethylformamide (10 mL) was stirred at 15° C. for 2 h, diluted with water (20 mL) and extracted with EtOAc (30 mL×3). The combined organic layers were washed with water (20 mL×2) and brine (20 mL), dried over MgSO$_4$ and concentrated. The residue was purified by chromatography on silica gel (5% methanol in dichloromethane, Rf=0.5) to obtain Compound 141-C (30 mg, 94.5% yield) as a white solid.

Compound 141 (formic acid salt) was prepared as a white solid in 7% yield using the TFA/HFIP deprotection method (Example 6). LCMS (Method 5-95 AB, ESI): $t_R$=0.615 min, [M/2+H]$^+$=452.1. LCMS (Method 5-95 AB, ESI): $t_R$=0.615 min, [M/2+H]$^+$=452.1.

Example 48: Synthesis of Compound 142
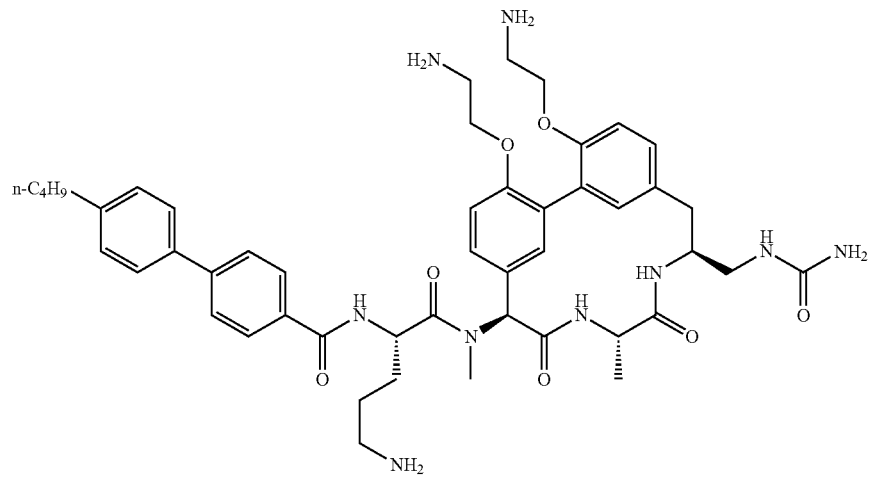
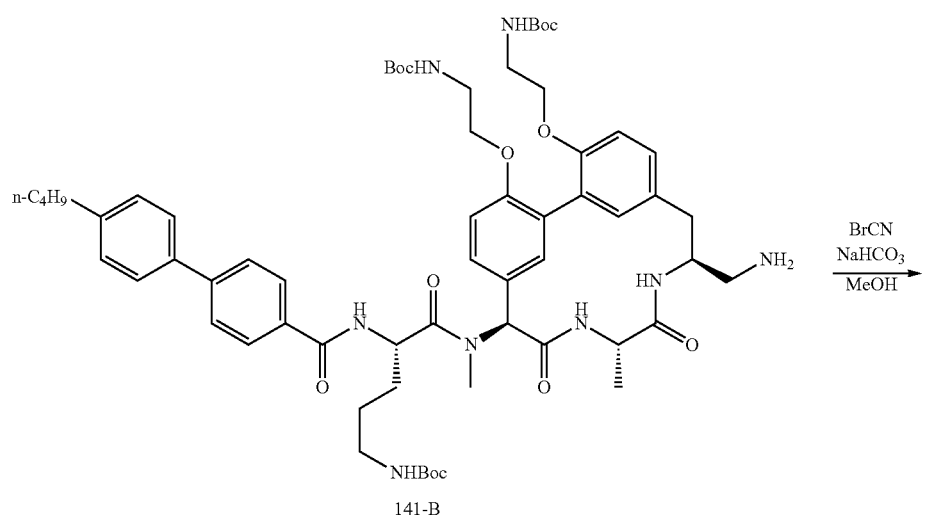

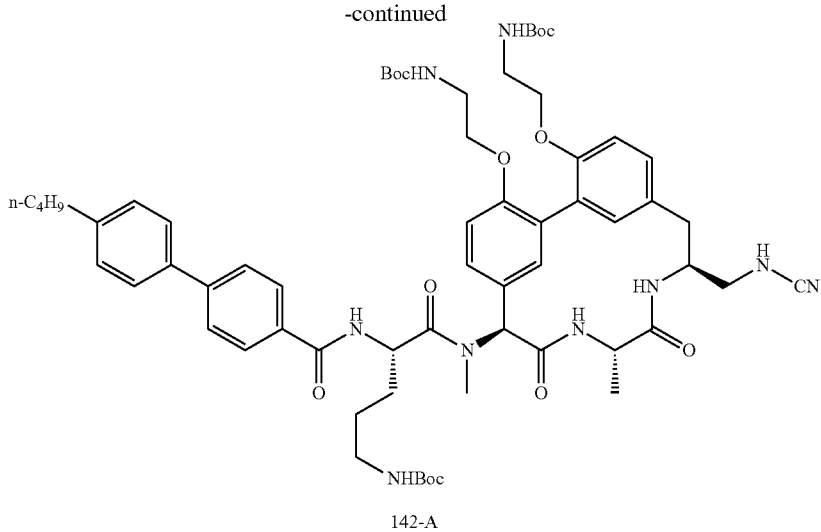

142-A

To a solution of Compound 141-B (Example 47) (60.0 mg, 0.05 mmol) in methanol (10 mL) were added sodium bicarbonate (88.8 mg, 1.06 mmol) and cyanic bromide (11.2 mg, 0.11 mmol) at 0° C. The reaction mixture was stirred at 0° C. for 3 h, diluted with water (20 mL) and extracted with EtOAc (30 mL×3). The combined organic layers were washed with water (20 mL×2) and brine (20 mL), dried over MgSO$_4$ and concentrated. The residue was purified by prep-TLC (5% methanol in dichloromethane, Rf=0.4) to obtain Compound 142-A (50 mg, 81.6% yield) as a white solid. LCMS (Method 5-95 AB, ESI): t$_R$=1.094 min, [M+H]$^+$=1160.9.

Compound 142 (formic acid salt) was prepared as a white solid in 8% yield using the TFA/HFIP deprotection method (Example 6). LCMS (Method 5-95AB): RT=0.600 min/1.5 min, [M+H]$^+$=878.4.

Example 49: Synthesis of Compound 143

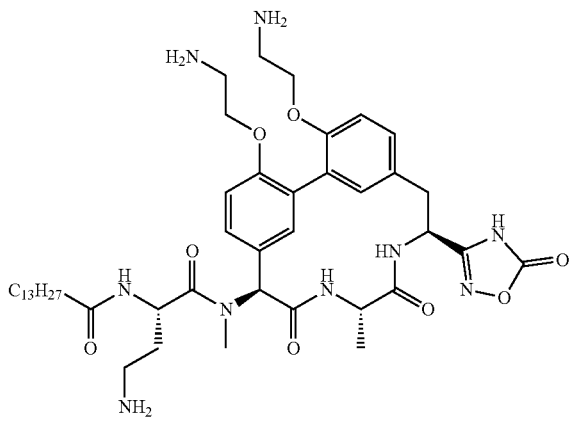

143

Compound 143 was prepared utilizing the methods similar to those in Example 31 (Compound 125). LCMS (Method 5-95 AB, ESI): t$_R$=0.793 min, [M+H]$^+$=850.6.

Example 50: Synthesis of Compound 144

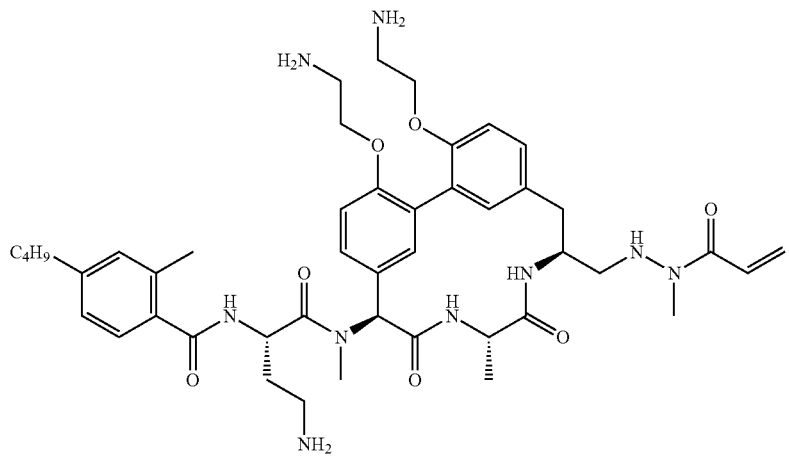

144

-continued
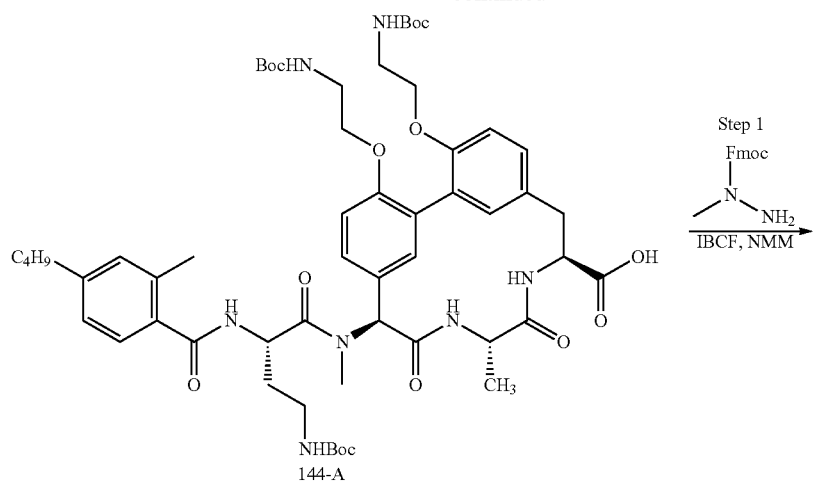
144-A
Step 1
Fmoc-N(Me)-NH2
IBCF, NMM
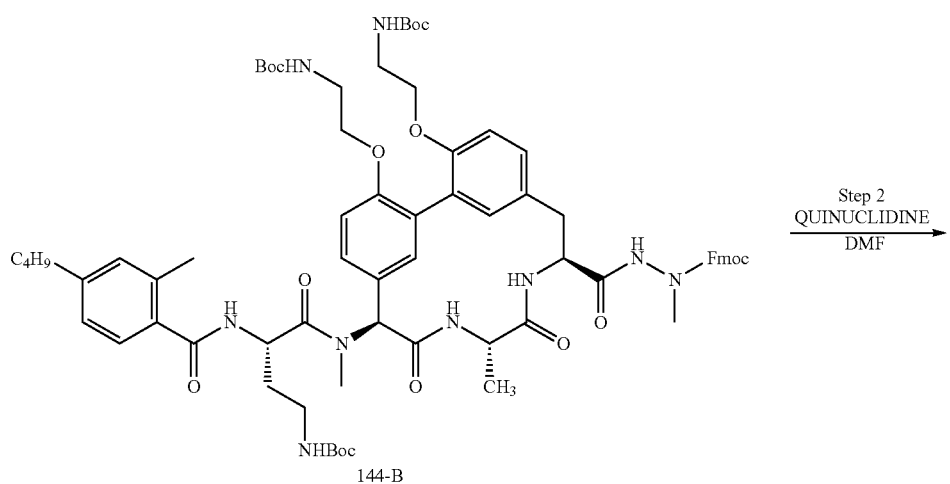
144-B
Step 2
QUINUCLIDINE
DMF
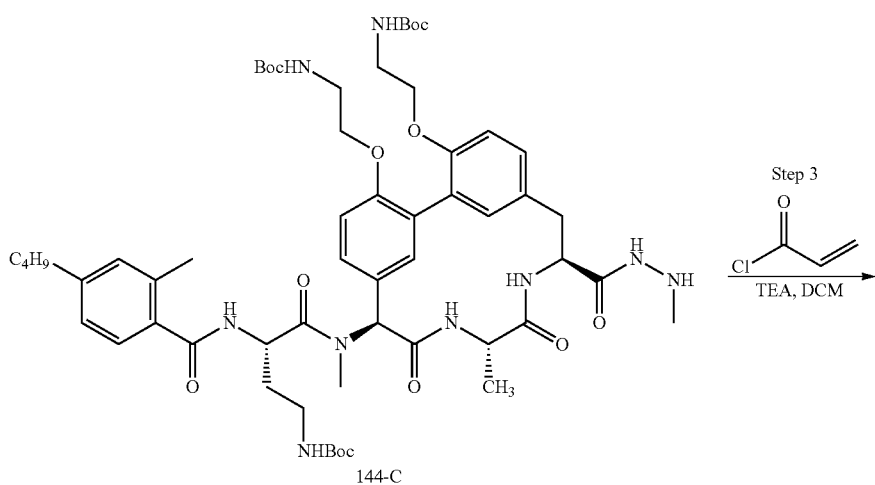
144-C
Step 3
acryloyl chloride
TEA, DCM

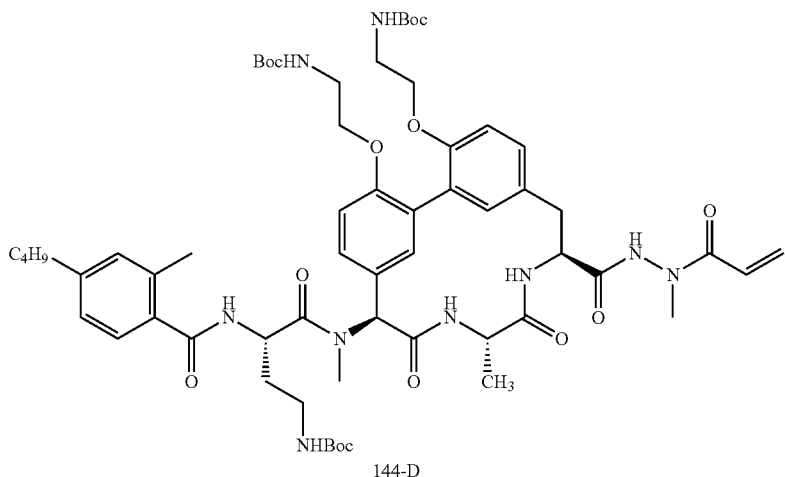

144-D

Compound 144-A was prepared utilizing the methods similar to Compound 101-N (Example 6).

Step 1: To a stirred solution of Compound 144-A (330 mg, 0.31 mmol) in DCM (10 mL) was added NMM (91 mg, 0.92 mmol) and IBCF (83 mg, 0.61 mmol) slowly at 0° C. and the mixture was stirred at the same temperature for 30 min, followed by the addition of (9H-fluoren-9-yl)methyl 1-methylhydrazinecarboxylate (165 mg, 0.61 mmol). The resulting mixture was then stirred at room temperature for 1 h. To the reaction mixture was added with DCM (30 mL), which was washed with brine (30 mL×2). The organic layer was dried over $Na_2SO_4$, concentrated and the residue was purified by silica gel flash column to give Compound 144-B (350 mg, 86% yield) as a white solid. LCMS (Method 5-95 AB, ESI): $t_R$=1.110, $[M+H]^+$=1325.3.

Step 2: To a stirred solution of Compound 144-B (50 mg, 0.04 mmol) in DCM (3 mL) was added quinuclidine (8.4 mg, 0.08 mmol) and the mixture was stirred at room temperature for 16 h. The volatiles were removed and the residue was then purified by prep-TLC to give Compound 144-C (35 mg, 84.1% yield) as a white solid.

Step 3: To a stirred solution of Compound 144-C (40 mg, 0.04 mmol) in DCM (2 mL) was added $Et_3N$ (11 mg, 0.11 mmol) and acryloyl chloride (3.6 mg, 0.04 mmol) at 0° C. and the mixture was warmed to room temperature while stirring and stirred at the same temperature for 0.5 h. The volatiles were removed and the residue was purified by prep-TLC to give Compound 144-D (30 mg, 71.5% yield) as a white solid. LCMS (Method 5-95 AB, ESI): $t_R$=1.021, $M+Na^+$=1179.1.

Compound 144 (formic acid salt) was prepared as a white solid in 22% yield using the TFA/HFIP deprotection method (Example 6). LCMS (Method 5-95 AB, ESI): $t_R$=0.695, $[M+H]^+$=856.6.

Example 51: Synthesis of Compound 145

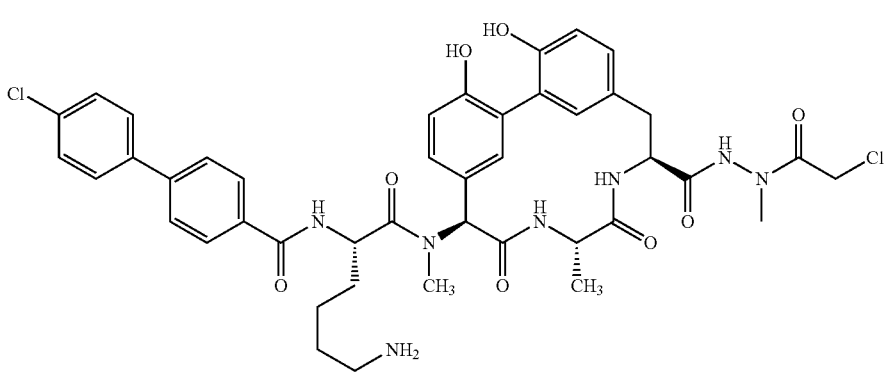

145

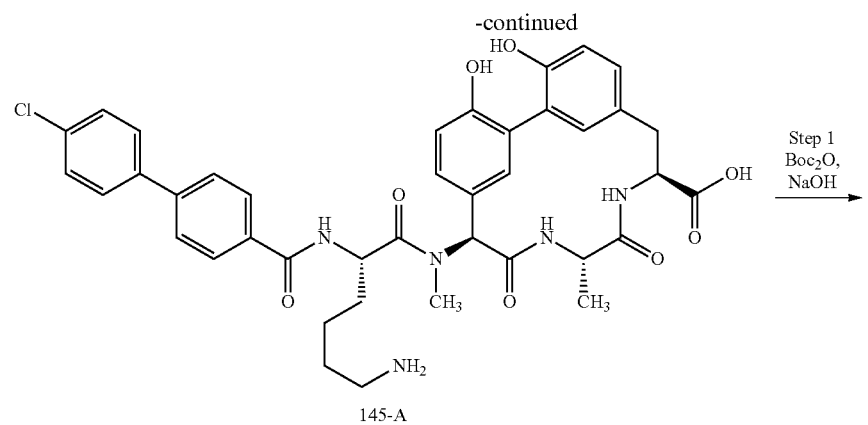
145-A
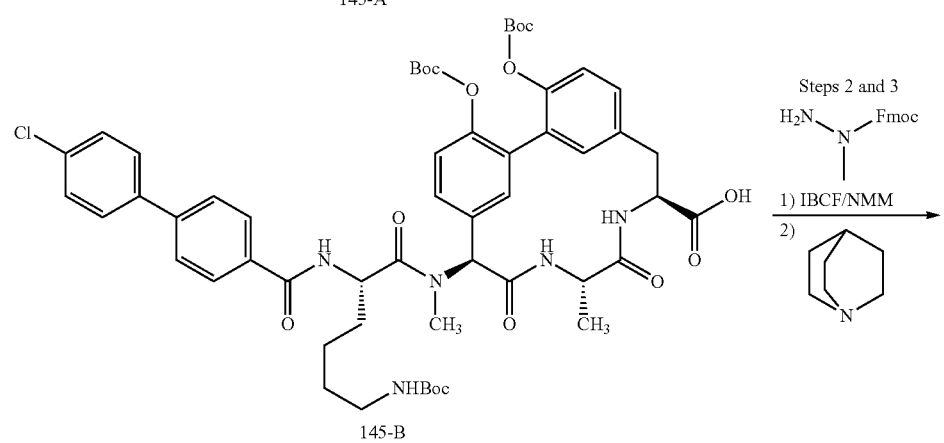
145-B
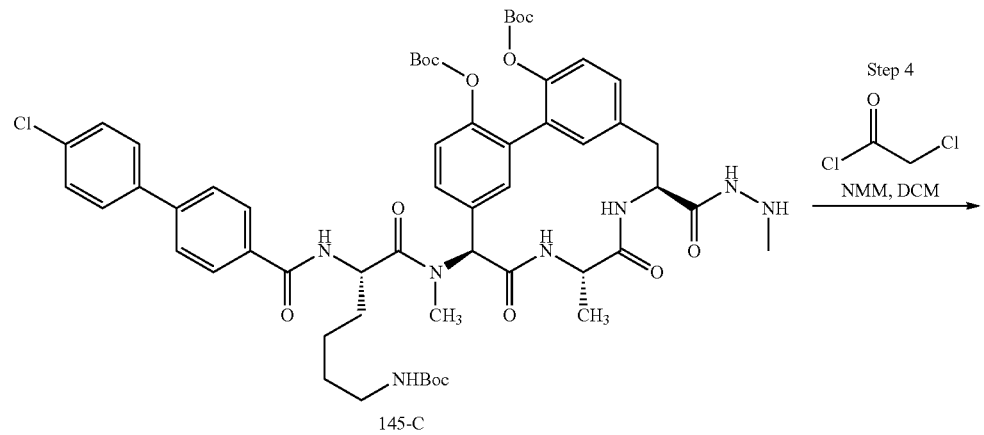
145-C
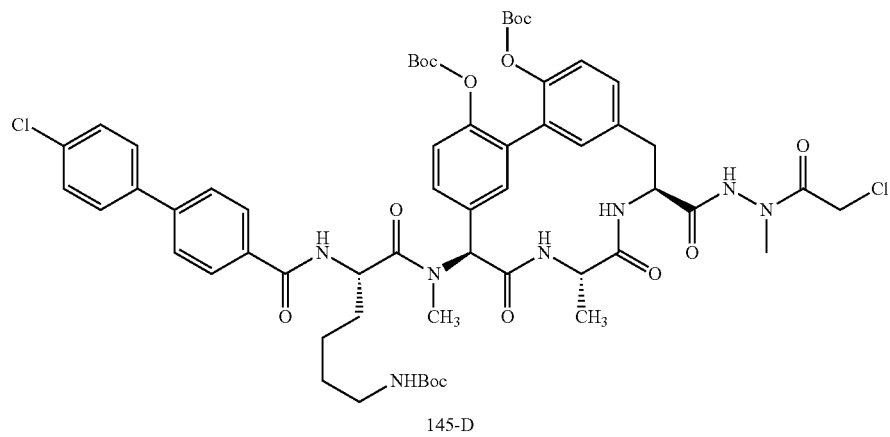
145-D

Compound 145-A was prepared utilizing the methods for Compound 119-D (Example 24).

Step 1: To a solution of Compound 145-A (500 mg, 0.5 mmol) in dioxane (20 mL) was added 1M NaOH (10 mL, 10 mmol) and (Boc)$_2$O (1.2 mL, 5 mmol). The reaction mixture was stirred at room temperature overnight. The dioxane was removed under reduced pressure and the mixture was acidified with 1M HCl. The resultant white pasty material was dried to afford Compound 145-B (507 mg, 96%). MS (ESI) for (C$_{55}$H$_{66}$ClN$_5$O$_{14}$): m/z 1056 (M+H)$^+$.

Steps 2 and 3: Starting from Compound 145-B, amide coupling with (9H-fluoren-9-yl)methyl 1-methylhydrazinecarboxylate (IBCF/NMM) and Fmoc removal procedure as described in Example 50 was utilized to afford Compound 145-C (100 mg, 75.3% yield) as a white solid.

Step 4: To a stirred solution of Compound 145-C (80 mg, 0.07 mmol) in DCM (5 mL) was added chloroacetyl chloride (16.7 mg, 0.15 mmol) and NMM (22.4 mg, 0.22 mmol) dropwise at 0° C. and the mixture was stirred at that temperature for another 1 h. The volatiles were removed and the residue was purified by Prep-TLC to give the Compound 145-D (55 mg, 64.2% yield) as a white solid.

Compound 145 (formic acid salt) was prepared as a white solid in 22% yield using the TFA/HFIP deprotection method (Example 6). LCMS (Method 5-95 AB, ESI): t$_R$=0.805, [M+H]$^+$=860.2.

Example 52: Synthesis of Compound 146

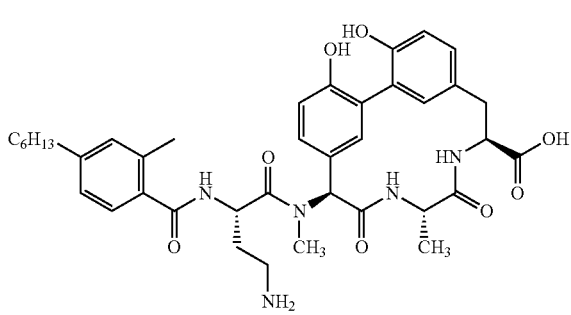

146

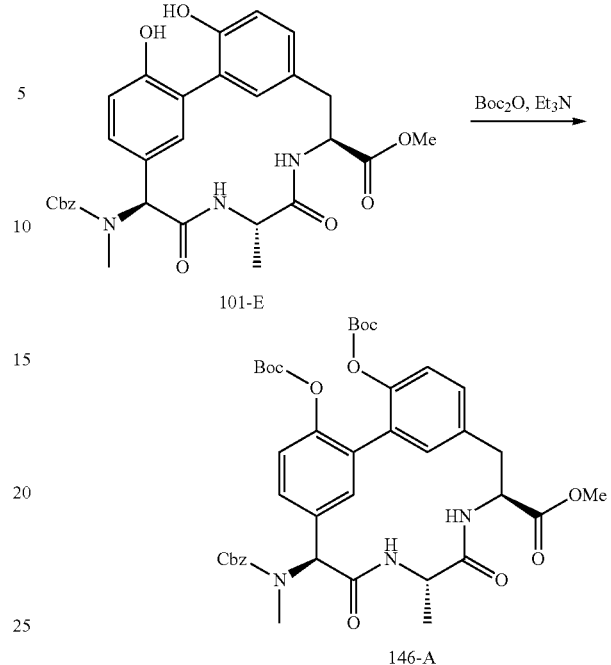

101-E

146-A

Compound 101-E (Example 4) (2.0 g, 3.56 mmol) was dissolved in CH$_2$Cl$_2$ (10 mL) and to this stirred solution Et$_3$N (2.47 mL, 17.8 mmol) and (Boc)$_2$O (2.45 mL, 10.68 mmol) was added. The reaction mixture was stirred at rt for overnight. After the reaction was complete, brine solution was added and the mixture was extracted with ethyl acetate. The combined organic layers washed with brine, dried over anhydrous Na$_2$SO$_4$, filtered and solvent was removed in vacuum. The residue was purified by flash chromatography (DCM—5% DCM—MeOH) to afford 2 g (74%) of Compound 146-A.

Starting from Compound 146-A, Compound 146 was prepared as a white solid using the methods in Example 4 and Example 8 utilizing hydrogenation (Pd/C), amide coupling (HATU/DIEA), ester hydrolysis (LiOH/THF) and global Boc de-protection (TFA/HFIP). LCMS (Method 5-95 AB, ESI): t$_R$=0.825, [M+H]$^+$=716.6.

Example 53: Synthesis of Compound 147

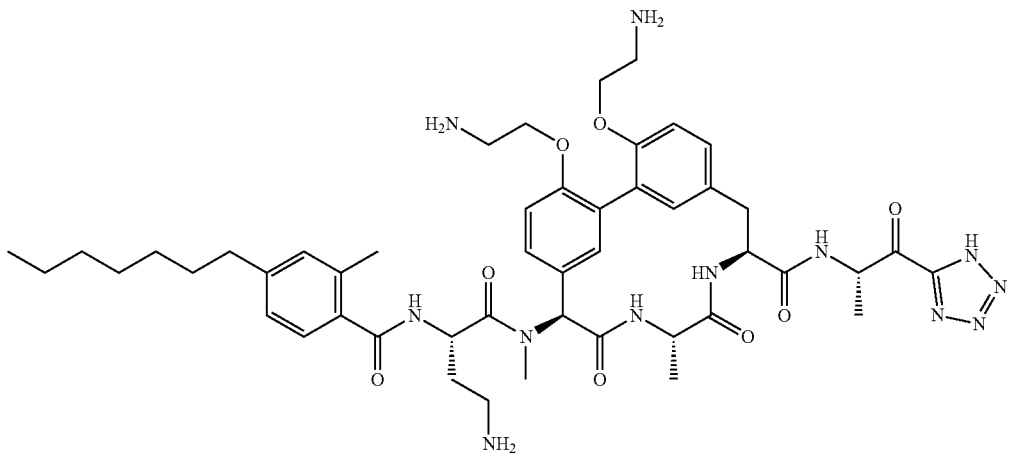 [SMILES: CCCCCCCc1ccc(C(=O)N[C@@H](CCN)C(=O)N(C)[C@@H]2C(=O)N[C@@H](C)C(=O)N[C@H](C(=O)N[C@@H](C)C(=O)c3nnn[nH]3)Cc3ccc(OCCN)c(c3)-c3cc2ccc3OCCN)c(C)c1]

Compound 147 (formic acid salt) was prepared from 4-heptyl-2-methylbenzoic acid (Example 6) utilizing methods analogous to those described in Example 21. LCMS (Method 5-95 AB, ESI): $t_R$=0.619, [M+H]$^+$=925.7; $^1$H NMR (400 MHz, MeOH-d$_4$) δ 8.51 (br s, 2H), 7.37-6.98 (m, 5H), 6.94-6.59 (m, 4H), 6.48 (s, 1H), 5.56-5.35 (m, 2H), 5.25-5.20 (m, 1H), 4.49-4.07 (m, 5H), 3.30-2.71 (m, 11H), 2.70-1.95 (m, 7H), 1.91-1.65 (m, 3H), 1.64-1.08 (m, 11H), 0.89 (t, J=6.8 Hz, 3H).
Example 54: Synthesis of Compound 148
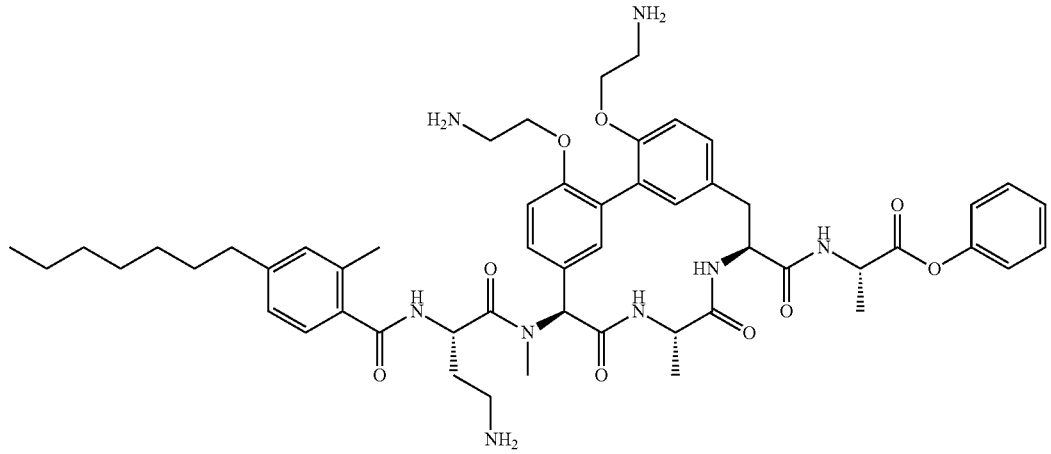
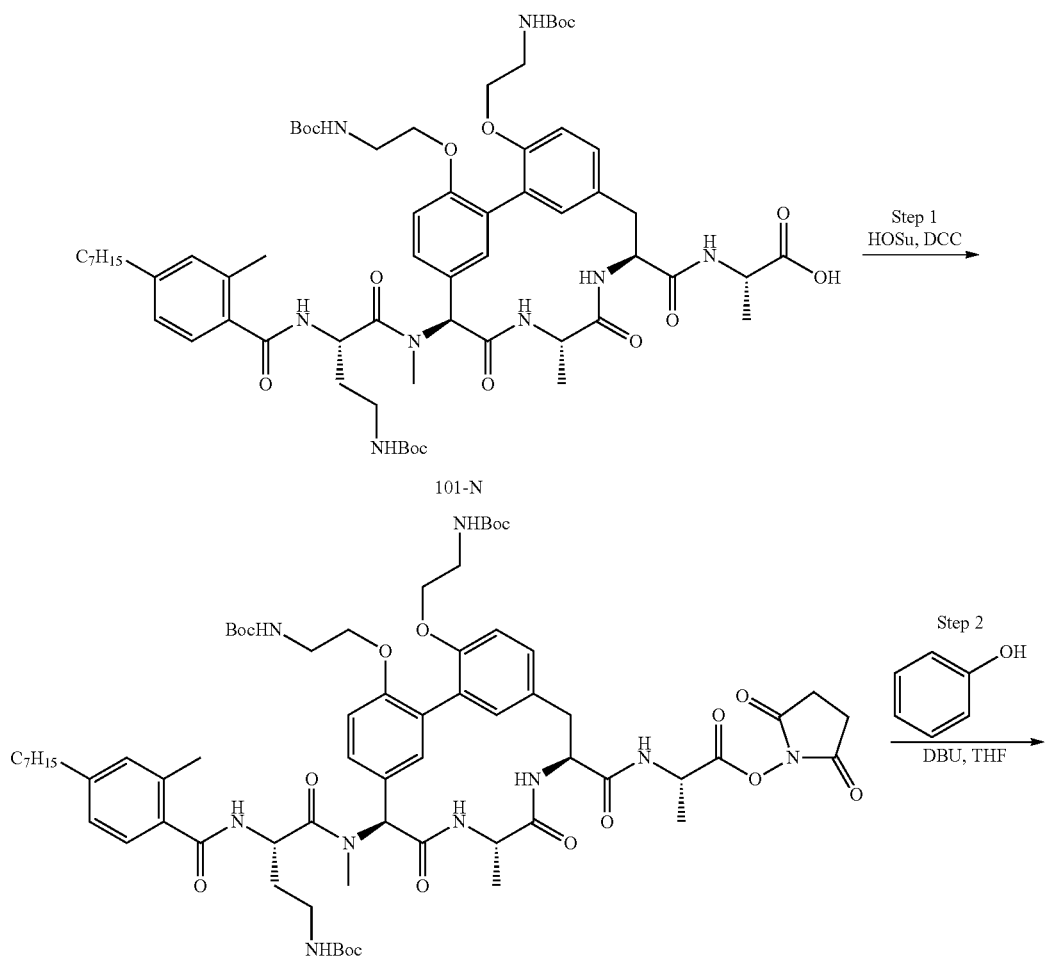

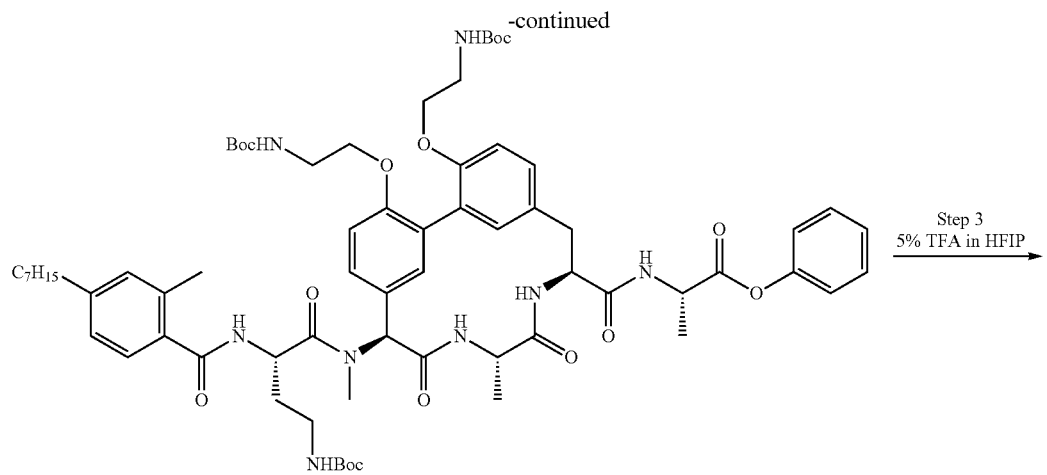

148-3

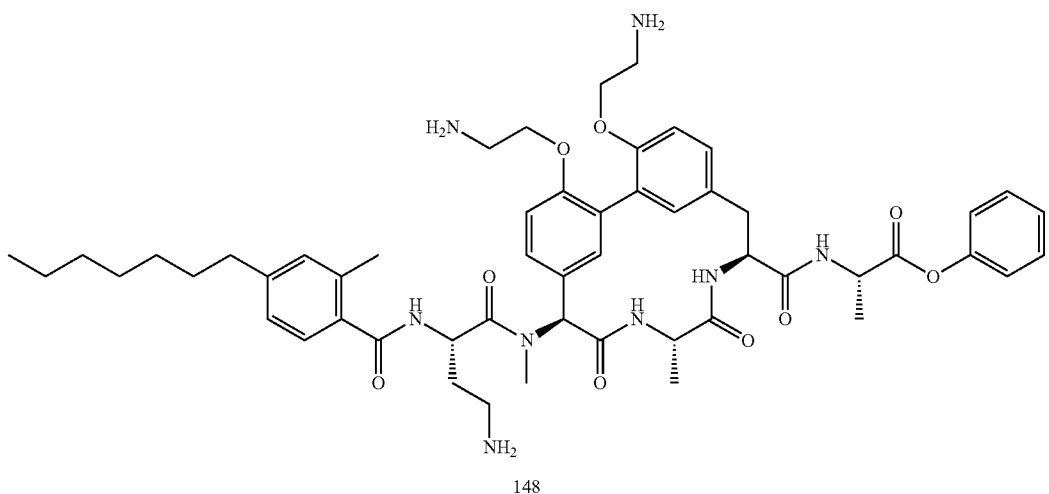

148

Step 1: To a stirred solution of compound 101-N (Example 6) (60 mg, 0.05 mmol) in THF (3 mL) was added HOSu (35 mg, 0.30 mmol) and DCC (63 mg, 0.30 mmol). The mixture was stirred at 20° C. for 2 h. The mixture was then concentrated in vacuo to give compound 148-2 (60 mg, 92.5% yield) as a white solid, which was used directly without purification. LCMS (Method 5-95 AB, ESI): $t_R$=0.984, [M+H]$^+$=1285.0

Step 2: A mixture of phenol (27 mg, 0.28 mmol) and 1,8-diazabicyclo[5.4.0]undec-7-ene (57 mg, 0.37 mmol) in THF (5 mL) was stirred at 20° C. for 0.5 h, followed by the addition of compound 148-2 (60 mg, 0.05 mmol). The resulting mixture was stirred at the same temperature for another 1 h. The mixture was concentrated and purified by Prep-TLC (10% MeOH in DCM) to afford compound 148-3 (11 mg, 18.6% yield) as a white solid. LCMS (Method 5-95 AB, ESI): $t_R$=1.019, [M+H]$^+$=1264.7.

Step 3: Compound 148 (formic acid salt) was prepared from 148-3 following typical Boc removal condition (TFA/HFIP) as described in Example 6 to afford 1.9 mg (24.5% yield) as a white solid. LCMS (Method 5-95 AB, ESI): $t_R$=0.786, [M+H]$^+$=963.9; $^1$H NMR (400 MHz, MeOH-d$_4$) δ 8.52 (brs, 2H), 7.32-7.08 (m, 10H), 6.85-6.76 (m, 4H), 6.34 (s, 1H), 5.14-5.11 (m, 1H), 4.82-4.77 (m, 1H), 4.19-4.15 (m, 6H), 3.48-3.40 (m, 2H), 3.21-3.10 (m, 6H), 2.92 (s, 3H), 2.63-2.61 (m, 3H), 2.41 (s, 3H), 2.22-2.09 (m, 2H), 1.61-1.57 (m, 4H), 1.37-1.29 (m, 11H), 0.91 (t, J=6.8 Hz, 3H).

Example 55: Synthesis of Compound 149
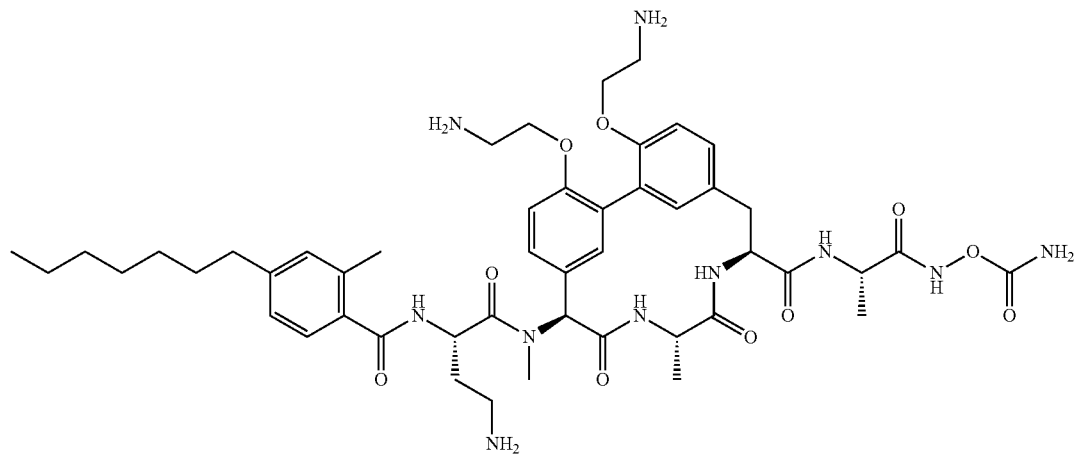
149
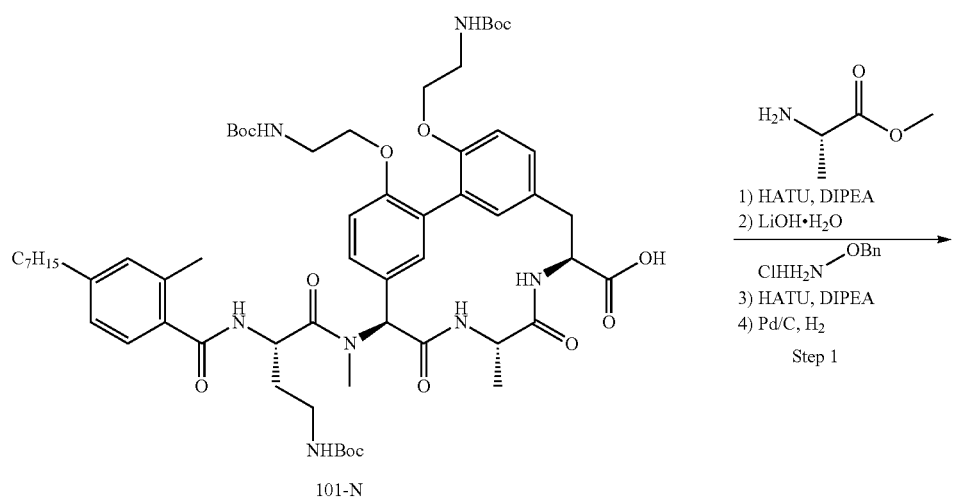
101-N
1) HATU, DIPEA
2) LiOH·H₂O
   ClHH₂N—OBn
3) HATU, DIPEA
4) Pd/C, H₂
Step 1
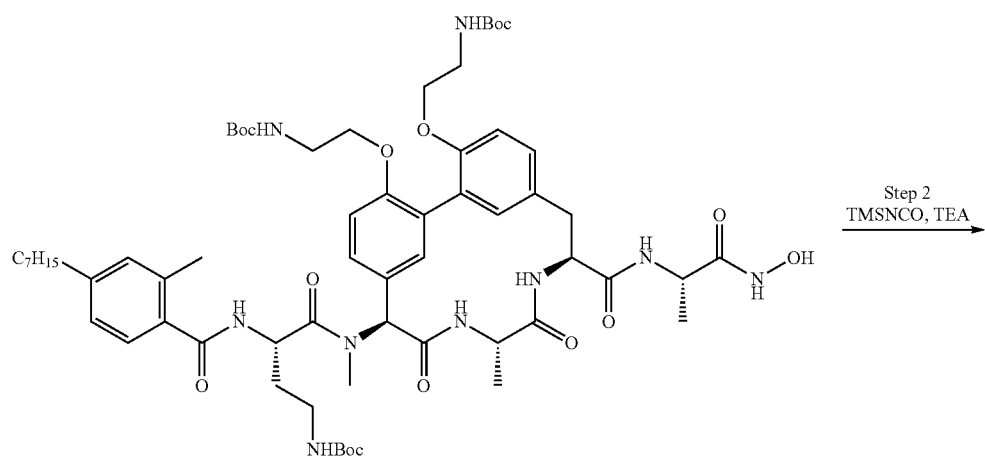
149-2
Step 2
TMSNCO, TEA

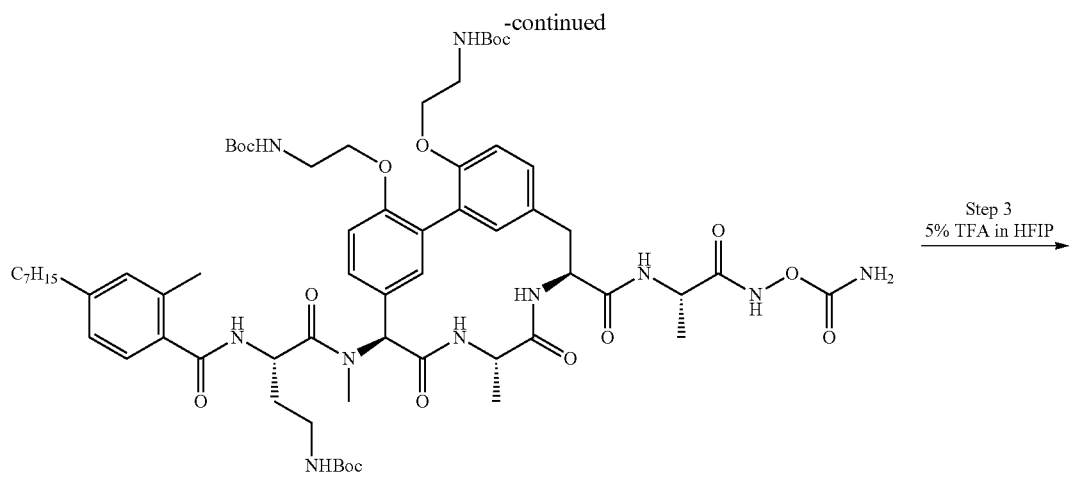

149-3

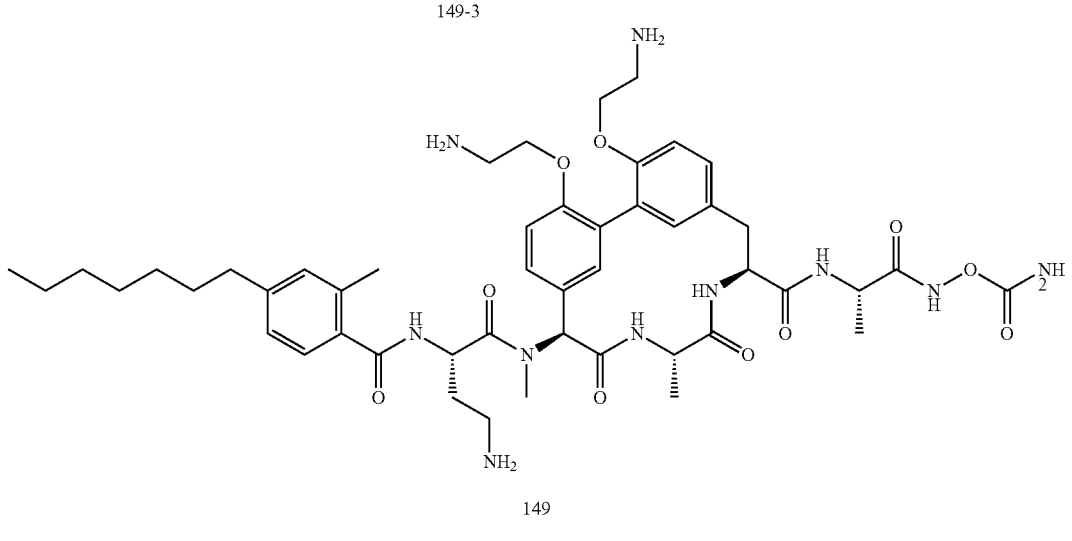

149

Step 1: Typical amide coupling (HATU/DIEA, Example 5), ester hydrolysis (LiOH in THF/H$_2$O, Example 6, Step 5), amide coupling (HATU/DIEA, Example 5) and hydrogenation (Pd/C, H$_2$, Example 4) conditions were applied to compound 101-N (Example 6) (110 mg, 0.099 mmol) to afford compound 149-2 (80 mg, 67% yield over 4 steps) as a white solid. LCMS (Method 5-95 AB, ESI): t$_R$=0.995, [M+H]$^+$=1202.6.

Step 2: To a solution of compound 149-2 (80 mg, 0.067 mmol) and triethylamine (46 µL, 0.33 mmol) in DMF (0.5 mL) was added trimethylsilyl isocyanate (38 mg, 0.33 mmol) at 0° C. and the mixture was gradually warmed up to 25° C. while stirring and stirred at the same temperature for 2 h. The reaction was taken up in EtOAc (30 mL) and the organic layer was washed with water and brine (30 mL each). The organic layer was then separated, dried over MgSO$_4$ and evaporated to dryness. The crude product was purified by prep-TLC (5% methanol in DCM) to afford compound 149-3 (20 mg) as a white solid.

Step 3: Compound 149 (formic acid salt) was prepared from compound 149-3 utilizing typical Boc removal condition (TFA/HFIP) as described in Example 6 to afford the title compound as a white solid. LCMS (Method 5-95 AB, ESI): t$_R$=0.762, [M+H]$^+$=945.6; $^1$H NMR (400 MHz, MeOH-d$_4$) δ 8.53 (br s, 3H), 7.42-7.15 (m, 4H), 7.14-6.99 (m, 3H), 6.89-6.73 (m, 2H), 6.42 (s, 1H), 5.18-5.15 (m, 1H), 4.37-4.28 (m, 2H), 4.27-4.10 (m, 4H), 3.53-3.28 (m, 2H), 3.21-3.04 (m, 6H), 2.95 (s, 3H), 2.70-2.49 (m, 3H), 2.38 (s, 3H), 2.34-2.07 (m, 2H), 1.69-1.55 (m, 2H), 1.46-1.20 (m, 13H), 0.92 (t, J=6.8 Hz, 3H).

Example 56: Synthesis of Compound 150-A

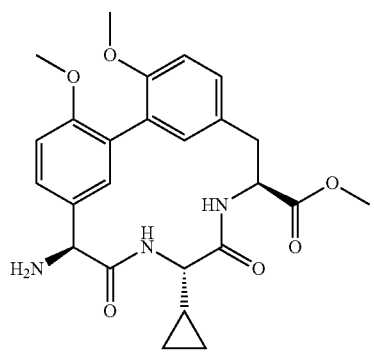 [SMILES: COC(=O)[C@@H]1Cc2ccc(OC)c(c2)-c2cc(ccc2OC)[C@H](N)C(=O)N[C@@H](C2CC2)C(=O)N1]

Compound 150-A was synthesized following procedures analogous to those described for Example 3 (Compound 101-B), in which (S)-2-((tert-butoxycarbonyl)amino)-2-(4-hydroxyphenyl)acetic acid and methyl (S)-2-amino-2-cyclopropylacetate were used in Step 1, to afford the title compound as brown solid. LCMS (ESI): (M+H)$^+$=354.

Example 57: Synthesis of Compound 150-B

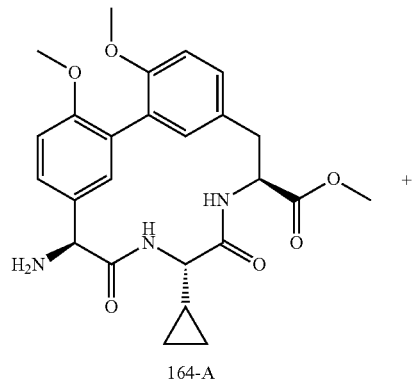

164-A

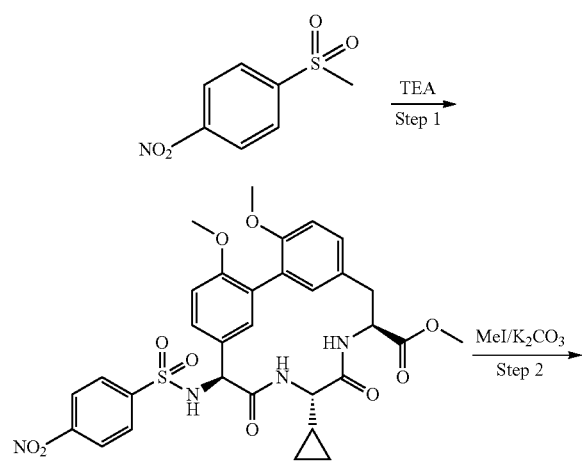

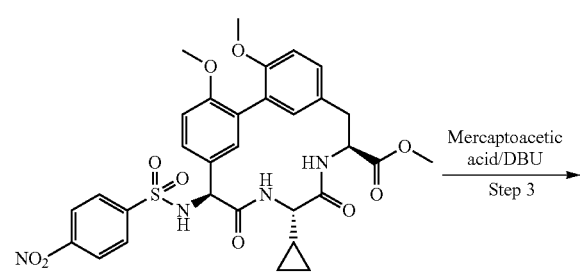

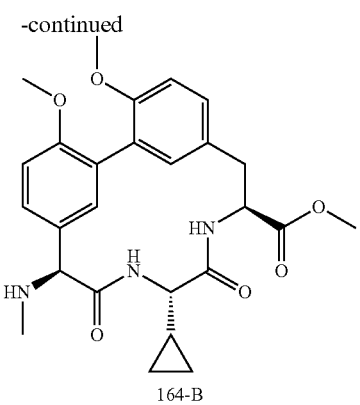

164-B

Step 1: To a solution of Compound 150-A (1.16 g, 2.48 mmol) and triethylamine (0.86 mL, 6.20 mmol) in acetonitrile (25 mL) was added 4-nitrobenzenesulfonyl chloride (660 mg, 2.98 mmol) in portions, and the resulting reaction mixture was stirred at room temperature for 4 h. The precipitate was collected by filtration, washed with small amount of acetonitrile, and dried under vacuum overnight to give 1.14 g (70%) of methyl (4S,7S,10S)-7-cyclopropyl-1$^6$,2$^6$-dimethoxy-10-((4-nitrophenyl)sulfonamido)-6,9-dioxo-5,8-diaza-1,2(1,3)-dibenzenacyclodecaphane-4-carboxylate as an off white solid, which was carried forward without further purification. LCMS (ESI): (M+H)$^+$=653.

Step 2: To a mixture of (4S,7S,10S)-7-cyclopropyl-1$^6$,2$^6$-dimethoxy-10-((4-nitrophenyl)sulfonamido)-6,9-dioxo-5,8-diaza-1,2(1,3)-dibenzenacyclodecaphane-4-carboxylate (1.14 g, 1.75 mmol) and K$_2$CO$_3$ (1.93 g, 14.0 mmol) in acetone (20 mL) was added iodomethane (0.870 mL, 14.0 mmol). The resulting reaction mixture was stirred at room temperature overnight. The mixture was filtered and evaporated in vacuo. The residue was diluted with water, extracted with isopropyl acetate (2×100 ml), dried over Mg$_2$SO$_4$, filtered, evaporated in vacuo, and dried under vacuum to give 1.21 g (100%) of methyl (4S,7S,10S)-7-cyclopropyl-1$^6$,2$^6$-dimethoxy-10-((N-methyl-4-nitrophenyOsulfonamido)-6,9-dioxo-5,8-diaza-1,2(1,3)-dibenzenacyclodecaphane-4-carboxylate as off white solid, which was carried forward without purification. LCMS (ESI): (M+H)$^+$=667.

Step 3: To a solution methyl (4S,7S,10S)-7-cyclopropyl-1$^6$,2$^6$-dimethoxy-10-((N-methyl-4-nitrophenyOsulfonamido)-6,9-dioxo-5,8-diaza-1,2(1,3)-dibenzenacyclodecaphane-4-carboxylate (1.11 g, 1.66 mmol) in acetonitrile (22 mL) was added mercaptoacetic acid (6.6 equiv., 1.01 g, 11.0 mmol) and DBU (2.50 mL, 16.6 mmol), and the resulting mixture stirred at room temperature for 3 h. The reaction mixture was evaporated in vacuo, diluted with isopropyl acetate (50 mL) and washed with saturated aqueous NaHCO$_3$ (50 mL). The aqueous layer was again extracted with iPrOAc (50 mL). The combined organics were washed with water and brine, dried over Mg$_2$SO$_4$, filtered, evaporated in vacuo, and dried under vacuum to give 776 mg (96.8%) of Compound 164-B as an off white solid. LCMS (ESI): (M+H)$^+$=482.

Example 58: Synthesis of Compound 150

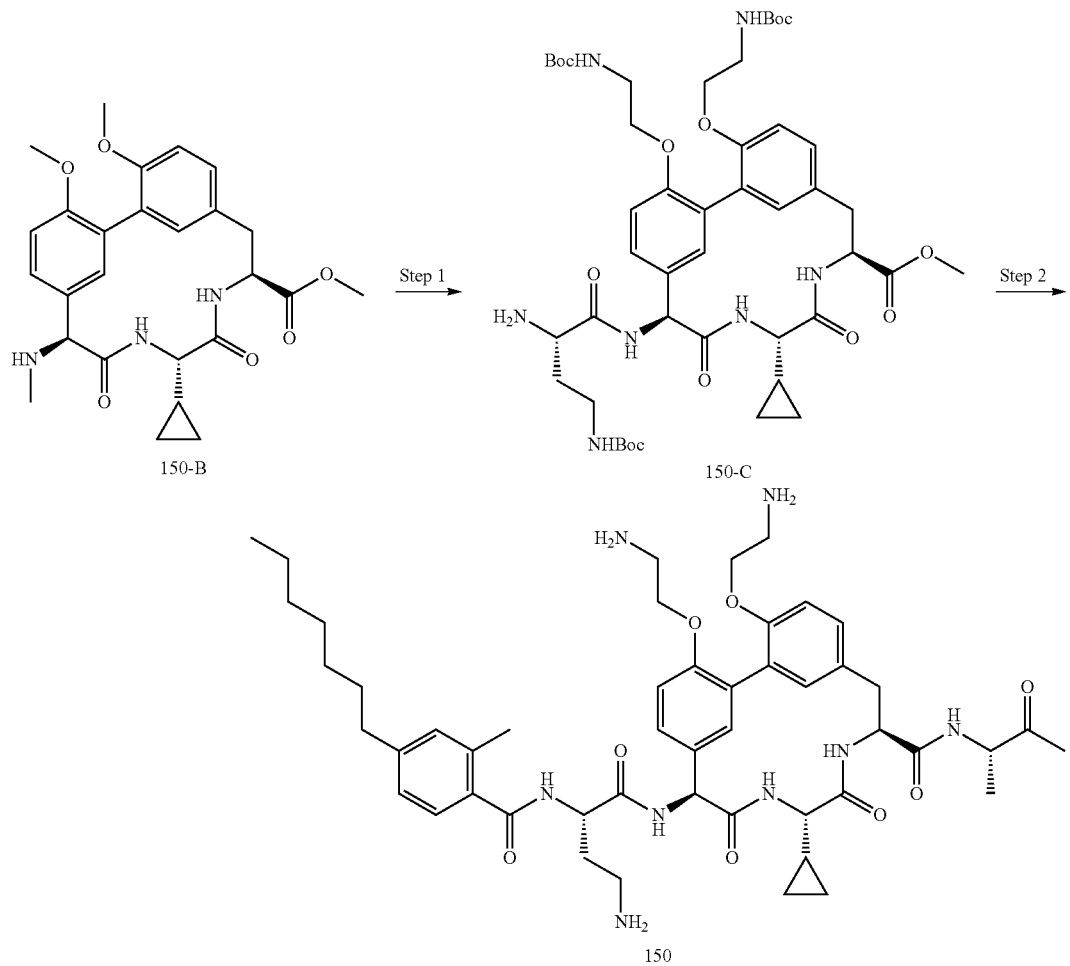 [SMILES: CN[C@@H]1C(=O)N[C@@H](C2CC2)C(=O)N[C@H](C(=O)OC)Cc2ccc(OC)c(c2)-c2cc1ccc2OC ; COC(=O)[C@@H]1Cc2ccc(OCCNC(=O)OC(C)(C)C)c(c2)-c2cc(ccc2OCCNC(=O)OC(C)(C)C)[C@H](NC(=O)[C@@H](N)CCNC(=O)OC(C)(C)C)C(=O)N[C@@H](C2CC2)C(=O)N1 ; CCCCCCCc1ccc(C(=O)N[C@@H](CCN)C(=O)N[C@@H]2C(=O)N[C@@H](C3CC3)C(=O)N[C@H](C(=O)N[C@@H](C)C(C)=O)Cc3ccc(OCCN)c(c3)-c3cc2ccc3OCCN)c(C)c1]

Step 1: Compound 150-C was synthesized from Compound 150-B following the General Method 4 as described in Example 5. LCMS (ESI): (M+H)⁺=940.

Step 2: Compound 150 (trifluoroacetic acid salt) was synthesized as an off-white solid from Compound 150-C following procedures analogous to those described in Example 6 (Compound 101-O) using (3S)-3-aminobutan-2-one hydrochloride instead of 2-aminoethan-1-ol in Step 6. LCMS (ESI): (M+H)⁺=911. ¹H NMR (400 MHz, Methanol-d4)) δ 7.33 (d, J=7.7 Hz, 2H), 7.30-7.21 (m, 1H), 7.19 (d, J=8.7 Hz, 1H), 7.13-7.06 (m, 3H), 6.79 (d, J=2.3 Hz, 2H), 6.46 (d, J=2.9 Hz, 1H), 5.16 (dd, J=8.2, 5.3 Hz, 1H), 4.96-4.89 (m, 1H), 4.53-4.41 (m, 1H), 4.36 (s, 1H), 4.26-4.15 (m, 6H), 3.23 (d, J=5.1 Hz, 1H), 3.19-3.08 (m, 8H), 2.94 (s, 3H), 2.66-2.56 (m, 2H), 2.40 (s, 3H), 2.32-2.25 (m, 1H), 2.23 (s, 1H), 2.20 (s, 1H), 2.19-2.11 (m, 1H), 1.94 (dd, J=7.1, 3.3 Hz, 1H), 1.69-1.57 (m, 2H), 1.41-1.18 (m, 8H), 0.96-0.89 (m, 4H), 0.57-0.48 (m, 4H).

Biological Assays

Example A1: Determination of Minimum Inhibitory Concentration

In vitro antimicrobial activity of each compound was determined by measuring minimal inhibitor concentrations (MICs) using the broth micro-dilution technique as approved by the Clinical and Laboratory Standards Institute (CLSI) (Methods for Dilution Antimicrobial Susceptibility Tests for Bacteria that Grow Aerobically; Approved Standard—Eighth Edition. CLSI document M07-A8. Wayne, Pa.: Clinical and Laboratory Standards; 2009). Antibacterial activity was measure against three strains of bacteria: a Methicillin Resistant *Staphylococcus aureus* strain USA 300, NRS384 (*S. aureus*); a strain of *Escherichia coli* MC4100 harboring the IMP4213 (*E. coli* IMP), which results in increased outer-membrane permeability (B Martin and Silhavy T. Imp/OstA is required for cell envelope biogenesis in *Escherichia coli*. (2002) Molecular Microbiology, 45(5), 1289-1302), and *Escherichia coli* ATCC 25922 (*E. coli*), a clinically relevant Gram-negative strain. Cells were inoculated onto plates of Trypyticase Soy Agar or Luria Agar respectively and grown at 35° C. for 20 hours. Inocula suspensions were prepared by scraping cells into 1 mL of testing media (cation adjusted Mueller Hinton Broth supplemented with 0.002% v/v Tween-80) and diluting to a final OD$_{600\,nm}$ of 0.01.

Test compounds were prepared in DMSO at a concentration of 10 mg/mL. The compounds were tested under several different dilution formats and the data are reported in Table 1. In protocol 1, the compound stocks were diluted into testing media at a concentration of 64 µg/ml and serial 2-fold dilutions were made in the same media, in 96-well U bottom microtiter dishes, for a total of 10 compound concentrations. In protocol 2, the compound stocks were diluted into testing media at a concentration of 4 µg/mL and serial 2-fold dilutions were made in the same media, in 96-well U bottom microtiter dishes, for a total of 10 compound concentrations. In protocol 3, compound stocks were diluted into testing media at a concentration of 0.5 µg/mL, with serial 2-fold dilutions conducted as described above. In protocol 4, compound stocks were diluted into testing media at a concentration of 0.13 µg/mL, with serial 2-fold dilutions conducted as described above. Inocula suspensions were added to the 2-fold serial dilutions of test compounds to a final density of OD $OD_{600\ nm}$ of 0.0005 and incubated at 35° C. for 22 hours. After incubation the plates were examined visually and the lowest concentration of test compound that completely prevented bacterial growth were recorded as the MICs. The results are listed in Table 2.

TABLE 2

| Compound | MIC (µg/mL) S. aureus | MIC (µg/mL) E. coli IMP | MIC (µg/mL) E. coli |
|---|---|---|---|
| 101 | 0.094 | 0.031 | 4 |
| 102 | 0.13 | 0.094 | 8 |
| 103 | 0.17 | 0.0078 | 0.75 |
| 104 | 0.75 | 0.023 | 4 |
| 105 | 1 | 0.13 | 12 |
| 106 | 0.031 | 0.016 | 1 |
| 107 | 0.5 | 0.5 | 32 |
| 108 | 0.75 | 0.5 | 32 |
| 109 | 0.25 | 0.5 | 64 |
| 110 | 0.38 | >0.13 | 64 |
| 111 | 0.25 | 0.063 | 8 |
| 112 | 1 | 0.031 | 4 |
| 113 | 0.063 | 0.047 | 4 |
| 114 | 0.5 | 0.13 | 8 |
| 115 | 0.19 | 0.25 | 8 |
| 116 | 0.063 | 0.063 | 4 |
| 117 | 0.0078 | 2 | 64 |
| 118 | 0.016 | 2 | >64 |
| 119 | NT | 1 | 24 |
| 120 | 2 | 0.5 | 16 |
| 121 | 4 | 0.25 | 8 |
| 122 | 1.5 | 0.094 | 3 |
| 123 | 1.5 | <0.063 | 8 |
| 124 | 1 | 0.5 | 8 |
| 125 | 0.38 | 0.036 | 0.5 |
| 126 | 4 | 0.031 | 1 |
| 127 | 2 | 2 | 32 |
| 128 | 1.5 | 0.012 | 0.75 |
| 129 | 0.5 | 0.094 | 4 |
| 130 | 0.38 | 0.13 | 6 |
| 131 | 0.094 | 0.0078 | 0.5 |
| 132 | 4 | 0.25 | 8 |
| 133 | 1 | 0.094 | 8 |
| 134 | 1 | 0.13 | 4 |
| 135 | >4.0 | 1.5 | 32 |
| 136 | 0.38 | 0.13 | 2 |
| 137 | 0.5 | 0.094 | 3 |
| 138 | 4 | 0.5 | 16 |
| 139 | 1 | 1.5 | 24 |
| 140 | 4 | 1 | 32 |
| 141 | 4 | 2 | 64 |
| 142 | 3 | 4 | >64 |
| 143 | 0.13 | 0.023 | 0.5 |
| 144 | >4.0 | 2 | 64 |
| 145 | 2 | 4 | >64 |
| 146 | >4.0 | 0.75 | >64 |
| 147 | 0.01 | NT | 4.12 |
| 148 | 0.5 | NT | 15.85 |
| 149 | 0.25 | NT | 16.14 |
| 150 | 0.068 | NT | 4.39 |

NT = not tested

Example A2: Whole-Cell SpsB Biochemical Screening Assay

A kinetic fluorogenic enzyme activity assay was used to assess inhibition of SpsB (*Staphylococcus aureus* signal peptidase) activity and $IC_{50}$s were determined. This assay uses a suspension of *Staphylococcus aureus* cells as a source of SpsB instead of recombinant SpsB protein.

Cell preparation: Luria broth (LB) was inoculated with *S. aureus* (USA300 background, overexpressing SpsB) and shaken at 37° C. until an $OD_{600\ nm}$ of 1.5-2.0 was reached (~4 hr). The culture was then diluted to an $OD_{600\ nm}$ of 1.0 with LB, aliquoted and centrifuged at 10,000×g for 2 mins. The supernatant was removed and the pellet was resuspended in phosphate buffer (1×PBS, 12.5 mg/L $MgCl_2$, 25 mg/L $CaCl_2$, 0.1% Tween-80) to an $OD_{600\ nm}$ of 0.5, then centrifuged again at 10,000×g for 2 mins. The supernatant was removed and the pellets were frozen at −20° C.

Test compounds were prepared in DMSO at a concentration of 10 mg/mL. These compound stocks were diluted into DMSO to a concentration of 25 µg/mL and serial 3-fold dilutions were made in DMSO, for a total of 11 compound concentrations. 20 nL of each compound solution was pre-spotted into a white 384-well plate (50 µL/well polypropylene, Nunc) using acoustic fluid transfer (Echo).

Frozen *S. aureus* pellets were resuspended in assay buffer (1×PBS, 12.5 mg/L MgCl2, 25 mg/L CaCl2, 0.1% Tween-80) to an OD600 nm of 0.05, then mixed 1:1 (v/v) with 20 µM substrate ((Dabcyl)βAla-KPAKAAE(Edans)) in assay buffer, and this solution was added (20 µL/well) to the 384-well plate that had been pre-spotted with compound. Fluorescence intensity was then immediately read kinetically for 30 minutes with 2 minute read intervals to monitor cleavage of the internally quenched peptide substrate (excitation wavelength=340 nm, emission wavelength=490 nm, Molecular Devices Spectramax M5). Reaction rate (slope) was plotted against inhibitor concentration to derive the $IC_{50}$. The results are listed in Table 3.

TABLE 3

| Compound | SpsB IC50 (nM) |
|---|---|
| 101 | NT |
| 102 | NT |
| 103 | NT |
| 104 | NT |
| 105 | NT |
| 106 | NT |
| 107 | NT |
| 108 | NT |
| 109 | NT |
| 110 | NT |
| 111 | NT |
| 112 | NT |
| 113 | 1.2 |
| 114 | NT |
| 115 | NT |
| 116 | NT |
| 117 | NT |
| 118 | NT |
| 119 | 71 |
| 120 | 18 |
| 121 | 12 |

TABLE 3-continued

| Compound | SpsB IC50 (nM) |
|---|---|
| 122 | NT |
| 123 | 15 |
| 124 | 14 |
| 125 | 1 |
| 126 | 6.2 |
| 127 | 2.7 |
| 128 | 1.5 |
| 129 | 2.2 |
| 130 | NT |
| 131 | 2.1 |
| 132 | NT |
| 133 | 2.3 |
| 134 | 7.1 |
| 135 | NT |
| 136 | 1.2 |
| 137 | 1.4 |
| 138 | NT |
| 139 | 110 |
| 140 | 370 |
| 141 | NT |
| 142 | NT |
| 143 | 1.5 |
| 144 | NT |
| 145 | NT |
| 146 | NT |

NT = not tested

Example A3: Clinical Trial of the Safety and Efficacy of Compounds of Formula (I), (Ia), (Ib), (Ic), (Id), or (II) in Patients with C. Difficile-Associated Diarrhea Purpose:

This study aims to determine the safety and efficacy of compounds presented herein for the treatment of symptoms of C. difficile-associated diarrhea and lowering the risk of repeat episodes of diarrhea. The compounds are evaluated in comparison to current standard antibiotic treatment, so all patients will receive active medication. All study-related care is provided including doctor visits, physical exams, laboratory tests and study medication. Total length of participation is approximately 10 weeks.

Patients:

Eligible subjects will be men and women 18 years and older.

Criteria:
Inclusion Criteria:
Be at least 18 years old;
Have active mild to moderate C. difficile-Associated Diarrhea (CDAD);
Be able to tolerate oral medication;
Not be pregnant or breast-feeding; and
Sign and date an informed consent form.

Study Design:

This is a randomized, double-blind, active control study of the efficacy, safety, and tolerability of a compound of Formula (I), (Ia), (Ib), (Ic), (Id), or (II) in patients with C. difficile-associated diarrhea.

Example A4: Clinical Trial Comparing a Compound of Formula (I), (Ia), (Ib), (Ic), (Id), or (II) with Vancomycin for the Treatment of MRSA Osteomyleitis Purpose:

This study aims to determine the efficacy of compounds presented herein as compared to vancomycin for the treatment of methicillin-resistant Staphylococcus aureus (MRSA) osteomyelitis.

Patients:

Eligible subjects will be men and women 18 years and older.

Criteria:
Inclusion Criteria:

Culture-proven MRSA, obtained in operating room or sterile biopsy procedure from bone site. The infection and sampling site is either within the bone or a deep soft-tissue site that is contiguous with bone; OR radiographic abnormality consistent with osteomyelitis in conjunction with a positive blood culture for MRSA;

Surgical debridement of infection site, as needed;
Subject is capable of providing written informed consent; and
Subject capable of receiving outpatient parenteral therapy for 12 weeks.

Exclusion Criteria:
Hypersensitivity to a compound of Formula (I), (Ia), (Ib), (Ic), (Id), or (II) or vancomycin;
S. aureus resistant to a compound of Formula (I), (Ia), (Ib), (Ic), (Id), or (II) or vancomycin;
Osteomyelitis that develops directly from a chronic, open wound;
Polymicrobial culture (the only exception is if coagulase-negative Staphylococcus is present in the culture and the clinical assessment is that it is a contaminant);
Subject has a positive pregnancy test at study enrollment;
Baseline renal or hepatic insufficiency that would preclude administration of study drugs;
Active injection drug use without safe conditions to administer intravenous antibiotics for 3 months; and
Anticipated use of antibiotics for greater than 14 days for an infection other than osteomyelitis.

Study Design:

This is a randomized, open-label, active control, efficacy trial comparing vancomycin with a compound of Formula (I), (Ia), (Ib), (Ic), (Id), or (II) for the treatment of MRSA Osteomyelitis.

Example A5: Clinical Trial Evaluating a Compound of Formula (I), (Ia), (Ib), (Ic), (Id), or (II) in Selected Serious Infections Caused by Vancomycin-Resistant Enterococcus (VRE)

Purpose:

This study aims to determine the safety and efficacy of a compound of Formula (I), (Ia), (Ib), (Ic), (Id), or (II) in the treatment of selected serious infections caused by VRE.

Patients:

Eligible subjects will be men and women 18 years and older.

Criteria:
Inclusion Criteria:

Isolation of one of the following multi-antibiotic resistant bacteria: vancomycin-resistant Enterococcus faecium, vancomycin-resistant Enterococcus faecalis alone or as part of a polymicrobial infection; and Have a confirmed diagnosis of a serious infection (eg, bacteremia [unless due to an excluded infection], complicated intra-abdominal infection, complicated skin and skin structure infection, or pneumonia) requiring administration of intravenous (IV) antibiotic therapy.

Exclusion Criteria:

Subjects with any concomitant condition or taking any concomitant medication that, in the opinion of the investigator, could preclude an evaluation of a response or make it unlikely that the contemplated course of therapy or followup assessment will be completed or that will substantially increase the risk associated with the subject's participation in this study.

Anticipated length of antibiotic therapy less than 7 days

Study Design:

This is a randomized, double-blind, safety and efficacy study of a compound of Formula (I), (Ia), (Ib), (Ic), (Id), or (II) in the treatment of selected serious infections caused by VRE.

Pharmaceutical Compositions

Parenteral Composition

To prepare a parenteral pharmaceutical composition suitable for administration by injection, 100 mg of a compound of Formula (I), (Ia), (Ib), (Ic), (Id), or (II) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
| --- | --- |
| Compound of Formula (I), (Ia), (Ib), (Ic), (Id), or (II) | 1.2 g |
| sodium acetate buffer solution (0.4M) | 2.0 mL |
| HCl (1N) or NaOH (1M) | q.s. to suitable pH |
| water (distilled, sterile) | q.s.to 20 mL |

All of the above ingredients, except water, are combined and stirred and if necessary, with slight heating if necessary. A sufficient quantity of water is then added.

Oral Composition

To prepare a pharmaceutical composition for oral delivery, 100 mg of a compound of Formula (I), (Ia), (Ib), (Ic), (Id), or (II) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
| --- | --- |
| compound of Formula (I), (Ia), (Ib), (Ic), (Id), or (II) | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| compound of Formula (I), (Ia), (Ib), (Ic), (Id), or (II) | 200 |
| lactose, spray-dried | 148 |
| magnesium stearate | 2 |

In yet another embodiment, the following ingredients are mixed to form a solution/suspension for oral administration:

| Ingredient | Amount |
| --- | --- |
| Compound of Formula (I), (Ia), (Ib), (Ic), (Id), or (II) | 1 g |
| Anhydrous Sodium Carbonate | 0.1 g |
| Ethanol (200 proof), USP | 10 mL |
| Purified Water, USP | 90 mL |
| Aspartame | 0.003 g |

Topical Gel Composition

To prepare a pharmaceutical topical gel composition, 100 mg of a compound of Formula (I), (Ia), (Ib), (Ic), (Id), or (II) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A compound of Formula (I):

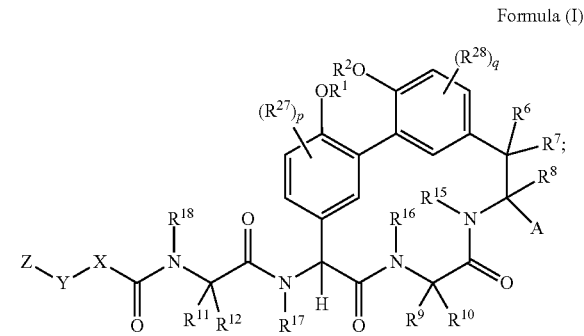

Formula (I)

wherein:

$R^1$ and $R^2$ are each independently H, —$(C_1$-$C_6)$alkyl, —$(C_1$-$C_6)$alkyl-$OR^{23}$, —$CH_2CH(OH)CH_2NH_2$, —$CH_2CH$(heterocycloalkyl)$CH_2NH_2$, —$CH_2C(O)$ $NH_2$, —$CH_2C(O)N(H)CH_2CN$, —$(C_1$-$C_6)$alkyl-$C(O)$ $OR^{23}$, —$(C_1$-$C_6)$alkyl-$NR^{21}R^{22}$, —$(C_1$-$C_6)$alkyl-$C(O)$ $NR^{25}R^{26}$, —$(C_1$-$C_6)$alkyl-$N(R^{23})C(O)(C_1$-$C_6)$ alkyl$NR^{21}R^{22}$, or —$(C_1$-$C_6)$alkyl-$C(O)N(R^{23})(C_1$-$C_6)$ alkyl, or optionally substituted heterocycloalkyl;

$R^6$, $R^7$, and $R^8$ are each independently H, or —$(C_1$-$C_6)$ alkyl;

$R^9$ is H, —$(C_1$-$C_6)$alkyl, —$(C_1$-$C_6)$haloalkyl, or —$(C_3$-$C_6)$cycloalkyl;

$R^{10}$ is H, or —$(C_1$-$C_6)$alkyl;

$R^{11}$ and $R^{12}$ are each independently H, —$NH_2$, —$(C_1$-$C_6)$alkyl, —$(C_1$-$C_6)$alkyl-$OR^{23}$, —$(C_1$-$C_6)$alkyl-$SR^{23}$, —$(C_1$-$C_6)$alkyl-$C(O)OR^{23}$, —$(C_1$-$C_6)$alkyl-$NR^{21}R^{22}$, —$(C_1$-$C_6)$alkyl-CN, —$(C_1$-$C_6)$alkyl-$C(O)NR^{25}R^{26}$, —$(C_1$-$C_6)$alkyl-$S(O)$—$(C_1$-$C_6)$alkyl, —$(C_1$-$C_6)$alkyl-$N(H)CH$=$NH$, —$(C_1$-$C_6)$alkyl-$N(H)C(NH)NH_2$, —$(C_1$-$C_6)$alkyl-heterocycloalkyl, optionally substituted —(C$_1$-C$_6$)alkyl-N(H)heterocycloalkyl, or —(C$_1$-C$_6$)alkyl-heteroaryl; or R$^{11}$ and R$^{18}$ are combined to form an optionally substituted heterocycloalkyl ring, and R$^{12}$ is H;

R$^{15}$, R$^{16}$, R$^{17}$, and R$^{18}$ are each independently H, —(C$_1$-C$_6$)alkyl, —(C$_3$-C$_6$)cycloalkyl, —(C$_1$-C$_6$)alkyl-OR$^{23}$, —(C$_1$-C$_6$)alkyl-C(O)OR$^{23}$, or —(C$_1$-C$_6$)alkyl-NR$^{21}$R$^{22}$;

A is —CN, —CH$_2$CN, —CH═CHCN, —CH$_2$N(H)C(O)CH$_2$CN, —CH$_2$N(H)C(O)N(H)R$^{24}$, —C(O)N(H)R$^{34}$, —C(O)N(H)C(R$^{23}$)$_2$C(O)OR$^{29}$, —C(O)N(H)C(R$^{23}$)$_2$C(O)NR$^{32}$R$^{33}$, —C(O)N(H)C(R$^{23}$)$_2$C═NR$^{30}$, —C(O)N(H)SO$_3$H, —C(O)N(H)SO$_2$CH═CH$_2$, —C(O)N(H)N(R$^{24}$)C(O)CH═CH$_2$, —C(O)N(H)N(R$^{24}$)C(O)CH$_2$Cl,

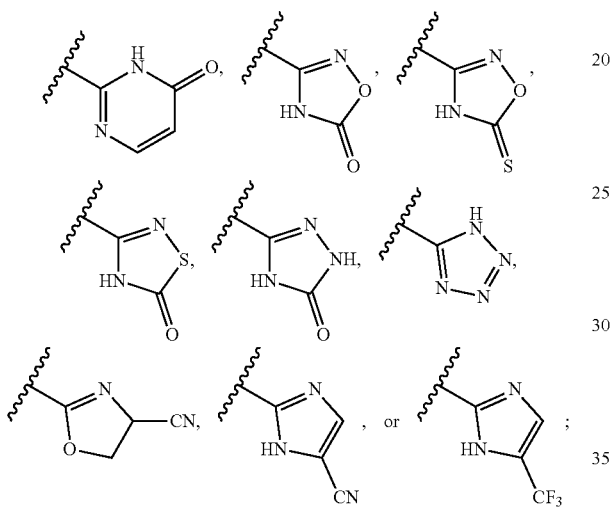

X is optionally substituted —(C$_1$-C$_6$)alkyl-, —(C$_2$-C$_6$)alkenyl-, —(C$_2$-C$_6$)alkynyl, —(C$_3$-C$_7$)cycloalkyl-, optionally substituted heterocycloalkyl, optionally substituted aryl, optionally substituted heteroaryl, —O—(C$_1$-C$_6$)alkyl-, —N(R$^{24}$)(C$_1$-C$_6$)alkyl-, —N(R$^{24}$)(C$_6$-C$_{10}$)aryl-, or —SO$_2$(C$_1$-C$_6$)alkyl-;

Y is a bond, optionally substituted —(C$_1$-C$_6$)alkyl-, —(C$_2$-C$_6$)alkenyl-, —(C$_2$-C$_6$)alkynyl, —(C$_1$-C$_6$)alkyl-N(R$^{24}$)(C$_1$-C$_6$)alkyl-, —O—(C$_1$-C$_6$)alkyl-, —O(C$_6$-C$_{10}$)aryl-, —N(R$^{24}$)(C$_1$-C$_6$)alkyl-, —N(R$^{24}$)SO$_2$(C$_1$-C$_6$)alkyl-, —N(R$^{24}$)C(O)(C$_1$-C$_6$)alkyl-, —C(O)(C$_1$-C$_6$)alkyl-, —S(C$_1$-C$_6$)alkyl-, —SO$_2$(C$_1$-C$_6$)alkyl-, —C(O)NH(C$_1$-C$_6$)alkyl-, —(C$_3$-C$_7$)cycloalkyl-, optionally substituted —C(O)N(R$^{24}$)aryl-, optionally substituted —N(R$^{24}$)C(O)aryl-, optionally substituted —N(R$^{24}$)SO$_2$aryl-, optionally substituted aryl, or optionally substituted heteroaryl;

Z is H, halogen, —NH$_2$, —CN, —CF$_3$, —CO$_2$H, —(C$_1$-C$_{12}$)alkyl, —(C$_2$-C$_{12}$)alkenyl, —(C$_2$-C$_{12}$)alkynyl, —C(O)NR$^{25}$R$^{26}$, —O—(C$_1$-C$_{12}$)alkyl, —N(R$^{24}$)(C$_1$-C$_{12}$)alkyl, —N(R$^{24}$)C(O)(C$_1$-C$_{12}$)alkyl, optionally substituted —(C$_3$-C$_7$)cycloalkyl, —(C$_1$-C$_6$)alkyl-heterocycloalkyl, optionally substituted aryl, or optionally substituted heteroaryl;

each R$^{21}$ and R$^{22}$ is independently H, —(C$_1$-C$_6$)alkyl, —(C$_1$-C$_6$)heteroalkyl, —(C$_1$-C$_6$)alkyl-CO$_2$H, —C(O)(C$_1$-C$_6$)alkyl, —C(O)N(R$^{31}$)$_2$, —SO$_2$N(R$^{31}$)$_2$; or R$^{21}$ and R$^{22}$ and the nitrogen atom to which they are attached form a heterocycloalkyl ring;

each R$^{31}$ is independently H or —(C$_1$-C$_6$)alkyl; or two R$^{31}$ and the nitrogen atom to which they are attached form a heterocycloalkyl ring;

each R$^{23}$ is independently H or —(C$_1$-C$_6$)alkyl;

each R$^{24}$ is independently H or —(C$_1$-C$_6$)alkyl;

each R$^{25}$ and R$^{26}$ is independently H or optionally substituted —(C$_1$-C$_6$)alkyl; or R$^{25}$ and R$^{26}$ and the nitrogen atom to which they are attached form a heterocycloalkyl ring;

each R$^{27}$ is independently halogen, —(C$_1$-C$_6$)alkyl, or —(C$_1$-C$_6$)heteroalkyl;

each R$^{28}$ is independently halogen, —(C$_1$-C$_6$)alkyl, or —(C$_1$-C$_6$)heteroalkyl;

R$^{29}$ is —CH$_2$C(O)NH$_2$ or optionally substituted aryl;

R$^{30}$ is

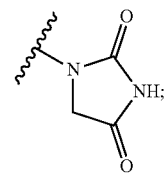

R$^{32}$ is H or —(C$_1$-C$_6$)alkyl;

R$^{33}$ is —CH$_2$CN, —OC(O)(C$_1$-C$_6$)alkyl, or —SO$_2$NH$_2$;

R$^{34}$ is —OH, —NH$_2$, —CN, —CH$_2$CH$_2$CN, —O(C$_1$-C$_6$)alkyl, —C(O)(C$_1$-C$_6$)alkyl, —SO$_2$NH$_2$,

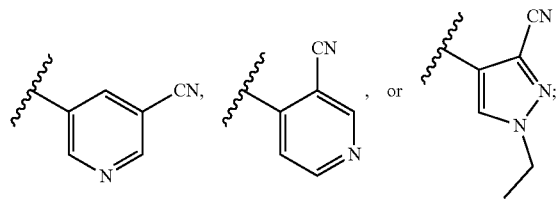

p is 0, 1, or 2; and q is 0, 1, or 2;

or a pharmaceutically acceptable salt or solvate, thereof.

2. The compound of claim 1 having the structure of Formula (Ia):

Formula (Ia)

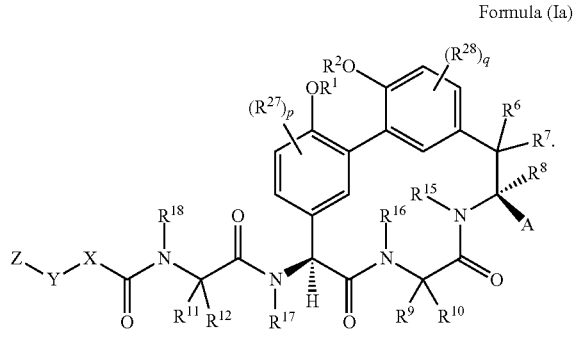

3. The compound of claim 1 having the structure of Formula (Ib):

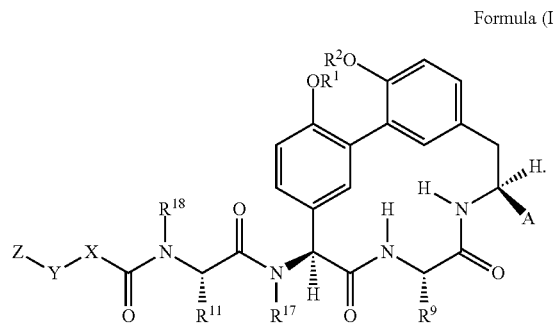

Formula (Ib)

4. The compound of claim 1, wherein $R^{17}$ is —$CH_3$ and $R^{18}$ is H.

5. The compound of claim 1, wherein $R^9$ is —$(C_1-C_6)$alkyl.

6. The compound of claim 1 having the structure of Formula (Ic):

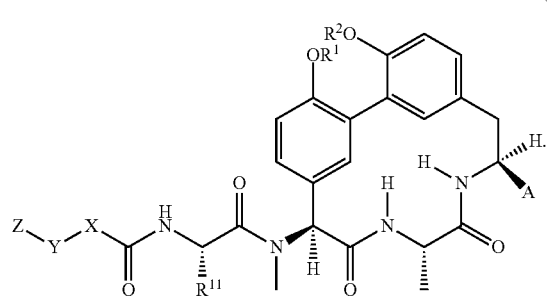

Formula (Ic)

7. The compound of claim 1, wherein $R^{11}$ is —$(C_1-C_6)$alkyl-$NR^{21}R^{22}$.

8. The compound of claim 1, wherein $R^1$ and $R^2$ are each independently H or —$(C_1-C_6)$alkyl-$NR^{21}R^{22}$.

9. The compound of claim 1 having the structure of Formula (Id):

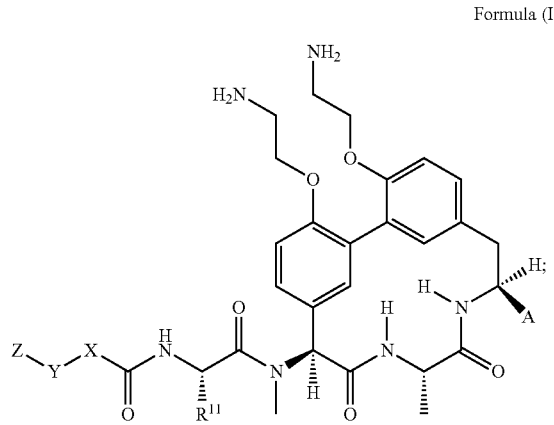

Formula (Id)

wherein $R^{11}$ is —$CH_2NH_2$, —$CH_2CH_2NH_2$, or —$CH_2CH_2CH_2NH_2$.

10. The compound of claim 1, wherein X is optionally substituted aryl, optionally substituted heteroaryl, or optionally substituted —$(C_1-C_6)$alkyl-.

11. The compound of claim 1, wherein Y is a bond, optionally substituted aryl, optionally substituted heteroaryl, optionally substituted —$(C_1-C_6)$alkyl-, —O—$(C_1-C_6)$alkyl-, or —N(H)—$(C_1-C_6)$alkyl-.

12. The compound of claim 1, wherein Z is —$(C_1-C_6)$alkyl, optionally substituted aryl, optionally substituted heteroaryl, optionally substituted —$(C_3-C_7)$cycloalkyl, or halogen.

13. The compound of claim 1, wherein —X—Y—Z is

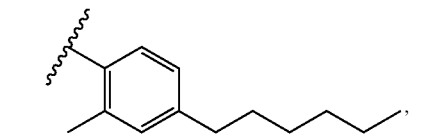

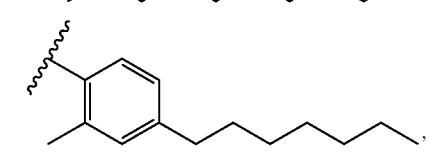

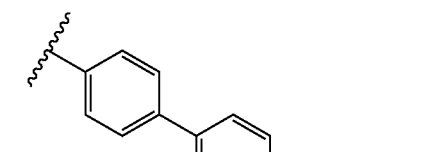

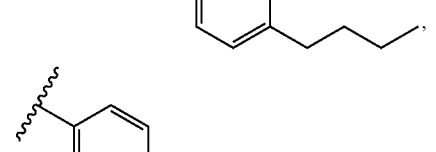

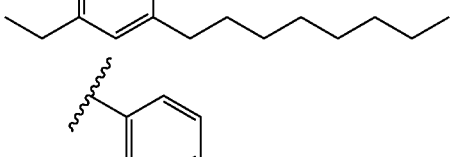

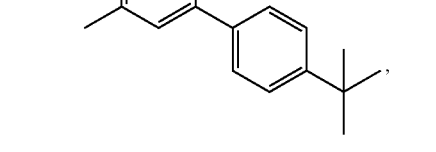

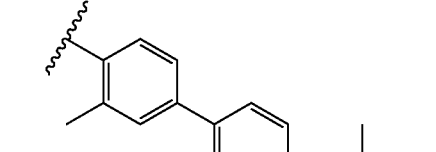

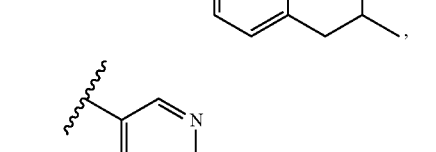

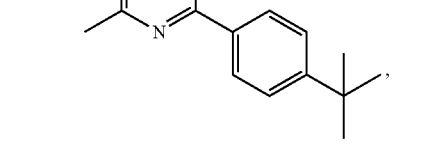

281
-continued
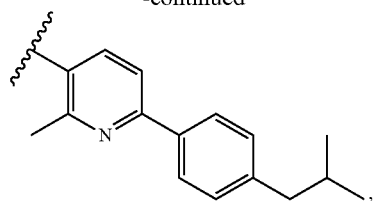
,
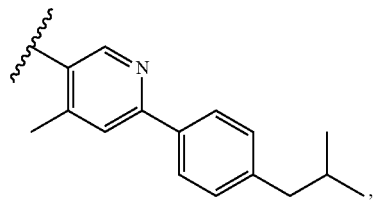
,
282
-continued
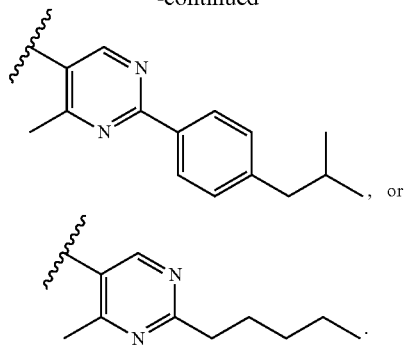
, or
14. The compound of claim 1, wherein the compound is selected from the group consisting of:
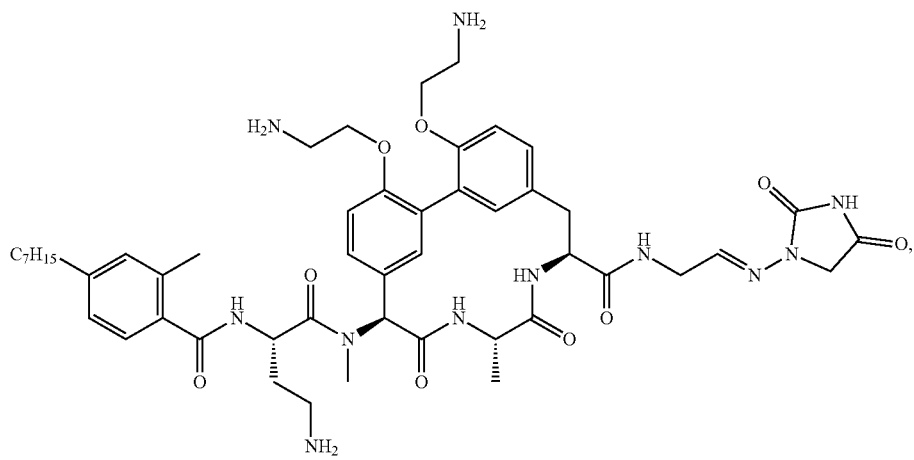
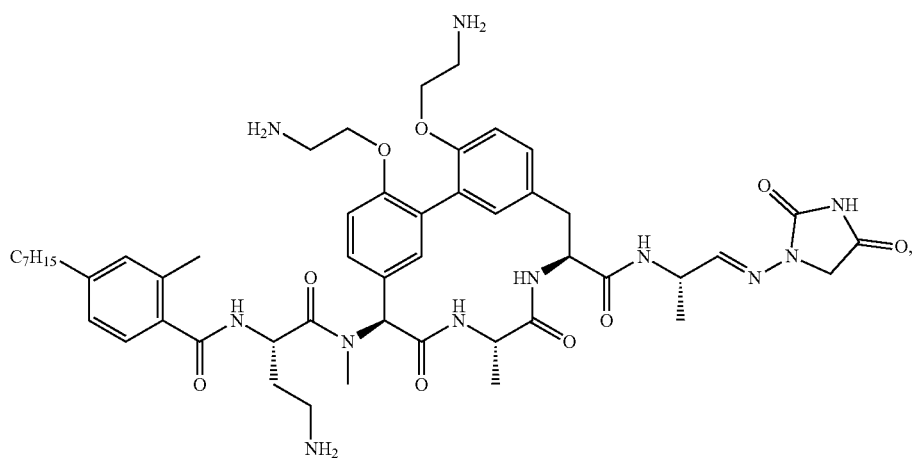

-continued
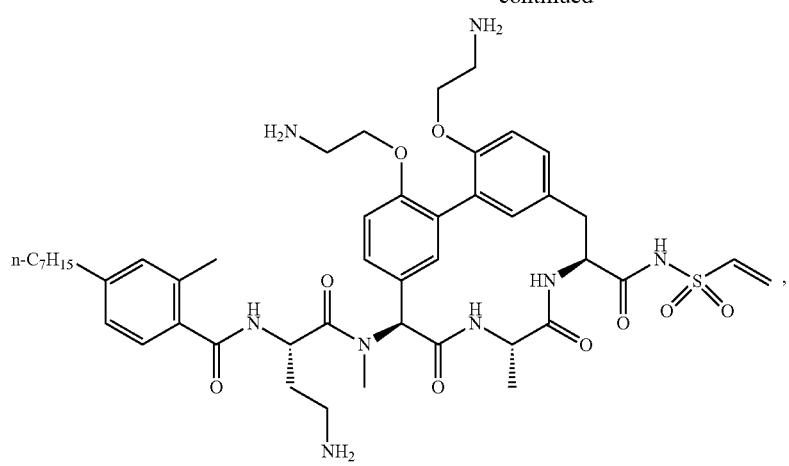
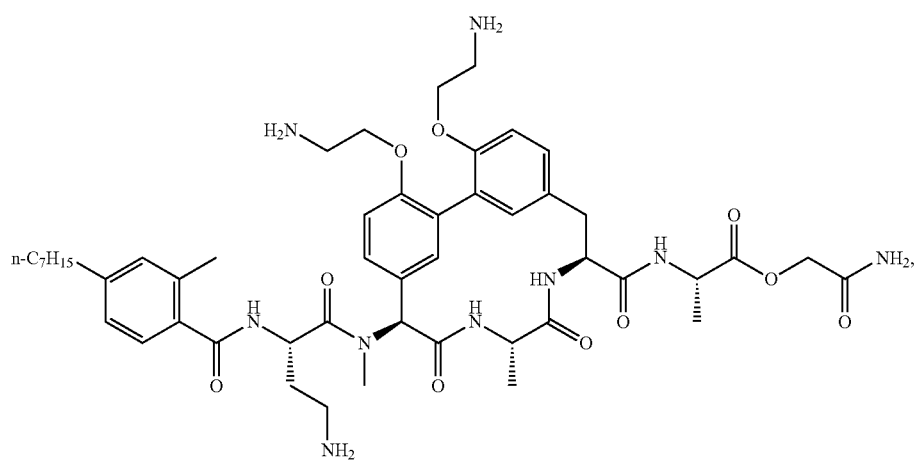
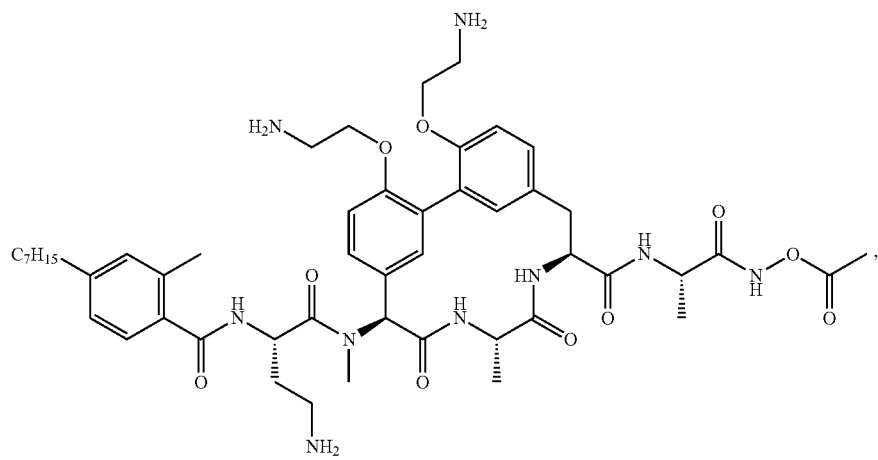

-continued
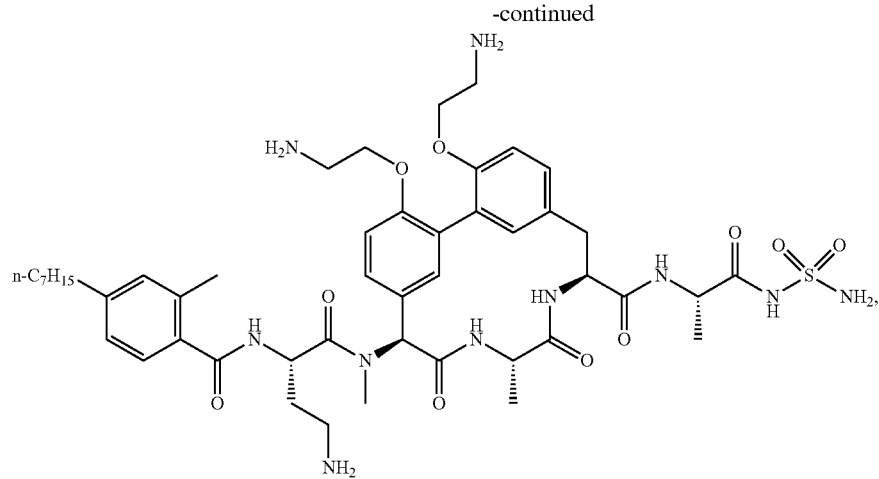
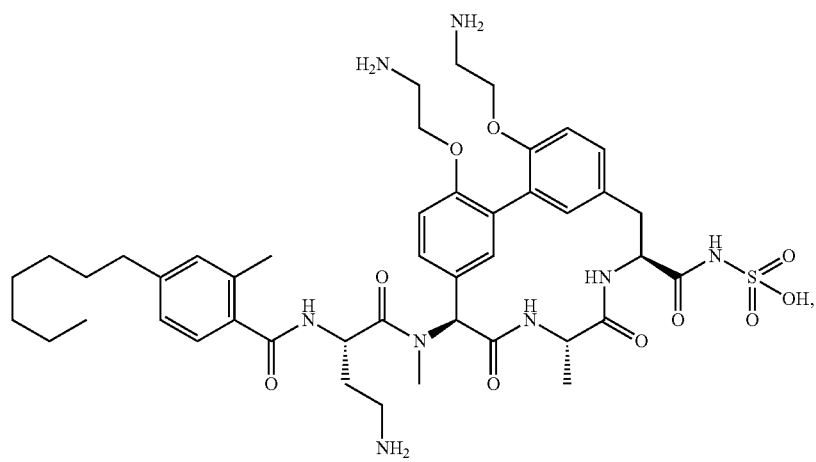
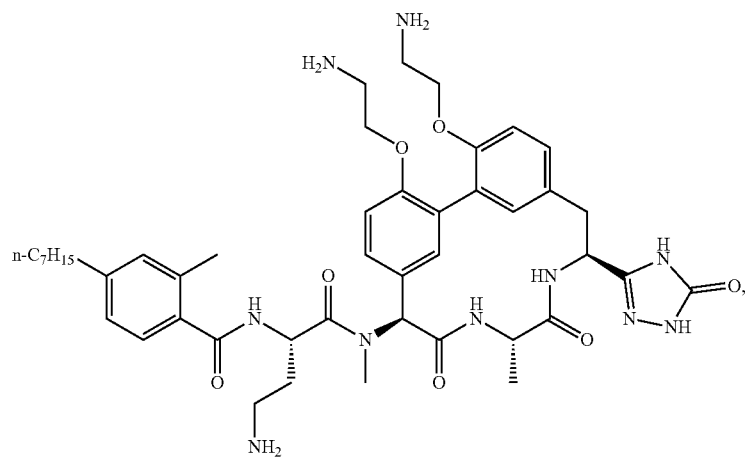

-continued
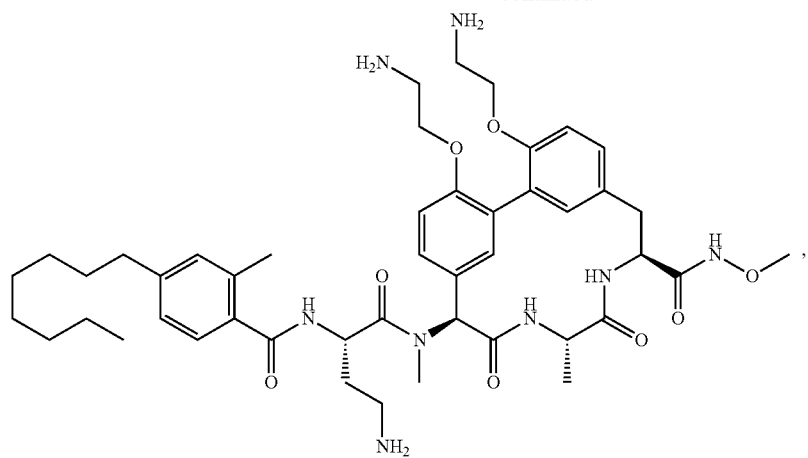
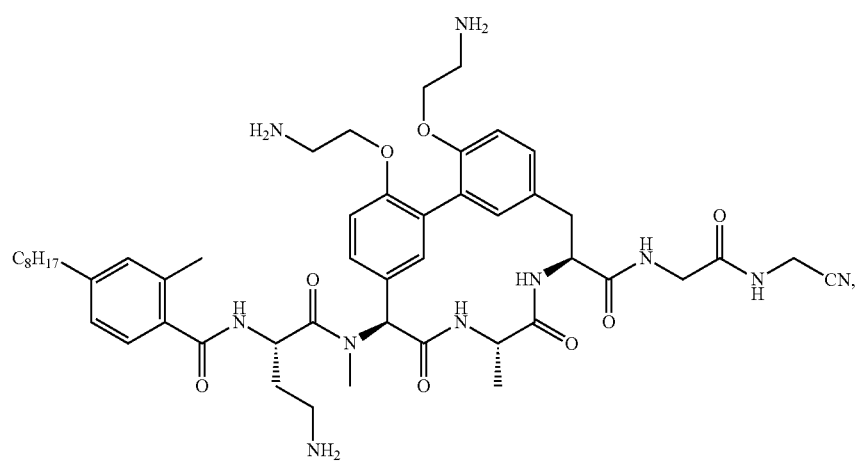
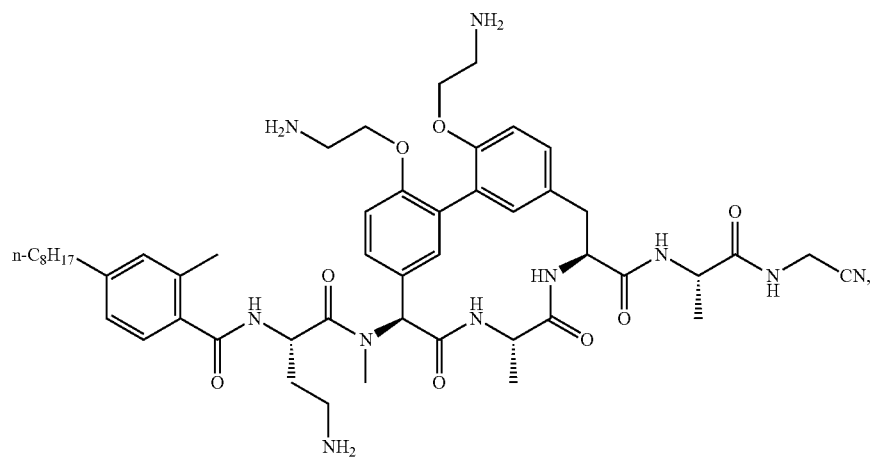

-continued
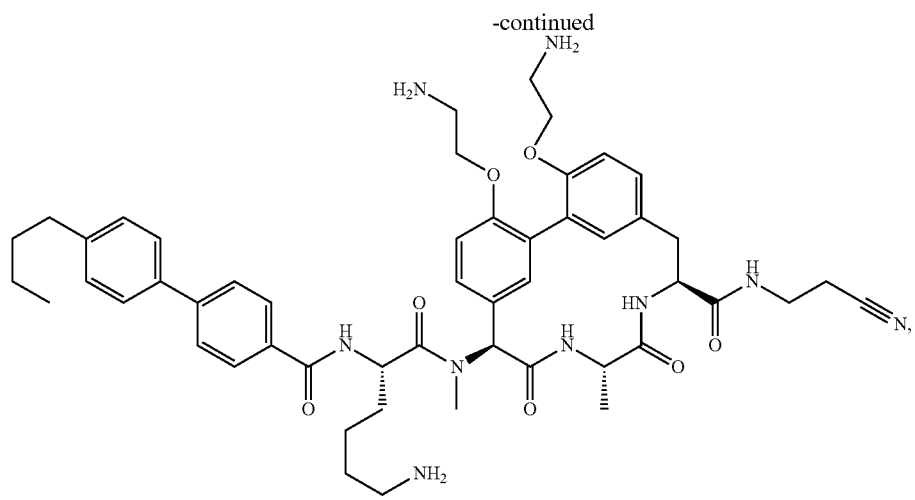
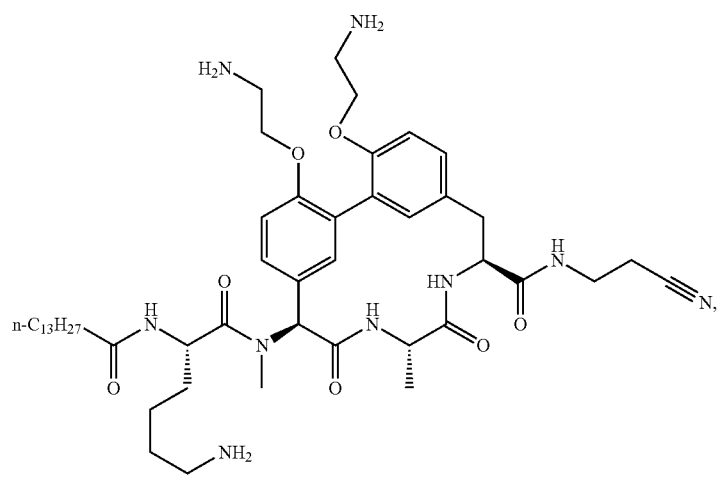
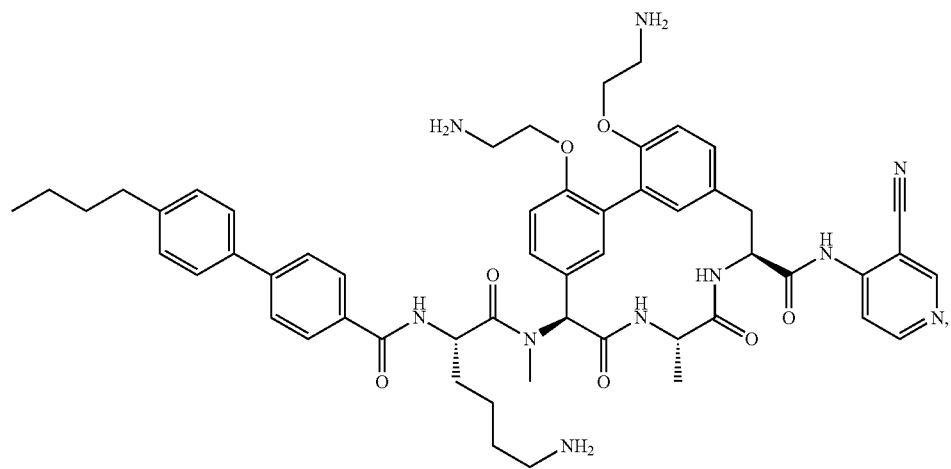

-continued
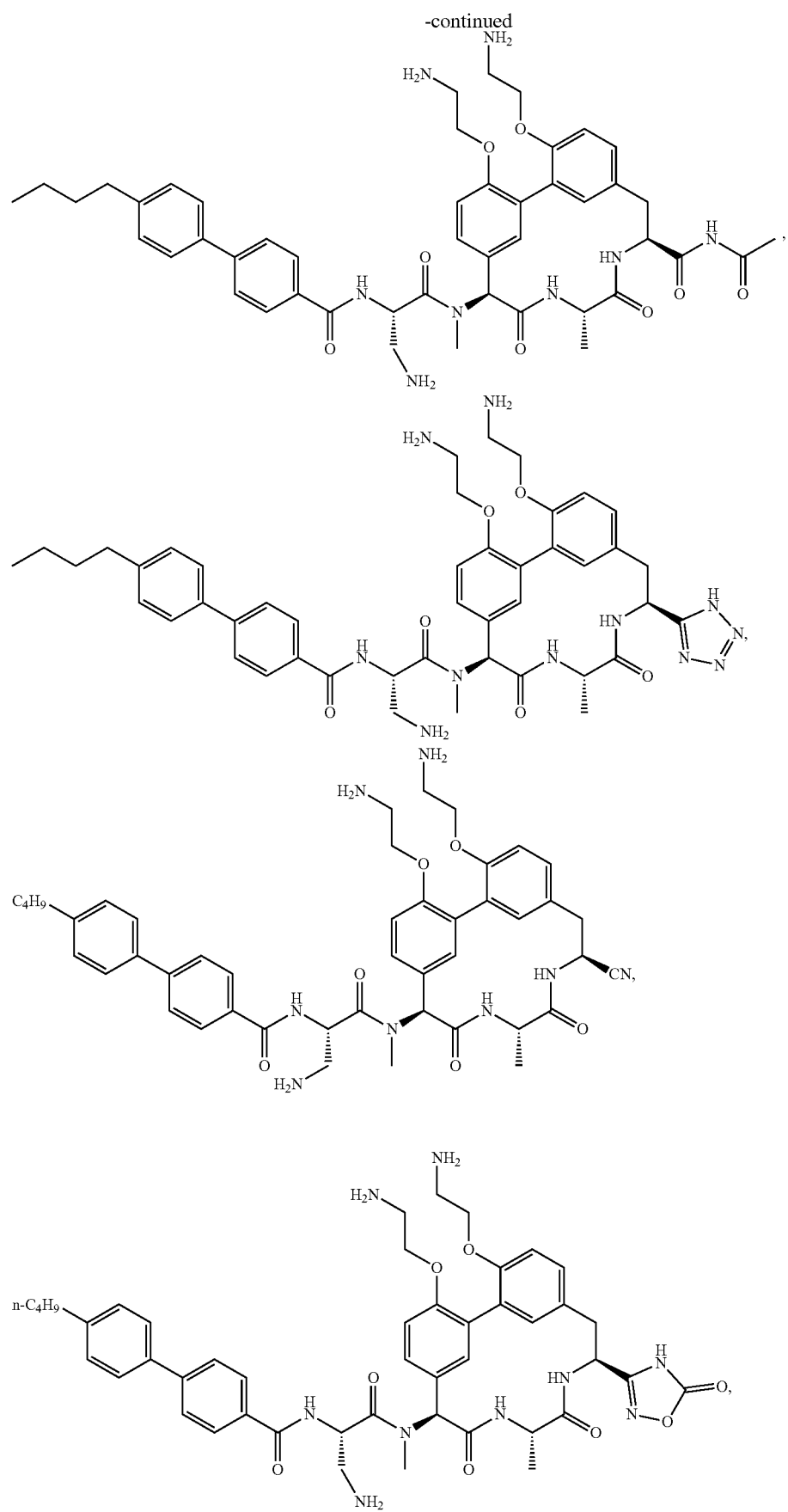

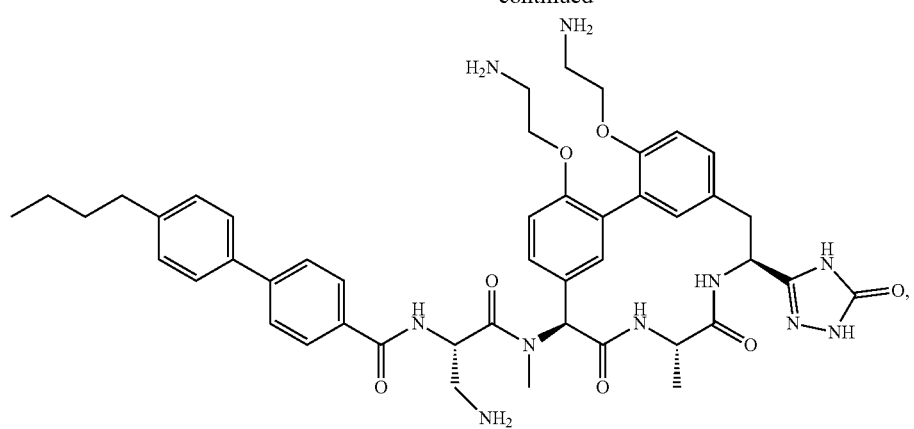
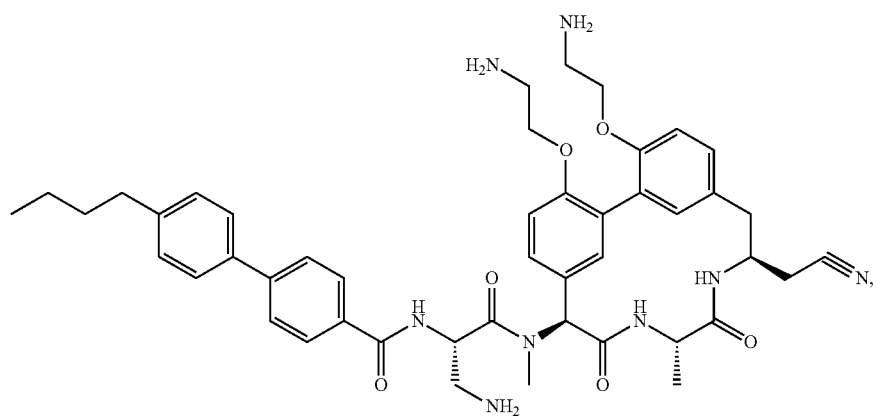
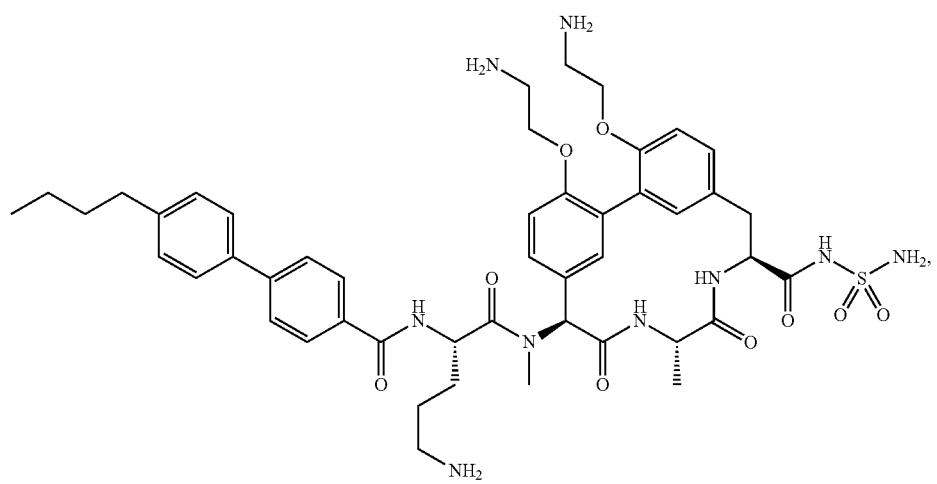

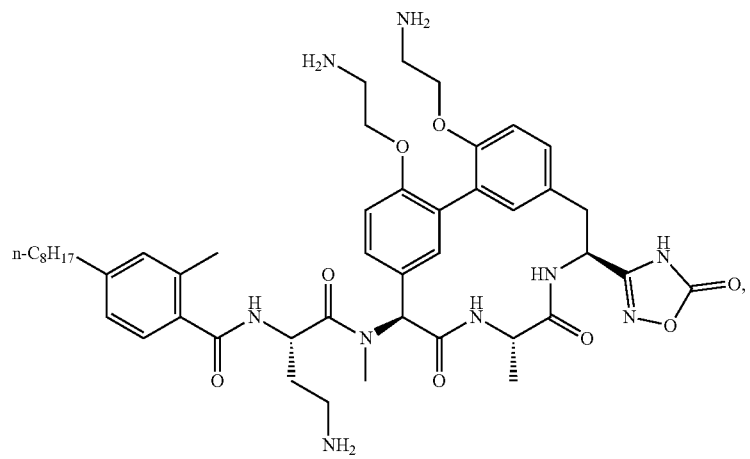
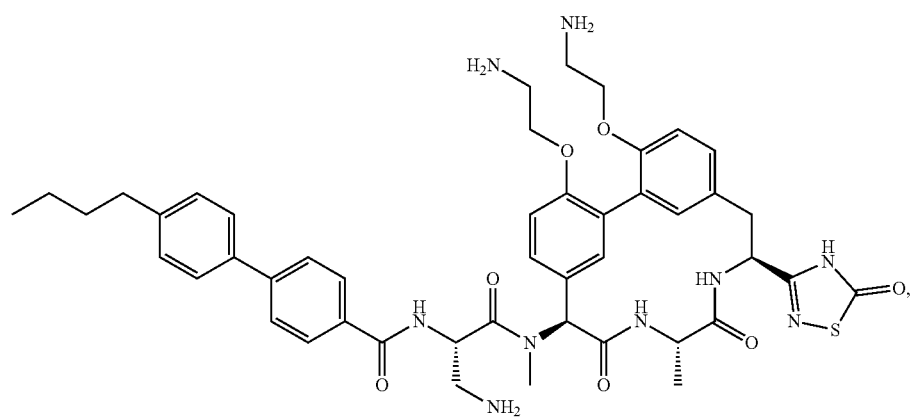
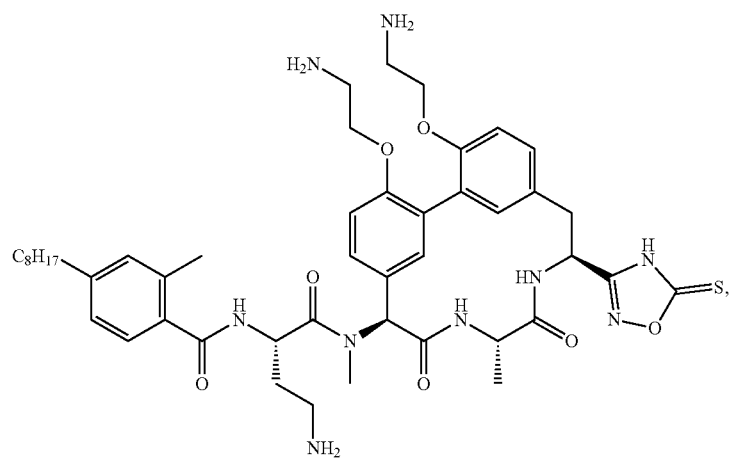

-continued
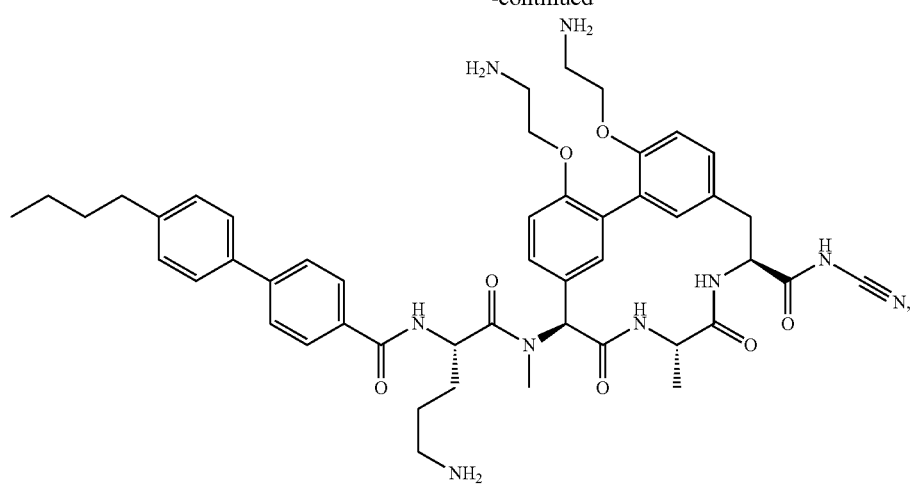
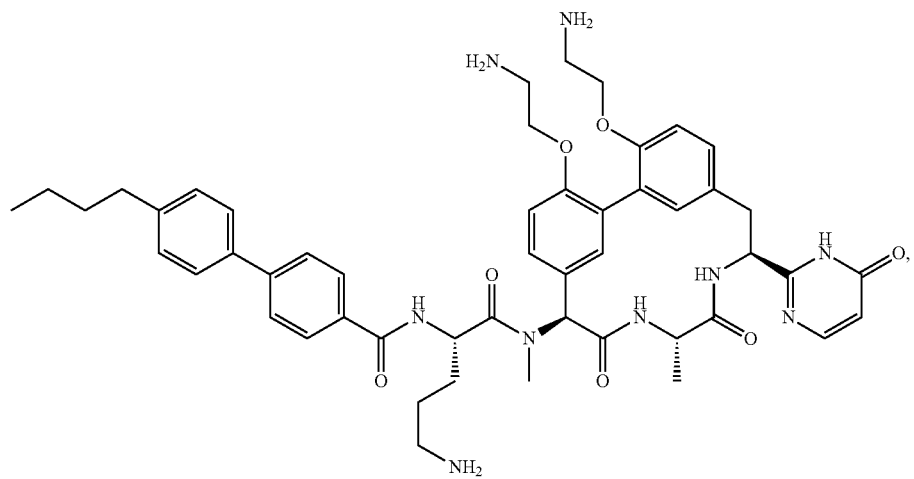
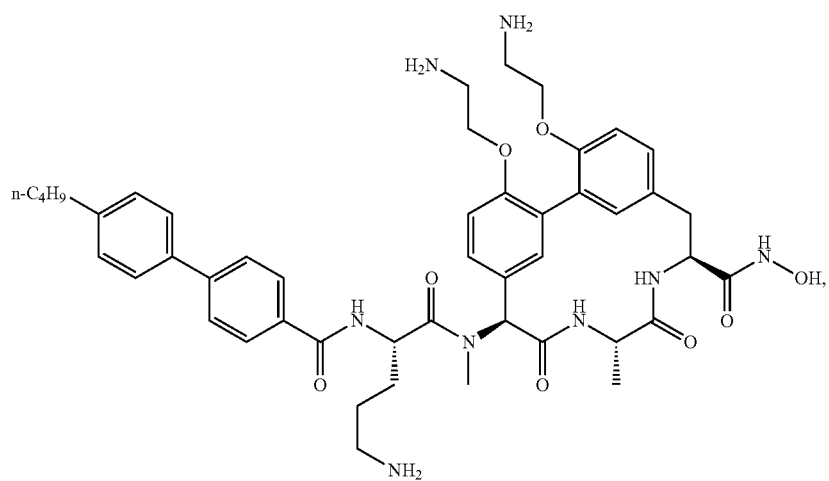

-continued
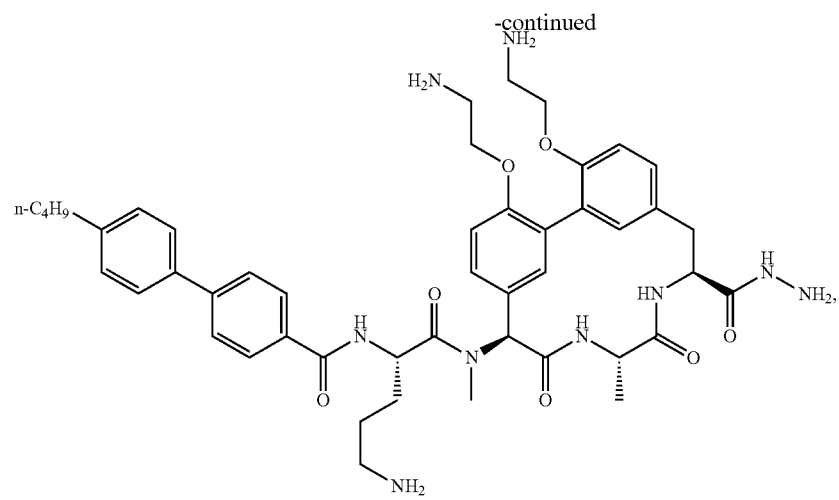
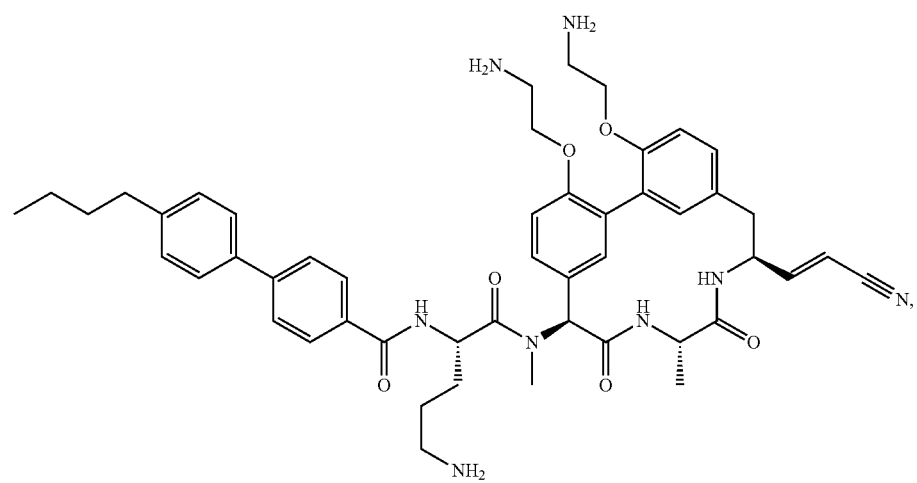
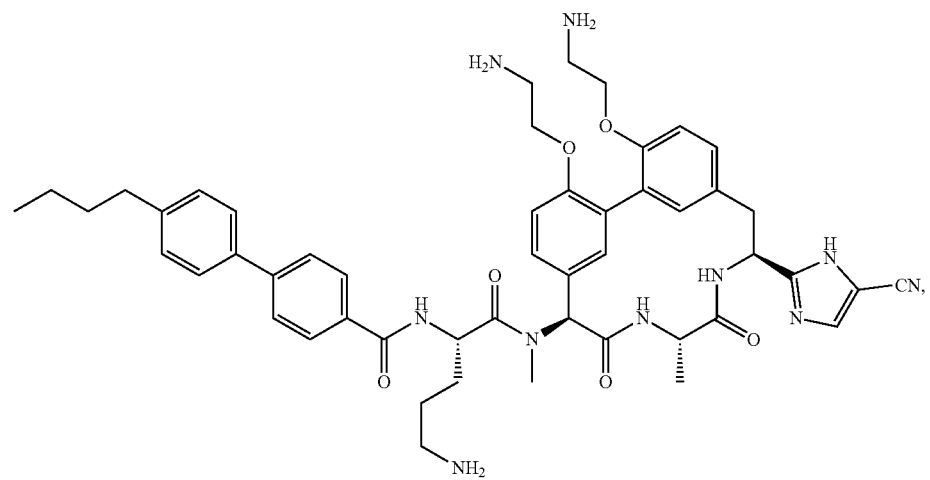

-continued
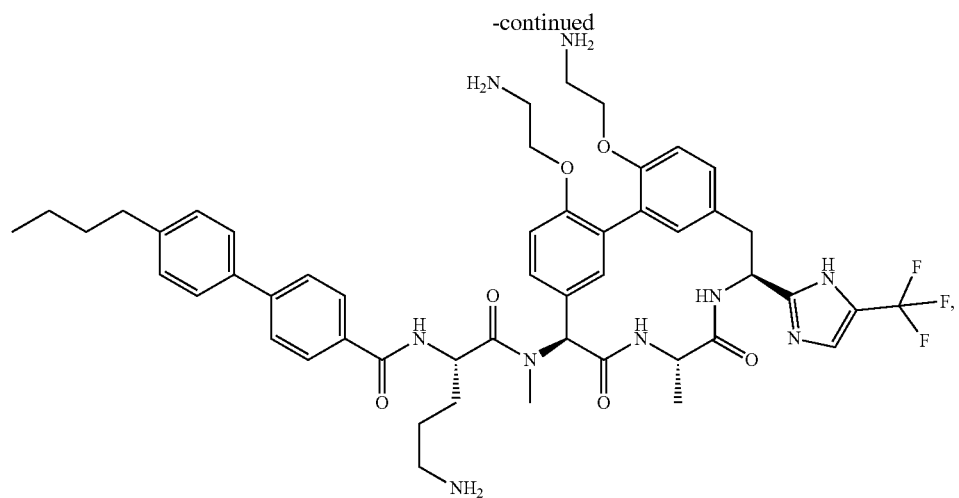
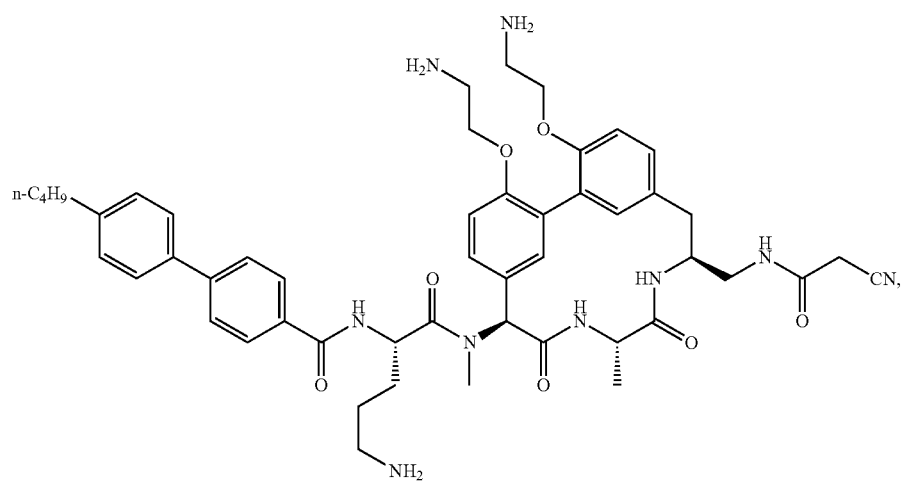
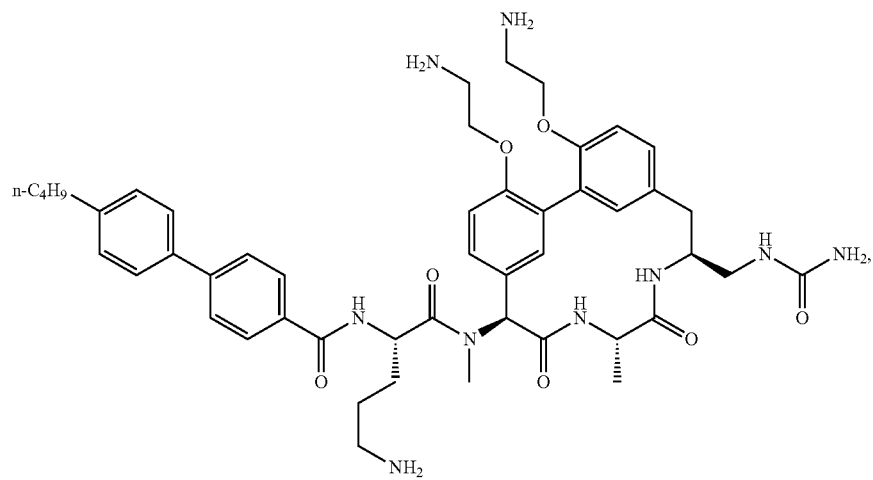

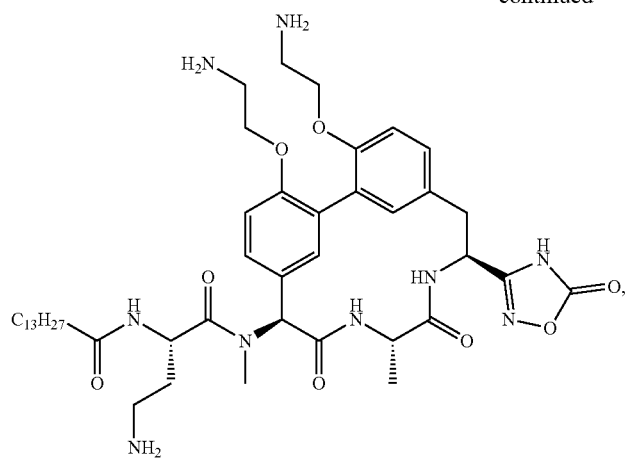
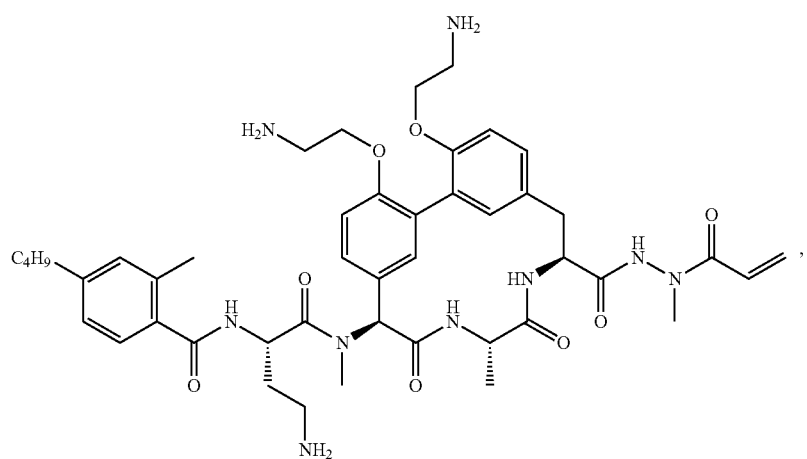
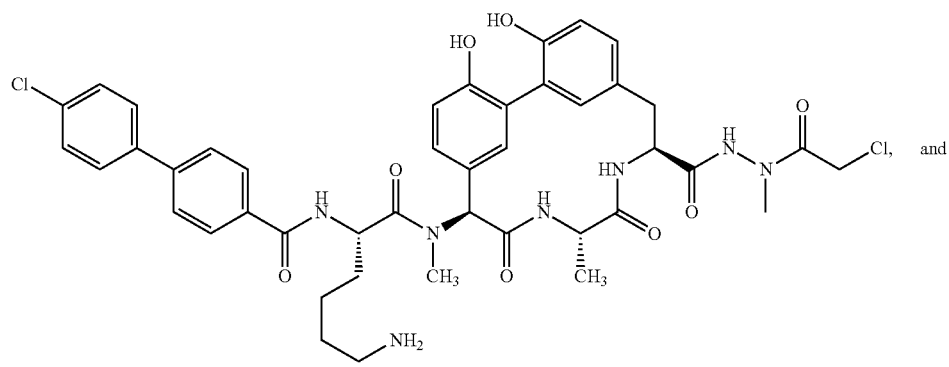

-continued
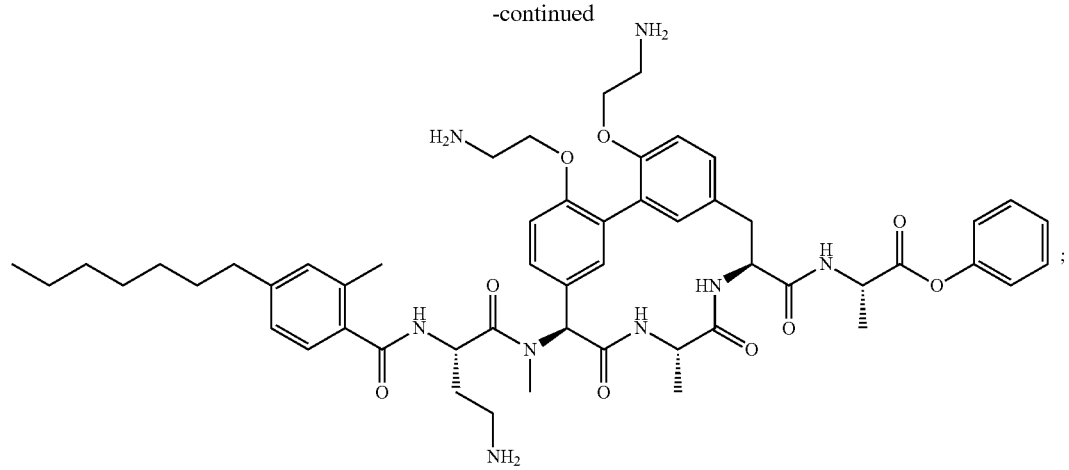
or a pharmaceutically acceptable salt or solvate, thereof.
15. A compound selected from the group consisting of:
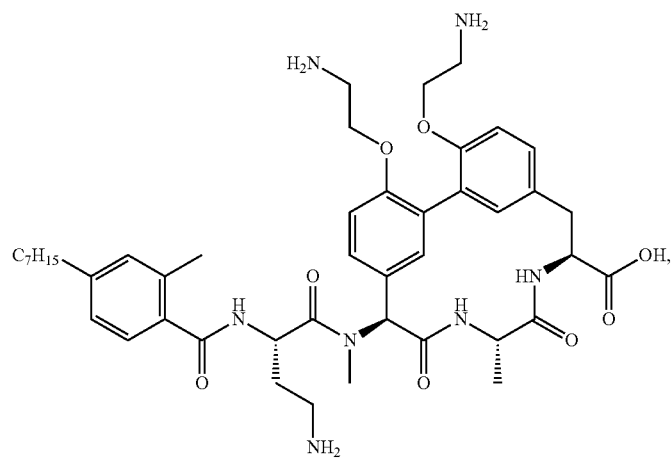
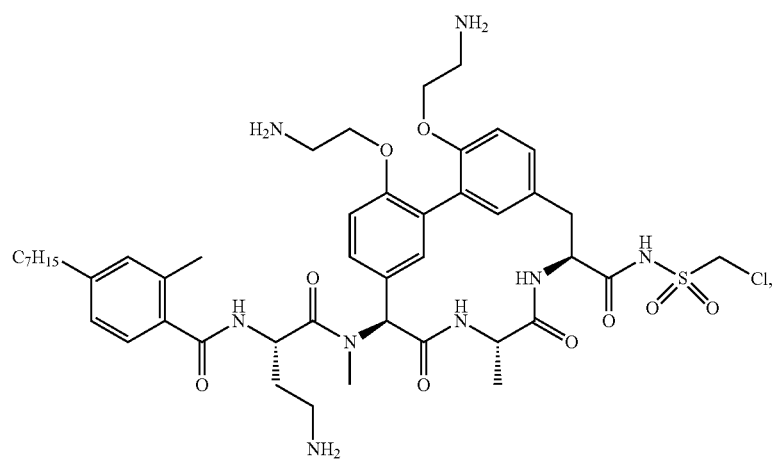

-continued
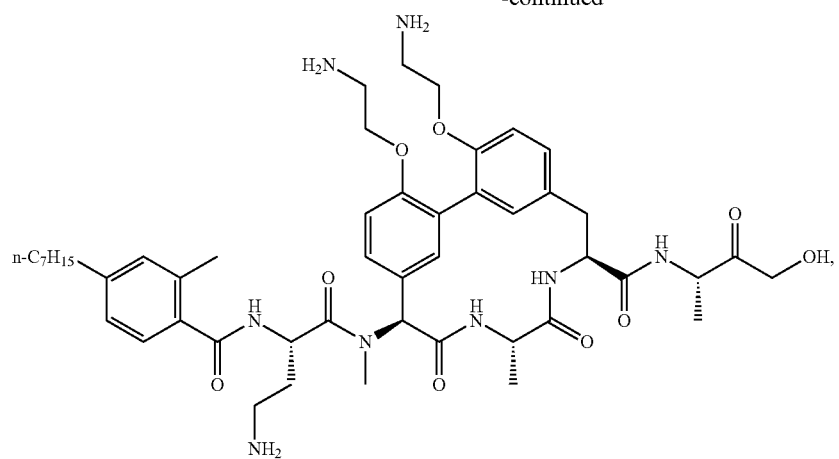
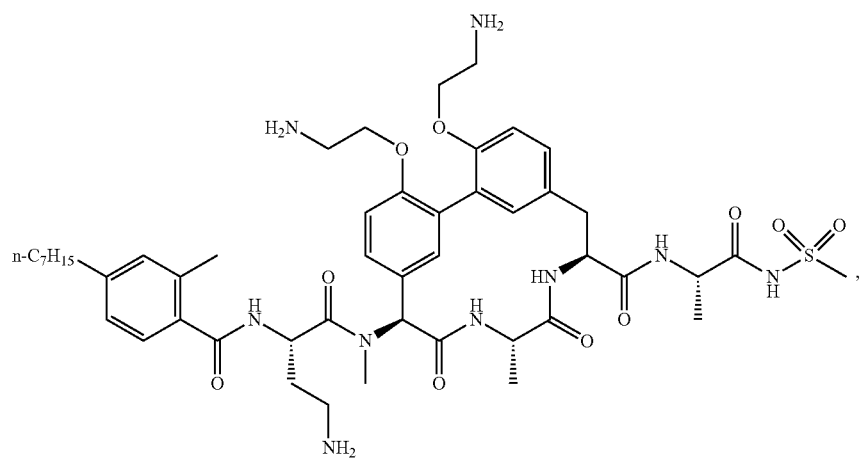
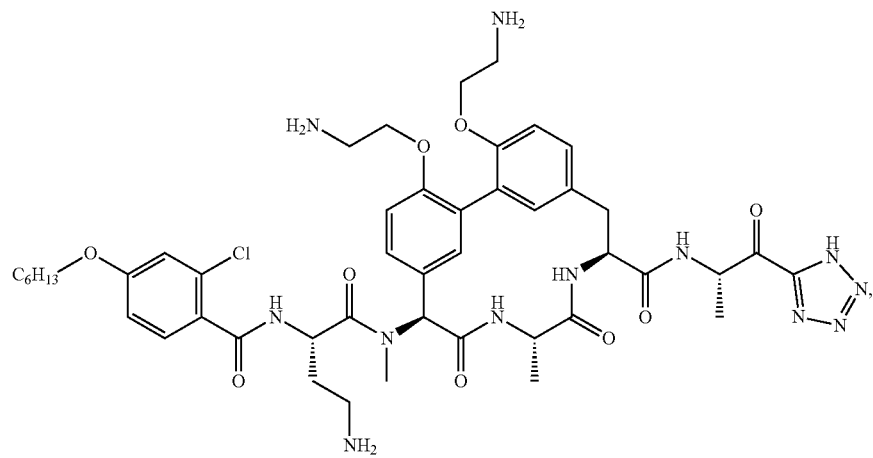

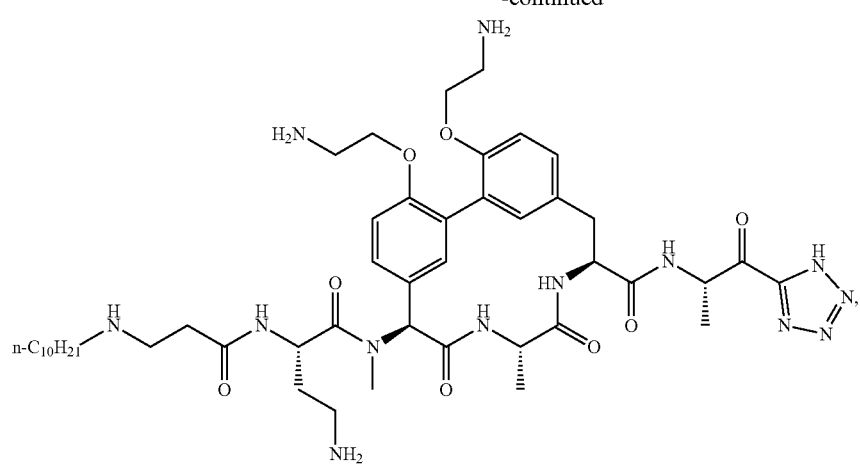
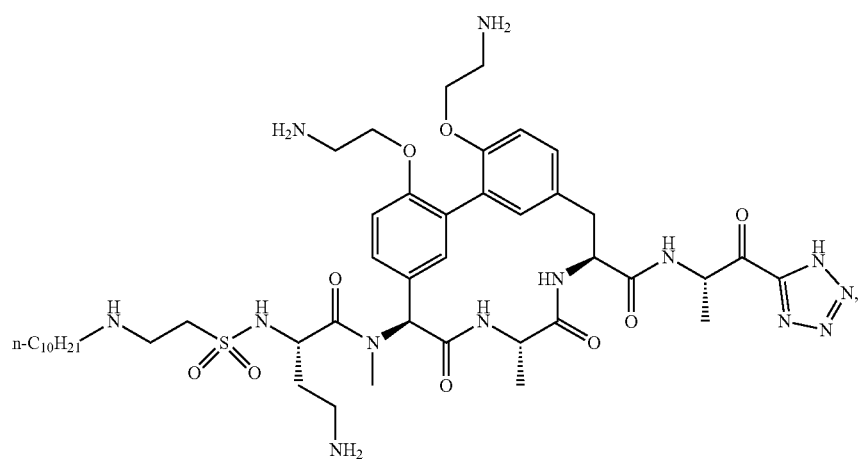
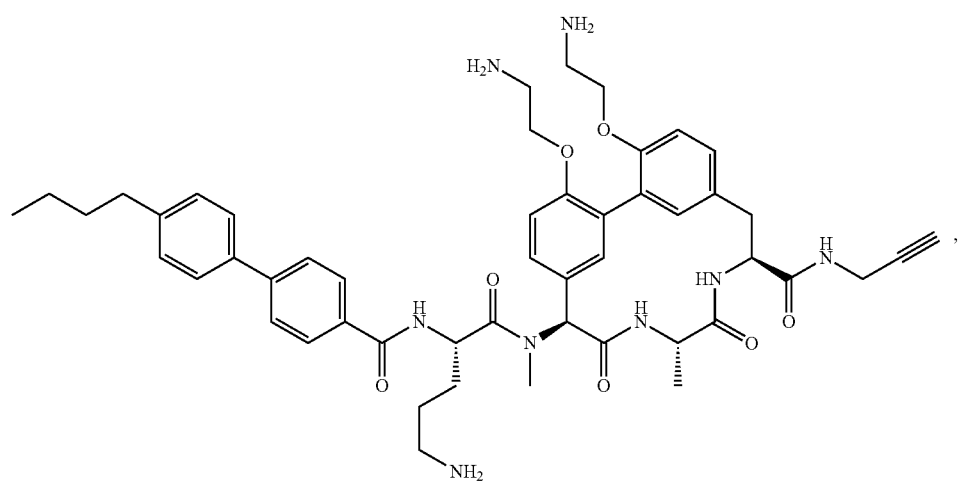

-continued
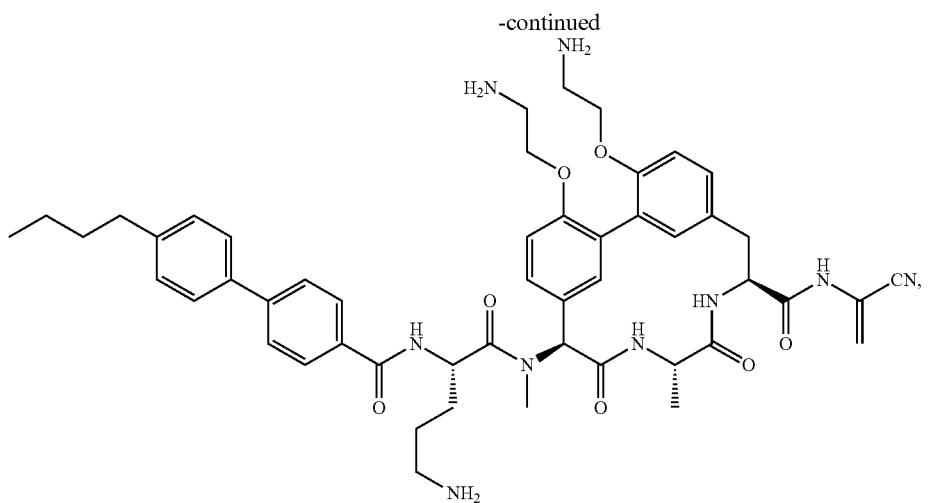
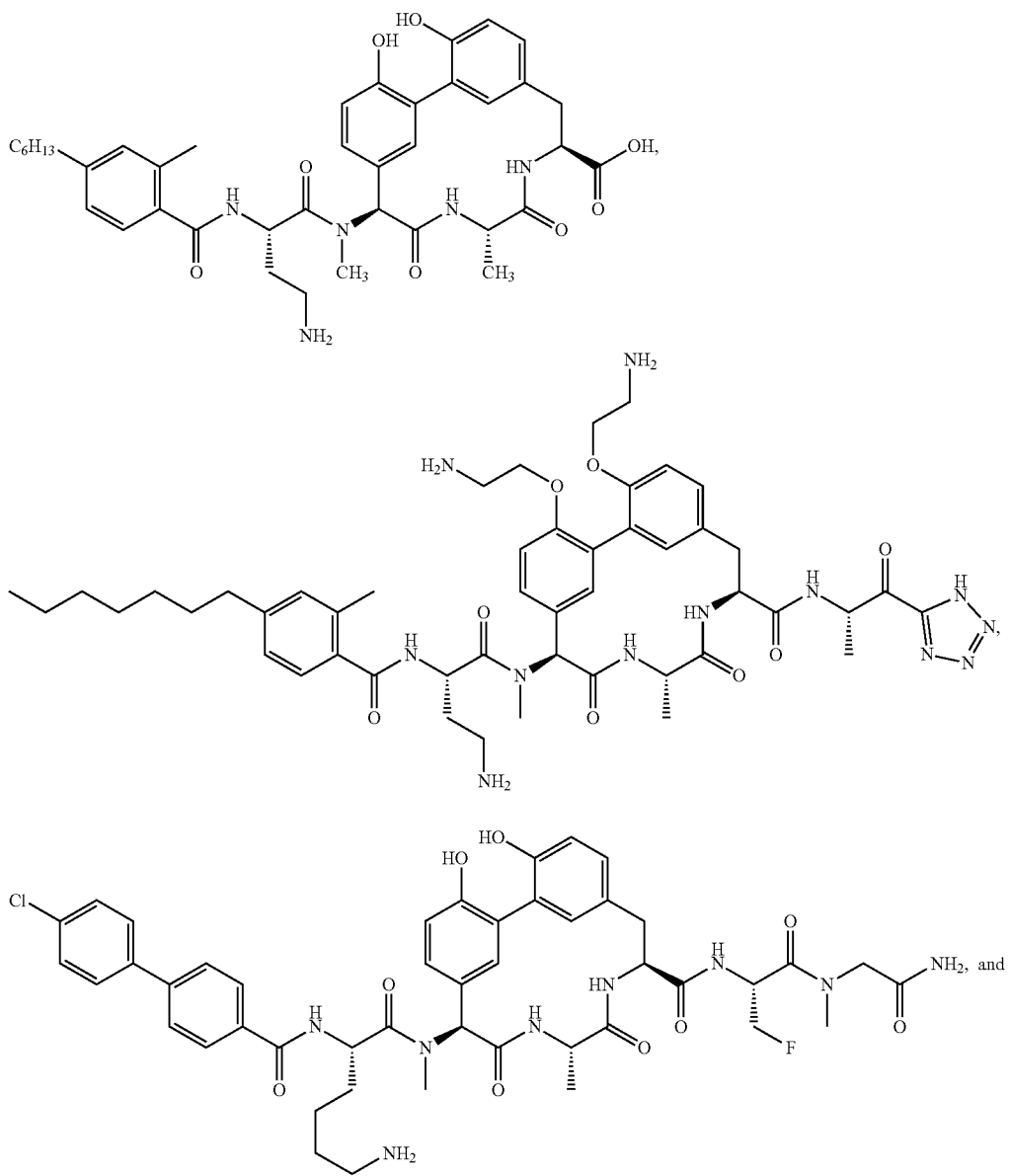

-continued

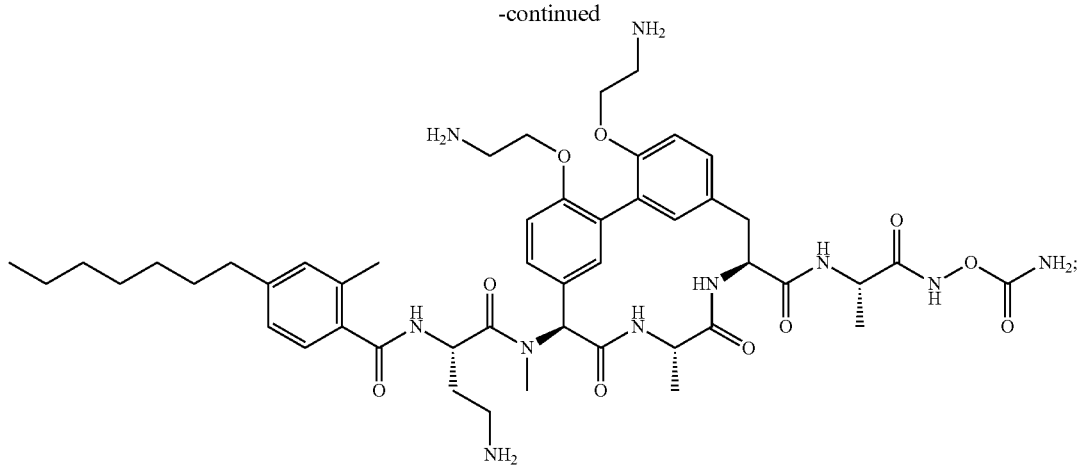

or a pharmaceutically acceptable salt or solvate, thereof.

16. A pharmaceutical composition comprising the compound, or a pharmaceutically acceptable salt or solvate, thereof, of claim 1 and a pharmaceutically acceptable excipient.

17. A method of treating a bacterial infection in a mammal, comprising administering an effective amount of a compound of claim 1, or a pharmaceutically acceptable salt or solvate thereof, to the mammal in need thereof.

18. The method of claim 17 further comprising administering a second therapeutic agent.

19. The method of claim 18, wherein the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

20. The method of claim 17, wherein the bacterial infection is an infection involving *Escherichia coli, Clostridium difficile, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

\* \* \* \* \*